(12) United States Patent
Ohta et al.

(10) Patent No.: US 10,815,489 B2
(45) Date of Patent: Oct. 27, 2020

(54) MODIFIED AMINOACYL-TRNA SYNTHETASE AND USE THEREOF

(71) Applicant: Chugai Seiyaku Kabushiki Kaisha, Kita-ku, Tokyo (JP)

(72) Inventors: Atsushi Ohta, Kanagawa (JP); Yusuke Yamagishi, Kanagawa (JP); Atsushi Matsuo, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/557,532

(22) PCT Filed: Mar. 11, 2016

(86) PCT No.: PCT/JP2016/057707
§ 371 (c)(1),
(2) Date: Sep. 12, 2017

(87) PCT Pub. No.: WO2016/148044
PCT Pub. Date: Sep. 22, 2016

(65) Prior Publication Data
US 2018/0127761 A1     May 10, 2018

(30) Foreign Application Priority Data

Mar. 13, 2015 (JP) ................................. 2015-051202

(51) Int. Cl.
| | |
|---|---|
| *C12N 15/00* | (2006.01) |
| *C12N 15/70* | (2006.01) |
| *C12P 19/34* | (2006.01) |
| *C12N 9/00* | (2006.01) |
| *C12N 5/10* | (2006.01) |
| *C12N 15/09* | (2006.01) |
| *C12P 21/00* | (2006.01) |
| *C12N 9/22* | (2006.01) |
| *C12P 21/02* | (2006.01) |

(52) U.S. Cl.
CPC ............... *C12N 15/70* (2013.01); *C12N 5/10* (2013.01); *C12N 9/00* (2013.01); *C12N 9/22* (2013.01); *C12N 9/93* (2013.01); *C12N 15/09* (2013.01); *C12P 19/34* (2013.01); *C12P 21/00* (2013.01); *C12P 21/02* (2013.01)

(58) Field of Classification Search
None
See application file for complete search history.

(56) References Cited

U.S. PATENT DOCUMENTS

| | | | |
|---|---|---|---|
| 5,057,415 | A | 10/1991 | Schuetz et al. |
| 7,288,372 | B2 | 10/2007 | Olejnik et al. |
| 8,809,280 | B2 | 8/2014 | Strom et al. |
| 9,133,245 | B2 | 9/2015 | Gao et al. |
| 9,913,245 | B2 | 3/2018 | Batchu et al. |
| 2003/0219780 | A1 | 11/2003 | Olejnik et al. |
| 2008/0044854 | A1* | 2/2008 | Wang ..................... C12N 15/67 435/69.1 |
| 2014/0194369 | A1 | 7/2014 | Gao et al. |
| 2015/0080549 | A1 | 3/2015 | Shiori et al. |
| 2016/0311858 | A1 | 10/2016 | Shiori et al. |
| 2019/0338050 | A1 | 11/2019 | Nakano et al. |
| 2020/0040372 | A1 | 2/2020 | Tanaka et al. |

FOREIGN PATENT DOCUMENTS

| | | |
|---|---|---|
| EP | 1424395 A1 | 6/2004 |
| EP | 1964916 A1 | 9/2008 |
| EP | 2088202 A1 | 8/2009 |
| EP | 2141175 A1 | 1/2010 |
| EP | 2177533 A1 | 4/2010 |
| EP | 2380596 A1 | 10/2011 |
| EP | 2492344 A1 | 8/2012 |
| EP | 2610348 A1 | 7/2013 |
| EP | 2615455 A1 | 7/2013 |
| EP | 2088202 B1 | 8/2013 |
| EP | 2647720 A1 | 10/2013 |
| EP | 2813512 A1 | 12/2014 |
| EP | 3031915 A1 | 6/2016 |
| EP | 3031915 B1 | 3/2019 |
| JP | S62143698 A | 6/1987 |
| JP | H01222795 A | 9/1989 |
| JP | 2003508408 A | 3/2003 |
| JP | 2003531199 A | 10/2003 |

(Continued)

OTHER PUBLICATIONS

Final Office Action dated Dec. 11, 2018 in U.S. Appl. No. 15/166,550, filed May 27, 2016.
Josephson, K., et al., "Ribosomal Synthesis of Unnatural Peptides," J Am Chem Soc 127:11727-11735 (2005).
Shimizu, Y., et al., "Cell-free translation reconstituted with purified components," Nat Biotechnol 19(8):751-755 (2001).
Liu, D. R., et al., "Engineering a tRNA and aminoacyl-tRNA synthetase for the site-specific incorporation of unnatural amino acids into proteins in vivo," Proc Natl Acad Sci 94:10092-10097 (1997).
U.S. Appl. No. 16/081,522, 371(c) date Aug. 31, 2018, Nakano, K., et al., related application.

(Continued)

*Primary Examiner* — Catherine S Hibbert
(74) *Attorney, Agent, or Firm* — Nixon & Vanderhye P.C.

(57) ABSTRACT

The present invention provides modified aminoacyl-tRNA synthetases (ARSs) having increased reactivity with N-methyl amino acids compared to natural aminoacyl-tRNA synthetases. The modified aminoacyl-tRNA synthetases according to the present invention can aminoacylate tRNAs with their corresponding N-methyl-substituted amino acids such as N-methyl-phenylalanine, N-methyl-valine, N-methyl-serine, N-methyl-threonine, N-methyl-tryptophan, and N-methyl-leucine more efficiently than natural aminoacyl-tRNA synthetases. The present invention enables a more efficient production of polypeptides containing N-methyl amino acids.

21 Claims, 14 Drawing Sheets
Specification includes a Sequence Listing.

(56) References Cited

FOREIGN PATENT DOCUMENTS

| | | |
|---|---|---|
| JP | 2007319064 A | 12/2007 |
| JP | 2008125396 A | 6/2008 |
| JP | 2009-528824 A | 8/2009 |
| JP | 5200241 B2 | 6/2013 |
| WO | WO 98/031700 A1 | 7/1998 |
| WO | WO-0181325 A2 | 11/2001 |
| WO | WO 02/085923 A2 | 10/2002 |
| WO | WO 03/014354 A1 | 2/2003 |
| WO | WO-03068990 A1 | 8/2003 |
| WO | WO 03/089454 A2 | 10/2003 |
| WO | WO 2007/066627 A1 | 6/2007 |
| WO | WO 2007/103307 A2 | 9/2007 |
| WO | WO 2008/117833 A1 | 10/2008 |
| WO | WO 2011/049157 A1 | 4/2011 |
| WO | WO 2011/051692 A1 | 5/2011 |
| WO | WO 2012/033154 A1 | 3/2012 |
| WO | WO-2012026566 A1 | 3/2012 |
| WO | WO 2012/074130 A1 | 6/2012 |
| WO | WO 2013/100132 A1 | 7/2013 |
| WO | WO-2015/019192 A2 | 2/2015 |
| WO | WO-2015019999 A1 | 2/2015 |
| WO | WO-2015185162 A1 | 12/2015 |
| WO | WO-2017150732 A1 | 9/2017 |
| WO | WO-2018143145 A1 | 8/2018 |
| WO | WO-2018225851 A1 | 12/2018 |
| WO | WO-2018225864 A1 | 12/2018 |

OTHER PUBLICATIONS

Beck et al., "Intestinal Permeability of Cyclic Peptides: Common Key Backbone Motifs Identified," Journal of the American Chemical Society, Jul. 25, 2012 (epub Jul. 12, 2012), 134(29):12125-12133.

Chatterjee et al., "N-Methylation of Peptides: A New Perspective in Medicinal Chemistry," Accounts of Chemical Research, Oct. 2008, 41(10):1331-1342.

Chen et al., "Effect of Alanine-293 Replacement on the Activity, ATP Binding, and Editing of *Escherichia coli* Leucyl-tRNA Synthetase," Biochemistry, Feb. 6, 2001, 40(5):1144-1149.

Chen et al., "Structurally Diverse Cyclisation Linkers Impose Different Backbone Conformations in Bicyclic Peptides," ChemBioChem, May 7, 2012, 13(7):1032-1038.

Cusack et al., "The 2 A crystal structure of leucyl-tRNA synthetase and its complex with a leucyl-adenylate analogue," The EMBO Journal, May 15, 2000, 19(10):2351-2361.

Dawson et al., "Synthesis of Proteins by Native Chemical Ligation," Science, Nov. 4, 1994, 266(5186):776-779.

Doublié et al., "Tryptophanyl-tRNA synthetase crystal structure reveals an unexpected homology to tyrosyl-tRNA synthetase," Structure, Jan. 15, 1995, 3(1):17-31.

Frankel et al., "Encodamers: Unnatural Peptide Oligomers Encoded in RNA," Chemistry & Biology, Nov. 2003, 10(11):1043-1050.

Fukunaga et al., "Structural Basis for Non-cognate Amino Acid Discrimination by the Valyl-tRNA Editing Domain," The Journal of Biological Chemistry, Aug. 19, 2005(epub Jun. 21, 2005), 280(33):29937-29945.

Ganesan, A., "The impact of natural products upon modern drug discovery," Current Opinion in Chemical Biology, Jun. 2008, 12(3):306-317.

Goto et al., "Flexizymes for genetic code reprogramming," Nature Protocols, Jun. 2011, 6(6):779-790.

Goto et al., "Translation Initiation with Initiator tRNA Charged with Exotic Peptides," J. Am. Chem. Soc., 2009, 131(14):5040-5041.

Goto et al., Kagaku Kogyo, 2007, 58(4):255-262 (relevance found in International Search Report of PCT/JP2012/084103).

Gracia et al., "Synthesis of chemically modified bioactive peptides: recent advances, challenges and developments for medicinal chemistry," Future Med. Chem., Oct. 2009, 1(7):1289-1310.

Hartman et al. "Enzymatic aminoacylation of tRNA with unnatural amino acids," PNAS, Mar. 21, 2006 (epub Mar. 13, 2006), 103(12):4356-4361.

Hartman et al., "An Expanded Set of Amino Acid Analogs for the Ribosomal Translation of Unnatural Peptides," PLoS One, Oct. 3, 2007, 10:e972, 17 pages.

Hayashi et al., Journal of Japanese Biochemical Society, Jun. 2010, 82(6):505-514 (relevance found in International Search Report of PCT/JP2012/084103).

Hecht et al., "Chemical Aminoacylation' of tRNA's," The Journal of Biological Chemistry, Jul. 10, 1978, 253(13):4517-4520.

Heinis et al., "Phage-encoded combinatorial chemical libraries based on bicyclic peptides,"Nature Chemical Biology, Jul. 2009, 5(7):502-507.

Higuchi et al., "Programmed Synthesis of Natural Product-like Non-standard Peptides Using the Translation System and Its Application," Journal of Synthetic Organic Chemistry, Japan, Mar. 2010, 68(3):217-227, with English abstract on first page (relevance found in International Search Report of PCT/JP2012/084103).

Hoogenboom, Hennie R., "Selecting and screening recombinant antibody libraries," Nature Biotechnology, Sep. 2005, 23(9):1105-1116.

Hountondji et al., "Crucial Role of Conserved Lysine 277 in the Fidelity of tRNA Aminoacylation by *Eschericia coli* Valyl-tRNA Synthetase," Biochemistry, Dec. 17, 2002, 41(50):14856-14865.

Itoh et al., "Crystallographic and mutational studies of seryl-tRNA synthetase from the archaeon *Pyrococcus horikoshii*," RNA Biology, Jul.-Sep. 2008 (epub Jul. 28, 2008), 5(3):169-177.

Kato et al., "2. Enzymes Involved in Drug Metabolism and Reaction Mechanisms Thereof," Yakubutsutaishagaku, Oct. 2000, $2^{nd}$ Edition, 9-13, with English translation.

Katoh et al., "Ribosomal synthesis of backbone macrocyclic peptides," Chem. Commun., Sep. 28, 2011, 47(36):9946-9958.

Kawakami et al., "Diverse backbone-cyclized peptides via codon reprogramming," Nature Chemical Biology, Dec. 2009, 5(12):888-890.

Kawakami et al., "In Vitro Selection of Multiple Libraries Created by Genetic Code Reprogramming to Discover Macrocyclic Peptides that Antagonize VEGFR2 Activity in Living Cells," ACS Chem. Biol. 2013(epub Apr. 2, 2013), 8(6):1205-1214.

Kawakami et al., "Messenger RNA-Programmed Incorporation of Multiple N-Methyl-Amino Acids into Linear and Cyclic Peptides," Chemistry & Biology, Jan. 2008, 15(1):32-42.

Kawakami et al., "Sequential peptide ligation by using a controlled cysteinyl prolyl ester (CPE) autoactivating unit," Tetrahedron Letters, 2007, 48:1903-1905.

Kleineweischede et al., "Chemoselective Peptide Cyclization by Traceless Staudinger Ligation," Angew. Chem. Int. Ed., 2008, 47(32):5984-5988.

Kobayashi et al., "Recognition of Non-α-amino Substrates by Pyrrolysyl-tRNA Synthetase," J. Mol. Biol., Feb. 6, 2009 (epub Dec. 11, 2008), 385(5):1342-1360.

Laufer et al., "The Impact of Amino Acid Side Chain Mutations in Conformational Design of Peptides and Proteins," Chem. Eur. J., May 10, 2010, 16(18):5385-5390.

Lee et al., "Molecular Modeling Study of the Editing Active Site of *Escherichia coli* Leucyl-tRNA Synthetase: Two Amino Acid Binding Sites in the Editing Domain," Proteins, Mar. 1, 2004, 54(4):693-704.

Li et al., "In Vitro Selection of mRNA Display Libraries Containing an Unnatural Amino Acid," J. Am. Chem. Soc., Aug. 28, 2002, 124(34):9972-9973.

Li et al., "Salicylaldehyde Ester-Induced Chemoselective Peptide Ligations: Enabling Generation of Natural Peptidic Linkages at the Serine/Threonine Sites," Organic Letters, Apr. 16, 2010, 12(8):1724-1727.

Mas-Moruno et al., "Cilengitide: The First Anti-Angiogenic Small Molecule Drug Canditate. Design, Synthesis and Clinical Evaluation," Anti-Cancer Agents in Medicinal Chemistry, Dec. 2010, 10(10):753-768.

(56) References Cited

OTHER PUBLICATIONS

Mermershtain et al., "Idiosyncrasy and identity in the prokaryotic phe-system: Crystal structure of *E. coli* phenylalanyl-tRNA synthetase complexed with phenylalanine and AMP," Protein Science, Jan. 2011, 20(1):160-167.
Merryman et al., "Transformation of Aminoacyl tRNAs for the In Vitro Selection of "Drug-like" Molecules," Chemistry & Biology, Apr. 2004, 11(4):575-582.
Millward et al., A General Route for Post-Translational Cyclization of mRNA Display Libraries, J. Am. Chem. Soc., Oct. 19, 2005, 127(41):14142-14143.
Millward et al., "Design of Cyclic Peptides That Bind Protein Surfaces with Antibody-Like Affinity," ACS Chemical Biology, Sep. 21, 2007, 2(9):625-634.
Ohta et al., "Synthesis of Polyester by Means of Genetic Code Reprogramming," Chemistry & Biology, Dec. 2007, 14(12):1315-1322.
Ovadia et al., "Improvement of drug-like properties of peptides: the somatostatin paradigm," Expert Opin. Drug Discov., Jul. 2010, 5(7):655-671.
Parthasarathy et al., "Sortase A as a Novel Molecular 'Stapler' for Sequence-Specific Protein Conjugation," Bioconjugate Chem., Mar.-Apr. 2007, 18(2):469-476.
Peacock et al., "Amino acid-dependent stability of the acyl linkage in aminoacyl-tRNA," RNA, Jun. 2014 (epub Apr. 21, 2014), 20(6):758-764.
Perona et al., "Structural Diversity and Protein Engineering of the Aminoacyl-tRNA Synthetases," Biochemistry, Nov. 6, 2012 (epub Oct. 26, 2012), 51(44):8705-8729.
Reddy et al., "Synthesis of small cyclic peptides via intramolecular Heck reactions," Tetrahedron Letters, 2003, 44:353-356.
Rezai et al., "Testing the Conformational Hypothesis of Passive Membrane Permeability Using Synthetic Cyclic Peptide Diastereomers," J. Am. Chem. Soc., Mar. 1, 2006, 128(8):2510-2511.
Sankaranarayanan et al., "The Structure of Threonyl-tRNA Synthetase-tRNA$^{Thr}$ Complex Enlightens Its Repressor Activity and Reveals an Essential Zinc Ion in the Active Site," Cell, Apr. 30, 1999, 97(3):371-381.
Satyanarayanajois et al., "Medicinal chemistry for 2020," Future Med. Chem., Oct. 2011, 3(14):1765-1786.
Sever et al., "*Escherichia coli* Tryptophanyl-tRNA Synthetase Mutants Selected for Tryptophan Auxotrophy Implicate the Dimer Interface in Optimizing Amino Acid Binding," Biochemistry, Jan. 9, 1996, 35(1):32-40.
Shukla et al., "Phage-Displayed Combinatorial Peptide Libraries in Fusion to Beta-Lactamase as Reporter for an Accelerated Clone Screening: Potential Uses of Selected Enzyme-Linked Affinity Reagents in Downstream Applications," Combinatorial Chemistry & High Throughput Screening, Jan. 2010, 13(1):75-87.
Subtelny et al., "Optimal Codon Choice Can Improve the Efficiency and Fidelity of N-Methyl Amino Acid Incorporation into Peptides by In-Vitro Translation," Angew. Chem. Int. Ed., Mar. 28, 2011 (epub Mar. 4, 2011), 50:3164-3167.
Subtelny et al., "Ribosomal Synthesis of N-Methyl Peptides," The Journal of the American Chemical Society, May 14, 2008 (epub Apr. 11, 2008), 130(19):6131-6136.
Tan et al., "Amino Acid Backbone Specificity of the *Escherichia coli* Translation Machinery," J. Am. Chem. Soc., Oct. 13, 2004, 126(40):12752-12753.
Terasaka et al., "Recent Developments of Engineered Translational Machineries for the Incorporation of Non-Canonical Amino Acids into Polypeptides," Int. J. Mol. Sci., Mar. 20, 2015, 16(3):6513-6531.
Tsukiji et al., "Sortase-Mediated Ligation: A Gift from Gram-Positive Bacteria to Protein Engineering," ChemBioChem, Mar. 23, 2009, 10(5):787-798.
Wells et al., "Reaching for high-hanging fruit in drug discovery at protein-protein interfaces," Nature, Dec. 13, 2007, 450(7172):1001-1009.

White et al., "Contemporary strategies for peptide macrocyclization," Nature Chemistry, Jul. 2011 (published online Jun. 23, 2011), 3(7):509-524.
White et al., "On-resin N-methylation of cyclic peptides for discovery of orally bioavailable scaffolds," Nature Chemical Biology, Nov. 2011 (epub Sep. 25, 2011), 7(11):810-817.
Wu et al., "A Genetically Encoded Photocaged Amino Acid," J. Am. Chem. Soc., Nov. 10, 2004, 126(44): 14306-14307.
Yamagishi et al., "Natural Product-Like Macrocyclic N-Methyl-Peptide Inhibitors against a Ubiquitin Ligase Uncovered from a Ribosome-Expressed De Novo Library," Chemistry & Biology, Dec. 23, 2011, 18(12):1562-1570.
Yanagisawa et al., "Multistep Engineering of Pyrrolsyl-tRNA Synthetase to Genetically Encode $N^{249}$-(o-Azidobenzyloxycarbonyl)lysine for Site-Specific Protein Modification," Chemistry & Biology, Nov. 24, 2008, 15(11):1187-1197.
Zhai et al., "Two Conserved Threonines Collaborate in the *Escherichia coli* Leucyl-tRNA Synthetase Amino Acid Editing Mechanism," Biochemistry, Nov. 29, 2005, 44(47):15437-15443.
Zhang et al., "Specificity of Translation for N-Alkyl Amino Acids," J. Am. Chem. Soc., Sep. 19, 2007, 129(37):11316-11317.
Goto et al., "Ribosomal Synthesis of Combinatorial Polypeptides containing unusual amino acid blocks," Kagaku Kogyo, 2007, 58(4):255-262, English translation, 12 pages.
Hayashi et al., "Ribosomal synthesis of nonstandard cyclic peptides and its application to drug discovery," Journal of Japanese Biochemical Society, Jun. 2010, 82(6):505-514, English translation, 15 pages.
Higuchi et al., "Programmed Synthesis of Natural Product-like Non-standard Peptides Using the Translation System and Its Application," Journal of Synthetic Organic Chemistry, Japan, Mar. 2010, 68(3):217-227, English translation, 19 pages.
Terasaka et al., "Construction of nonstandard peptide library by genetic code reprogramming and bioactive peptide discovery," Experimental Medicine, May 2011, 29(7):1063-1070, with English translation, 10 pages.
U.S. Appl. No. 15/166,550, filed May 27, 2016, Kariyuki, S. et al., related application, now published.
Bock, et al., "Getting in Shape: Controlling Peptide Bioactivity and Bioavailability Using Conformational Constraints," ACS Chem Biol., 8(3):488-499 (2013).
International Search Report for International Application No. PCT/JP2017/008623, dated May 30, 2017, 2 pages.
Josephson, et al., "mRNA display: from basic principles to macrocycle drug discovery," Drug Discov Today, 19(4):388-399 (2014).
Meinnel, et al., "Methionine as translation start signal: A review of the enzymes of the pathway in *Escherichia coli*," Biochimie., 75(12):1061-1075 (1993).
Montalbetti, C. A. G. and Falque, V., "Amide bond formation and peptide coupling," Tetrahedron, 61:10827-10852 (2005).
Schlippe, et al., "In Vitro Selection of Highly Modified Cyclic Peptides That Act as Tight Binding Inhibitors," J Am Chem Soc., 134(25):10469-77 (2012).
Albericio, F., et al., "Fmoc Methodology: Cleavage from the Resin and Final Deprotection," Amino Acids, Peptides and Proteins in Organic Chemistry, 3:349-369 (2011).
Behrendt, R., et al., "Advances in Fmoc solid-phase peptide synthesis," J Pept Sci., 22:4-27 (2016).
Carpino, L. A., et al., "Dramatically enhanced N → acyl migration during the trifluoroacetic acid-based deprotection step in solid phase peptide synthesis," Tetrahedron Letters, 46:1361-1364 (2005).
Doi, Y., et al., "Elongation Factor Tu Mutants Expand Amino Acid Tolerance of Protein Biosynthesis System," Journal of the American Chemical Society, 129:14458-14462 (2007).
Eberhard, H. and Seitz, O., "N → Acyl shift in Fmoc-based synthesis of phosphopeptides," Org Biomol Chem., 6:1349-1355 (2008).
Fang, W.-J., et al., "Deletion of Ac-NMePhe From [NMePhe]arodyn Under Acidic Conditions, Part 1: Effects of Cleavage Conditions and N-Terminal Functionality," PeptideScience, 96(1):97-102 (2011).
Fujino, T., et al., "Reevaluation of the D-Amino Acid Compatibility with the Elongation Event in Translation," Journal of the American Chemical Society, 135:1830-1837 (2013).

(56) References Cited

OTHER PUBLICATIONS

Fujino, T., et al., "Ribosomal Synthesis of Peptides with Multiple β-Amino Acids," Journal of the American Chemical Society, 138:1962-1969 (2016).

Gilon, C., et al., "Backbone Cyclization: A New Method for Conferring Conformational Constraint on Peptides," Biopolymers, 31:745-750 (1991).

Hruby, V. J., et al., "Emerging approaches in the molecular design of receptor-selective peptide ligands: conformational, topographical and dynamic considerations," Biochem J., 268:249-262 (1990).

Kato, et al., "Enzymes Involved in Drug Metabolism and Reaction Mechanisms Thereof," Yakubutsutaishagaku, $3^{rd}$ Edition, 43-46, (2010).

Kawakami, T., et al., "Ribosomal Synthesis of Polypeptides and Peptoid-Peptide Hybrids," Journal of American Chemical Society, 130:16861-16863 (2008).

Kawakami, T., et al., "Incorporation of electrically charged N-alkyl amino acids into ribosomally synthesized peptides via post-translational conversion," Chem Sci., 5:887-893 (2014).

Loos, P., et al., "Unified Azoline and Azole Syntheses by Optimized Aza-Wittig Chemistry," Eur J Org Chem., 2013:3290-3315 (2013).

Lundquist IV, J. T. and Pelletier, J. C., "Improved Solid-Phase Peptide Synthesis Method Utilizing α-Azide-Protected Amino Acids," Org Lett., 3(5):781-783 (2001).

Maini, R., et al., "Protein Synthesis with Ribosomes Selected for the Incorporation of β-Amino Acids," Biochemistry, 54:3694-3706 (2015).

Maini, R., et al., "Ribosome-mediated synthesis of natural product-like peptides via cell-free translation," Current Opinion in Chemical Biology, 34:44-52 (2016).

Marcucci, E., et al., "Solid-Phase Synthesis of NMe-IB-01212, a Highly N-Methylated Cyclic Peptide," Org Lett., 14(2):612-615 (2012).

Rodriguez, H., et al., "A convenient microwave-enhanced solid-phase synthesis of short chain N-methyl-rich peptides," J Pept Sci., 16:136-140 (2010).

Roodbeen, R., et al., "Microwave Heating in the Solid-Phase Synthesis of N-Methylated Peptides: When Is Room Temperature Better?" Eur J Org Chem., 2012:7106-7111 (2012).

Teixidó, M., et al., "Solid-phase synthesis and characterization of N-methyl-rich peptides," J Peptide Res., 65:153-166 (2005).

Urban, J., et al., "Lability of N-alkylated peptides towards TFA cleavage," Int J Peptide Protein Res., 47:182-189 (1996).

Wang, J., et al., "Kinetics of Ribosome-Catalyzed Polymerization Using Artificial Aminoacyl-tRNA Substrates Clarifies Inefficiencies and Improvements," ACS Chemical Biology, 10:2187-2192 (2015).

Wenschuh, H., et al., "Stepwise Automated Solid Phase Synthesis of Naturally Occurring Peptaibols Using FMOC Amino Acid Fluorides," J Org Chem., 60:405-410 (1995).

U.S. Appl. No. 16/619,388, 371(c) date Dec. 4, 2019, Nomura, K., et al., related application.

U.S. Appl. No. 16/619,014, 371(c) date Dec. 3, 2019, Muraoka, T., et al., related application.

U.S. Appl. No. 251,176, filed Sep. 30, 1988, Schuetz, H.-J., et al.

U.S. Appl. No. 14/125,906, 371(c) date Mar. 10, 2014, Gao, J., et al.

U.S. Appl. No. 16/479,736, 371(c) date Jul. 22, 2019, Tanaka, S., et al., related application.

\* cited by examiner

[Figure 1]
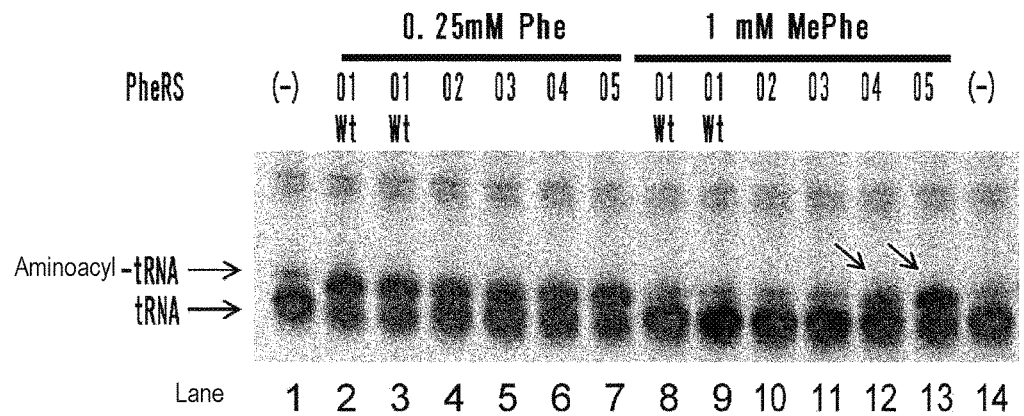
[Figure 2]
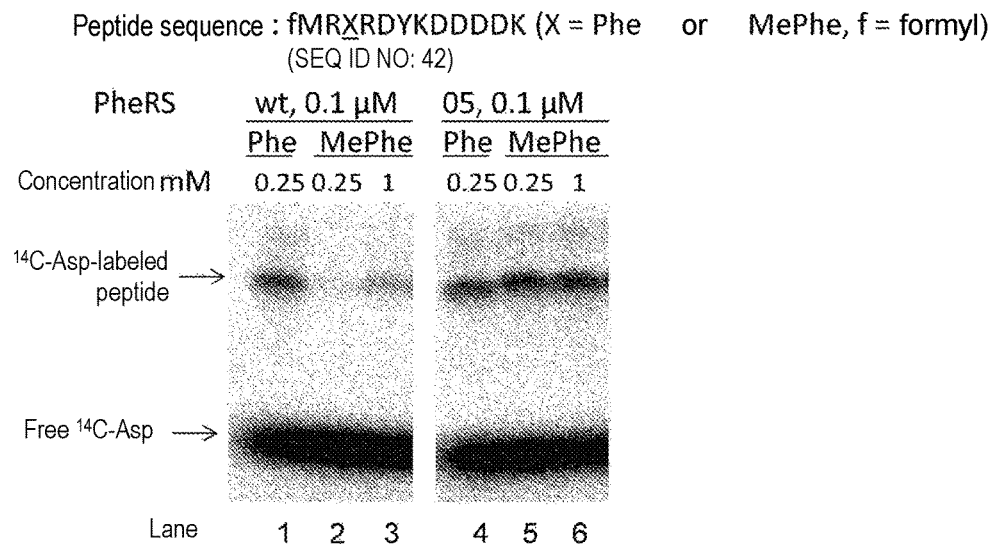

[Figure 3-1]
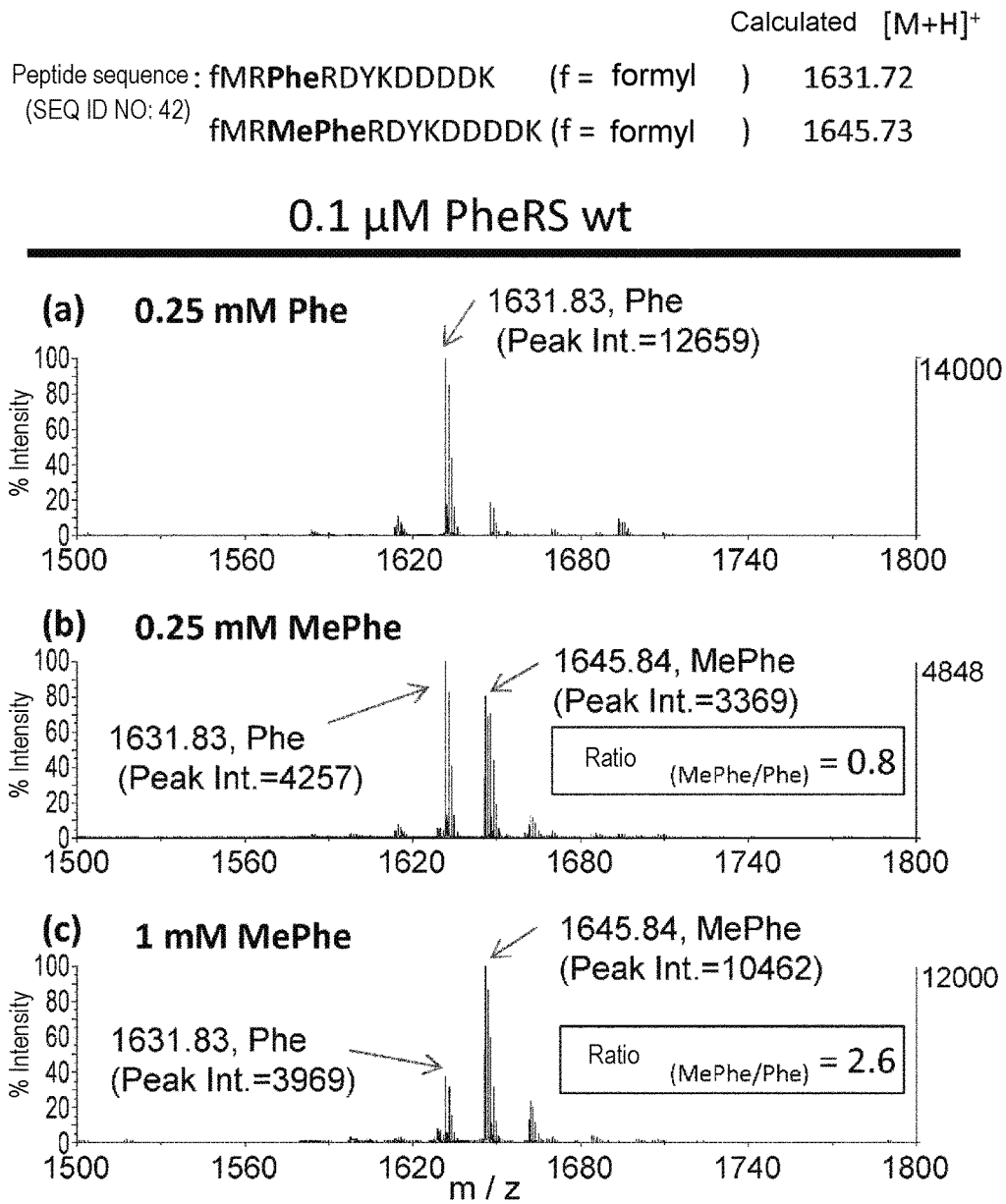

[Figure 3-2]
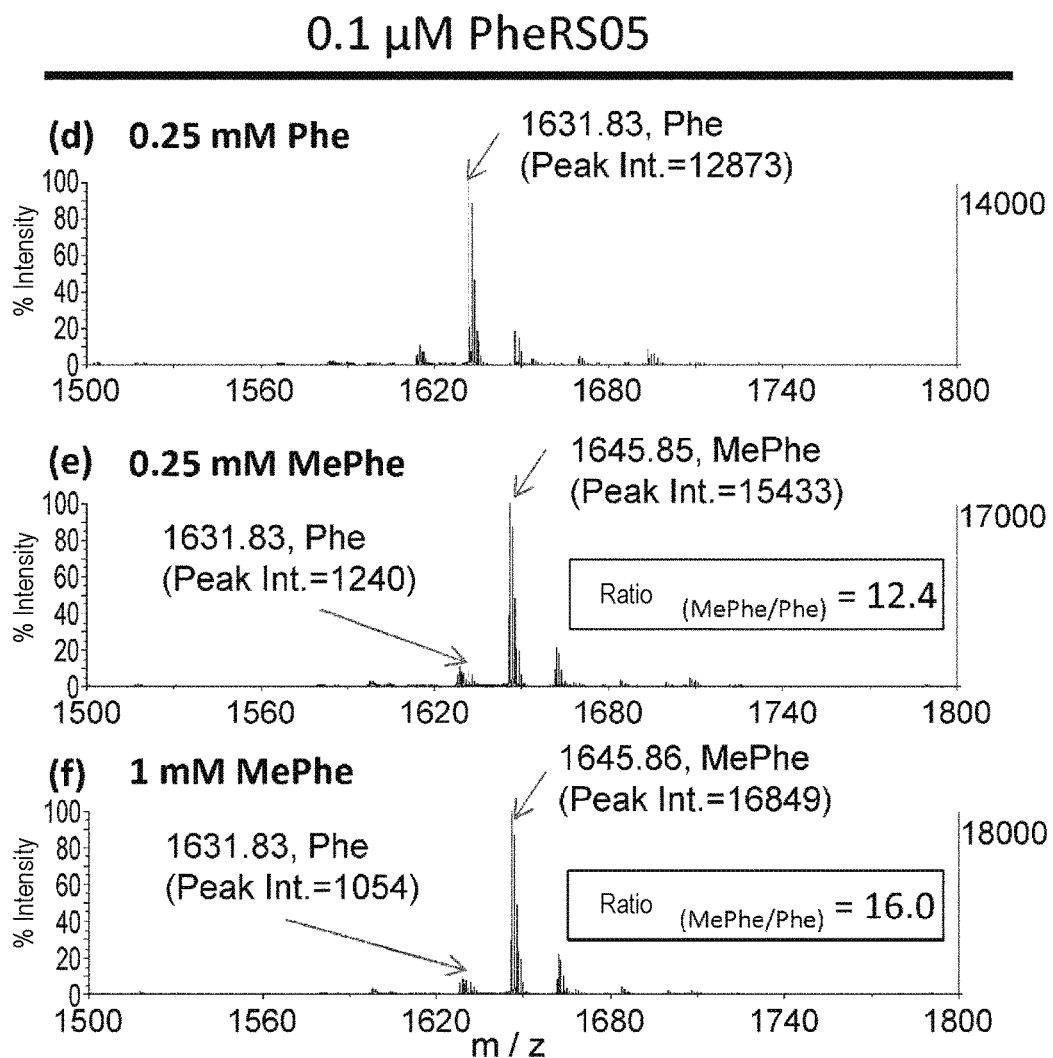

[Figure 4]
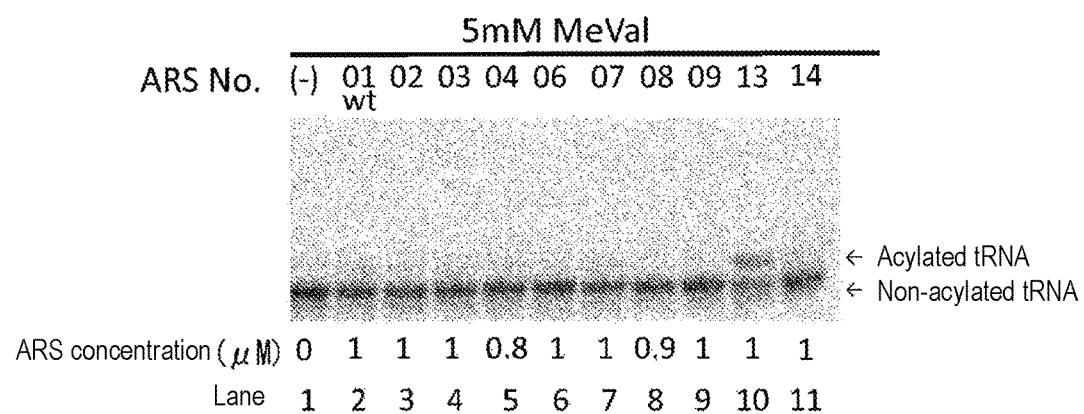

[Figure 5]
(a) ValRS01(wt)
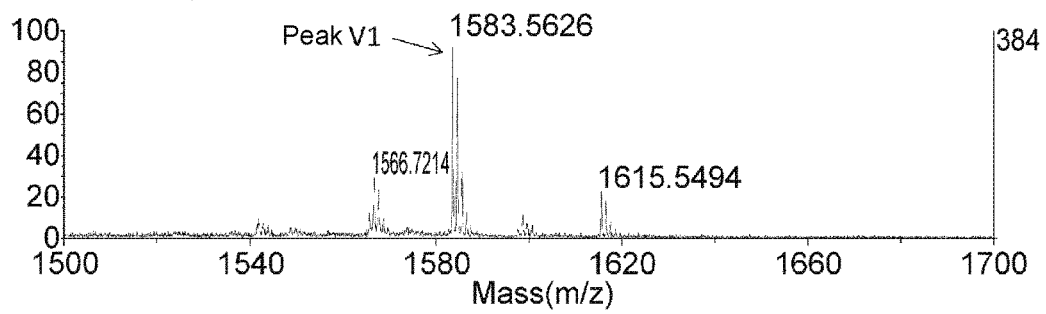
(b) ValRS13
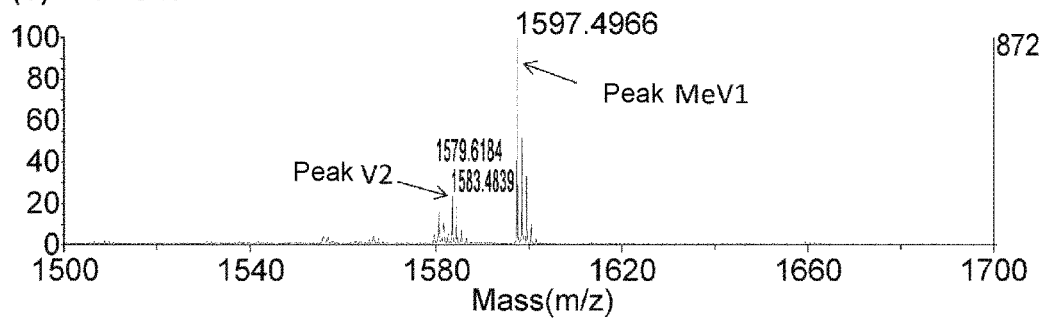
(c) ValRS04
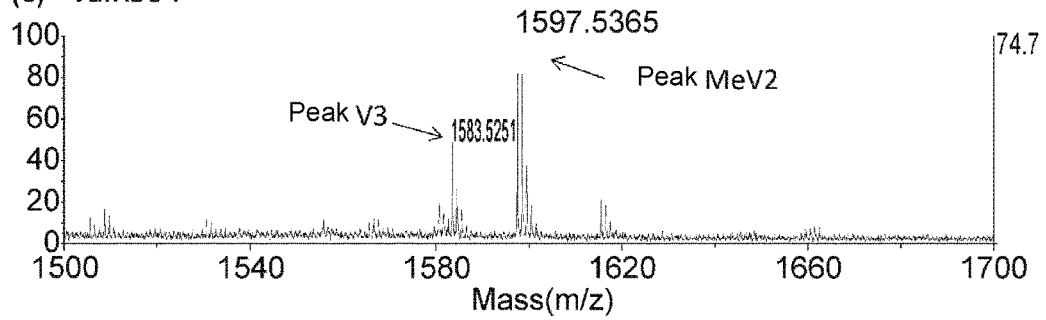

[Figure 6]
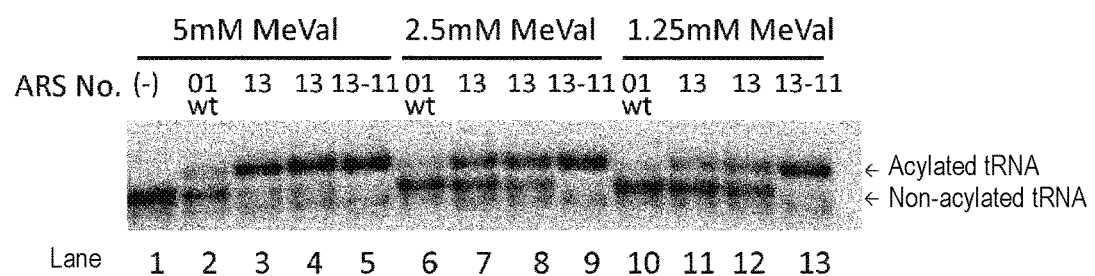

[Figure 7]
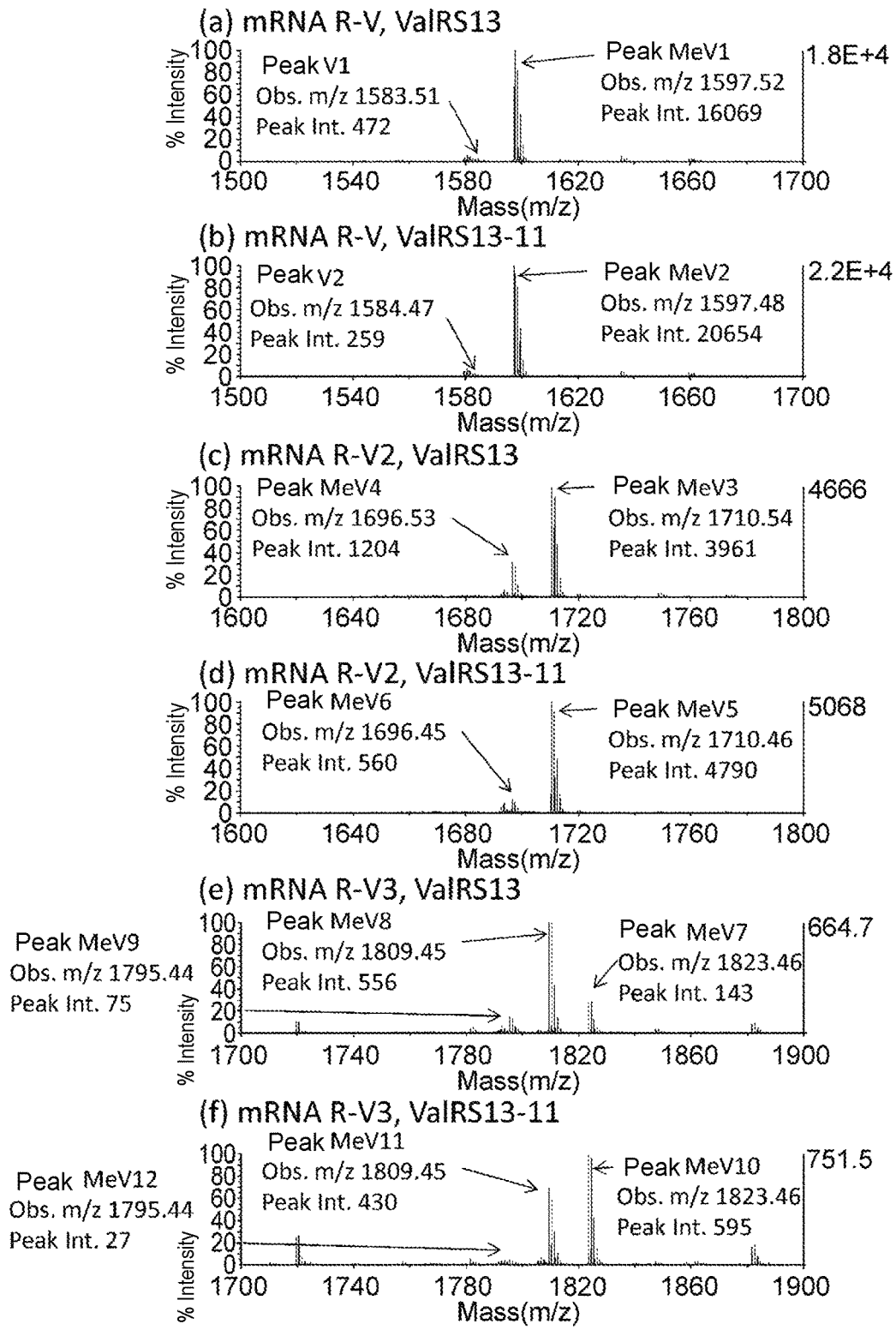

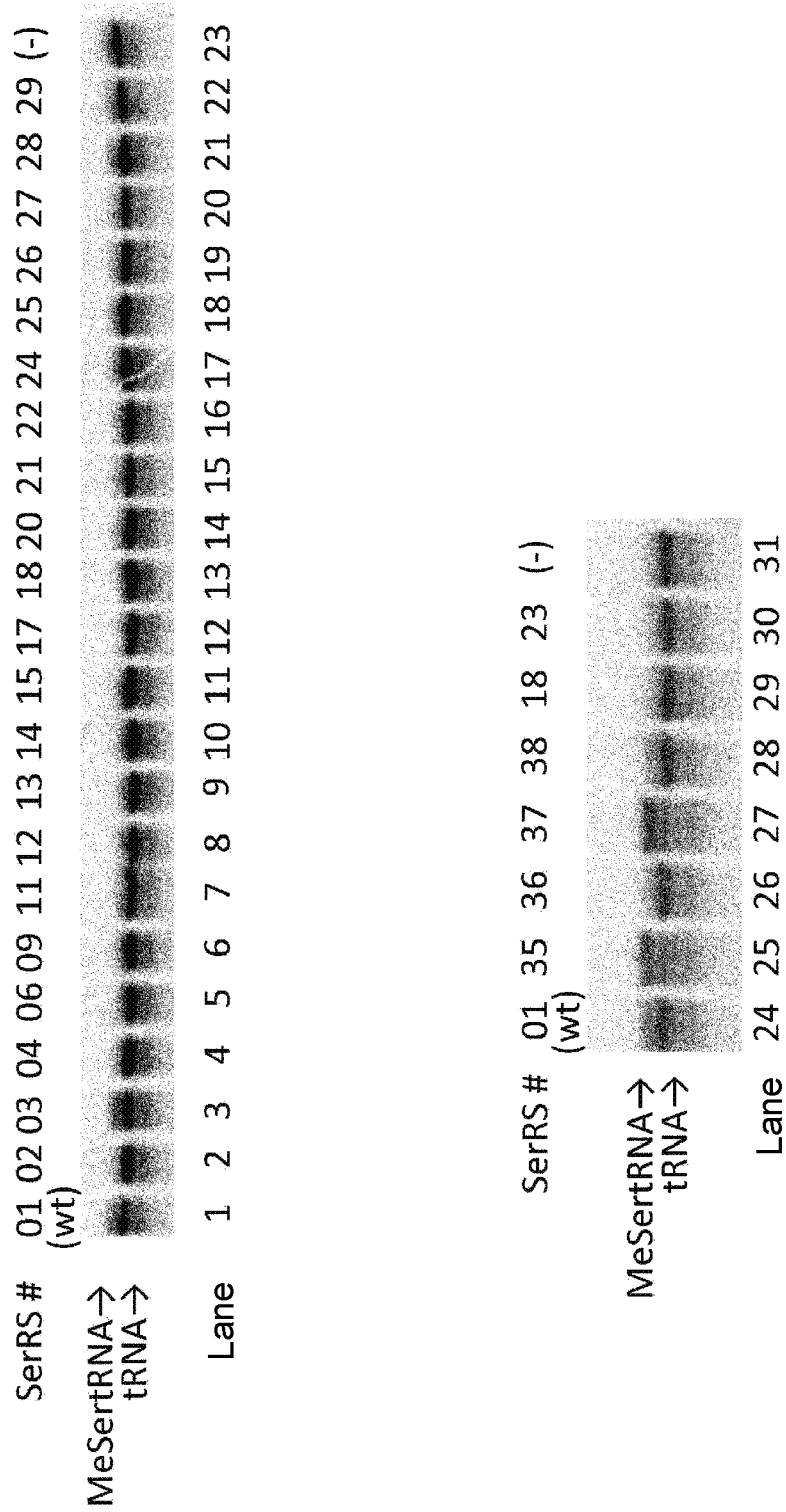
[Figure 8]

[Figure 9]
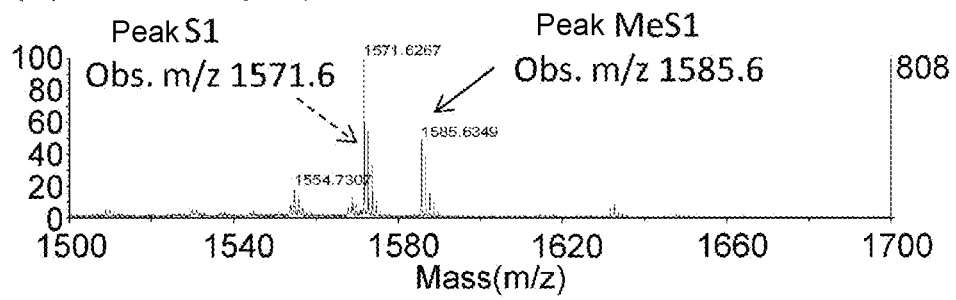
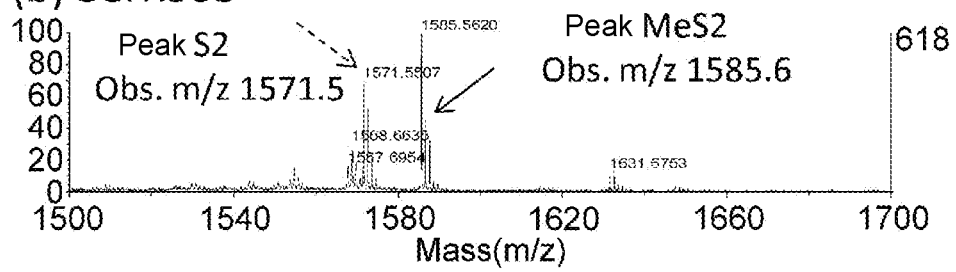
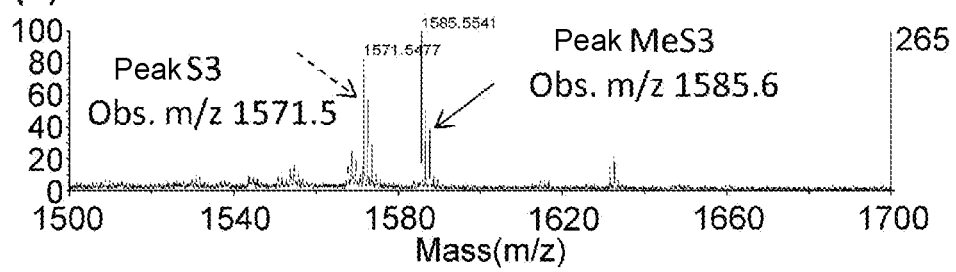
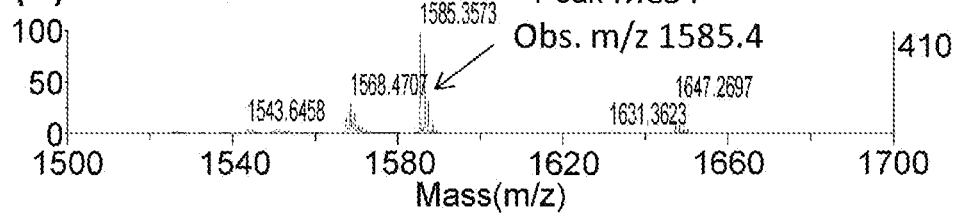
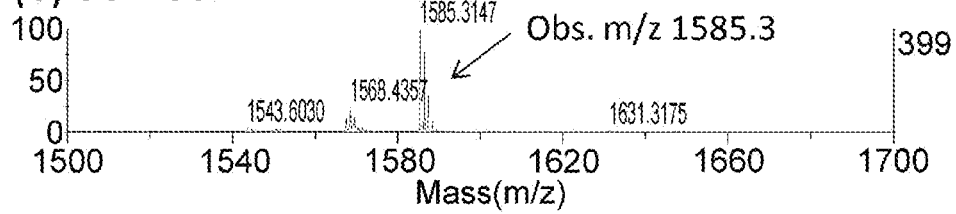

[Figure 10]
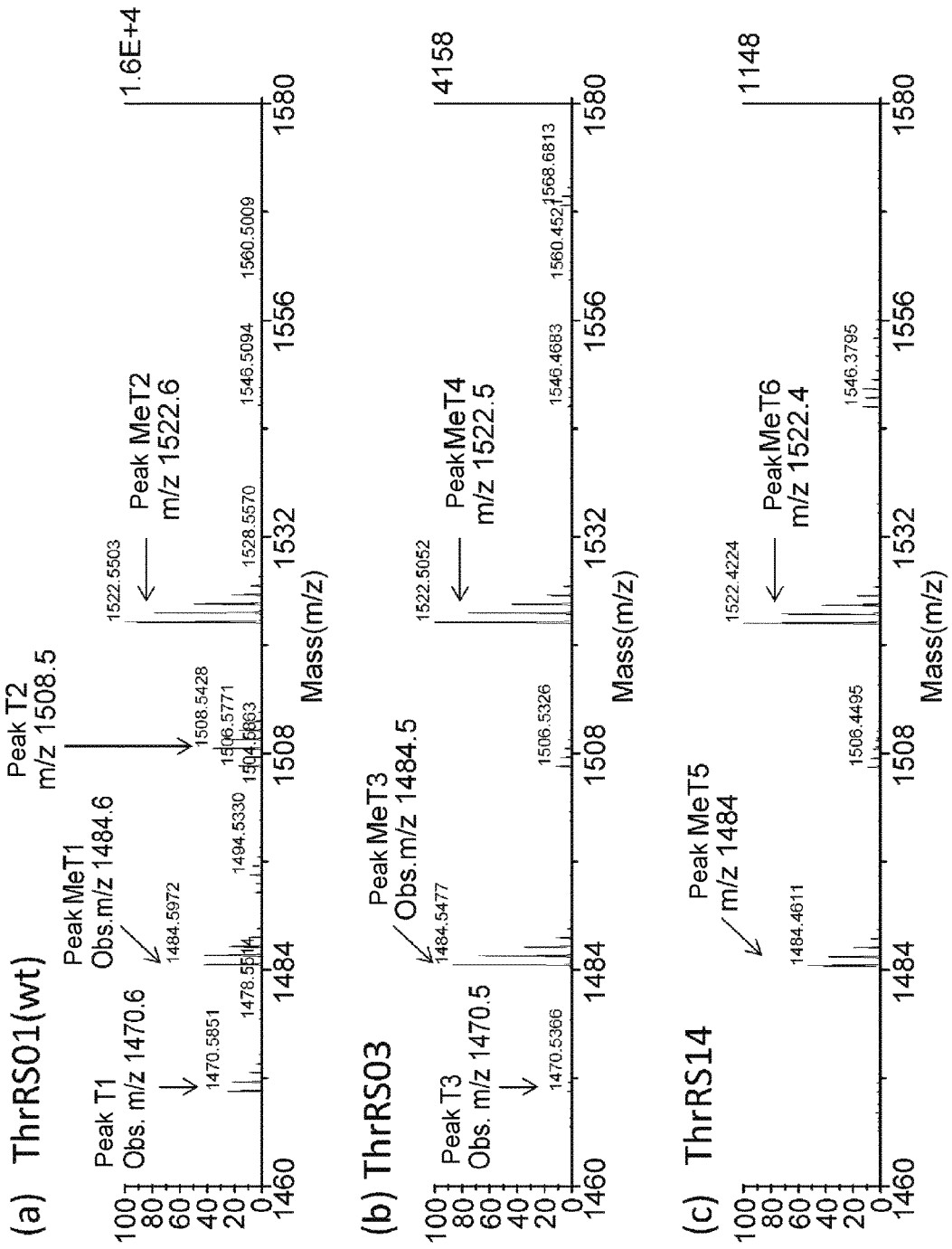

[Figure 11]
(a) TrpRS01(wt)
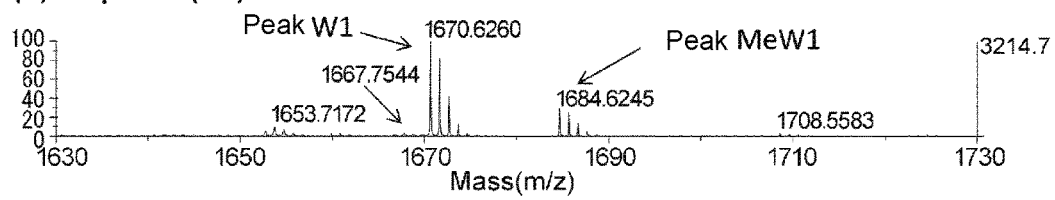
(b) TrpRS04
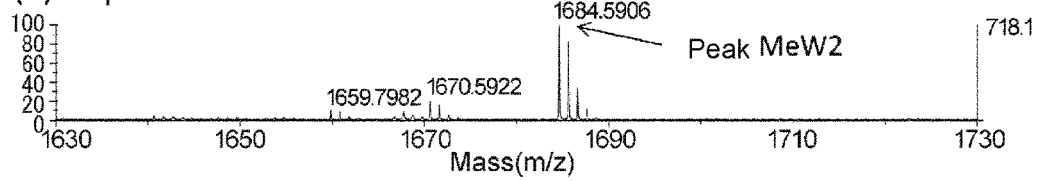
(c) TrpRS05
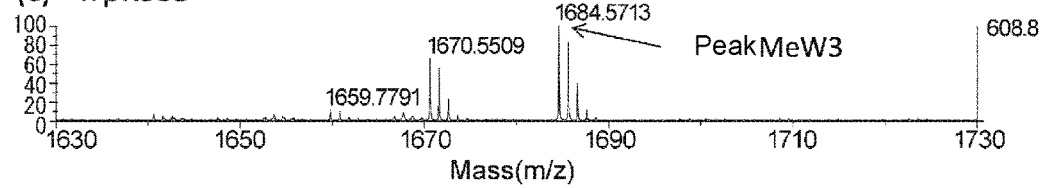
(d) TrpRS18
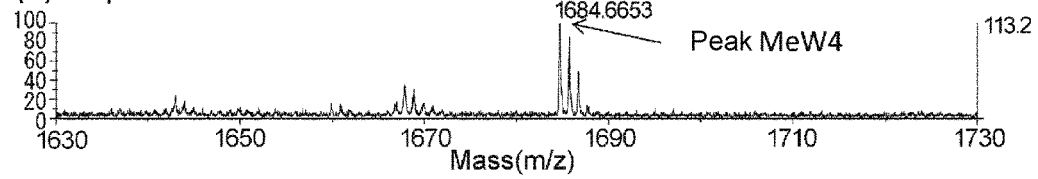

[Figure 12]
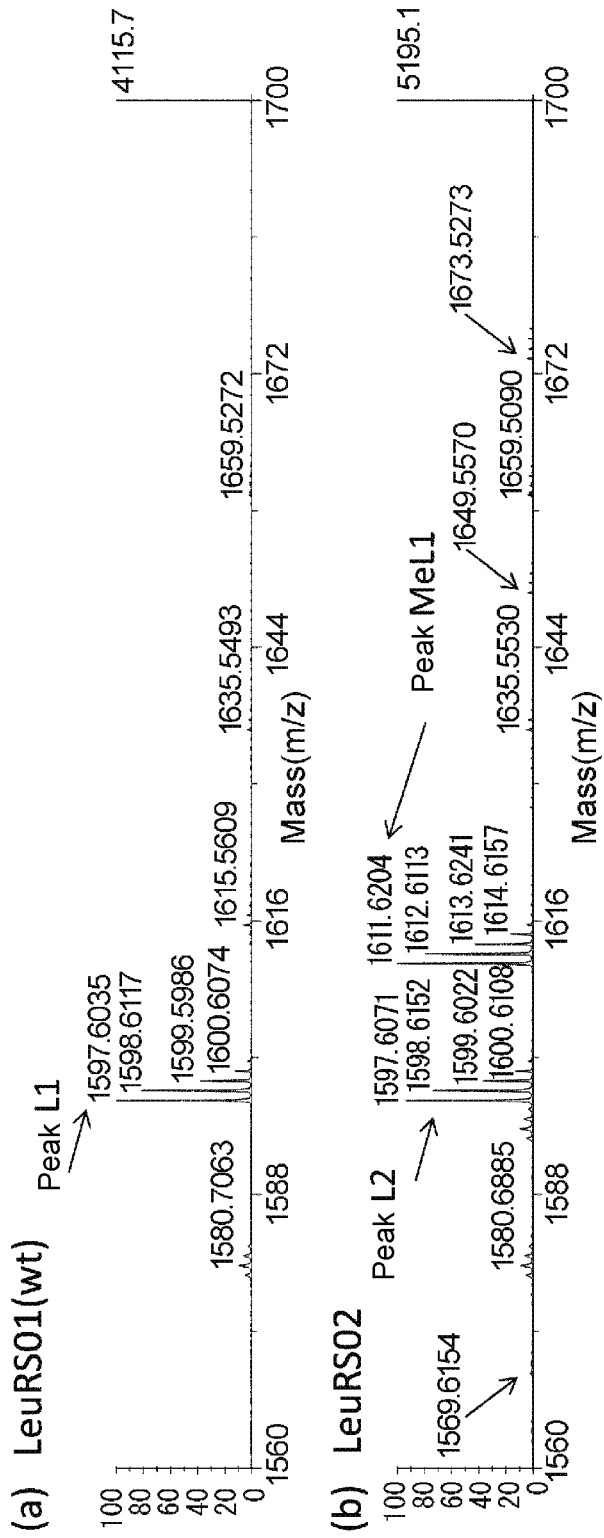

[Figure 13]
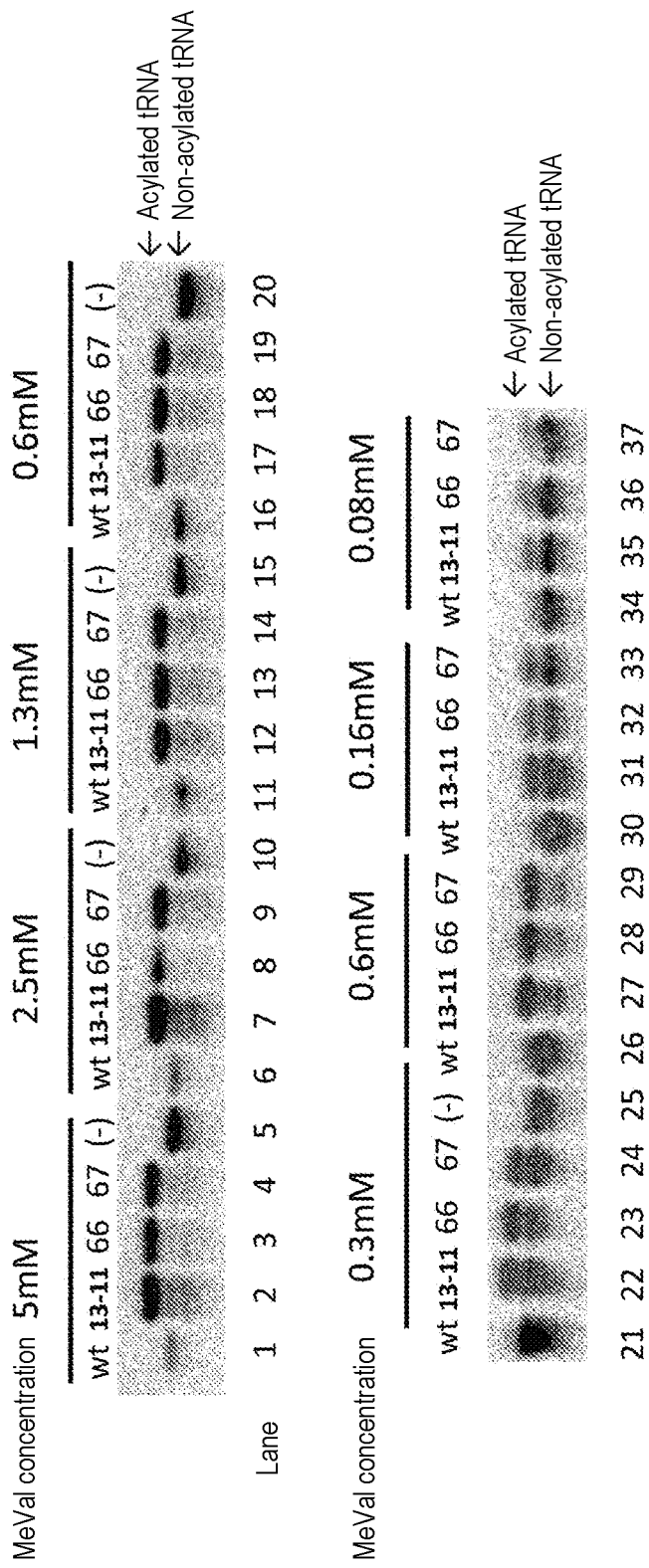

[Figure 14]
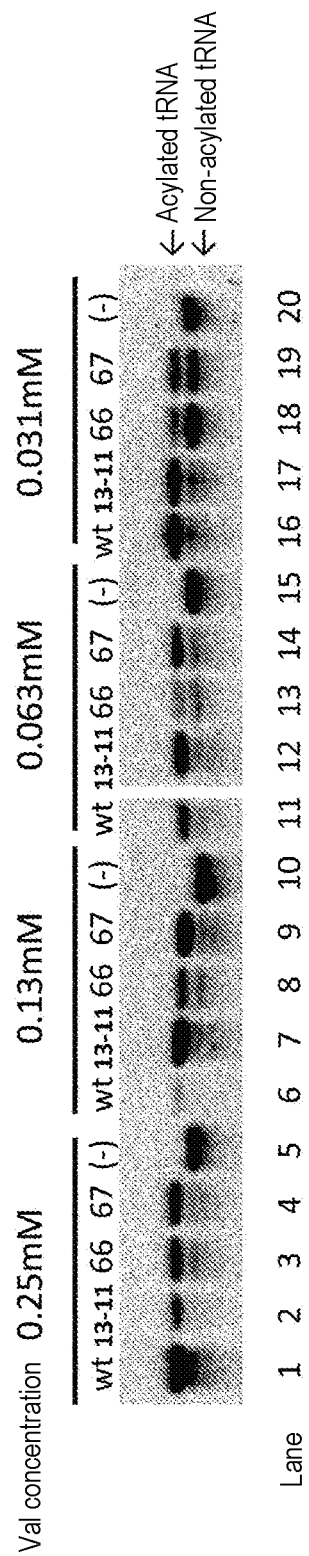

SEQUENCE LISTING

```
<160> NUMBER OF SEQ ID NOS: 205

<210> SEQ ID NO 1
<211> LENGTH: 327
<212> TYPE: PRT
<213> ORGANISM: Artificial
<220> FEATURE:
<223> OTHER INFORMATION: artificially synthesized sequence

<400> SEQUENCE: 1

Met Ser His Leu Ala Glu Leu Val Ala Ser Ala Lys Ala Ala Ile Ser
1               5                   10                  15

Gln Ala Ser Asp Val Ala Ala Leu Asp Asn Val Arg Val Glu Tyr Leu
            20                  25                  30

Gly Lys Lys Gly His Leu Thr Leu Gln Met Thr Thr Leu Arg Glu Leu
        35                  40                  45

Pro Pro Glu Glu Arg Pro Ala Ala Gly Ala Val Ile Asn Glu Ala Lys
    50                  55                  60

Glu Gln Val Gln Gln Ala Leu Asn Ala Arg Lys Ala Glu Leu Glu Ser
65                  70                  75                  80

Ala Ala Leu Asn Ala Arg Leu Ala Ala Glu Thr Ile Asp Val Ser Leu
                85                  90                  95

Pro Gly Arg Arg Ile Glu Asn Gly Gly Leu His Pro Val Thr Arg Thr
            100                 105                 110

Ile Asp Arg Ile Glu Ser Phe Phe Gly Glu Leu Gly Phe Thr Val Ala
        115                 120                 125

Thr Gly Pro Glu Ile Glu Asp Asp Tyr His Asn Phe Asp Ala Leu Asn
    130                 135                 140

Ile Pro Gly His His Pro Ala Arg Ala Asp His Asp Thr Phe Trp Phe
145                 150                 155                 160

Asp Thr Thr Arg Leu Leu Arg Thr Ala Thr Ser Gly Val Gln Ile Arg
                165                 170                 175

Thr Met Lys Ala Gln Gln Pro Pro Ile Arg Ile Ile Ala Pro Gly Arg
            180                 185                 190

Val Tyr Arg Asn Asp Tyr Asp Gln Thr His Thr Pro Met Phe His Gln
        195                 200                 205

Met Glu Gly Leu Ile Val Asp Thr Asn Ile Ser Phe Thr Asn Leu Lys
    210                 215                 220

Gly Thr Leu His Asp Phe Leu Arg Asn Phe Phe Glu Glu Asp Leu Gln
225                 230                 235                 240
```

Ile Arg Phe Arg Pro Ser Tyr Phe Pro Phe Thr Glu Pro Ser Ala Glu
                245                 250                 255

Val Asp Val Met Gly Lys Asn Gly Lys Trp Leu Glu Val Leu Gly Cys
            260                 265                 270

Gly Met Val His Pro Asn Val Leu Arg Asn Val Gly Ile Asp Pro Glu
            275                 280                 285

Val Tyr Ser Gly Phe Ala Phe Gly Met Gly Met Glu Arg Leu Thr Met
        290                 295                 300

Leu Arg Tyr Gly Val Thr Asp Leu Arg Ser Phe Glu Asn Asp Leu
305                 310                 315                 320

Arg Phe Leu Lys Gln Phe Lys
                325

<210> SEQ ID NO 2
<211> LENGTH: 327
<212> TYPE: PRT
<213> ORGANISM: Artificial
<220> FEATURE:
<223> OTHER INFORMATION: artificially synthesized sequence

<400> SEQUENCE: 2

Met Ser His Leu Ala Glu Leu Val Ala Ser Ala Lys Ala Ala Ile Ser
1               5                   10                  15

Gln Ala Ser Asp Val Ala Ala Leu Asp Asn Val Arg Val Glu Tyr Leu
            20                  25                  30

Gly Lys Lys Gly His Leu Thr Leu Gln Met Thr Thr Leu Arg Glu Leu
        35                  40                  45

Pro Pro Glu Glu Arg Pro Ala Ala Gly Ala Val Ile Asn Glu Ala Lys
    50                  55                  60

Glu Gln Val Gln Gln Ala Leu Asn Ala Arg Lys Ala Glu Leu Glu Ser
65                  70                  75                  80

Ala Ala Leu Asn Ala Arg Leu Ala Ala Glu Thr Ile Asp Val Ser Leu
                85                  90                  95

Pro Gly Arg Arg Ile Glu Asn Gly Gly Leu His Pro Val Thr Arg Thr
            100                 105                 110

Ile Asp Arg Ile Glu Ser Phe Phe Gly Glu Leu Gly Phe Thr Val Ala
        115                 120                 125

Thr Gly Pro Glu Ile Glu Asp Asp Tyr His Asn Phe Asp Ala Leu Asn
    130                 135                 140

Ile Pro Gly His His Pro Ala Arg Ala Asp His Asp Thr Phe Trp Phe
145                 150                 155                 160

Asp Thr Thr Arg Leu Leu Arg Thr Gly Thr Ser Gly Val Gln Ile Arg
                165                 170                 175

Thr Met Lys Ala Gln Gln Pro Pro Ile Arg Ile Ala Pro Gly Arg
            180                 185                 190

Val Tyr Arg Asn Asp Tyr Asp Gln Thr His Thr Pro Met Phe His Gln
        195                 200                 205

Met Glu Gly Leu Ile Val Asp Thr Asn Ile Ser Phe Thr Asn Leu Lys
    210                 215                 220

Gly Thr Leu His Asp Phe Leu Arg Asn Phe Phe Glu Glu Asp Leu Gln
225                 230                 235                 240

Ile Arg Phe Arg Pro Ser Tyr Phe Pro Phe Thr Glu Pro Ser Ala Glu
                245                 250                 255

Val Asp Val Met Gly Lys Asn Gly Lys Trp Leu Glu Val Leu Gly Cys
            260                 265                 270

```
Gly Met Val His Pro Asn Val Leu Arg Asn Val Gly Ile Asp Pro Glu
        275                 280                 285

Val Tyr Ser Gly Phe Ala Phe Gly Met Gly Met Glu Arg Leu Thr Met
    290                 295                 300

Leu Arg Tyr Gly Val Thr Asp Leu Arg Ser Phe Phe Glu Asn Asp Leu
305                 310                 315                 320

Arg Phe Leu Lys Gln Phe Lys
                325

<210> SEQ ID NO 3
<211> LENGTH: 951
<212> TYPE: PRT
<213> ORGANISM: Artificial
<220> FEATURE:
<223> OTHER INFORMATION: artificially synthesized sequence

<400> SEQUENCE: 3

Met Glu Lys Thr Tyr Asn Pro Gln Asp Ile Glu Gln Pro Leu Tyr Glu
1               5                   10                  15

His Trp Glu Lys Gln Gly Tyr Phe Lys Pro Asn Gly Asp Glu Ser Gln
            20                  25                  30

Glu Ser Phe Cys Ile Met Ile Pro Pro Ala Val Thr Gly Ser Leu
        35                  40                  45

His Met Gly His Ala Phe Gln Gln Thr Ile Met Asp Thr Met Ile Arg
    50                  55                  60

Tyr Gln Arg Met Gln Gly Lys Asn Thr Leu Trp Gln Val Gly Thr Asp
65                  70                  75                  80

His Ala Gly Ile Ala Thr Gln Met Val Val Glu Arg Lys Ile Ala Ala
                85                  90                  95

Glu Glu Gly Lys Thr Arg His Asp Tyr Gly Arg Glu Ala Phe Ile Asp
            100                 105                 110

Lys Ile Trp Glu Trp Lys Ala Glu Ser Gly Gly Thr Ile Thr Arg Gln
        115                 120                 125

Met Arg Arg Leu Gly Asn Ser Val Asp Trp Glu Arg Glu Arg Phe Thr
    130                 135                 140

Met Asp Glu Gly Leu Ser Asn Ala Val Lys Glu Val Phe Val Arg Leu
145                 150                 155                 160

Tyr Lys Glu Asp Leu Ile Tyr Arg Gly Lys Arg Leu Val Asn Trp Asp
                165                 170                 175

Pro Lys Leu Arg Thr Ala Ile Ser Asp Leu Glu Val Glu Asn Arg Glu
            180                 185                 190

Ser Lys Gly Ser Met Trp His Ile Arg Tyr Pro Leu Ala Asp Gly Ala
        195                 200                 205

Lys Thr Ala Asp Gly Lys Asp Tyr Leu Val Val Ala Thr Thr Arg Pro
    210                 215                 220

Glu Thr Leu Leu Gly Asp Thr Gly Val Ala Val Asn Pro Glu Asp Pro
225                 230                 235                 240

Arg Tyr Lys Asp Leu Ile Gly Lys Tyr Val Ile Leu Pro Leu Val Asn
                245                 250                 255

Arg Arg Ile Pro Ile Val Gly Asp Glu His Ala Asp Met Glu Lys Gly
            260                 265                 270

Thr Gly Cys Val Lys Ile Thr Pro Ala His Asp Phe Asn Asp Tyr Glu
        275                 280                 285

Val Gly Lys Arg His Ala Leu Pro Met Ile Asn Ile Leu Thr Phe Asp
    290                 295                 300
```

-continued

Gly Asp Ile Arg Glu Ser Ala Gln Val Phe Asp Thr Lys Gly Asn Glu
305                 310                 315                 320

Ser Asp Val Tyr Ser Ser Glu Ile Pro Ala Glu Phe Gln Lys Leu Glu
            325                 330                 335

Arg Phe Ala Ala Arg Lys Ala Val Val Ala Ala Val Asp Ala Leu Gly
            340                 345                 350

Leu Leu Glu Glu Ile Lys Pro His Asp Leu Thr Val Pro Tyr Gly Asp
        355                 360                 365

Arg Gly Gly Val Val Ile Glu Pro Met Leu Thr Asp Gln Trp Tyr Val
    370                 375                 380

Arg Ala Asp Val Leu Ala Lys Pro Ala Val Ala Val Glu Asn Gly
385                 390                 395                 400

Asp Ile Gln Phe Val Pro Lys Gln Tyr Glu Asn Met Tyr Phe Ser Trp
        405                 410                 415

Met Arg Asp Ile Gln Asp Trp Cys Ile Ser Arg Gln Leu Trp Trp Gly
        420                 425                 430

His Arg Ile Pro Ala Trp Tyr Asp Glu Ala Gly Asn Val Tyr Val Gly
        435                 440                 445

Arg Asn Glu Asp Glu Val Arg Lys Glu Asn Asn Leu Gly Ala Asp Val
    450                 455                 460

Val Leu Arg Gln Asp Glu Asp Val Leu Asp Thr Trp Phe Ser Ser Ala
465                 470                 475                 480

Leu Trp Thr Phe Ser Thr Leu Gly Trp Pro Glu Asn Thr Asp Ala Leu
            485                 490                 495

Arg Gln Phe His Pro Thr Ser Val Met Val Ser Gly Phe Asp Ile Ile
            500                 505                 510

Phe Phe Trp Ile Ala Arg Met Ile Met Met Thr Met His Phe Ile Lys
        515                 520                 525

Asp Glu Asn Gly Lys Pro Gln Val Pro Phe His Thr Val Tyr Met Thr
    530                 535                 540

Gly Leu Ile Arg Asp Asp Glu Gly Gln Lys Met Ser Lys Ser Lys Gly
545                 550                 555                 560

Asn Val Ile Asp Pro Leu Asp Met Val Asp Gly Ile Ser Leu Pro Glu
            565                 570                 575

Leu Leu Glu Lys Arg Thr Gly Asn Met Met Gln Pro Gln Leu Ala Asp
            580                 585                 590

Lys Ile Arg Lys Arg Thr Glu Lys Gln Phe Pro Asn Gly Ile Glu Pro
        595                 600                 605

His Gly Thr Asp Ala Leu Arg Phe Thr Leu Ala Ala Leu Ala Ser Thr
    610                 615                 620

Gly Arg Asp Ile Asn Trp Asp Met Lys Arg Leu Glu Gly Tyr Arg Asn
625                 630                 635                 640

Phe Cys Asn Lys Leu Trp Asn Ala Ser Arg Phe Val Leu Met Asn Thr
            645                 650                 655

Glu Gly Gln Asp Cys Gly Phe Asn Gly Gly Glu Met Thr Leu Ser Leu
            660                 665                 670

Ala Asp Arg Trp Ile Leu Ala Glu Phe Asn Gln Thr Ile Lys Ala Tyr
        675                 680                 685

Arg Glu Ala Leu Asp Ser Phe Arg Phe Asp Ile Ala Ala Gly Ile Leu
    690                 695                 700

Tyr Glu Phe Thr Trp Asn Gln Phe Cys Asp Trp Tyr Leu Glu Leu Thr
705                 710                 715                 720

Lys Pro Val Met Asn Gly Gly Thr Glu Ala Glu Leu Arg Gly Thr Arg
                725                 730                 735

His Thr Leu Val Thr Val Leu Glu Gly Leu Leu Arg Leu Ala His Pro
            740                 745                 750

Ile Ile Pro Phe Ile Thr Glu Thr Ile Trp Gln Arg Val Lys Val Leu
            755                 760                 765

Cys Gly Ile Thr Ala Asp Thr Ile Met Leu Gln Pro Phe Pro Gln Tyr
            770                 775                 780

Asp Ala Ser Gln Val Asp Glu Ala Leu Ala Asp Thr Glu Trp Leu
785                 790                 795                 800

Lys Gln Ala Ile Val Ala Val Arg Asn Ile Arg Ala Glu Met Asn Ile
                805                 810                 815

Ala Pro Gly Lys Pro Leu Glu Leu Leu Arg Gly Cys Ser Ala Asp
            820                 825                 830

Ala Glu Arg Arg Val Asn Glu Asn Arg Gly Phe Leu Gln Thr Leu Ala
            835                 840                 845

Arg Leu Glu Ser Ile Thr Val Leu Pro Ala Asp Lys Gly Pro Val
            850                 855                 860

Ser Val Thr Lys Ile Ile Asp Gly Ala Glu Leu Leu Ile Pro Met Ala
865                 870                 875                 880

Gly Leu Ile Asn Lys Glu Asp Glu Leu Ala Arg Leu Ala Lys Glu Val
                885                 890                 895

Ala Lys Ile Glu Gly Glu Ile Ser Arg Ile Glu Asn Lys Leu Ala Asn
                900                 905                 910

Glu Gly Phe Val Ala Arg Ala Pro Glu Ala Val Ile Ala Lys Glu Arg
            915                 920                 925

Glu Lys Leu Glu Gly Tyr Ala Glu Ala Lys Ala Lys Leu Ile Glu Gln
            930                 935                 940

Gln Ala Val Ile Ala Ala Leu
945                 950

<210> SEQ ID NO 4
<211> LENGTH: 951
<212> TYPE: PRT
<213> ORGANISM: Artificial
<220> FEATURE:
<223> OTHER INFORMATION: artificially synthesized sequence

<400> SEQUENCE: 4

Met Glu Lys Thr Tyr Asn Pro Gln Asp Ile Glu Gln Pro Leu Tyr Glu
1               5                   10                  15

His Trp Glu Lys Gln Gly Tyr Phe Lys Pro Asn Gly Asp Glu Ser Gln
                20                  25                  30

Glu Ser Phe Cys Ile Met Ile Pro Pro Pro Gly Val Thr Gly Ser Leu
            35                  40                  45

His Met Gly His Ala Phe Gln Gln Thr Ile Met Asp Thr Met Ile Arg
        50                  55                  60

Tyr Gln Arg Met Gln Gly Lys Asn Thr Leu Trp Gln Val Gly Thr Asp
65                  70                  75                  80

His Ala Gly Ile Ala Thr Gln Met Val Val Glu Arg Lys Ile Ala Ala
                85                  90                  95

Glu Glu Gly Lys Thr Arg His Asp Tyr Gly Arg Glu Ala Phe Ile Asp
            100                 105                 110

Lys Ile Trp Glu Trp Lys Ala Glu Ser Gly Gly Thr Ile Thr Arg Gln
            115                 120                 125

-continued

```
Met Arg Arg Leu Gly Asn Ser Val Asp Trp Glu Arg Glu Phe Thr
130                 135                 140

Met Asp Glu Gly Leu Ser Asn Ala Val Lys Glu Val Phe Val Arg Leu
145                 150                 155                 160

Tyr Lys Glu Asp Leu Ile Tyr Arg Gly Lys Arg Leu Val Asn Trp Asp
                165                 170                 175

Pro Lys Leu Arg Thr Ala Ile Ser Asp Leu Glu Val Glu Asn Arg Glu
            180                 185                 190

Ser Lys Gly Ser Met Trp His Ile Arg Tyr Pro Leu Ala Asp Gly Ala
        195                 200                 205

Lys Thr Ala Asp Gly Lys Asp Tyr Leu Val Val Ala Thr Thr Arg Pro
210                 215                 220

Glu Thr Leu Leu Gly Asp Thr Gly Val Ala Val Asn Pro Glu Asp Pro
225                 230                 235                 240

Arg Tyr Lys Asp Leu Ile Gly Lys Tyr Val Ile Leu Pro Leu Val Asn
                245                 250                 255

Arg Arg Ile Pro Ile Val Gly Asp Glu His Ala Asp Met Glu Lys Gly
            260                 265                 270

Thr Gly Cys Val Lys Ile Thr Pro Ala His Asp Phe Asn Asp Tyr Glu
        275                 280                 285

Val Gly Lys Arg His Ala Leu Pro Met Ile Asn Ile Leu Thr Phe Asp
290                 295                 300

Gly Asp Ile Arg Glu Ser Ala Gln Val Phe Asp Thr Lys Gly Asn Glu
305                 310                 315                 320

Ser Asp Val Tyr Ser Ser Glu Ile Pro Ala Glu Phe Gln Lys Leu Glu
                325                 330                 335

Arg Phe Ala Ala Arg Lys Ala Val Val Ala Val Asp Ala Leu Gly
            340                 345                 350

Leu Leu Glu Glu Ile Lys Pro His Asp Leu Thr Val Pro Tyr Gly Asp
        355                 360                 365

Arg Gly Gly Val Val Ile Glu Pro Met Leu Thr Asp Gln Trp Tyr Val
370                 375                 380

Arg Ala Asp Val Leu Ala Lys Pro Ala Val Glu Ala Val Glu Asn Gly
385                 390                 395                 400

Asp Ile Gln Phe Val Pro Lys Gln Tyr Glu Asn Met Tyr Phe Ser Trp
                405                 410                 415

Met Arg Asp Ile Gln Asp Trp Cys Ile Ser Arg Gln Leu Trp Trp Gly
            420                 425                 430

His Arg Ile Pro Ala Trp Tyr Asp Glu Ala Gly Asn Val Tyr Val Gly
        435                 440                 445

Arg Asn Glu Asp Glu Val Arg Lys Glu Asn Asn Leu Gly Ala Asp Val
450                 455                 460

Val Leu Arg Gln Asp Glu Asp Val Leu Asp Thr Trp Phe Ser Ser Ala
465                 470                 475                 480

Leu Trp Thr Phe Ser Thr Leu Gly Trp Pro Glu Asn Thr Asp Ala Leu
                485                 490                 495

Arg Gln Phe His Pro Thr Ser Val Met Val Ser Gly Phe Asp Ile Ile
            500                 505                 510

Phe Phe Trp Ile Ala Arg Met Ile Met Met Thr Met His Phe Ile Lys
        515                 520                 525

Asp Glu Asn Gly Lys Pro Gln Val Pro Phe His Thr Val Tyr Met Thr
530                 535                 540

Gly Leu Ile Arg Asp Asp Glu Gly Gln Lys Met Ser Lys Ser Lys Gly
```

```
               545                 550                 555                 560
        Asn Val Ile Asp Pro Leu Asp Met Val Asp Gly Ile Ser Leu Pro Glu
                            565                 570                 575

Leu Leu Glu Lys Arg Thr Gly Asn Met Met Gln Pro Gln Leu Ala Asp
                    580                 585                 590

Lys Ile Arg Lys Arg Thr Glu Lys Gln Phe Pro Asn Gly Ile Glu Pro
                595                 600                 605

His Gly Thr Asp Ala Leu Arg Phe Thr Leu Ala Ala Leu Ala Ser Thr
            610                 615                 620

Gly Arg Asp Ile Asn Trp Asp Met Lys Arg Leu Glu Gly Tyr Arg Asn
        625                 630                 635                 640

Phe Cys Asn Lys Leu Trp Asn Ala Ser Arg Phe Val Leu Met Asn Thr
                        645                 650                 655

Glu Gly Gln Asp Cys Gly Phe Asn Gly Gly Glu Met Thr Leu Ser Leu
                    660                 665                 670

Ala Asp Arg Trp Ile Leu Ala Glu Phe Asn Gln Thr Ile Lys Ala Tyr
                675                 680                 685

Arg Glu Ala Leu Asp Ser Phe Arg Phe Asp Ile Ala Ala Gly Ile Leu
            690                 695                 700

Tyr Glu Phe Thr Trp Asn Gln Phe Cys Asp Trp Tyr Leu Glu Leu Thr
        705                 710                 715                 720

Lys Pro Val Met Asn Gly Gly Thr Glu Ala Glu Leu Arg Gly Thr Arg
                        725                 730                 735

His Thr Leu Val Thr Val Leu Glu Gly Leu Leu Arg Leu Ala His Pro
                    740                 745                 750

Ile Ile Pro Phe Ile Thr Glu Thr Ile Trp Gln Arg Val Lys Val Leu
                755                 760                 765

Cys Gly Ile Thr Ala Asp Thr Ile Met Leu Gln Pro Phe Pro Gln Tyr
            770                 775                 780

Asp Ala Ser Gln Val Asp Glu Ala Ala Leu Ala Asp Thr Glu Trp Leu
        785                 790                 795                 800

Lys Gln Ala Ile Val Ala Val Arg Asn Ile Arg Ala Glu Met Asn Ile
                        805                 810                 815

Ala Pro Gly Lys Pro Leu Glu Leu Leu Leu Arg Gly Cys Ser Ala Asp
                    820                 825                 830

Ala Glu Arg Arg Val Asn Glu Asn Arg Gly Phe Leu Gln Thr Leu Ala
                835                 840                 845

Arg Leu Glu Ser Ile Thr Val Leu Pro Ala Asp Asp Lys Gly Pro Val
            850                 855                 860

Ser Val Thr Lys Ile Ile Asp Gly Ala Glu Leu Leu Ile Pro Met Ala
        865                 870                 875                 880

Gly Leu Ile Asn Lys Glu Asp Glu Leu Ala Arg Leu Ala Lys Glu Val
                        885                 890                 895

Ala Lys Ile Glu Gly Glu Ile Ser Arg Ile Glu Asn Lys Leu Ala Asn
                    900                 905                 910

Glu Gly Phe Val Ala Arg Ala Pro Glu Ala Val Ile Ala Lys Glu Arg
                915                 920                 925

Glu Lys Leu Glu Gly Tyr Ala Glu Ala Lys Ala Lys Leu Ile Glu Gln
            930                 935                 940

Gln Ala Val Ile Ala Ala Leu
        945                 950

<210> SEQ ID NO 5
```

```
<211> LENGTH: 951
<212> TYPE: PRT
<213> ORGANISM: Artificial
<220> FEATURE:
<223> OTHER INFORMATION: artificially synthesized sequence

<400> SEQUENCE: 5

Met Glu Lys Thr Tyr Asn Pro Gln Asp Ile Glu Gln Pro Leu Tyr Glu
1               5                   10                  15

His Trp Glu Lys Gln Gly Tyr Phe Lys Pro Asn Gly Asp Glu Ser Gln
            20                  25                  30

Glu Ser Phe Cys Ile Met Ile Pro Pro Gly Val Ser Gly Ser Leu
        35                  40                  45

His Met Gly His Ala Phe Gln Gln Thr Ile Met Asp Thr Met Ile Arg
50                  55                  60

Tyr Gln Arg Met Gln Gly Lys Asn Thr Leu Trp Gln Val Gly Thr Asp
65                  70                  75                  80

His Ala Gly Ile Ala Thr Gln Met Val Val Glu Arg Lys Ile Ala Ala
                85                  90                  95

Glu Glu Gly Lys Thr Arg His Asp Tyr Gly Arg Glu Ala Phe Ile Asp
            100                 105                 110

Lys Ile Trp Glu Trp Lys Ala Glu Ser Gly Gly Thr Ile Thr Arg Gln
        115                 120                 125

Met Arg Arg Leu Gly Asn Ser Val Asp Trp Glu Arg Glu Arg Phe Thr
130                 135                 140

Met Asp Glu Gly Leu Ser Asn Ala Val Lys Glu Val Phe Val Arg Leu
145                 150                 155                 160

Tyr Lys Glu Asp Leu Ile Tyr Arg Gly Lys Arg Leu Val Asn Trp Asp
                165                 170                 175

Pro Lys Leu Arg Thr Ala Ile Ser Asp Leu Glu Val Glu Asn Arg Glu
            180                 185                 190

Ser Lys Gly Ser Met Trp His Ile Arg Tyr Pro Leu Ala Asp Gly Ala
        195                 200                 205

Lys Thr Ala Asp Gly Lys Asp Tyr Leu Val Val Ala Thr Thr Arg Pro
210                 215                 220

Glu Thr Leu Leu Gly Asp Thr Gly Val Ala Val Asn Pro Glu Asp Pro
225                 230                 235                 240

Arg Tyr Lys Asp Leu Ile Gly Lys Tyr Val Ile Leu Pro Leu Val Asn
                245                 250                 255

Arg Arg Ile Pro Ile Val Gly Asp Glu His Ala Asp Met Glu Lys Gly
            260                 265                 270

Thr Gly Cys Val Lys Ile Thr Pro Ala His Asp Phe Asn Asp Tyr Glu
        275                 280                 285

Val Gly Lys Arg His Ala Leu Pro Met Ile Asn Ile Leu Thr Phe Asp
290                 295                 300

Gly Asp Ile Arg Glu Ser Ala Gln Val Phe Asp Thr Lys Gly Asn Glu
305                 310                 315                 320

Ser Asp Val Tyr Ser Ser Glu Ile Pro Ala Glu Phe Gln Lys Leu Glu
                325                 330                 335

Arg Phe Ala Ala Arg Lys Ala Val Val Ala Val Asp Ala Leu Gly
            340                 345                 350

Leu Leu Glu Glu Ile Lys Pro His Asp Leu Thr Val Pro Tyr Gly Asp
        355                 360                 365

Arg Gly Gly Val Val Ile Glu Pro Met Leu Thr Asp Gln Trp Tyr Val
370                 375                 380
```

```
Arg Ala Asp Val Leu Ala Lys Pro Ala Val Glu Ala Val Glu Asn Gly
385                 390                 395                 400

Asp Ile Gln Phe Val Pro Lys Gln Tyr Glu Asn Met Tyr Phe Ser Trp
            405                 410                 415

Met Arg Asp Ile Gln Asp Trp Cys Ile Ser Arg Gln Leu Trp Trp Gly
        420                 425                 430

His Arg Ile Pro Ala Trp Tyr Asp Glu Ala Gly Asn Val Tyr Val Gly
            435                 440                 445

Arg Asn Glu Asp Glu Val Arg Lys Glu Asn Asn Leu Gly Ala Asp Val
    450                 455                 460

Val Leu Arg Gln Asp Glu Asp Val Leu Asp Thr Trp Phe Ser Ser Ala
465                 470                 475                 480

Leu Trp Thr Phe Ser Thr Leu Gly Trp Pro Glu Asn Thr Asp Ala Leu
                485                 490                 495

Arg Gln Phe His Pro Thr Ser Val Met Val Ser Gly Phe Asp Ile Ile
            500                 505                 510

Phe Phe Trp Ile Ala Arg Met Ile Met Met Thr Met His Phe Ile Lys
        515                 520                 525

Asp Glu Asn Gly Lys Pro Gln Val Pro Phe His Thr Val Tyr Met Thr
530                 535                 540

Gly Leu Ile Arg Asp Asp Glu Gly Gln Lys Met Ser Lys Ser Lys Gly
545                 550                 555                 560

Asn Val Ile Asp Pro Leu Asp Met Val Asp Gly Ile Ser Leu Pro Glu
                565                 570                 575

Leu Leu Glu Lys Arg Thr Gly Asn Met Met Gln Pro Gln Leu Ala Asp
                580                 585                 590

Lys Ile Arg Lys Arg Thr Glu Lys Gln Phe Pro Asn Gly Ile Glu Pro
            595                 600                 605

His Gly Thr Asp Ala Leu Arg Phe Thr Leu Ala Ala Leu Ala Ser Thr
    610                 615                 620

Gly Arg Asp Ile Asn Trp Asp Met Lys Arg Leu Glu Gly Tyr Arg Asn
625                 630                 635                 640

Phe Cys Asn Lys Leu Trp Asn Ala Ser Arg Phe Val Leu Met Asn Thr
                645                 650                 655

Glu Gly Gln Asp Cys Gly Phe Asn Gly Gly Glu Met Thr Leu Ser Leu
                660                 665                 670

Ala Asp Arg Trp Ile Leu Ala Glu Phe Asn Gln Thr Ile Lys Ala Tyr
            675                 680                 685

Arg Glu Ala Leu Asp Ser Phe Arg Phe Asp Ile Ala Ala Gly Ile Leu
            690                 695                 700

Tyr Glu Phe Thr Trp Asn Gln Phe Cys Asp Trp Tyr Leu Glu Leu Thr
705                 710                 715                 720

Lys Pro Val Met Asn Gly Gly Thr Glu Ala Glu Leu Arg Gly Thr Arg
                725                 730                 735

His Thr Leu Val Thr Val Leu Glu Gly Leu Leu Arg Leu Ala His Pro
            740                 745                 750

Ile Ile Pro Phe Ile Thr Glu Thr Ile Trp Gln Arg Val Lys Val Leu
            755                 760                 765

Cys Gly Ile Thr Ala Asp Thr Ile Met Leu Gln Pro Phe Pro Gln Tyr
        770                 775                 780

Asp Ala Ser Gln Val Asp Glu Ala Ala Leu Ala Asp Thr Glu Trp Leu
785                 790                 795                 800
```

```
Lys Gln Ala Ile Val Ala Val Arg Asn Ile Arg Ala Glu Met Asn Ile
                805                 810                 815

Ala Pro Gly Lys Pro Leu Glu Leu Leu Leu Arg Gly Cys Ser Ala Asp
            820                 825                 830

Ala Glu Arg Arg Val Asn Glu Asn Arg Gly Phe Leu Gln Thr Leu Ala
            835                 840                 845

Arg Leu Glu Ser Ile Thr Val Leu Pro Ala Asp Asp Lys Gly Pro Val
        850                 855                 860

Ser Val Thr Lys Ile Ile Asp Gly Ala Glu Leu Ile Pro Met Ala
865                 870                 875                 880

Gly Leu Ile Asn Lys Glu Asp Glu Leu Ala Arg Leu Ala Lys Glu Val
                885                 890                 895

Ala Lys Ile Glu Gly Glu Ile Ser Arg Ile Glu Asn Lys Leu Ala Asn
            900                 905                 910

Glu Gly Phe Val Ala Arg Ala Pro Glu Ala Val Ile Ala Lys Glu Arg
            915                 920                 925

Glu Lys Leu Glu Gly Tyr Ala Glu Ala Lys Ala Lys Leu Ile Glu Gln
        930                 935                 940

Gln Ala Val Ile Ala Ala Leu
945                 950

<210> SEQ ID NO 6
<211> LENGTH: 430
<212> TYPE: PRT
<213> ORGANISM: Artificial
<220> FEATURE:
<223> OTHER INFORMATION: artificially synthesized sequence

<400> SEQUENCE: 6

Met Leu Asp Pro Asn Leu Leu Arg Asn Glu Pro Asp Ala Val Ala Glu
1               5                   10                  15

Lys Leu Ala Arg Arg Gly Phe Lys Leu Asp Val Asp Lys Leu Gly Ala
            20                  25                  30

Leu Glu Glu Arg Arg Lys Val Leu Gln Val Lys Thr Glu Asn Leu Gln
        35                  40                  45

Ala Glu Arg Asn Ser Arg Ser Lys Ser Ile Gly Gln Ala Lys Ala Arg
    50                  55                  60

Gly Glu Asp Ile Glu Pro Leu Arg Leu Glu Val Asn Lys Leu Gly Glu
65                  70                  75                  80

Glu Leu Asp Ala Ala Lys Ala Glu Leu Asp Ala Leu Gln Ala Glu Ile
                85                  90                  95

Arg Asp Ile Ala Leu Thr Ile Pro Asn Leu Pro Ala Asp Glu Val Pro
            100                 105                 110

Val Gly Lys Asp Glu Asn Asp Asn Val Glu Val Ser Arg Trp Gly Thr
        115                 120                 125

Pro Arg Glu Phe Asp Phe Glu Val Arg Asp His Val Thr Leu Gly Glu
    130                 135                 140

Met His Ser Gly Leu Asp Phe Ala Ala Ala Val Lys Leu Thr Gly Ser
145                 150                 155                 160

Arg Phe Val Val Met Lys Gly Gln Ile Ala Arg Met His Arg Ala Leu
                165                 170                 175

Ser Gln Phe Met Leu Asp Leu His Thr Glu Gln His Gly Tyr Ser Glu
            180                 185                 190

Asn Tyr Val Pro Tyr Leu Val Asn Gln Asp Thr Leu Tyr Gly Thr Gly
        195                 200                 205
```

Gln Leu Pro Lys Phe Ala Gly Asp Leu Phe His Thr Arg Pro Leu Glu
210                 215                 220

Glu Glu Ala Asp Thr Ser Asn Tyr Ala Leu Ile Pro Ser Ala Glu Val
225                 230                 235                 240

Pro Leu Thr Asn Leu Val Arg Gly Ile Ile Asp Glu Asp Leu
        245                 250                 255

Pro Ile Lys Met Thr Ala His Thr Pro Cys Phe Arg Ser Glu Ala Gly
        260                 265                 270

Ser Tyr Gly Arg Asp Thr Arg Gly Leu Ile Arg Met His Gln Phe Asp
        275                 280                 285

Lys Val Glu Met Val Gln Ile Val Arg Pro Glu Asp Ser Met Ala Ala
290                 295                 300

Leu Glu Glu Met Thr Gly His Ala Glu Lys Val Leu Gln Leu Leu Gly
305                 310                 315                 320

Leu Pro Tyr Arg Lys Ile Ile Leu Cys Thr Gly Asp Met Gly Phe Gly
                325                 330                 335

Ala Cys Lys Thr Tyr Asp Leu Glu Val Trp Ile Pro Ala Gln Asn Thr
                340                 345                 350

Tyr Arg Glu Ile Ser Ser Cys Ser Asn Val Trp Asp Phe Gln Ala Arg
                355                 360                 365

Arg Met Gln Ala Arg Cys Arg Ser Lys Ser Asp Lys Lys Thr Arg Leu
370                 375                 380

Val His Thr Leu Asn Gly Ser Gly Leu Ala Val Gly Arg Thr Leu Val
385                 390                 395                 400

Ala Val Met Glu Asn Tyr Gln Gln Ala Asp Gly Arg Ile Glu Val Pro
                405                 410                 415

Glu Val Leu Arg Pro Tyr Met Asn Gly Leu Glu Tyr Ile Gly
                420                 425                 430

<210> SEQ ID NO 7
<211> LENGTH: 430
<212> TYPE: PRT
<213> ORGANISM: Artificial
<220> FEATURE:
<223> OTHER INFORMATION: artificially synthesized sequence

<400> SEQUENCE: 7

Met Leu Asp Pro Asn Leu Leu Arg Asn Glu Pro Asp Ala Val Ala Glu
1               5                   10                  15

Lys Leu Ala Arg Arg Gly Phe Lys Leu Asp Val Asp Lys Leu Gly Ala
                20                  25                  30

Leu Glu Glu Arg Arg Lys Val Leu Gln Val Lys Thr Glu Asn Leu Gln
                35                  40                  45

Ala Glu Arg Asn Ser Arg Ser Lys Ser Ile Gly Gln Ala Lys Ala Arg
    50                  55                  60

Gly Glu Asp Ile Glu Pro Leu Arg Leu Glu Val Asn Lys Leu Gly Glu
65                  70                  75                  80

Glu Leu Asp Ala Ala Lys Ala Glu Leu Asp Ala Leu Gln Ala Glu Ile
                85                  90                  95

Arg Asp Ile Ala Leu Thr Ile Pro Asn Leu Pro Ala Asp Glu Val Pro
                100                 105                 110

Val Gly Lys Asp Glu Asn Asp Asn Val Glu Val Ser Arg Trp Gly Thr
            115                 120                 125

Pro Arg Glu Phe Asp Phe Glu Val Arg Asp His Val Thr Leu Gly Glu
        130                 135                 140

```
Met His Ser Gly Leu Asp Phe Ala Ala Ala Val Lys Leu Thr Gly Ser
145                 150                 155                 160

Arg Phe Val Val Met Lys Gly Gln Ile Ala Arg Met His Arg Ala Leu
                165                 170                 175

Ser Gln Phe Met Leu Asp Leu His Thr Glu Gln His Gly Tyr Ser Glu
            180                 185                 190

Asn Tyr Val Pro Tyr Leu Val Asn Gln Asp Thr Leu Tyr Gly Thr Gly
        195                 200                 205

Gln Leu Pro Lys Phe Ala Gly Asp Leu Phe His Thr Arg Pro Leu Glu
    210                 215                 220

Glu Glu Ala Asp Thr Ser Asn Tyr Ala Leu Ile Pro Thr Ala Ala Val
225                 230                 235                 240

Pro Leu Thr Asn Leu Val Arg Gly Glu Ile Ile Asp Glu Asp Asp Leu
                245                 250                 255

Pro Ile Lys Met Thr Ala His Thr Pro Cys Phe Arg Ser Glu Ala Gly
                260                 265                 270

Ser Tyr Gly Arg Asp Thr Arg Gly Leu Ile Arg Met His Gln Phe Asp
            275                 280                 285

Lys Val Glu Met Val Gln Ile Val Arg Pro Glu Asp Ser Met Ala Ala
        290                 295                 300

Leu Glu Glu Met Thr Gly His Ala Glu Lys Val Leu Gln Leu Leu Gly
305                 310                 315                 320

Leu Pro Tyr Arg Lys Ile Ile Leu Cys Thr Gly Asp Met Gly Phe Gly
                325                 330                 335

Ala Cys Lys Thr Tyr Asp Leu Glu Val Trp Ile Pro Ala Gln Asn Thr
                340                 345                 350

Tyr Arg Glu Ile Ser Ser Cys Ser Asn Val Trp Asp Phe Gln Ala Arg
            355                 360                 365

Arg Met Gln Ala Arg Cys Arg Ser Lys Ser Asp Lys Lys Thr Arg Leu
        370                 375                 380

Val His Thr Leu Asn Gly Ser Gly Leu Ala Val Gly Arg Thr Leu Val
385                 390                 395                 400

Ala Val Met Glu Asn Tyr Gln Gln Ala Asp Gly Arg Ile Glu Val Pro
                405                 410                 415

Glu Val Leu Arg Pro Tyr Met Asn Gly Leu Glu Tyr Ile Gly
                420                 425                 430

<210> SEQ ID NO 8
<211> LENGTH: 430
<212> TYPE: PRT
<213> ORGANISM: Artificial
<220> FEATURE:
<223> OTHER INFORMATION: artificially synthesized sequence

<400> SEQUENCE: 8

Met Leu Asp Pro Asn Leu Leu Arg Asn Glu Pro Asp Ala Val Ala Glu
1               5                   10                  15

Lys Leu Ala Arg Arg Gly Phe Lys Leu Asp Val Asp Lys Leu Gly Ala
                20                  25                  30

Leu Glu Glu Arg Arg Lys Val Leu Gln Val Lys Thr Glu Asn Leu Gln
            35                  40                  45

Ala Glu Arg Asn Ser Arg Ser Lys Ser Ile Gly Gln Ala Lys Ala Arg
        50                  55                  60

Gly Glu Asp Ile Glu Pro Leu Arg Leu Glu Val Asn Lys Leu Gly Glu
65                  70                  75                  80
```

```
Glu Leu Asp Ala Ala Lys Ala Glu Leu Asp Ala Leu Gln Ala Glu Ile
                85                  90                  95

Arg Asp Ile Ala Leu Thr Ile Pro Asn Leu Pro Ala Asp Glu Val Pro
            100                 105                 110

Val Gly Lys Asp Glu Asn Asp Asn Val Glu Val Ser Arg Trp Gly Thr
        115                 120                 125

Pro Arg Glu Phe Asp Phe Glu Val Arg Asp His Val Thr Leu Gly Glu
    130                 135                 140

Met His Ser Gly Leu Asp Phe Ala Ala Val Lys Leu Thr Gly Ser
145                 150                 155                 160

Arg Phe Val Val Met Lys Gly Gln Ile Ala Arg Met His Arg Ala Leu
                165                 170                 175

Ser Gln Phe Met Leu Asp Leu His Thr Glu Gln His Gly Tyr Ser Glu
            180                 185                 190

Asn Tyr Val Pro Tyr Leu Val Asn Gln Asp Thr Leu Tyr Gly Thr Gly
        195                 200                 205

Gln Leu Pro Lys Phe Ala Gly Asp Leu Phe His Thr Arg Pro Leu Glu
    210                 215                 220

Glu Glu Ala Asp Thr Ser Asn Tyr Ala Leu Ile Pro Thr Ala Gly Val
225                 230                 235                 240

Pro Leu Thr Asn Leu Val Arg Gly Glu Ile Ile Asp Glu Asp Leu
                245                 250                 255

Pro Ile Lys Met Thr Ala His Thr Pro Cys Phe Arg Ser Glu Ala Gly
            260                 265                 270

Ser Tyr Gly Arg Asp Thr Arg Gly Leu Ile Arg Met His Gln Phe Asp
        275                 280                 285

Lys Val Glu Met Val Gln Ile Val Arg Pro Glu Asp Ser Met Ala Ala
    290                 295                 300

Leu Glu Glu Met Thr Gly His Ala Glu Lys Val Leu Gln Leu Leu Gly
305                 310                 315                 320

Leu Pro Tyr Arg Lys Ile Ile Leu Cys Thr Gly Asp Met Gly Phe Gly
                325                 330                 335

Ala Cys Lys Thr Tyr Asp Leu Glu Val Trp Ile Pro Ala Gln Asn Thr
            340                 345                 350

Tyr Arg Glu Ile Ser Ser Cys Ser Asn Val Trp Asp Phe Gln Ala Arg
        355                 360                 365

Arg Met Gln Ala Arg Cys Arg Ser Lys Ser Asp Lys Lys Thr Arg Leu
    370                 375                 380

Val His Thr Leu Asn Gly Ser Gly Leu Ala Val Gly Arg Thr Leu Val
385                 390                 395                 400

Ala Val Met Glu Asn Tyr Gln Gln Ala Asp Gly Arg Ile Glu Val Pro
                405                 410                 415

Glu Val Leu Arg Pro Tyr Met Asn Gly Leu Glu Tyr Ile Gly
            420                 425                 430

<210> SEQ ID NO 9
<211> LENGTH: 430
<212> TYPE: PRT
<213> ORGANISM: Artificial
<220> FEATURE:
<223> OTHER INFORMATION: artificially synthesized sequence

<400> SEQUENCE: 9

Met Leu Asp Pro Asn Leu Leu Arg Asn Glu Pro Asp Ala Val Ala Glu
1               5                   10                  15
```

```
Lys Leu Ala Arg Arg Gly Phe Lys Leu Asp Val Asp Lys Leu Gly Ala
             20                  25                  30

Leu Glu Glu Arg Arg Lys Val Leu Gln Val Lys Thr Glu Asn Leu Gln
         35                  40                  45

Ala Glu Arg Asn Ser Arg Ser Lys Ser Ile Gly Gln Ala Lys Ala Arg
     50                  55                  60

Gly Glu Asp Ile Glu Pro Leu Arg Leu Glu Val Asn Lys Leu Gly Glu
 65                  70                  75                  80

Glu Leu Asp Ala Ala Lys Ala Glu Leu Asp Ala Leu Gln Ala Glu Ile
                 85                  90                  95

Arg Asp Ile Ala Leu Thr Ile Pro Asn Leu Pro Ala Asp Glu Val Pro
            100                 105                 110

Val Gly Lys Asp Glu Asn Asp Asn Val Glu Val Ser Arg Trp Gly Thr
        115                 120                 125

Pro Arg Glu Phe Asp Phe Glu Val Arg Asp His Val Thr Leu Gly Glu
    130                 135                 140

Met His Ser Gly Leu Asp Phe Ala Ala Val Lys Leu Thr Gly Ser
145                 150                 155                 160

Arg Phe Val Val Met Lys Gly Gln Ile Ala Arg Met His Arg Ala Leu
                165                 170                 175

Ser Gln Phe Met Leu Asp Leu His Thr Glu Gln His Gly Tyr Ser Glu
            180                 185                 190

Asn Tyr Val Pro Tyr Leu Val Asn Gln Asp Thr Leu Tyr Gly Thr Gly
        195                 200                 205

Gln Leu Pro Lys Phe Ala Gly Asp Leu Phe His Thr Arg Pro Leu Glu
    210                 215                 220

Glu Glu Ala Asp Thr Ser Asn Tyr Ala Leu Ile Pro Ser Ala Gly Val
225                 230                 235                 240

Pro Leu Thr Asn Leu Val Arg Gly Glu Ile Ile Asp Glu Asp Asp Leu
                245                 250                 255

Pro Ile Lys Met Thr Ala His Thr Pro Cys Phe Arg Ser Glu Ala Gly
            260                 265                 270

Ser Tyr Gly Arg Asp Thr Arg Gly Leu Ile Arg Met His Gln Phe Asp
        275                 280                 285

Lys Val Glu Met Val Gln Ile Val Arg Pro Glu Asp Ser Met Ala Ala
    290                 295                 300

Leu Glu Glu Met Thr Gly His Ala Glu Lys Val Leu Gln Leu Leu Gly
305                 310                 315                 320

Leu Pro Tyr Arg Lys Ile Ile Leu Cys Thr Gly Asp Met Gly Phe Gly
                325                 330                 335

Ala Cys Lys Thr Tyr Asp Leu Glu Val Trp Ile Pro Ala Gln Asn Thr
            340                 345                 350

Tyr Arg Glu Ile Ser Ser Cys Ser Asn Val Trp Asp Phe Gln Ala Arg
        355                 360                 365

Arg Met Gln Ala Arg Cys Arg Ser Lys Ser Asp Lys Thr Arg Leu
    370                 375                 380

Val His Thr Leu Asn Gly Ser Gly Leu Ala Val Gly Arg Thr Leu Val
385                 390                 395                 400

Ala Val Met Glu Asn Tyr Gln Gln Ala Asp Gly Arg Ile Glu Val Pro
                405                 410                 415

Glu Val Leu Arg Pro Tyr Met Asn Gly Leu Glu Tyr Ile Gly
            420                 425                 430
```

```
<210> SEQ ID NO 10
<211> LENGTH: 642
<212> TYPE: PRT
<213> ORGANISM: Artificial
<220> FEATURE:
<223> OTHER INFORMATION: artificially synthesized sequence

<400> SEQUENCE: 10
```

| | | | | | | | | | | | | | | | |
|---|---|---|---|---|---|---|---|---|---|---|---|---|---|---|---|
| Met | Pro | Val | Ile | Thr | Leu | Pro | Asp | Gly | Ser | Gln | Arg | His | Tyr | Asp | His |
| 1 | | | | 5 | | | | | 10 | | | | | 15 | |
| Ala | Val | Ser | Pro | Met | Asp | Val | Ala | Leu | Asp | Ile | Gly | Pro | Gly | Leu | Ala |
| | | | 20 | | | | | 25 | | | | | 30 | | |
| Lys | Ala | Cys | Ile | Ala | Gly | Arg | Val | Asn | Gly | Glu | Leu | Val | Asp | Ala | Cys |
| | | | 35 | | | | | 40 | | | | | 45 | | |
| Asp | Leu | Ile | Glu | Asn | Asp | Ala | Gln | Leu | Ser | Ile | Thr | Ala | Lys | Asp |
| 50 | | | | | 55 | | | | | 60 | | | | | |
| Glu | Glu | Gly | Leu | Glu | Ile | Ile | Arg | His | Ser | Cys | Ala | His | Leu | Leu | Gly |
| 65 | | | | | 70 | | | | | 75 | | | | | 80 |
| His | Ala | Ile | Lys | Gln | Leu | Trp | Pro | His | Thr | Lys | Met | Ala | Ile | Gly | Pro |
| | | | | 85 | | | | | 90 | | | | | 95 | |
| Val | Ile | Asp | Asn | Gly | Phe | Tyr | Tyr | Asp | Val | Asp | Leu | Asp | Arg | Thr | Leu |
| | | | | 100 | | | | | 105 | | | | | 110 | |
| Thr | Gln | Glu | Asp | Val | Glu | Ala | Leu | Glu | Lys | Arg | Met | His | Glu | Leu | Ala |
| | | | 115 | | | | | 120 | | | | | 125 | | |
| Glu | Lys | Asn | Tyr | Asp | Val | Ile | Lys | Lys | Lys | Val | Ser | Trp | His | Glu | Ala |
| | | | 130 | | | | | 135 | | | | | 140 | | |
| Arg | Glu | Thr | Phe | Ala | Asn | Arg | Gly | Glu | Ser | Tyr | Lys | Val | Ser | Ile | Leu |
| 145 | | | | | 150 | | | | | 155 | | | | | 160 |
| Asp | Glu | Asn | Ile | Ala | His | Asp | Asp | Lys | Pro | Gly | Leu | Tyr | Phe | His | Glu |
| | | | | 165 | | | | | 170 | | | | | 175 | |
| Glu | Tyr | Val | Asp | Met | Cys | Arg | Gly | Pro | His | Val | Pro | Asn | Met | Arg | Phe |
| | | | | 180 | | | | | 185 | | | | | 190 | |
| Cys | His | His | Phe | Lys | Leu | Met | Lys | Thr | Ala | Gly | Ala | Tyr | Trp | Arg | Gly |
| | | | 195 | | | | | 200 | | | | | 205 | | |
| Asp | Ser | Asn | Asn | Lys | Met | Leu | Gln | Arg | Ile | Tyr | Gly | Thr | Ala | Trp | Ala |
| | | | 210 | | | | | 215 | | | | | 220 | | |
| Asp | Lys | Lys | Ala | Leu | Asn | Ala | Tyr | Leu | Gln | Arg | Leu | Glu | Glu | Ala | Ala |
| 225 | | | | | 230 | | | | | 235 | | | | | 240 |
| Lys | Arg | Asp | His | Arg | Lys | Ile | Gly | Lys | Gln | Leu | Asp | Leu | Tyr | His | Met |
| | | | | 245 | | | | | 250 | | | | | 255 | |
| Gln | Glu | Glu | Ala | Pro | Gly | Met | Val | Phe | Trp | His | Asn | Asp | Gly | Trp | Thr |
| | | | | 260 | | | | | 265 | | | | | 270 | |
| Ile | Phe | Arg | Glu | Leu | Glu | Val | Phe | Val | Arg | Ser | Lys | Leu | Lys | Glu | Tyr |
| | | | 275 | | | | | 280 | | | | | 285 | | |
| Gln | Tyr | Gln | Glu | Val | Lys | Gly | Pro | Phe | Met | Met | Asp | Arg | Val | Leu | Trp |
| | | | 290 | | | | | 295 | | | | | 300 | | |
| Glu | Lys | Thr | Gly | His | Trp | Asp | Asn | Tyr | Lys | Asp | Ala | Met | Phe | Thr | Thr |
| 305 | | | | | 310 | | | | | 315 | | | | | 320 |
| Ser | Ser | Glu | Asn | Arg | Glu | Tyr | Cys | Ile | Lys | Pro | Gly | Asn | Cys | Pro | Gly |
| | | | | 325 | | | | | 330 | | | | | 335 | |
| His | Val | Gln | Ile | Phe | Asn | Gln | Gly | Leu | Lys | Ser | Tyr | Arg | Asp | Leu | Pro |
| | | | | 340 | | | | | 345 | | | | | 350 | |
| Leu | Arg | Met | Ala | Glu | Phe | Gly | Ser | Cys | His | Arg | Asn | Glu | Pro | Ser | Gly |
| | | | 355 | | | | | 360 | | | | | 365 | | |
| Ser | Leu | His | Gly | Leu | Met | Arg | Val | Arg | Gly | Phe | Thr | Gln | Asp | Asp | Ala |

His Ile Phe Cys Thr Glu Glu Gln Ile Arg Asp Glu Val Asn Gly Cys
385                 390                 395                 400

Ile Arg Leu Val Tyr Asp Met Tyr Ser Thr Phe Gly Phe Glu Lys Ile
                405                 410                 415

Val Val Lys Leu Ser Thr Arg Pro Glu Lys Arg Ile Gly Ser Asp Glu
            420                 425                 430

Met Trp Asp Arg Ala Glu Ala Asp Leu Ala Val Ala Leu Glu Glu Asn
        435                 440                 445

Asn Ile Pro Phe Glu Tyr Gln Leu Gly Glu Gly Ala Phe Tyr Gly Pro
    450                 455                 460

Lys Ile Glu Phe Thr Leu Tyr Asp Cys Leu Asp Arg Ala Trp Gln Cys
465                 470                 475                 480

Gly Thr Val Gln Leu Asp Phe Ser Leu Pro Ser Arg Leu Ser Ala Ser
                485                 490                 495

Tyr Val Gly Glu Asp Asn Glu Arg Lys Val Pro Val Met Ile His Arg
                500                 505                 510

Ala Ile Leu Gly Ser Met Glu Arg Phe Ile Gly Ile Leu Thr Glu Glu
            515                 520                 525

Phe Ala Gly Phe Phe Pro Thr Trp Leu Ala Pro Val Gln Val Val Ile
530                 535                 540

Met Asn Ile Thr Asp Ser Gln Ser Glu Tyr Val Asn Glu Leu Thr Gln
545                 550                 555                 560

Lys Leu Ser Asn Ala Gly Ile Arg Val Lys Ala Asp Leu Arg Asn Glu
                565                 570                 575

Lys Ile Gly Phe Lys Ile Arg Glu His Thr Leu Arg Arg Val Pro Tyr
                580                 585                 590

Met Leu Val Cys Gly Asp Lys Glu Val Glu Ser Gly Lys Val Ala Val
            595                 600                 605

Arg Thr Arg Arg Gly Lys Asp Leu Gly Ser Met Asp Val Asn Glu Val
        610                 615                 620

Ile Glu Lys Leu Gln Gln Glu Ile Arg Ser Arg Ser Leu Lys Gln Leu
625                 630                 635                 640

Glu Glu

<210> SEQ ID NO 11
<211> LENGTH: 642
<212> TYPE: PRT
<213> ORGANISM: Artificial
<220> FEATURE:
<223> OTHER INFORMATION: artificially synthesized sequence

<400> SEQUENCE: 11

Met Pro Val Ile Thr Leu Pro Asp Gly Ser Gln Arg His Tyr Asp His
1               5                   10                  15

Ala Val Ser Pro Met Asp Val Ala Leu Asp Ile Gly Pro Gly Leu Ala
            20                  25                  30

Lys Ala Cys Ile Ala Gly Arg Val Asn Gly Glu Leu Val Asp Ala Cys
        35                  40                  45

Asp Leu Ile Glu Asn Asp Ala Gln Leu Ser Ile Ile Thr Ala Lys Asp
    50                  55                  60

Glu Glu Gly Leu Glu Ile Ile Arg His Ser Cys Ala His Leu Leu Gly
65                  70                  75                  80

His Ala Ile Lys Gln Leu Trp Pro His Thr Lys Met Ala Ile Gly Pro
                85                  90                  95

```
Val Ile Asp Asn Gly Phe Tyr Tyr Asp Val Asp Leu Asp Arg Thr Leu
            100                 105                 110

Thr Gln Glu Asp Val Glu Ala Leu Glu Lys Arg Met His Glu Leu Ala
            115                 120                 125

Glu Lys Asn Tyr Asp Val Ile Lys Lys Val Ser Trp His Glu Ala
            130                 135                 140

Arg Glu Thr Phe Ala Asn Arg Gly Glu Ser Tyr Lys Val Ser Ile Leu
145                 150                 155                 160

Asp Glu Asn Ile Ala His Asp Lys Pro Gly Leu Tyr Phe His Glu
                165                 170                 175

Glu Tyr Val Asp Met Cys Arg Gly Pro His Val Pro Asn Met Arg Phe
            180                 185                 190

Cys His His Phe Lys Leu Met Lys Thr Ala Gly Ala Tyr Trp Arg Gly
            195                 200                 205

Asp Ser Asn Asn Lys Met Leu Gln Arg Ile Tyr Gly Thr Ala Trp Ala
        210                 215                 220

Asp Lys Lys Ala Leu Asn Ala Tyr Leu Gln Arg Leu Glu Glu Ala Ala
225                 230                 235                 240

Lys Arg Asp His Arg Lys Ile Gly Lys Gln Leu Asp Leu Tyr His Met
                245                 250                 255

Gln Glu Glu Ala Pro Gly Met Val Phe Trp His Asn Asp Gly Trp Thr
            260                 265                 270

Ile Phe Arg Glu Leu Glu Val Phe Val Arg Ser Lys Leu Lys Glu Tyr
            275                 280                 285

Gln Tyr Gln Glu Val Lys Gly Pro Phe Met Met Asp Arg Val Leu Trp
            290                 295                 300

Glu Lys Thr Gly His Trp Asp Asn Tyr Lys Asp Ala Met Phe Thr Thr
305                 310                 315                 320

Ser Ser Glu Asn Arg Glu Tyr Cys Ile Lys Pro Met Asn Cys Pro Gly
                325                 330                 335

His Val Gln Ile Phe Asn Gln Gly Leu Lys Ser Tyr Arg Asp Leu Pro
            340                 345                 350

Leu Arg Met Ala Glu Phe Gly Ser Cys His Arg Asn Glu Pro Ser Gly
            355                 360                 365

Ser Leu His Gly Leu Met Arg Val Arg Gly Phe Thr Gln Asp Asp Ala
        370                 375                 380

His Ile Phe Cys Thr Glu Glu Gln Ile Arg Asp Glu Val Asn Gly Cys
385                 390                 395                 400

Ile Arg Leu Val Tyr Asp Met Tyr Ser Thr Phe Gly Phe Glu Lys Ile
                405                 410                 415

Val Val Lys Leu Ser Thr Arg Pro Glu Lys Arg Ile Gly Ser Asp Glu
            420                 425                 430

Met Trp Asp Arg Ala Glu Ala Asp Leu Ala Val Ala Leu Glu Glu Asn
            435                 440                 445

Asn Ile Pro Phe Glu Tyr Gln Leu Gly Glu Gly Ala Phe Tyr Gly Pro
        450                 455                 460

Lys Ile Glu Phe Thr Leu Tyr Asp Cys Leu Asp Arg Ala Trp Gln Cys
465                 470                 475                 480

Gly Thr Val Gln Leu Asp Phe Ser Leu Pro Ser Arg Leu Ser Ala Ser
                485                 490                 495

Tyr Val Gly Glu Asp Asn Glu Arg Lys Val Pro Val Met Ile Gly Arg
            500                 505                 510
```

```
Ala Ile Leu Gly Ser Met Glu Arg Phe Ile Gly Ile Leu Thr Glu Glu
            515                 520                 525

Phe Ala Gly Phe Phe Pro Thr Trp Leu Ala Pro Val Gln Val Val Ile
530                 535                 540

Met Asn Ile Thr Asp Ser Gln Ser Glu Tyr Val Asn Glu Leu Thr Gln
545                 550                 555                 560

Lys Leu Ser Asn Ala Gly Ile Arg Val Lys Ala Asp Leu Arg Asn Glu
                565                 570                 575

Lys Ile Gly Phe Lys Ile Arg Glu His Thr Leu Arg Arg Val Pro Tyr
            580                 585                 590

Met Leu Val Cys Gly Asp Lys Glu Val Glu Ser Gly Lys Val Ala Val
            595                 600                 605

Arg Thr Arg Arg Gly Lys Asp Leu Gly Ser Met Asp Val Asn Glu Val
610                 615                 620

Ile Glu Lys Leu Gln Gln Glu Ile Arg Ser Arg Ser Leu Lys Gln Leu
625                 630                 635                 640

Glu Glu

<210> SEQ ID NO 12
<211> LENGTH: 981
<212> TYPE: DNA
<213> ORGANISM: Artificial
<220> FEATURE:
<223> OTHER INFORMATION: artificially synthesized sequence

<400> SEQUENCE: 12
atgtcacatc tcgcagaact ggttgccagt gcgaaggcgg ccattagcca ggcgtcagat      60
gttgccgcgt tagataatgt gcgcgtcgaa tatttgggta aaaagggca cttaaccctt     120 cagatgacga ccctgcgtga gctgccgcca aagagcgtc cggcagctgg tgcggttatc     180
aacgaagcga aagagcaggt tcagcaggcg ctgaatgcgc gtaaagcgga actggaaagc     240
gctgcactga atgcgcgtct ggcggcggaa acgattgatg tctctctgcc aggtcgtcgc     300
attgaaaacg gcggtctgca tccggttacc cgtaccatcg accgtatcga agtttcttc     360 ggtgagcttg gctttaccgt ggcaaccggg ccggaaatcg aagacgatta tcataacttc     420
gatgctctga acattcctgg tcaccaccg gcgcgcgctg accacgacac tttctggttt     480
gacactaccc gcctgctgcg taccgcgacc tctggcgtac agatccgcac catgaaagcc     540
cagcagccac cgattcgtat catcgcgcct ggccgtgttt atcgtaacga ctacgaccag     600
actcacacgc cgatgttcca tcagatggaa ggtctgattg ttgataccaa catcagcttt     660
accaacctga aaggcacgct gcacgacttc ctgcgtaact tctttgagga agatttgcag     720
attcgcttcc gtccttccta cttcccgttt accgaacctt ctgcagaagt ggacgtcatg     780
ggtaaaaacg gtaaatggct ggaagtgctg ggctgcggga tggtgcatcc gaacgtgttg     840
cgtaacgttg gcatcgaccc ggaagtttac tctggtttcg ccttcgggat ggggatggag     900
cgtctgacta tgttgcgtta cggcgtcacc gacctgcgtt cattcttcga aaacgatctg     960
cgtttcctca aacagtttaa a                                              981

<210> SEQ ID NO 13
<211> LENGTH: 981
<212> TYPE: DNA
<213> ORGANISM: Artificial
<220> FEATURE:
<223> OTHER INFORMATION: artificially synthesized sequence

<400> SEQUENCE: 13
```

-continued

```
atgtcacatc tcgcagaact ggttgccagt gcgaaggcgg ccattagcca ggcgtcagat      60
gttgccgcgt tagataatgt gcgcgtcgaa tatttgggta aaaaagggca cttaacccTT     120
cagatgacga ccctgcgtga gctgccgcca gaagagcgtc cggcagctgg tgcggttatc    180
aacgaagcga aagagcaggt tcagcaggcg ctgaatgcgc gtaaagcgga actggaaagc    240
gctgcactga atgcgcgtct ggcggcggaa acgattgatg tctctctgcc aggtcgtcgc    300
attgaaaacg gcggtctgca tccggttacc cgtaccatcg accgtatcga agtttcttc    360 ggtgagcttg gctttaccgt ggcaaccggg ccggaaatcg aagacgatta tcataacttc    420
gatgctctga acattcctgg tcaccacccg gcgcgcgctg accacgacac tttctggttt    480
gacactaccc gcctgctgcg taccggcacc tctggcgtac agatccgcac catgaaagcc    540
cagcagccac cgattcgtat catcgcgcct ggccgtgttt atcgtaacga ctacgaccag    600
actcacacgc cgatgttcca tcagatggaa ggtctgattg ttgataccaa catcagcttt    660
accaacctga aaggcacgct gcacgacttc ctgcgtaact tctttgagga agatttgcag    720
attcgcttcc gtccttccta cttcccgttt accgaacctt ctgcagaagt ggacgtcatg    780
ggtaaaaacg gtaaatggct ggaagtgctg ggctgcggga tggtgcatcc gaacgtgttg    840
cgtaacgttg gcatcgaccc ggaagtttac tctggtttcg ccttcgggat ggggatggag    900
cgtctgacta tgttgcgtta cggcgtcacc gacctgcgtt cattcttcga aaacgatctg    960
cgtttcctca aacagtttaa a                                              981
```

<210> SEQ ID NO 14
<211> LENGTH: 2853
<212> TYPE: DNA
<213> ORGANISM: Artificial
<220> FEATURE:
<223> OTHER INFORMATION: artificially synthesized sequence

<400> SEQUENCE: 14

```
atggaaaaga catataaccc acaagatatc gaacagccgc tttacgagca ctgggaaaag     60
cagggctact ttaagcctaa tggcgatgaa agccaggaaa gtttctgcat catgatcccg    120
ccgccggctg tcaccggcag tttgcatatg ggtcacgcct tccagcaaac catcatggat    180
accatgatcc gctatcagcg catgcagggc aaaaacaccc tgtggcaggt cggtactgac    240
cacgccggga tcgctaccca gatggtcgtt gagcgcaaga ttgccgcaga agaaggtaaa    300
acccgtcacg actacggccg cgaagctttc atcgacaaaa tctgggaatg gaaagcggaa    360
tctggcggca ccattacccg tcagatgcgc cgtctcggca actccgtcga ctgggagcgt    420
gaacgcttca ccatggacga aggcctgtcc aatgcggtga agaagtttt cgttcgtctg    480 tataagaag acctgattta ccgtggcaaa cgcctggtaa actgggatcc gaaactgcgc    540
accgctatct ctgacctgga agtcgaaaac cgcgaatcga aggttcgat gtggcacatc    600 cgctatccgc tggctgacgg tgcgaaaacc gcagacggta agattatct ggtggtcgcg    660 actacccgtc cagaaaccct gctgggcgat actggcgtag ccgttaaccc ggaagatccg    720
cgttacaaag atctgattgg caaatatgtc attctgccgc tggttaaccg tcgtattccg    780
atcgttggcg acgaacacgc cgacatgaaa aaggcaccg gctgcgtgaa atcactccg    840 gcgcacgact ttaacgacta tgaagtgggt aaacgtcacg ccctgccgat gatcaacatc    900
ctgacctttg acggcgatat ccgtgaaagc gcccaggtgt cgataccaa aggtaacgaa    960 tctgacgttt attccagcga aatccctgca gagttccaga aactggagcg ttttgctgca   1020
```

```
cgtaaagcag tcgttgccgc agttgacgcg cttggcctgc tggaagaaat taaaccgcac      1080
gacctgaccg ttccttacgg cgaccgtggc ggcgtagtta tcgaaccaat gctgaccgac      1140
cagtggtacg tgcgtgccga tgtcctggcg aaaccggcgg ttgaagcggt tgagaacggc      1200
gacattcagt tcgtaccgaa gcagtacgaa aacatgtact tctcctggat gcgcgatatt      1260
caggactggt gtatctctcg tcagttgtgg tggggtcacc gtatcccggc atggtatgac      1320
gaagcgggta acgtttatgt tggccgcaac gaagacgaag tgcgtaaaga aaataacctc      1380
ggtgctgatg ttgtcctgcg tcaggacgaa gacgttctcg atacctggtt ctcttctgcg      1440
ctgtggacct tctctaccct tggctggccg gaaaataccg acgccctgcg tcagttccac      1500
ccaaccagcg tgatggtatc tggtttcgac atcatttttct tctggattgc ccgcatgatc      1560
atgatgacca tgcacttcat caaagatgaa aatggcaaac cgcaggtgcc gttccacacc      1620
gtttacatga ccggcctgat tcgtgatgac gaaggccaga agatgtccaa atccaagggt      1680
aacgttatcg acccactgga tatggttgac ggtatttcgc tgccagaact gctggaaaaa      1740
cgtaccggca atatgatgca gccgcagctg gcggacaaaa tccgtaagcg caccgagaag      1800
cagttcccga acggtattga gccgcacggt actgacgcgc tgcgcttcac cctggcggcg      1860
ctggcgtcta ccggtcgtga catcaactgg gatatgaagg tctggaaggg ttaccgtaac      1920
ttctgtaaca gctgtggaaa cgccagccgc tttgtgctga tgaacacaga aggtcaggat      1980
tgcggcttca acggcggcga aatgacgctg tcgctggcgg accgctggat tctggcggag      2040
ttcaaccaga ccatcaaagc gtaccgcgaa gcgctggaca gcttccgctt cgatatcgcc      2100
gcaggcattc tgtatgagtt cacctggaac cagttctgtg actggtatct cgagctgacc      2160
aagccggtaa tgaacggtgg caccgaagca gaactgcgcg gtactcgcca tacgctggtg      2220
actgtactgg aaggtctgct cgcgctcgcg catccgatca ttccgttcat caccgaaaacc      2280 atctggcagc gtgtgaaagt actttgcggt atcactgccg acaccatcat gctgcagccg      2340
ttcccgcagt acgatgcatc tcaggttgat gaagccgcac tggccgacac cgaatggctg      2400
aaacaggcga tcgttgcggt acgtaacatc cgtgcagaaa tgaacatcgc gccgggcaaa      2460
ccgctggagc tgctgctgcg tggttgcagc gcggatgcag aacgtcgcgt aaatgaaaac      2520
cgtggcttcc tgcaaacccct ggcgcgtctg gaaagtatca ccgtgctgcc tgccgatgac      2580
aaaggtccgg tttccgttac gaagatcatc gacggtgcag agctgctgat cccgatggct      2640
ggcctcatca acaaagaaga tgagctggcg cgtctggcga agaagtggc gaagattgaa      2700 ggtgaaatca gccgtatcga gaacaaactg gcgaacgaag ctttgtcgc ccgcgcaccg      2760 gaagcggtca tcgcgaaaga gcgtgagaag ctggaaggct atgcggaagc gaaagcgaaa      2820
ctgattgaac agcaggctgt tatcgccgcg ctg                                   2853
```

<210> SEQ ID NO 15
<211> LENGTH: 2853
<212> TYPE: DNA
<213> ORGANISM: Artificial
<220> FEATURE:
<223> OTHER INFORMATION: artificially synthesized sequence

<400> SEQUENCE: 15

```
atggaaaaga catataaccc acaagatatc gaacagccgc tttacgagca ctgggaaaag        60
cagggctact ttaagcctaa tggcgatgaa agccaggaaa gtttctgcat catgatcccg       120
ccgccgggtg tcaccggcag tttgcatatg ggtcacgcct tccagcaaac catcatggat       180
accatgatcc gctatcagcg catgcagggc aaaaacaccc tgtggcaggt cggtactgac       240
```

```
cacgccggga tcgctaccca gatggtcgtt gagcgcaaga ttgccgcaga agaaggtaaa    300
acccgtcacg actacggccg cgaagctttc atcgacaaaa tctgggaatg gaaagcggaa    360
tctggcggca ccattacccg tcagatgcgc cgtctcggca actccgtcga ctgggagcgt    420
gaacgcttca ccatggacga aggcctgtcc aatgcggtga agaagttttt cgttcgtctg    480
tataaagaag acctgattta ccgtggcaaa cgcctggtaa actgggatcc gaaactgcgc    540
accgctatct ctgacctgga agtcgaaaac cgcgaatcga aaggttcgat gtggcacatc    600
cgctatccgc tggctgacgg tgcgaaaacc gcagacggta agattatct ggtggtcgcg    660 actacccgtc cagaaaccct gctgggcgat actggcgtag ccgttaaccc ggaagatccg    720
cgttacaaag atctgattgg caaatatgtc attctgccgc tggttaaccg tcgtattccg    780
atcgttggcg acgaacacgc cgacatggaa aaaggcaccg gctgcgtgaa aatcactccg    840
gcgcacgact ttaacgacta tgaagtgggt aaacgtcacg ccctgccgat gatcaacatc    900
ctgacctttg acggcgatat ccgtgaaagc gcccaggtgt tcgataccaa aggtaacgaa    960
tctgacgttt attccagcga aatccctgca gagttccaga actggagcg ttttgctgca    1020 cgtaaagcag tcgttgccgc agttgacgcg cttggcctgc tggaagaaat taaaccgcac    1080
gacctgaccg ttccttacgg cgaccgtggc ggcgtagtta tcgaaccaat gctgaccgac    1140
cagtggtacg tgcgtgccga tgtcctggcg aaaccggcgg ttgaagcggt tgagaacggc    1200
gacattcagt tcgtaccgaa gcagtacgaa acatgtact tctcctggat gcgcgatatt    1260
caggactggt gtatctctcg tcagttgtgg tggggtcacc gtatcccggc atggtatgac    1320
gaagcgggta acgtttatgt tggccgcaac gaagacgaag tgcgtaaaga aaataacctc    1380
ggtgctgatg ttgtcctgcg tcaggacgaa gacgttctcg atacctggtt ctcttctgcg    1440
ctgtggacct tctctaccct tggctggccg gaaaataccg acgccctgcg tcagttccac    1500
ccaaccagcg tgatggtatc tggtttcgac atcattttct tctggattgc ccgcatgatc    1560
atgatgacca tgcacttcat caaagatgaa aatggcaaac cgcaggtgcc gttccacacc    1620
gtttacatga ccggcctgat tcgtgatgac gaaggccaga agatgtccaa atccaagggt    1680
aacgttatcg acccactgga tatggttgac ggtatttcgc tgccagaact gctggaaaaa    1740
cgtaccggca atatgatgca gccgcagctg gcggacaaaa tccgtaagcg caccgagaag    1800
cagttcccga acggtattga gccgcacggt actgacgcgc tgcgcttcac cctggcggcg    1860
ctggcgtcta ccggtcgtga catcaactgg gatatgaagc gtctggaagg ttaccgtaac    1920
ttctgtaaca agctgtggaa cgccagccgc tttgtgctga tgaacacaga aggtcaggat    1980
tgcggcttca acggcggcga aatgacgctg tcgctggcgg accgctggat tctggcggag    2040
ttcaaccaga ccatcaaagc gtaccgcgaa gcgctggaca gcttccgctt cgatatcgcc    2100
gcaggcattc tgtatgagtt cacctggaac cagttctgtg actggtatct cgagctgacc    2160
aagccggtaa tgaacggtgg caccgaagca gaactgcgcg gtactcgcca tacgctggtg    2220
actgtactgg aaggtctgct gcgcctcgcg catccgatca ttccgttcat caccgaaacc    2280
atctggcagc gtgtgaaagt actttgcggt atcactgccg acaccatcat gctgcagccg    2340
ttcccgcagt acgatgcatc tcaggttgat gaagccgcac tggccgacac cgaatggctg    2400
aaacaggcga tcgttgcggt acgtaacatc cgtgcagaaa tgaacatcgc gccgggcaaa    2460
ccgctggagc tgctgctgcg tggttgcagc gcggatgcag aacgtcgcgt aaatgaaaac    2520
cgtggcttcc tgcaaacct ggcgcgtctg gaaagtatca ccgtgctgcc tgccgatgac    2580
```

```
aaaggtccgg tttccgttac gaagatcatc gacggtgcag agctgctgat cccgatggct    2640
ggcctcatca acaaagaaga tgagctggcg cgtctggcga agaagtggc gaagattgaa     2700 ggtgaaatca gccgtatcga gaacaaactg gcgaacgaag gctttgtcgc ccgcgcaccg    2760
gaagcggtca tcgcgaaaga gcgtgagaag ctggaaggct atgcggaagc gaaagcgaaa    2820
ctgattgaac agcaggctgt tatcgccgcg ctg                                 2853
```

<210> SEQ ID NO 16
<211> LENGTH: 2853
<212> TYPE: DNA
<213> ORGANISM: Artificial
<220> FEATURE:
<223> OTHER INFORMATION: artificially synthesized sequence

<400> SEQUENCE: 16

```
atggaaaaga catataaccc acaagatatc gaacagccgc tttacgagca ctgggaaaag      60
cagggctact ttaagcctaa tggcgatgaa agccaggaaa gtttctgcat catgatcccg     120
ccgccgggtg tctcaggcag tttgcatatg ggtcacgcct ccagcaaac catcatggat     180 accatgatcc gctatcagcg catgcagggc aaaaacaccc tgtggcaggt cggtactgac     240
cacgcccgga tcgctaccca gatggtcgtt gagcgcaaga ttgccgcaga agaaggtaaa     300
acccgtcacg actacggccg cgaagctttc atcgacaaaa tctgggaatg gaaagcggaa     360
tctggcggca ccattacccg tcagatgcgc cgtctcggca actccgtcga ctgggagcgt     420
gaacgcttca ccatggacga aggcctgtcc aatgcggtga agaagttttt cgttcgtctg     480 tataagaag acctgattta ccgtggcaaa cgcctggtaa actgggatcc gaaactgcgc     540
accgctatct ctgacctgga agtcgaaaac cgcgaatcga aggttcgat gtggcacatc     600 cgctatccgc tggctgacgg tgcgaaaacc gcagacggta agattatct ggtggtcgcg     660 actacccgtc agaaacccct gctgggcgat actggcgtag ccgttaaccc ggaagatccg     720
cgttacaaag atctgattgg caaatatgtc attctgccgc tggttaaccg tcgtattccg     780
atcgttggcg acgaacacgc cgacatggaa aaaggcaccg gctgcgtgaa aatcactccg     840
gcgcacgact taacgacta tgaagtgggt aaacgtcacg ccctgccgat gatcaacatc     900
ctgacctttg acggcgatat ccgtgaaagc gcccaggtgt cgataccaa aggtaacgaa     960 tctgacgttt attccagcga aatccctgca gagttccaga aactggagcg ttttgctgca    1020
cgtaaagcag tcgttgccgc agttgacgcg cttggcctgc tggaagaaat taaaccgcac    1080
gacctgaccg ttccttacgg cgaccgtggc ggcgtagtta tcgaaccaat gctgaccgac    1140
cagtggtacg tgcgtgccga tgtcctggcg aaaccggcgg ttgaagcggt tgagaacggc    1200
gacattcagt tcgtaccgaa gcagtacgaa aacatgtact ctcctggat gcgcgatatt    1260 caggactggt gtatctctcg tcagttgtgg tggggtcacc gtatcccggc atggtatgac    1320
gaagcgggta acgtttatgt tggccgcaac gaagacgaag tgcgtaaaga aaataacctc    1380
ggtgctgatg ttgtcctgcg tcaggacgaa gacgttctcg atacctggtt ctcttctgcg    1440
ctgtggacct tctctaccct tggctggccg gaaaataccg acgccctgcg tcagttccac    1500
ccaaccagcg tgatggtatc tggtttcgac atcattttct ctggattgc ccgcatgatc    1560 atgatgacca tgcacttcat caaagatgaa aatggcaaac cgcaggtgcc gttccacacc    1620
gtttacatga ccggcctgat tcgtgatgac gaaggccaga gatgtccaa atccaagggt    1680 aacgttatcg acccactgga tatggttgac ggtatttcgc tgccagaact gctgaaaaaa    1740
cgtaccggca atatgatgca gccgcagctg gcggacaaaa tccgtaagcg caccgagaag    1800
```

-continued

```
cagttcccga acggtattga gccgcacggt actgacgcgc tgcgcttcac cctggcggcg    1860
ctggcgtcta ccggtcgtga catcaactgg gatatgaagc gtctggaagg ttaccgtaac    1920
ttctgtaaca agctgtggaa cgccagccgc tttgtgctga tgaacacaga aggtcaggat    1980
tgcggcttca acggcggcga aatgacgctg tcgctggcgg accgctggat tctggcggag    2040
ttcaaccaga ccatcaaagc gtaccgcgaa gcgctggaca gcttccgctt cgatatcgcc    2100
gcaggcattc tgtatgagtt cacctggaac cagttctgtg actggtatct cgagctgacc    2160
aagccggtaa tgaacggtgg caccgaagca gaactgcgcg gtactcgcca tacgctggtg    2220
actgtactgg aaggtctgct gcgcctcgcg catccgatca ttccgttcat caccgaaacc    2280
atctggcagc gtgtgaaagt actttgcggt atcactgccg acaccatcat gctgcagccg    2340
ttcccgcagt acgatgcatc tcaggttgat gaagccgcac tggccgacac cgaatggctg    2400
aaacaggcga tcgttgcggt acgtaacatc cgtgcagaaa tgaacatcgc gccgggcaaa    2460 ccgctgagc tgctgctgcg tggttgcagc gcggatgcag aacgtcgcgt aaatgaaaac    2520
cgtggcttcc tgcaaaccct ggcgcgtctg gaaagtatca ccgtgctgcc tgccgatgac    2580
aaaggtccgg tttccgttac gaagatcatc gacggtgcag agctgctgat cccgatggct    2640
ggcctcatca acaaagaaga tgagctggcg cgtctggcga agaagtggc gaagattgaa    2700 ggtgaaatca ccgtatcga gaacaaactg gcgaacgaag ctttgtcgc ccgcgcaccg    2760 gaagcggtca tcgcgaaaga gcgtgagaag ctggaaggct atgcggaagc gaaagcgaaa    2820
ctgattgaac agcaggctgt tatcgccgcg ctg                                 2853
```

<210> SEQ ID NO 17  
<211> LENGTH: 1290  
<212> TYPE: DNA  
<213> ORGANISM: Artificial  
<220> FEATURE:  
<223> OTHER INFORMATION: artificially synthesized sequence

<400> SEQUENCE: 17

```
atgctcgatc ccaatctgct gcgtaatgag ccagacgcag tcgctgaaaa actggcacgc      60
cggggcttta agctggatgt agataagctg ggcgctcttg aagagcgtcg taaagtattg     120
caggtcaaaa cggaaaacct gcaagcggag cgtaactccc gatcgaaatc cattggccag     180
gcgaaagcgc gcggggaaga tatcgagcct ttacgtctgg aagtgaacaa actgggcgaa     240
gagctggatg cagcaaaagc cgagctggat gctttacagg ctgaaattcg cgatatcgcg     300
ctgaccatcc ctaacctgcc tgcagatgaa gtgccggtag gtaaagacga aaatgacaac     360
gttgaagtca ccgctggggg tacccgcgt gagtttgact ttgaagttcg tgaccacgtg     420
acgctgggtg aaatgcactc tggcctcgac tttgcagctg cagttaagct gactggttcc     480
cgctttgtgg taatgaaagg gcagattgct cgcatgcacc gcgcactgtc gcagtttatg     540
ctggatctgc ataccgaaca gcatggctac agtgagaact atgttccgta cctggttaac     600
caggacacgc tgtacggtac gggtcaactg ccgaaatttg ctggcgatct gttccatact     660
cgtccgctgg aagaagaagc agacaccagt aactatgcgc tgatcccaag tgcagaagtt     720
ccgctgacta acctggtgcg cggtgaaatc atcgatgaag atgatctgcc aattaagatg     780
accgcccaca ccccatgctt ccgttctgaa gccggttcat atggtcgtga cacccgtggt     840
ctgatccgta tgcaccagtt cgacaaagtt gaaatggtgc agatcgtgcg cccagaagac     900
tcaatggcgg cgctggaaga gatgactggt catgcagaaa agtcctgca gttgctgggc     960
```

| | |
|---|---|
| ctgccgtacc gtaaaatcat cctttgcact ggcgacatgg gctttggcgc ttgcaaaact | 1020 |
| tacgacctgg aagtatggat cccggcacag aacacctacc gtgagatctc ttcctgctcc | 1080 |
| aacgtttggg atttccaggc acgtcgtatg caggcacgtt gccgcagcaa gtcggacaag | 1140 |
| aaaacccgtc tggttcatac cctgaacggt tctggtctgg ctgttggtcg tacgctggtt | 1200 |
| gcagtaatgg aaaactatca gcaggctgat ggtcgtattg aagtaccaga agttctgcgt | 1260 |
| ccgtatatga acggactgga atatattggc | 1290 |

```
<210> SEQ ID NO 18
<211> LENGTH: 1290
<212> TYPE: DNA
<213> ORGANISM: Artificial
<220> FEATURE:
<223> OTHER INFORMATION: artificially synthesized sequence

<400> SEQUENCE: 18
```

| | |
|---|---|
| atgctcgatc ccaatctgct gcgtaatgag ccagacgcag tcgctgaaaa actggcacgc | 60 |
| cggggcttta agctggatgt agataagctg ggcgctcttg aagagcgtcg taaagtattg | 120 |
| caggtcaaaa cggaaaacct gcaagcggag cgtaactccc gatcgaaatc cattggccag | 180 |
| gcgaaagcgc gcggggaaga tatcgagcct ttacgtctgg aagtgaacaa actgggcgaa | 240 |
| gagctggatg cagcaaaagc cgagctggat gctttacagg ctgaaattcg cgatatcgcg | 300 |
| ctgaccatcc ctaacctgcc tgcagatgaa gtgccggtag gtaaagacga aaatgacaac | 360 |
| gttgaagtca gccgctgggg taccccgcgt gagtttgact ttgaagttcg tgaccacgtg | 420 |
| acgctgggtg aaatgcactc tggcctcgac tttgcagctg cagttaagct gactggttcc | 480 |
| cgctttgtgg taatgaaagg gcagattgct cgcatgcacc gcgcactgtc gcagtttatg | 540 |
| ctggatctgc ataccgaaca gcatggctac agtgagaact atgttccgta cctggttaac | 600 |
| caggacacgc tgtacggtac gggtcaactg ccgaaatttg ctggcgatct gttccatact | 660 |
| cgtccgctgg aagaagaagc agacaccagt aactatgcgc tgatcccaac ggcagctgtt | 720 |
| ccgctgacta acctggtgcg cggtgaaatc atcgatgaag atgatctgcc aattaagatg | 780 |
| accgcccaca ccccatgctt ccgttctgaa gccggttcat atggtcgtga cacccgtggt | 840 |
| ctgatccgta tgcaccagtt cgacaaagtt gaaatggtgc agatcgtgcg cccagaagac | 900 |
| tcaatggcgg cgctggaaga gatgactggt catgcagaaa aagtcctgca gttgctgggc | 960 |
| ctgccgtacc gtaaaatcat cctttgcact ggcgacatgg gctttggcgc ttgcaaaact | 1020 |
| tacgacctgg aagtatggat cccggcacag aacacctacc gtgagatctc ttcctgctcc | 1080 |
| aacgtttggg atttccaggc acgtcgtatg caggcacgtt gccgcagcaa gtcggacaag | 1140 |
| aaaacccgtc tggttcatac cctgaacggt tctggtctgg ctgttggtcg tacgctggtt | 1200 |
| gcagtaatgg aaaactatca gcaggctgat ggtcgtattg aagtaccaga agttctgcgt | 1260 |
| ccgtatatga acggactgga atatattggc | 1290 |

```
<210> SEQ ID NO 19
<211> LENGTH: 1290
<212> TYPE: DNA
<213> ORGANISM: Artificial
<220> FEATURE:
<223> OTHER INFORMATION: artificially synthesized sequence

<400> SEQUENCE: 19
```

| | |
|---|---|
| atgctcgatc ccaatctgct gcgtaatgag ccagacgcag tcgctgaaaa actggcacgc | 60 |
| cggggcttta agctggatgt agataagctg ggcgctcttg aagagcgtcg taaagtattg | 120 |

```
caggtcaaaa cggaaaacct gcaagcggag cgtaactccc gatcgaaatc cattggccag    180
gcgaaagcgc gcggggaaga tatcgagcct ttacgtctgg aagtgaacaa actgggcgaa    240
gagctggatg cagcaaaagc cgagctggat gctttacagg ctgaaattcg cgatatcgcg    300
ctgaccatcc ctaacctgcc tgcagatgaa gtgccggtag gtaaagacga aaatgacaac    360
gttgaagtca gccgctgggg taccccgcgt gagtttgact ttgaagttcg tgaccacgtg    420
acgctgggtg aaatgcactc tggcctcgac tttgcagctg cagttaagct gactggttcc    480
cgctttgtgg taatgaaagg gcagattgct cgcatgcacc gcgcactgtc gcagtttatg    540
ctggatctgc ataccgaaca gcatggctac agtgagaact atgttccgta cctggttaac    600
caggacacgc tgtacggtac gggtcaactg ccgaaatttg ctggcgatct gttccatact    660
cgtccgctgg aagaagaagc agacaccagt aactatgcgc tgatcccaac ggcaggtgtt    720
ccgctgacta acctggtgcg cggtgaaatc atcgatgaag atgatctgcc aattaagatg    780
accgcccaca ccccatgctt ccgttctgaa gccggttcat atggtcgtga cacccgtggt    840
ctgatccgta tgcaccagtt cgacaaagtt gaaatggtgc agatcgtgcg cccagaagac    900
tcaatggcgg cgctggaaga gatgactggt catgcagaaa aagtcctgca gttgctgggc    960
ctgccgtacc gtaaaatcat cctttgcact ggcgacatgg gctttggcgc ttgcaaaact   1020
tacgacctgg aagtatggat cccggcacag aacacctacc gtgagatctc ttcctgctcc   1080
aacgtttggg atttccaggc acgtcgtatg caggcacgtt gccgcagcaa gtcggacaag   1140
aaaacccgtc tggttcatac cctgaacggt tctggtctgg ctgttggtcg tacgctggtt   1200
gcagtaatgg aaaactatca gcaggctgat ggtcgtattg aagtaccaga agttctgcgt   1260
ccgtatatga acggactgga atatattggc                                    1290

<210> SEQ ID NO 20
<211> LENGTH: 1290
<212> TYPE: DNA
<213> ORGANISM: Artificial
<220> FEATURE:
<223> OTHER INFORMATION: artificially synthesized sequence

<400> SEQUENCE: 20
atgctcgatc ccaatctgct gcgtaatgag ccagacgcag tcgctgaaaa actggcacgc     60 cggggctttta agctggatgt agataagctg ggcgctcttg aagagcgtcg taaagtattg    120
caggtcaaaa cggaaaacct gcaagcggag cgtaactccc gatcgaaatc cattggccag    180
gcgaaagcgc gcggggaaga tatcgagcct ttacgtctgg aagtgaacaa actgggcgaa    240
gagctggatg cagcaaaagc cgagctggat gctttacagg ctgaaattcg cgatatcgcg    300
ctgaccatcc ctaacctgcc tgcagatgaa gtgccggtag gtaaagacga aaatgacaac    360
gttgaagtca gccgctgggg taccccgcgt gagtttgact ttgaagttcg tgaccacgtg    420
acgctgggtg aaatgcactc tggcctcgac tttgcagctg cagttaagct gactggttcc    480
cgctttgtgg taatgaaagg gcagattgct cgcatgcacc gcgcactgtc gcagtttatg    540
ctggatctgc ataccgaaca gcatggctac agtgagaact atgttccgta cctggttaac    600
caggacacgc tgtacggtac gggtcaactg ccgaaatttg ctggcgatct gttccatact    660
cgtccgctgg aagaagaagc agacaccagt aactatgcgc tgatcccaag tgcaggtgtt    720
ccgctgacta acctggtgcg cggtgaaatc atcgatgaag atgatctgcc aattaagatg    780
accgcccaca ccccatgctt ccgttctgaa gccggttcat atggtcgtga cacccgtggt    840
```

| | |
|---|---:|
| ctgatccgta tgcaccagtt cgacaaagtt gaaatggtgc agatcgtgcg cccagaagac | 900 |
| tcaatggcgg cgctggaaga gatgactggt catgcagaaa aagtcctgca gttgctgggc | 960 |
| ctgccgtacc gtaaaatcat cctttgcact ggcgacatgg gctttggcgc ttgcaaaact | 1020 |
| tacgacctgg aagtatggat cccggcacag aacacctacc gtgagatctc ttcctgctcc | 1080 |
| aacgtttggg atttccaggc acgtcgtatg caggcacgtt gccgcagcaa gtcggacaag | 1140 |
| aaaacccgtc tggttcatac cctgaaccggt tctggtctgg ctgttggtcg tacgctggtt | 1200 |
| gcagtaatgg aaaactatca gcaggctgat ggtcgtattg aagtaccaga agttctgcgt | 1260 |
| ccgtatatga acggactgga atatattggc | 1290 |

<210> SEQ ID NO 21
<211> LENGTH: 1926
<212> TYPE: DNA
<213> ORGANISM: Artificial
<220> FEATURE:
<223> OTHER INFORMATION: artificially synthesized sequence

<400> SEQUENCE: 21

| | |
|---|---:|
| atgccggtta ttaccctgcc ggacggttcg caacgtcatt acgatcacgc tgttagcccg | 60 |
| atggatgtcg cactggatat tggcccgggt ctggcaaaag cttgcattgc aggccgcgtt | 120 |
| aatggtgaac tggtcgacgc ttgtgatctg atcgaaaacg acgcgcagct gagcattatc | 180 |
| accgccaaag atgaagaagg cctggaaatt atccgtcatt cttgcgcgca cctgctgggt | 240 |
| catgccatta acagctgtg ccgcatacc aaaatggcga ttggcccggt catcgacaat | 300 |
| ggttttatt acgatgtgga cctggatcgc accctgacgc aggaagatgt ggaagcgctg | 360 |
| gaaaaacgta tgcacgaact ggccgagaaa aactacgacg tgattaagaa aaaagttagt | 420 |
| tggcatgaag cacgtgaaac cttgctaat cgcggcgaat catacaaagt ttcgattctg | 480 |
| gatgaaaaca tcgcccacga tgacaaaccg ggcctgtatt ccatgaaga atacgtggat | 540 |
| atgtgccgtg gtccgcacgt tccgaatatg cgcttttgtc atcacttcaa actgatgaaa | 600 |
| accgcaggtg catattggcg tggtgacagc aacaataaaa tgctgcagcg tatttatggt | 660 |
| acggcatggg ctgataaaaa agcgctgaat gcctacctgc aacgcctgga agaagcggcc | 720 |
| aaacgtgacc accgcaaaat tggcaaacag ctggatctgt atcatatgca agaagaagcg | 780 |
| ccgggcatgt gtttttggca taacgatggt tggaccatct ttcgtgaact ggaagttttc | 840 |
| gtccgcagca aactgaaaga atatcagtac caagaagtta aaggcccgtt tatgatggat | 900 |
| cgcgtcctgt gggaaaaaac cggtcactgg acaactata aagatgccat gttcaccacg | 960 |
| agctctgaaa accgtgaata ctgcattaaa ccgggcaatt gtccgggtca tgtgcagatc | 1020 |
| tttaaccaag gcctgaaaag ttatcgtgat ctgccgctgc gcatggcaga attcggttcc | 1080 |
| tgccaccgca atgaaccgag tggctccctg catggtctga tgcgtgttcg cggttttacc | 1140 |
| caggatgacg cccatatttt ctgcacggaa gaacaaatcc gtgacgaagt taacggctgt | 1200 |
| attcgcctgg tctatgatat gtactctacc tttggtttcg aaaaaattgt ggttaaactg | 1260 |
| agcacgcgtc ggaaaaacg catcggctct gacgaaatgt gggatcgtgc ggaagccgat | 1320 |
| ctggcagtgg ctctggaaga aaacaatatt ccgtttgaat atcagctggg cgagggtgcg | 1380 |
| ttttacggcc cgaaaatcga attcaccctg tatgactgcc tggatcgcgc tggcagtgt | 1440 |
| ggtacggtcc aactggactt cagtctgccg tcccgtctgt cagcatcgta cgtgggcgaa | 1500 |
| gataatgaac gtaaagtgcc ggttatgatt caccgcgcta tcctgggcag tatggaacgt | 1560 |
| tttattggta tcctgaccga agaattcgca ggcttttttcc cgacgtggct ggctccggtt | 1620 |

```
caggtcgtga ttatgaatat caccgatagc cagtctgaat atgtgaacga actgacgcaa    1680
aaactgtcca atgcaggcat tcgtgttaaa gctgatctgc gcaacgaaaa aatcggtttc    1740
aaaatccgcg aacatacccT gcgtcgcgtc ccgtacatgc tggtgtgtgg cgataaagaa    1800
gttgaaagcg gtaaagtcgc ggtgcgtacg cgtcgcggca aagacctggg ttcgatggat    1860
gtcaacgaag tcattgaaaa actgcaacaa gaaatccgta ccgctcgct gaaacaactg     1920 gaagaa                                                               1926
```

<210> SEQ ID NO 22
<211> LENGTH: 1926
<212> TYPE: DNA
<213> ORGANISM: Artificial
<220> FEATURE:
<223> OTHER INFORMATION: artificially synthesized sequence

<400> SEQUENCE: 22

```
atgccggtca ttaccctgcc ggatggctct cagcgtcact acgatcatgc ggtctcgccg      60
atggatgttg ctctggatat tggcccgggt ctggcaaaag cttgcattgc aggccgcgtt     120
aatggtgaac tggtcgacgc ttgtgatctg atcgaaaacg acgcgcagct gagcattatc     180
accgccaaag atgaagaagg cctggaaatt atccgtcatt cttgcgcgca cctgctgggt     240
catgccatta gcagctgtg ccgcataccc aaaatggcga ttggcccggt catcgacaat     300
ggtttttatt acgatgtgga cctggatcgc accctgacgc aggaagatgt ggaagcgctg    360
gaaaagcgta tgcacgaact ggccgaaaag aactatgacg tgatcaaaaa gaaagttagt    420
tggcatgaag cacgtgaaac ctttgctaat cgcggcgaat catacaaggt ttcgattctg    480
gatgaaaaca tcgcccacga tgacaaaccg ggcctgtatt ccatgaaga atacgtggat     540 atgtgccgtg gtccgcacgt tccgaatatg cgcttttgtc atcacttcaa gctgatgaaa    600
accgcaggtg catattggcg tggtgacagc aacaataaaa tgctgcagcg tatttatggt    660
acggcatggg ctgataagaa agcgctgaat gcctacctgc aacgcctgga agaagcggcc    720
aaacgtgacc accgcaagat tggcaaacag ctggatctgt atcatatgca agaagaagcg    780
ccgggcatgg tgttttggca taacgatggt tggaccatct ttcgtgaact ggaagttttc    840
gtccgcagca agctgaaaga atatcagtac caagaagtta aaggcccgtt tatgatggat    900
cgcgtcctgt gggaaaagac cggtcactgg gacaactata agatgccat gttcaccacg    960 agctctgaaa accgtgaata ctgcattaag ccgatgaatt gtccgggcca tgtgcagatc    1020
tttaaccaag gtctgaaaag ttatcgtgat ctgccgctgc gcatggcaga attcggttcc    1080
tgccaccgca atgaaccgag tggctccctg catggtctga tgcgtgttcg cggctttacc    1140
caggatgacg cccacatttt ctgcacggaa gaacaaatcc gtgacgaagt aacggctgt    1200 attcgcctgg tctatgatat gtactctacc tttggtttcg aaaagattgt ggttaaactg    1260
agcacgcgtc cggaaaaacg catcggttct gacgaaatgt gggatcgtgc ggaagccgat    1320
ctggcagtgg ctctggaaga aaacaatatt ccgtttgaat atcagctggg cgagggtgcg    1380
ttttacggcc cgaaaatcga attcacccTg tatgactgcc tggatcgcgc ctggcagtgt    1440
ggtacggtcc aactggactt cagtctgccg tcccgtctgt cagcatcgta cgtgggcgaa    1500
gataatgaac gtaaagtgcc ggttatgatt ggccgcgcta tcctgggtag tatggaacgt    1560
tttattggca tcctgaccga agaattcgca ggcttttttcc cgacgtggct ggctccggtt    1620
caggtcgtga ttatgaatat caccgatagc cagtctgaat atgtgaacga actgacgcaa    1680
```

| | |
|---|---:|
| aagctgtcca atgcaggcat tcgtgttaaa gctgatctgc gcaacgaaaa gattggtttt | 1740 |
| aaaatccgcg aacataccct gcgtcgcgtc ccgtacatgc tggtgtgtgg cgataaggaa | 1800 |
| gttgaaagcg gtaaagtcgc ggtgcgtacg cgtcgcggca agacctggg ttcgatggat | 1860 |
| gtcaacgaag tcattgaaaa actgcaacaa gaaatccgct cacgctcgct gaaacaactg | 1920 |
| gaagaa | 1926 |

<210> SEQ ID NO 23
<211> LENGTH: 2853
<212> TYPE: DNA
<213> ORGANISM: E. coli

<400> SEQUENCE: 23

| | |
|---|---:|
| atggaaaaga catataaccc acaagatatc gaacagccgc tttacgagca ctgggaaaag | 60 |
| cagggctact ttaagcctaa tggcgatgaa agccaggaaa gtttctgcat catgatcccg | 120 |
| ccgccgaacg tcaccggcag tttgcatatg ggtcacgcct tccagcaaac catcatggat | 180 |
| accatgatcc gctatcagcg catgcagggc aaaaacaccc tgtggcaggt cggtactgac | 240 |
| cacgccggga tcgctaccca gatggtcgtt gagcgcaaga ttgccgcaga agaaggtaaa | 300 |
| acccgtcacg actacggccg cgaagctttc atcgacaaaa tctgggaatg gaaagcggaa | 360 |
| tctggcggca ccattacccg tcagatgcgc cgtctcggca actccgtcga ctggagcgt | 420 |
| gaacgcttca ccatgacga aggcctgtcc aatgcggtga agaagttttt cgttcgtctg | 480 |
| tataagaag acctgattta ccgtggcaaa cgcctggtaa actgggatcc gaaactgcgc | 540 |
| accgctatct ctgacctgga agtcgaaaac cgcgaatcga aggttcgat gtggcacatc | 600 |
| cgctatccgc tggctgacgg tgcgaaaacc gcagacggta agattatct ggtggtcgcg | 660 |
| actacccgtc cagaaaccct gctgggcgat actggcgtag ccgttaaccc ggaagatccg | 720 |
| cgttacaaag atctgattgg caaatatgtc attctgccgc tggttaaccg tcgtattccg | 780 |
| atcgttggcg acgaacacgc cgacatgaaa aaggcaccg gctgcgtgaa aatcactccg | 840 |
| gcgcacgact ttaacgacta tgaagtgggt aaacgtcacg ccctgccgat gatcaacatc | 900 |
| ctgacctttg acggcgatat ccgtgaaagc gcccaggtgt cgataccaa ggtaacgaa | 960 |
| tctgacgttt attccagcga aatccctgca gagttccaga aactggagcg ttttgctgca | 1020 |
| cgtaaagcag tcgttgccgc agttgacgcg cttggcctgc tggaagaaat taaccgcac | 1080 |
| gacctgaccg ttccttacgg cgaccgtggc ggcgtagtta tcgaaccaat gctgaccgac | 1140 |
| cagtggtacg tgcgtgccga tgtcctggcg aaaccggcgg ttgaagcggt tgagaacggc | 1200 |
| gacattcagt tcgtaccgaa gcagtacgaa acatgtact tctcctggat gcgcgatatt | 1260 |
| caggactggt gtatctctcg tcagttgtgg ggggtcacc gtatcccggc atggtatgac | 1320 |
| gaagcgggta acgtttatgt tggccgcaac gaagacgaag tgcgtaaaga aataaccctc | 1380 |
| ggtgctgatg ttgtcctgcg tcaggacgaa gacgttctcg atacctggtt ctcttctgcg | 1440 |
| ctgtggacct tctctaccct ggctggccg gaaaataccg acgccctgcg tcagttccac | 1500 |
| ccaaccagcg tgatggtatc tggtttcgac atcattttct tctggattgc ccgcatgatc | 1560 |
| atgatgacca tgcacttcat caaagatgaa atggcaaac gcaggtgcc gttccacacc | 1620 |
| gtttacatga ccggcctgat tcgtgatgac gaaggccaga agatgtccaa atccaaggt | 1680 |
| aacgttatcg acccactgga tatggttgac ggtatttcgc tgccagaact gctggaaaaa | 1740 |
| cgtaccggca atatgatgca gccgcagctg gcggacaaaa tccgtaagcg caccgagaag | 1800 |
| cagttcccga cggtattga ccgcacggt actgacgcgc tgcgcttcac cctggcggcg | 1860 |

```
ctggcgtcta ccggtcgtga catcaactgg gatatgaagc gtctggaagg ttaccgtaac    1920
ttctgtaaca agctgtggaa cgccagccgc tttgtgctga tgaacacaga aggtcaggat    1980
tgcggcttca acggcggcga aatgacgctg tcgctggcgg accgctggat tctggcggag    2040
ttcaaccaga ccatcaaagc gtaccgcgaa gcgctggaca gcttccgctt cgatatcgcc    2100
gcaggcattc tgtatgagtt cacctggaac cagttctgtg actggtatct cgagctgacc    2160
aagccggtaa tgaacggtgg caccgaagca gaactgcgcg gtactcgcca tacgctggtg    2220
actgtactgg aaggtctgct gcgcctcgcg catccgatca ttccgttcat caccgaaacc    2280
atctggcagc gtgtgaaagt actttgcggt atcactgccg acaccatcat gctgcagccg    2340
ttcccgcagt acgatgcatc tcaggttgat gaagccgcac tggccgacac cgaatggctg    2400
aaacaggcga tcgttgcggt acgtaacatc cgtgcagaaa tgaacatcgc gccgggcaaa    2460
ccgctggagc tgctgctgcg tggttgcagc gcggatgcag aacgtcgcgt aaatgaaaac    2520
cgtggcttcc tgcaaaccct ggcgcgtctg gaaagtatca ccgtgctgcc tgccgatgac    2580
aaaggtccgg tttccgttac gaagatcatc gacggtgcag agctgctgat cccgatggct    2640
ggcctcatca acaaagaaga tgagctggcg cgtctggcga agaagtggc gaagattgaa    2700 ggtgaaatca gccgtatcga gaacaaactg gcgaacgaag ctttgtcgc ccgcgcaccg    2760 gaagcggtca tcgcgaaaga gcgtgagaag ctggaaggct atgcggaagc gaaagcgaaa    2820
ctgattgaac agcaggctgt tatcgccgcg ctg                                 2853
```

<210> SEQ ID NO 24
<211> LENGTH: 951
<212> TYPE: PRT
<213> ORGANISM: E. coli

<400> SEQUENCE: 24

```
Met Glu Lys Thr Tyr Asn Pro Gln Asp Ile Glu Gln Pro Leu Tyr Glu
1               5                   10                  15

His Trp Glu Lys Gln Gly Tyr Phe Lys Pro Asn Gly Asp Glu Ser Gln
            20                  25                  30

Glu Ser Phe Cys Ile Met Ile Pro Pro Asn Val Thr Gly Ser Leu
        35                  40                  45

His Met Gly His Ala Phe Gln Gln Thr Ile Met Asp Thr Met Ile Arg
    50                  55                  60

Tyr Gln Arg Met Gln Gly Lys Asn Thr Leu Trp Gln Val Gly Thr Asp
65                  70                  75                  80

His Ala Gly Ile Ala Thr Gln Met Val Val Glu Arg Lys Ile Ala Ala
                85                  90                  95

Glu Glu Gly Lys Thr Arg His Asp Tyr Gly Arg Glu Ala Phe Ile Asp
            100                 105                 110

Lys Ile Trp Glu Trp Lys Ala Glu Ser Gly Gly Thr Ile Thr Arg Gln
        115                 120                 125

Met Arg Arg Leu Gly Asn Ser Val Asp Trp Glu Arg Glu Arg Phe Thr
    130                 135                 140

Met Asp Glu Gly Leu Ser Asn Ala Val Lys Glu Val Phe Val Arg Leu
145                 150                 155                 160

Tyr Lys Glu Asp Leu Ile Tyr Arg Gly Lys Arg Leu Val Asn Trp Asp
                165                 170                 175

Pro Lys Leu Arg Thr Ala Ile Ser Asp Leu Glu Val Glu Asn Arg Glu
            180                 185                 190
```

```
Ser Lys Gly Ser Met Trp His Ile Arg Tyr Pro Leu Ala Asp Gly Ala
            195                 200                 205
Lys Thr Ala Asp Gly Lys Asp Tyr Leu Val Val Ala Thr Thr Arg Pro
        210                 215                 220
Glu Thr Leu Leu Gly Asp Thr Gly Val Ala Val Asn Pro Glu Asp Pro
225                 230                 235                 240
Arg Tyr Lys Asp Leu Ile Gly Lys Tyr Val Ile Leu Pro Leu Val Asn
                245                 250                 255
Arg Arg Ile Pro Ile Val Gly Asp His Ala Asp Met Glu Lys Gly
            260                 265                 270
Thr Gly Cys Val Lys Ile Thr Pro Ala His Asp Phe Asn Asp Tyr Glu
        275                 280                 285
Val Gly Lys Arg His Ala Leu Pro Met Ile Asn Ile Leu Thr Phe Asp
290                 295                 300
Gly Asp Ile Arg Glu Ser Ala Gln Val Phe Asp Thr Lys Gly Asn Glu
305                 310                 315                 320
Ser Asp Val Tyr Ser Ser Glu Ile Pro Ala Glu Phe Gln Lys Leu Glu
                325                 330                 335
Arg Phe Ala Ala Arg Lys Ala Val Val Ala Ala Val Asp Ala Leu Gly
            340                 345                 350
Leu Leu Glu Glu Ile Lys Pro His Asp Leu Thr Val Pro Tyr Gly Asp
        355                 360                 365
Arg Gly Gly Val Val Ile Glu Pro Met Leu Thr Asp Gln Trp Tyr Val
        370                 375                 380
Arg Ala Asp Val Leu Ala Lys Pro Ala Val Glu Ala Val Glu Asn Gly
385                 390                 395                 400
Asp Ile Gln Phe Val Pro Lys Gln Tyr Glu Asn Met Tyr Phe Ser Trp
                405                 410                 415
Met Arg Asp Ile Gln Asp Trp Cys Ile Ser Arg Gln Leu Trp Trp Gly
            420                 425                 430
His Arg Ile Pro Ala Trp Tyr Asp Glu Ala Gly Asn Val Tyr Val Gly
        435                 440                 445
Arg Asn Glu Asp Glu Val Arg Lys Glu Asn Asn Leu Gly Ala Asp Val
450                 455                 460
Val Leu Arg Gln Asp Glu Asp Val Leu Asp Thr Trp Phe Ser Ser Ala
465                 470                 475                 480
Leu Trp Thr Phe Ser Thr Leu Gly Trp Pro Glu Asn Thr Asp Ala Leu
                485                 490                 495
Arg Gln Phe His Pro Thr Ser Val Met Val Ser Gly Phe Asp Ile Ile
            500                 505                 510
Phe Phe Trp Ile Ala Arg Met Ile Met Met Thr Met His Phe Ile Lys
        515                 520                 525
Asp Glu Asn Gly Lys Pro Gln Val Pro Phe His Thr Val Tyr Met Thr
530                 535                 540
Gly Leu Ile Arg Asp Asp Glu Gly Gln Lys Met Ser Lys Ser Lys Gly
545                 550                 555                 560
Asn Val Ile Asp Pro Leu Asp Met Val Asp Gly Ile Ser Leu Pro Glu
                565                 570                 575
Leu Leu Glu Lys Arg Thr Gly Asn Met Met Gln Pro Gln Leu Ala Asp
            580                 585                 590
Lys Ile Arg Lys Arg Thr Glu Lys Gln Phe Pro Asn Gly Ile Glu Pro
        595                 600                 605
His Gly Thr Asp Ala Leu Arg Phe Thr Leu Ala Ala Leu Ala Ser Thr
```

```
          610                 615                 620
Gly Arg Asp Ile Asn Trp Asp Met Lys Arg Leu Glu Gly Tyr Arg Asn
625                 630                 635                 640

Phe Cys Asn Lys Leu Trp Asn Ala Ser Arg Phe Val Leu Met Asn Thr
                645                 650                 655

Glu Gly Gln Asp Cys Gly Phe Asn Gly Gly Glu Met Thr Leu Ser Leu
            660                 665                 670

Ala Asp Arg Trp Ile Leu Ala Glu Phe Asn Gln Thr Ile Lys Ala Tyr
            675                 680                 685

Arg Glu Ala Leu Asp Ser Phe Arg Phe Asp Ile Ala Ala Gly Ile Leu
        690                 695                 700

Tyr Glu Phe Thr Trp Asn Gln Phe Cys Asp Trp Tyr Leu Glu Leu Thr
705                 710                 715                 720

Lys Pro Val Met Asn Gly Gly Thr Glu Ala Glu Leu Arg Gly Thr Arg
                725                 730                 735

His Thr Leu Val Thr Val Leu Glu Gly Leu Leu Arg Leu Ala His Pro
            740                 745                 750

Ile Ile Pro Phe Ile Thr Glu Thr Ile Trp Gln Arg Val Lys Val Leu
            755                 760                 765

Cys Gly Ile Thr Ala Asp Thr Ile Met Leu Gln Pro Phe Pro Gln Tyr
770                 775                 780

Asp Ala Ser Gln Val Asp Glu Ala Ala Leu Ala Asp Thr Glu Trp Leu
785                 790                 795                 800

Lys Gln Ala Ile Val Ala Val Arg Asn Ile Arg Ala Glu Met Asn Ile
                805                 810                 815

Ala Pro Gly Lys Pro Leu Glu Leu Leu Leu Arg Gly Cys Ser Ala Asp
            820                 825                 830

Ala Glu Arg Arg Val Asn Glu Asn Arg Gly Phe Leu Gln Thr Leu Ala
            835                 840                 845

Arg Leu Glu Ser Ile Thr Val Leu Pro Ala Asp Asp Lys Gly Pro Val
        850                 855                 860

Ser Val Thr Lys Ile Ile Asp Gly Ala Glu Leu Leu Ile Pro Met Ala
865                 870                 875                 880

Gly Leu Ile Asn Lys Glu Asp Glu Leu Ala Arg Leu Ala Lys Glu Val
                885                 890                 895

Ala Lys Ile Glu Gly Glu Ile Ser Arg Ile Glu Asn Lys Leu Ala Asn
            900                 905                 910

Glu Gly Phe Val Ala Arg Ala Pro Glu Ala Val Ile Ala Lys Glu Arg
            915                 920                 925

Glu Lys Leu Glu Gly Tyr Ala Glu Ala Lys Ala Lys Leu Ile Glu Gln
        930                 935                 940

Gln Ala Val Ile Ala Ala Leu
945                 950

<210> SEQ ID NO 25
<211> LENGTH: 1290
<212> TYPE: DNA
<213> ORGANISM: E. coli

<400> SEQUENCE: 25
atgctcgatc ccaatctgct gcgtaatgag ccagacgcag tcgctgaaaa actggcacgc      60
cggggcttta agctggatgt agataagctg ggcgctcttg aagagcgtcg taaagtattg     120
caggtcaaaa cggaaaacct gcaagcggag cgtaactccc gatcgaaatc cattggccag     180
```

```
gcgaaagcgc gcggggaaga tatcgagcct ttacgtctgg aagtgaacaa actgggcgaa    240
gagctggatg cagcaaaagc cgagctggat gctttacagg ctgaaattcg cgatatcgcg    300
ctgaccatcc ctaacctgcc tgcagatgaa gtgccggtag gtaaagacga aaatgacaac    360
gttgaagtca gccgctgggg taccccgcgt gagtttgact ttgaagttcg tgaccacgtg    420
acgctgggtg aaatgcactc tggcctcgac tttgcagctg cagttaagct gactggttcc    480
cgctttgtgg taatgaaagg gcagattgct cgcatgcacc gcgcactgtc gcagtttatg    540
ctggatctgc ataccgaaca gcatggctac agtgagaact atgttccgta cctggttaac    600
caggacacgc tgtacggtac gggtcaactg ccgaaatttg ctggcgatct gttccatact    660
cgtccgctgg aagaagaagc agacaccagt aactatgcgc tgatcccaac ggcagaagtt    720
ccgctgacta acctggtgcg cggtgaaatc atcgatgaag atgatctgcc aattaagatg    780
accgcccaca ccccatgctt ccgttctgaa gccggttcat atggtcgtga cacccgtggt    840
ctgatccgta tgcaccagtt cgacaaagtt gaaatggtgc agatcgtgcg cccagaagac    900
tcaatggcgg cgctggaaga gatgactggt catgcagaaa aagtcctgca gttgctgggc    960
ctgccgtacc gtaaaatcat cctttgcact ggcgacatgg gctttggcgc ttgcaaaact    1020
tacgacctgg aagtatggat cccggcacag aacacctacc gtgagatctc ttcctgctcc    1080
aacgtttggg atttccaggc acgtcgtatg caggcacgtt gccgcagcaa gtcggacaag    1140
aaaacccgtc tggttcatac cctgaacggt tctggtctgg ctgttggtcg tacgctggtt    1200
gcagtaatgg aaaactatca gcaggctgat ggtcgtattg aagtaccaga agttctgcgt    1260
ccgtatatga acggactgga atatattggc                                    1290
```

<210> SEQ ID NO 26
<211> LENGTH: 430
<212> TYPE: PRT
<213> ORGANISM: E. coli

<400> SEQUENCE: 26

```
Met Leu Asp Pro Asn Leu Leu Arg Asn Glu Pro Asp Ala Val Ala Glu
1               5                   10                  15

Lys Leu Ala Arg Arg Gly Phe Lys Leu Asp Val Asp Lys Leu Gly Ala
            20                  25                  30

Leu Glu Glu Arg Arg Lys Val Leu Gln Val Lys Thr Glu Asn Leu Gln
        35                  40                  45

Ala Glu Arg Asn Ser Arg Ser Lys Ser Ile Gly Gln Ala Lys Ala Arg
    50                  55                  60

Gly Glu Asp Ile Glu Pro Leu Arg Leu Glu Val Asn Lys Leu Gly Glu
65                  70                  75                  80

Glu Leu Asp Ala Ala Lys Ala Glu Leu Asp Ala Leu Gln Ala Glu Ile
                85                  90                  95

Arg Asp Ile Ala Leu Thr Ile Pro Asn Leu Pro Ala Asp Glu Val Pro
            100                 105                 110

Val Gly Lys Asp Glu Asn Asp Asn Val Glu Val Ser Arg Trp Gly Thr
        115                 120                 125

Pro Arg Glu Phe Asp Phe Glu Val Arg Asp His Val Thr Leu Gly Glu
    130                 135                 140

Met His Ser Gly Leu Asp Phe Ala Ala Ala Val Lys Leu Thr Gly Ser
145                 150                 155                 160

Arg Phe Val Val Met Lys Gly Gln Ile Ala Arg Met His Arg Ala Leu
                165                 170                 175
```

```
Ser Gln Phe Met Leu Asp Leu His Thr Glu Gln His Gly Tyr Ser Glu
            180                 185                 190

Asn Tyr Val Pro Tyr Leu Val Asn Gln Asp Thr Leu Tyr Gly Thr Gly
            195                 200                 205

Gln Leu Pro Lys Phe Ala Gly Asp Leu Phe His Thr Arg Pro Leu Glu
        210                 215                 220

Glu Glu Ala Asp Thr Ser Asn Tyr Ala Leu Ile Pro Thr Ala Glu Val
225                 230                 235                 240

Pro Leu Thr Asn Leu Val Arg Gly Glu Ile Ile Asp Glu Asp Leu
                245                 250                 255

Pro Ile Lys Met Thr Ala His Thr Pro Cys Phe Arg Ser Glu Ala Gly
        260                 265                 270

Ser Tyr Gly Arg Asp Thr Arg Gly Leu Ile Arg Met His Gln Phe Asp
        275                 280                 285

Lys Val Glu Met Val Gln Ile Val Arg Pro Glu Asp Ser Met Ala Ala
        290                 295                 300

Leu Glu Glu Met Thr Gly His Ala Glu Lys Val Leu Gln Leu Leu Gly
305                 310                 315                 320

Leu Pro Tyr Arg Lys Ile Ile Leu Cys Thr Gly Asp Met Gly Phe Gly
                325                 330                 335

Ala Cys Lys Thr Tyr Asp Leu Glu Val Trp Ile Pro Ala Gln Asn Thr
            340                 345                 350

Tyr Arg Glu Ile Ser Ser Cys Ser Asn Val Trp Asp Phe Gln Ala Arg
        355                 360                 365

Arg Met Gln Ala Arg Cys Arg Ser Lys Ser Asp Lys Lys Thr Arg Leu
    370                 375                 380

Val His Thr Leu Asn Gly Ser Gly Leu Ala Val Gly Arg Thr Leu Val
385                 390                 395                 400

Ala Val Met Glu Asn Tyr Gln Gln Ala Asp Gly Arg Ile Glu Val Pro
                405                 410                 415

Glu Val Leu Arg Pro Tyr Met Asn Gly Leu Glu Tyr Ile Gly
            420                 425                 430

<210> SEQ ID NO 27
<211> LENGTH: 981
<212> TYPE: DNA
<213> ORGANISM: E. coli

<400> SEQUENCE: 27
atgtcacatc tcgcagaact ggttgccagt gcgaaggcgg ccattagcca ggcgtcagat      60
gttgccgcgt tagataatgt gcgcgtcgaa tatttgggta aaaagggca cttaacccctt    120 cagatgacga ccctgcgtga gctgccgcca aagagcgtc cggcagctgg tgcggttatc     180
aacgaagcga aagagcaggt tcagcaggcg ctgaatgcgc gtaaagcgga actggaaagc     240
gctgcactga tgcgcgtct ggcggcggaa acgattgatg tctctctgcc aggtcgtcgc     300
attgaaaacg gcggtctgca tccggttacc cgtaccatcg accgtatcga agtttcttc    360 ggtgagcttg gctttaccgt ggcaaccggg ccggaaatcg aagacgatta tcataacttc    420
gatgctctga acattcctgg tcaccacccg gcgcgcgctg accacgacac tttctggttt    480
gacactaccc gcctgctgcg tacccagacc tctggcgtac agatccgcac catgaaagcc    540
cagcagccac cgattcgtat catcgcgcct ggccgtgttt atcgtaacga ctacgaccag    600
actcacacgc cgatgttcca tcagatggaa ggtctgattg ttgataccaa catcagcttt    660
accaacctga aaggcacgct gcacgacttc ctgcgtaact tctttgagga agatttgcag    720
```

```
attcgcttcc gtccttccta cttcccgttt accgaacctt ctgcagaagt ggacgtcatg    780
ggtaaaaacg gtaaatggct ggaagtgctg ggctgcggga tggtgcatcc gaacgtgttg    840
cgtaacgttg gcatcgaccc ggaagtttac tctggtttcg ccttcgggat ggggatggag    900
cgtctgacta tgttgcgtta cggcgtcacc gacctgcgtt cattcttcga aaacgatctg    960
cgtttcctca aacagtttaa a                                              981
```

<210> SEQ ID NO 28
<211> LENGTH: 327
<212> TYPE: PRT
<213> ORGANISM: E. coli

<400> SEQUENCE: 28

```
Met Ser His Leu Ala Glu Leu Val Ala Ser Lys Ala Ala Ile Ser
1               5                   10                  15

Gln Ala Ser Asp Val Ala Ala Leu Asp Asn Val Arg Val Glu Tyr Leu
                20                  25                  30

Gly Lys Lys Gly His Leu Thr Leu Gln Met Thr Thr Leu Arg Glu Leu
            35                  40                  45

Pro Pro Glu Glu Arg Pro Ala Ala Gly Ala Val Ile Asn Glu Ala Lys
        50                  55                  60

Glu Gln Val Gln Gln Ala Leu Asn Ala Arg Lys Ala Glu Leu Glu Ser
65                  70                  75                  80

Ala Ala Leu Asn Ala Arg Leu Ala Ala Glu Thr Ile Asp Val Ser Leu
                85                  90                  95

Pro Gly Arg Arg Ile Glu Asn Gly Gly Leu His Pro Val Thr Arg Thr
            100                 105                 110

Ile Asp Arg Ile Glu Ser Phe Phe Gly Glu Leu Gly Phe Thr Val Ala
        115                 120                 125

Thr Gly Pro Glu Ile Glu Asp Asp Tyr His Asn Phe Asp Ala Leu Asn
    130                 135                 140

Ile Pro Gly His His Pro Ala Arg Ala Asp His Asp Thr Phe Trp Phe
145                 150                 155                 160

Asp Thr Thr Arg Leu Leu Arg Thr Gln Thr Ser Gly Val Gln Ile Arg
                165                 170                 175

Thr Met Lys Ala Gln Gln Pro Pro Ile Arg Ile Ile Ala Pro Gly Arg
            180                 185                 190

Val Tyr Arg Asn Asp Tyr Asp Gln Thr His Thr Pro Met Phe His Gln
        195                 200                 205

Met Glu Gly Leu Ile Val Asp Thr Asn Ile Ser Phe Thr Asn Leu Lys
    210                 215                 220

Gly Thr Leu His Asp Phe Leu Arg Asn Phe Phe Glu Glu Asp Leu Gln
225                 230                 235                 240

Ile Arg Phe Arg Pro Ser Tyr Phe Pro Phe Thr Glu Pro Ser Ala Glu
                245                 250                 255

Val Asp Val Met Gly Lys Asn Gly Lys Trp Leu Glu Val Leu Gly Cys
            260                 265                 270

Gly Met Val His Pro Asn Val Leu Arg Asn Val Gly Ile Asp Pro Glu
        275                 280                 285

Val Tyr Ser Gly Phe Ala Phe Gly Met Gly Met Glu Arg Leu Thr Met
    290                 295                 300

Leu Arg Tyr Gly Val Thr Asp Leu Arg Ser Phe Phe Glu Asn Asp Leu
305                 310                 315                 320
```

```
Arg Phe Leu Lys Gln Phe Lys
            325

<210> SEQ ID NO 29
<211> LENGTH: 642
<212> TYPE: PRT
<213> ORGANISM: E. coli

<400> SEQUENCE: 29

Met Pro Val Ile Thr Leu Pro Asp Gly Ser Gln Arg His Tyr Asp His
1               5                   10                  15

Ala Val Ser Pro Met Asp Val Ala Leu Asp Ile Gly Pro Gly Leu Ala
            20                  25                  30

Lys Ala Cys Ile Ala Gly Arg Val Asn Gly Glu Leu Val Asp Ala Cys
        35                  40                  45

Asp Leu Ile Glu Asn Asp Ala Gln Leu Ser Ile Ile Thr Ala Lys Asp
    50                  55                  60

Glu Glu Gly Leu Glu Ile Ile Arg His Ser Cys Ala His Leu Leu Gly
65                  70                  75                  80

His Ala Ile Lys Gln Leu Trp Pro His Thr Lys Met Ala Ile Gly Pro
                85                  90                  95

Val Ile Asp Asn Gly Phe Tyr Tyr Asp Val Asp Leu Asp Arg Thr Leu
            100                 105                 110

Thr Gln Glu Asp Val Glu Ala Leu Glu Lys Arg Met His Glu Leu Ala
        115                 120                 125

Glu Lys Asn Tyr Asp Val Ile Lys Lys Lys Val Ser Trp His Glu Ala
    130                 135                 140

Arg Glu Thr Phe Ala Asn Arg Gly Glu Ser Tyr Lys Val Ser Ile Leu
145                 150                 155                 160

Asp Glu Asn Ile Ala His Asp Asp Lys Pro Gly Leu Tyr Phe His Glu
                165                 170                 175

Glu Tyr Val Asp Met Cys Arg Gly Pro His Val Pro Asn Met Arg Phe
            180                 185                 190

Cys His His Phe Lys Leu Met Lys Thr Ala Gly Ala Tyr Trp Arg Gly
        195                 200                 205

Asp Ser Asn Asn Lys Met Leu Gln Arg Ile Tyr Gly Thr Ala Trp Ala
    210                 215                 220

Asp Lys Lys Ala Leu Asn Ala Tyr Leu Gln Arg Leu Glu Glu Ala Ala
225                 230                 235                 240

Lys Arg Asp His Arg Lys Ile Gly Lys Gln Leu Asp Leu Tyr His Met
                245                 250                 255

Gln Glu Glu Ala Pro Gly Met Val Phe Trp His Asn Asp Gly Trp Thr
            260                 265                 270

Ile Phe Arg Glu Leu Glu Val Phe Val Arg Ser Lys Leu Lys Glu Tyr
        275                 280                 285

Gln Tyr Gln Glu Val Lys Gly Pro Phe Met Met Asp Arg Val Leu Trp
    290                 295                 300

Glu Lys Thr Gly His Trp Asp Asn Tyr Lys Asp Ala Met Phe Thr Thr
305                 310                 315                 320

Ser Ser Glu Asn Arg Glu Tyr Cys Ile Lys Pro Met Asn Cys Pro Gly
                325                 330                 335

His Val Gln Ile Phe Asn Gln Gly Leu Lys Ser Tyr Arg Asp Leu Pro
            340                 345                 350

Leu Arg Met Ala Glu Phe Gly Ser Cys His Arg Asn Glu Pro Ser Gly
        355                 360                 365
```

Ser Leu His Gly Leu Met Arg Val Arg Gly Phe Thr Gln Asp Asp Ala
        370                 375                 380

His Ile Phe Cys Thr Glu Glu Gln Ile Arg Asp Glu Val Asn Gly Cys
385                 390                 395                 400

Ile Arg Leu Val Tyr Asp Met Tyr Ser Thr Phe Gly Phe Glu Lys Ile
                405                 410                 415

Val Val Lys Leu Ser Thr Arg Pro Glu Lys Arg Ile Gly Ser Asp Glu
            420                 425                 430

Met Trp Asp Arg Ala Glu Ala Asp Leu Ala Val Ala Leu Glu Glu Asn
            435                 440                 445

Asn Ile Pro Phe Glu Tyr Gln Leu Gly Glu Gly Ala Phe Tyr Gly Pro
    450                 455                 460

Lys Ile Glu Phe Thr Leu Tyr Asp Cys Leu Asp Arg Ala Trp Gln Cys
465                 470                 475                 480

Gly Thr Val Gln Leu Asp Phe Ser Leu Pro Ser Arg Leu Ser Ala Ser
                485                 490                 495

Tyr Val Gly Glu Asp Asn Glu Arg Lys Val Pro Val Met Ile His Arg
            500                 505                 510

Ala Ile Leu Gly Ser Met Glu Arg Phe Ile Gly Ile Leu Thr Glu Glu
        515                 520                 525

Phe Ala Gly Phe Phe Pro Thr Trp Leu Ala Pro Val Gln Val Val Ile
    530                 535                 540

Met Asn Ile Thr Asp Ser Gln Ser Glu Tyr Val Asn Glu Leu Thr Gln
545                 550                 555                 560

Lys Leu Ser Asn Ala Gly Ile Arg Val Lys Ala Asp Leu Arg Asn Glu
                565                 570                 575

Lys Ile Gly Phe Lys Ile Arg Glu His Thr Leu Arg Arg Val Pro Tyr
            580                 585                 590

Met Leu Val Cys Gly Asp Lys Glu Val Glu Ser Gly Lys Val Ala Val
        595                 600                 605

Arg Thr Arg Arg Gly Lys Asp Leu Gly Ser Met Asp Val Asn Glu Val
    610                 615                 620

Ile Glu Lys Leu Gln Gln Glu Ile Arg Ser Arg Ser Leu Lys Gln Leu
625                 630                 635                 640

Glu Glu

<210> SEQ ID NO 30
<211> LENGTH: 41
<212> TYPE: DNA
<213> ORGANISM: Artificial
<220> FEATURE:
<223> OTHER INFORMATION: artificially synthesized sequence

<400> SEQUENCE: 30
gcctgctgcg tacccagacc gcgggcgtac agatccgcac c          41

<210> SEQ ID NO 31
<211> LENGTH: 41
<212> TYPE: DNA
<213> ORGANISM: Artificial
<220> FEATURE:
<223> OTHER INFORMATION: artificially synthesized sequence

<400> SEQUENCE: 31
gcctgctgcg tacccagacc ggcggcgtac agatccgcac c          41

```
<210> SEQ ID NO 32
<211> LENGTH: 42
<212> TYPE: DNA
<213> ORGANISM: Artificial
<220> FEATURE:
<223> OTHER INFORMATION: artificially synthesized sequence

<400> SEQUENCE: 32
ctacccgcct gctgcgtacc gcgacctctg gcgtacagat cc          42

<210> SEQ ID NO 33
<211> LENGTH: 42
<212> TYPE: DNA
<213> ORGANISM: Artificial
<220> FEATURE:
<223> OTHER INFORMATION: artificially synthesized sequence

<400> SEQUENCE: 33
ctacccgcct gctgcgtacc ggcacctctg gcgtacagat cc          42

<210> SEQ ID NO 34
<211> LENGTH: 41
<212> TYPE: DNA
<213> ORGANISM: Artificial
<220> FEATURE:
<223> OTHER INFORMATION: artificially synthesized sequence

<400> SEQUENCE: 34
ggtgcggatc tgtacgcccg cggtctgggt acgcagcagg c           41

<210> SEQ ID NO 35
<211> LENGTH: 41
<212> TYPE: DNA
<213> ORGANISM: Artificial
<220> FEATURE:
<223> OTHER INFORMATION: artificially synthesized sequence

<400> SEQUENCE: 35
ggtgcggatc tgtacgccgc cggtctgggt acgcagcagg c           41

<210> SEQ ID NO 36
<211> LENGTH: 42
<212> TYPE: DNA
<213> ORGANISM: Artificial
<220> FEATURE:
<223> OTHER INFORMATION: artificially synthesized sequence

<400> SEQUENCE: 36
ggatctgtac gccagaggtc gcggtacgca gcaggcgggt ag          42

<210> SEQ ID NO 37
<211> LENGTH: 42
<212> TYPE: DNA
<213> ORGANISM: Artificial
<220> FEATURE:
<223> OTHER INFORMATION: artificially synthesized sequence

<400> SEQUENCE: 37
ggatctgtac gccagaggtg ccggtacgca gcaggcgggt ag          42

<210> SEQ ID NO 38
<211> LENGTH: 97
<212> TYPE: DNA
<213> ORGANISM: Artificial
<220> FEATURE:
<223> OTHER INFORMATION: artificially synthesized sequence
```

<400> SEQUENCE: 38
ggcgtaatac gactcactat agcccggata gctcagtcgg tagagcaggg gattgaaaat    60
ccccgtgtcc ttggttcgat tccgagtccg ggcacca                             97

<210> SEQ ID NO 39
<211> LENGTH: 76
<212> TYPE: RNA
<213> ORGANISM: Artificial
<220> FEATURE:
<223> OTHER INFORMATION: artificially synthesized sequence

<400> SEQUENCE: 39
gcccggauag cucagucggu agagcagggg auugaaaauc cccguguccu ugguucgauu    60
ccgaguccgg gcacca                                                    76

<210> SEQ ID NO 40
<211> LENGTH: 92
<212> TYPE: DNA
<213> ORGANISM: Artificial
<220> FEATURE:
<223> OTHER INFORMATION: artificially synthesized sequence

<400> SEQUENCE: 40
ggcgtaatac gactcactat agggttaact ttaacaagga gaaaaacatg cgtttccgtg    60
actacaagga cgacgacgac aagtaagctt cg                                  92

<210> SEQ ID NO 41
<211> LENGTH: 71
<212> TYPE: RNA
<213> ORGANISM: Artificial
<220> FEATURE:
<223> OTHER INFORMATION: artificially synthesized sequence

<400> SEQUENCE: 41
ggguuaacuu uaacaaggag aaaaacaugc guuccguga cuacaaggac gacgacgaca    60
aguaagcuuc g                                                         71

<210> SEQ ID NO 42
<211> LENGTH: 12
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (3)..(3)
<223> OTHER INFORMATION: Xaa is phenylalanine or methyl phenylalanine

<400> SEQUENCE: 42

Met Arg Xaa Arg Asp Tyr Lys Asp Asp Asp Asp Lys
1               5                   10

<210> SEQ ID NO 43
<211> LENGTH: 49
<212> TYPE: DNA
<213> ORGANISM: Artificial
<220> FEATURE:
<223> OTHER INFORMATION: artificially synthesized sequence

<400> SEQUENCE: 43
gtttctgcat catgatcccg gctccgaacg tcaccggcag tttgcatat               49

<210> SEQ ID NO 44

<211> LENGTH: 49
<212> TYPE: DNA
<213> ORGANISM: Artificial
<220> FEATURE:
<223> OTHER INFORMATION: artificially synthesized sequence

<400> SEQUENCE: 44
gtttctgcat catgatcccg ggtccgaacg tcaccggcag tttgcatat         49

<210> SEQ ID NO 45
<211> LENGTH: 49
<212> TYPE: DNA
<213> ORGANISM: Artificial
<220> FEATURE:
<223> OTHER INFORMATION: artificially synthesized sequence

<400> SEQUENCE: 45
gtttctgcat catgatcccg ccgccggctg tcaccggcag tttgcatat         49

<210> SEQ ID NO 46
<211> LENGTH: 49
<212> TYPE: DNA
<213> ORGANISM: Artificial
<220> FEATURE:
<223> OTHER INFORMATION: artificially synthesized sequence

<400> SEQUENCE: 46
gtttctgcat catgatcccg gctccggctg tcaccggcag tttgcatat         49

<210> SEQ ID NO 47
<211> LENGTH: 49
<212> TYPE: DNA
<213> ORGANISM: Artificial
<220> FEATURE:
<223> OTHER INFORMATION: artificially synthesized sequence

<400> SEQUENCE: 47
gtttctgcat catgatcccg ggtccggctg tcaccggcag tttgcatat         49

<210> SEQ ID NO 48
<211> LENGTH: 49
<212> TYPE: DNA
<213> ORGANISM: Artificial
<220> FEATURE:
<223> OTHER INFORMATION: artificially synthesized sequence

<400> SEQUENCE: 48
gtttctgcat catgatcccg ccgccgagtg tcaccggcag tttgcatat         49

<210> SEQ ID NO 49
<211> LENGTH: 49
<212> TYPE: DNA
<213> ORGANISM: Artificial
<220> FEATURE:
<223> OTHER INFORMATION: artificially synthesized sequence

<400> SEQUENCE: 49
gtttctgcat catgatcccg gctccgagtg tcaccggcag tttgcatat         49

<210> SEQ ID NO 50
<211> LENGTH: 49
<212> TYPE: DNA
<213> ORGANISM: Artificial
<220> FEATURE:
<223> OTHER INFORMATION: artificially synthesized sequence

<400> SEQUENCE: 50
gtttctgcat catgatcccg ggtccgagtg tcaccggcag tttgcatat            49

<210> SEQ ID NO 51
<211> LENGTH: 49
<212> TYPE: DNA
<213> ORGANISM: Artificial
<220> FEATURE:
<223> OTHER INFORMATION: artificially synthesized sequence

<400> SEQUENCE: 51
gtttctgcat catgatcccg ccgccggtag tcaccggcag tttgcatat            49

<210> SEQ ID NO 52
<211> LENGTH: 49
<212> TYPE: DNA
<213> ORGANISM: Artificial
<220> FEATURE:
<223> OTHER INFORMATION: artificially synthesized sequence

<400> SEQUENCE: 52
gtttctgcat catgatcccg gctccggtag tcaccggcag tttgcatat            49

<210> SEQ ID NO 53
<211> LENGTH: 49
<212> TYPE: DNA
<213> ORGANISM: Artificial
<220> FEATURE:
<223> OTHER INFORMATION: artificially synthesized sequence

<400> SEQUENCE: 53
gtttctgcat catgatcccg ggtccggtag tcaccggcag tttgcatat            49

<210> SEQ ID NO 54
<211> LENGTH: 49
<212> TYPE: DNA
<213> ORGANISM: Artificial
<220> FEATURE:
<223> OTHER INFORMATION: artificially synthesized sequence

<400> SEQUENCE: 54
gtttctgcat catgatcccg ccgccgggtg tcaccggcag tttgcatat            49

<210> SEQ ID NO 55
<211> LENGTH: 49
<212> TYPE: DNA
<213> ORGANISM: Artificial
<220> FEATURE:
<223> OTHER INFORMATION: artificially synthesized sequence

<400> SEQUENCE: 55
gtttctgcat catgatcccg gctccgggtg tcaccggcag tttgcatat            49

<210> SEQ ID NO 56
<211> LENGTH: 49
<212> TYPE: DNA
<213> ORGANISM: Artificial
<220> FEATURE:
<223> OTHER INFORMATION: artificially synthesized sequence

<400> SEQUENCE: 56
gtttctgcat catgatcccg ggtccgggtg tcaccggcag tttgcatat            49

<210> SEQ ID NO 57
<211> LENGTH: 49
<212> TYPE: DNA

<213> ORGANISM: Artificial
<220> FEATURE:
<223> OTHER INFORMATION: artificially synthesized sequence

<400> SEQUENCE: 57
gtttctgcat catgatcccg ccgccggatg tcaccggcag tttgcatat        49

<210> SEQ ID NO 58
<211> LENGTH: 49
<212> TYPE: DNA
<213> ORGANISM: Artificial
<220> FEATURE:
<223> OTHER INFORMATION: artificially synthesized sequence

<400> SEQUENCE: 58
gtttctgcat catgatcccg gctccggatg tcaccggcag tttgcatat        49

<210> SEQ ID NO 59
<211> LENGTH: 49
<212> TYPE: DNA
<213> ORGANISM: Artificial
<220> FEATURE:
<223> OTHER INFORMATION: artificially synthesized sequence

<400> SEQUENCE: 59
gtttctgcat catgatcccg ggtccggatg tcaccggcag tttgcatat        49

<210> SEQ ID NO 60
<211> LENGTH: 33
<212> TYPE: DNA
<213> ORGANISM: Artificial
<220> FEATURE:
<223> OTHER INFORMATION: artificially synthesized sequence

<400> SEQUENCE: 60
tggcaggtcg gtactgctca cgccgggatc gct        33

<210> SEQ ID NO 61
<211> LENGTH: 33
<212> TYPE: DNA
<213> ORGANISM: Artificial
<220> FEATURE:
<223> OTHER INFORMATION: artificially synthesized sequence

<400> SEQUENCE: 61
tggcaggtcg gtactagtca cgccgggatc gct        33

<210> SEQ ID NO 62
<211> LENGTH: 33
<212> TYPE: DNA
<213> ORGANISM: Artificial
<220> FEATURE:
<223> OTHER INFORMATION: artificially synthesized sequence

<400> SEQUENCE: 62
tggcaggtcg gtactgtaca cgccgggatc gct        33

<210> SEQ ID NO 63
<211> LENGTH: 33
<212> TYPE: DNA
<213> ORGANISM: Artificial
<220> FEATURE:
<223> OTHER INFORMATION: artificially synthesized sequence

<400> SEQUENCE: 63
tggcaggtcg gtactggtca cgccgggatc gct        33

-continued

<210> SEQ ID NO 64
<211> LENGTH: 43
<212> TYPE: DNA
<213> ORGANISM: Artificial
<220> FEATURE:
<223> OTHER INFORMATION: artificially synthesized sequence

<400> SEQUENCE: 64
gtactgacca cgccgggatc tatacccaga tggtcgttga gcg    43

<210> SEQ ID NO 65
<211> LENGTH: 43
<212> TYPE: DNA
<213> ORGANISM: Artificial
<220> FEATURE:
<223> OTHER INFORMATION: artificially synthesized sequence

<400> SEQUENCE: 65
gtactgacca cgccgggatc tggacccaga tggtcgttga gcg    43

<210> SEQ ID NO 66
<211> LENGTH: 43
<212> TYPE: DNA
<213> ORGANISM: Artificial
<220> FEATURE:
<223> OTHER INFORMATION: artificially synthesized sequence

<400> SEQUENCE: 66
gtactgacca cgccgggatc tcaacccaga tggtcgttga gcg    43

<210> SEQ ID NO 67
<211> LENGTH: 43
<212> TYPE: DNA
<213> ORGANISM: Artificial
<220> FEATURE:
<223> OTHER INFORMATION: artificially synthesized sequence

<400> SEQUENCE: 67
gtactgacca cgccgggatc atgacccaga tggtcgttga gcg    43

<210> SEQ ID NO 68
<211> LENGTH: 43
<212> TYPE: DNA
<213> ORGANISM: Artificial
<220> FEATURE:
<223> OTHER INFORMATION: artificially synthesized sequence

<400> SEQUENCE: 68
gtactgacca cgccgggatc aaaacccaga tggtcgttga gcg    43

<210> SEQ ID NO 69
<211> LENGTH: 43
<212> TYPE: DNA
<213> ORGANISM: Artificial
<220> FEATURE:
<223> OTHER INFORMATION: artificially synthesized sequence

<400> SEQUENCE: 69
gtactgacca cgccgggatc aacacccaga tggtcgttga gcg    43

<210> SEQ ID NO 70
<211> LENGTH: 43
<212> TYPE: DNA
<213> ORGANISM: Artificial
<220> FEATURE:

<223> OTHER INFORMATION: artificially synthesized sequence

<400> SEQUENCE: 70
gtactgacca cgccgggatc gtgacccaga tggtcgttga gcg        43

<210> SEQ ID NO 71
<211> LENGTH: 43
<212> TYPE: DNA
<213> ORGANISM: Artificial
<220> FEATURE:
<223> OTHER INFORMATION: artificially synthesized sequence

<400> SEQUENCE: 71
gtactgacca cgccgggatc ctgacccaga tggtcgttga gcg        43

<210> SEQ ID NO 72
<211> LENGTH: 43
<212> TYPE: DNA
<213> ORGANISM: Artificial
<220> FEATURE:
<223> OTHER INFORMATION: artificially synthesized sequence

<400> SEQUENCE: 72
gatcccgccg ccgggtgtct atggcagttt gcatatgggt cac        43

<210> SEQ ID NO 73
<211> LENGTH: 43
<212> TYPE: DNA
<213> ORGANISM: Artificial
<220> FEATURE:
<223> OTHER INFORMATION: artificially synthesized sequence

<400> SEQUENCE: 73
gatcccgccg ccgggtgtct ggggcagttt gcatatgggt cac        43

<210> SEQ ID NO 74
<211> LENGTH: 43
<212> TYPE: DNA
<213> ORGANISM: Artificial
<220> FEATURE:
<223> OTHER INFORMATION: artificially synthesized sequence

<400> SEQUENCE: 74
gatcccgccg ccgggtgtct caggcagttt gcatatgggt cac        43

<210> SEQ ID NO 75
<211> LENGTH: 43
<212> TYPE: DNA
<213> ORGANISM: Artificial
<220> FEATURE:
<223> OTHER INFORMATION: artificially synthesized sequence

<400> SEQUENCE: 75
gatcccgccg ccgggtgtca tgggcagttt gcatatgggt cac        43

<210> SEQ ID NO 76
<211> LENGTH: 43
<212> TYPE: DNA
<213> ORGANISM: Artificial
<220> FEATURE:
<223> OTHER INFORMATION: artificially synthesized sequence

<400> SEQUENCE: 76
gatcccgccg ccgggtgtca aaggcagttt gcatatgggt cac        43

```
<210> SEQ ID NO 77
<211> LENGTH: 43
<212> TYPE: DNA
<213> ORGANISM: Artificial
<220> FEATURE:
<223> OTHER INFORMATION: artificially synthesized sequence

<400> SEQUENCE: 77
gatcccgccg ccgggtgtca acggcagttt gcatatgggt cac        43

<210> SEQ ID NO 78
<211> LENGTH: 43
<212> TYPE: DNA
<213> ORGANISM: Artificial
<220> FEATURE:
<223> OTHER INFORMATION: artificially synthesized sequence

<400> SEQUENCE: 78
gatcccgccg ccgggtgtcg tgggcagttt gcatatgggt cac        43

<210> SEQ ID NO 79
<211> LENGTH: 43
<212> TYPE: DNA
<213> ORGANISM: Artificial
<220> FEATURE:
<223> OTHER INFORMATION: artificially synthesized sequence

<400> SEQUENCE: 79
gatcccgccg ccgggtgtcc tgggcagttt gcatatgggt cac        43

<210> SEQ ID NO 80
<211> LENGTH: 49
<212> TYPE: DNA
<213> ORGANISM: Artificial
<220> FEATURE:
<223> OTHER INFORMATION: artificially synthesized sequence

<400> SEQUENCE: 80
atatgcaaac tgccggtgac gttcggagcc gggatcatga tgcagaaac        49

<210> SEQ ID NO 81
<211> LENGTH: 49
<212> TYPE: DNA
<213> ORGANISM: Artificial
<220> FEATURE:
<223> OTHER INFORMATION: artificially synthesized sequence

<400> SEQUENCE: 81
atatgcaaac tgccggtgac gttcggaccc gggatcatga tgcagaaac        49

<210> SEQ ID NO 82
<211> LENGTH: 49
<212> TYPE: DNA
<213> ORGANISM: Artificial
<220> FEATURE:
<223> OTHER INFORMATION: artificially synthesized sequence

<400> SEQUENCE: 82
atatgcaaac tgccggtgac agccggcggc gggatcatga tgcagaaac        49

<210> SEQ ID NO 83
<211> LENGTH: 49
<212> TYPE: DNA
<213> ORGANISM: Artificial
<220> FEATURE:
<223> OTHER INFORMATION: artificially synthesized sequence
```

-continued

<400> SEQUENCE: 83
atatgcaaac tgccggtgac agccggagcc gggatcatga tgcagaaac           49

<210> SEQ ID NO 84
<211> LENGTH: 49
<212> TYPE: DNA
<213> ORGANISM: Artificial
<220> FEATURE:
<223> OTHER INFORMATION: artificially synthesized sequence

<400> SEQUENCE: 84
atatgcaaac tgccggtgac agccggaccc gggatcatga tgcagaaac           49

<210> SEQ ID NO 85
<211> LENGTH: 49
<212> TYPE: DNA
<213> ORGANISM: Artificial
<220> FEATURE:
<223> OTHER INFORMATION: artificially synthesized sequence

<400> SEQUENCE: 85
atatgcaaac tgccggtgac actcggcggc gggatcatga tgcagaaac           49

<210> SEQ ID NO 86
<211> LENGTH: 49
<212> TYPE: DNA
<213> ORGANISM: Artificial
<220> FEATURE:
<223> OTHER INFORMATION: artificially synthesized sequence

<400> SEQUENCE: 86
atatgcaaac tgccggtgac actcggagcc gggatcatga tgcagaaac           49

<210> SEQ ID NO 87
<211> LENGTH: 49
<212> TYPE: DNA
<213> ORGANISM: Artificial
<220> FEATURE:
<223> OTHER INFORMATION: artificially synthesized sequence

<400> SEQUENCE: 87
atatgcaaac tgccggtgac actcggaccc gggatcatga tgcagaaac           49

<210> SEQ ID NO 88
<211> LENGTH: 49
<212> TYPE: DNA
<213> ORGANISM: Artificial
<220> FEATURE:
<223> OTHER INFORMATION: artificially synthesized sequence

<400> SEQUENCE: 88
atatgcaaac tgccggtgac taccggcggc gggatcatga tgcagaaac           49

<210> SEQ ID NO 89
<211> LENGTH: 49
<212> TYPE: DNA
<213> ORGANISM: Artificial
<220> FEATURE:
<223> OTHER INFORMATION: artificially synthesized sequence

<400> SEQUENCE: 89
atatgcaaac tgccggtgac taccggagcc gggatcatga tgcagaaac           49

<210> SEQ ID NO 90
<211> LENGTH: 49

```
<212> TYPE: DNA
<213> ORGANISM: Artificial
<220> FEATURE:
<223> OTHER INFORMATION: artificially synthesized sequence

<400> SEQUENCE: 90
atatgcaaac tgccggtgac taccggaccc gggatcatga tgcagaaac        49

<210> SEQ ID NO 91
<211> LENGTH: 49
<212> TYPE: DNA
<213> ORGANISM: Artificial
<220> FEATURE:
<223> OTHER INFORMATION: artificially synthesized sequence

<400> SEQUENCE: 91
atatgcaaac tgccggtgac acccggcggc gggatcatga tgcagaaac        49

<210> SEQ ID NO 92
<211> LENGTH: 49
<212> TYPE: DNA
<213> ORGANISM: Artificial
<220> FEATURE:
<223> OTHER INFORMATION: artificially synthesized sequence

<400> SEQUENCE: 92
atatgcaaac tgccggtgac acccggagcc gggatcatga tgcagaaac        49

<210> SEQ ID NO 93
<211> LENGTH: 49
<212> TYPE: DNA
<213> ORGANISM: Artificial
<220> FEATURE:
<223> OTHER INFORMATION: artificially synthesized sequence

<400> SEQUENCE: 93
atatgcaaac tgccggtgac acccggaccc gggatcatga tgcagaaac        49

<210> SEQ ID NO 94
<211> LENGTH: 49
<212> TYPE: DNA
<213> ORGANISM: Artificial
<220> FEATURE:
<223> OTHER INFORMATION: artificially synthesized sequence

<400> SEQUENCE: 94
atatgcaaac tgccggtgac atccggcggc gggatcatga tgcagaaac        49

<210> SEQ ID NO 95
<211> LENGTH: 49
<212> TYPE: DNA
<213> ORGANISM: Artificial
<220> FEATURE:
<223> OTHER INFORMATION: artificially synthesized sequence

<400> SEQUENCE: 95
atatgcaaac tgccggtgac atccggagcc gggatcatga tgcagaaac        49

<210> SEQ ID NO 96
<211> LENGTH: 49
<212> TYPE: DNA
<213> ORGANISM: Artificial
<220> FEATURE:
<223> OTHER INFORMATION: artificially synthesized sequence

<400> SEQUENCE: 96
```

-continued

```
atatgcaaac tgccggtgac atccggaccc gggatcatga tgcagaaac          49

<210> SEQ ID NO 97
<211> LENGTH: 33
<212> TYPE: DNA
<213> ORGANISM: Artificial
<220> FEATURE:
<223> OTHER INFORMATION: artificially synthesized sequence

<400> SEQUENCE: 97
agcgatcccg gcgtgagcag taccgacctg cca                           33

<210> SEQ ID NO 98
<211> LENGTH: 33
<212> TYPE: DNA
<213> ORGANISM: Artificial
<220> FEATURE:
<223> OTHER INFORMATION: artificially synthesized sequence

<400> SEQUENCE: 98
agcgatcccg gcgtgactag taccgacctg cca                           33

<210> SEQ ID NO 99
<211> LENGTH: 33
<212> TYPE: DNA
<213> ORGANISM: Artificial
<220> FEATURE:
<223> OTHER INFORMATION: artificially synthesized sequence

<400> SEQUENCE: 99
agcgatcccg gcgtgtacag taccgacctg cca                           33

<210> SEQ ID NO 100
<211> LENGTH: 33
<212> TYPE: DNA
<213> ORGANISM: Artificial
<220> FEATURE:
<223> OTHER INFORMATION: artificially synthesized sequence

<400> SEQUENCE: 100
agcgatcccg gcgtgaccag taccgacctg cca                           33

<210> SEQ ID NO 101
<211> LENGTH: 43
<212> TYPE: DNA
<213> ORGANISM: Artificial
<220> FEATURE:
<223> OTHER INFORMATION: artificially synthesized sequence

<400> SEQUENCE: 101
cgctcaacga ccatctgggt atagatcccg gcgtggtcag tac                43

<210> SEQ ID NO 102
<211> LENGTH: 43
<212> TYPE: DNA
<213> ORGANISM: Artificial
<220> FEATURE:
<223> OTHER INFORMATION: artificially synthesized sequence

<400> SEQUENCE: 102
cgctcaacga ccatctgggt ccagatcccg gcgtggtcag tac                43

<210> SEQ ID NO 103
<211> LENGTH: 43
<212> TYPE: DNA
<213> ORGANISM: Artificial
```

```
<220> FEATURE:
<223> OTHER INFORMATION: artificially synthesized sequence

<400> SEQUENCE: 103
cgctcaacga ccatctgggt tgagatcccg gcgtggtcag tac          43

<210> SEQ ID NO 104
<211> LENGTH: 43
<212> TYPE: DNA
<213> ORGANISM: Artificial
<220> FEATURE:
<223> OTHER INFORMATION: artificially synthesized sequence

<400> SEQUENCE: 104
cgctcaacga ccatctgggt catgatcccg gcgtggtcag tac          43

<210> SEQ ID NO 105
<211> LENGTH: 43
<212> TYPE: DNA
<213> ORGANISM: Artificial
<220> FEATURE:
<223> OTHER INFORMATION: artificially synthesized sequence

<400> SEQUENCE: 105
cgctcaacga ccatctgggt tttgatcccg gcgtggtcag tac          43

<210> SEQ ID NO 106
<211> LENGTH: 43
<212> TYPE: DNA
<213> ORGANISM: Artificial
<220> FEATURE:
<223> OTHER INFORMATION: artificially synthesized sequence

<400> SEQUENCE: 106
cgctcaacga ccatctgggt gttgatcccg gcgtggtcag tac          43

<210> SEQ ID NO 107
<211> LENGTH: 43
<212> TYPE: DNA
<213> ORGANISM: Artificial
<220> FEATURE:
<223> OTHER INFORMATION: artificially synthesized sequence

<400> SEQUENCE: 107
cgctcaacga ccatctgggt cacgatcccg gcgtggtcag tac          43

<210> SEQ ID NO 108
<211> LENGTH: 43
<212> TYPE: DNA
<213> ORGANISM: Artificial
<220> FEATURE:
<223> OTHER INFORMATION: artificially synthesized sequence

<400> SEQUENCE: 108
cgctcaacga ccatctgggt caggatcccg gcgtggtcag tac          43

<210> SEQ ID NO 109
<211> LENGTH: 43
<212> TYPE: DNA
<213> ORGANISM: Artificial
<220> FEATURE:
<223> OTHER INFORMATION: artificially synthesized sequence

<400> SEQUENCE: 109
gtgacccata tgcaaactgc catagacacc cggcggcggg atc          43
```

<210> SEQ ID NO 110
<211> LENGTH: 43
<212> TYPE: DNA
<213> ORGANISM: Artificial
<220> FEATURE:
<223> OTHER INFORMATION: artificially synthesized sequence

<400> SEQUENCE: 110
gtgacccata tgcaaactgc cccagacacc cggcggcggg atc        43

<210> SEQ ID NO 111
<211> LENGTH: 43
<212> TYPE: DNA
<213> ORGANISM: Artificial
<220> FEATURE:
<223> OTHER INFORMATION: artificially synthesized sequence

<400> SEQUENCE: 111
gtgacccata tgcaaactgc ctgagacacc cggcggcggg atc        43

<210> SEQ ID NO 112
<211> LENGTH: 43
<212> TYPE: DNA
<213> ORGANISM: Artificial
<220> FEATURE:
<223> OTHER INFORMATION: artificially synthesized sequence

<400> SEQUENCE: 112
gtgacccata tgcaaactgc ccatgacacc cggcggcggg atc        43

<210> SEQ ID NO 113
<211> LENGTH: 43
<212> TYPE: DNA
<213> ORGANISM: Artificial
<220> FEATURE:
<223> OTHER INFORMATION: artificially synthesized sequence

<400> SEQUENCE: 113
gtgacccata tgcaaactgc ctttgacacc cggcggcggg atc        43

<210> SEQ ID NO 114
<211> LENGTH: 43
<212> TYPE: DNA
<213> ORGANISM: Artificial
<220> FEATURE:
<223> OTHER INFORMATION: artificially synthesized sequence

<400> SEQUENCE: 114
gtgacccata tgcaaactgc cgttgacacc cggcggcggg atc        43

<210> SEQ ID NO 115
<211> LENGTH: 43
<212> TYPE: DNA
<213> ORGANISM: Artificial
<220> FEATURE:
<223> OTHER INFORMATION: artificially synthesized sequence

<400> SEQUENCE: 115
gtgacccata tgcaaactgc ccacgacacc cggcggcggg atc        43

<210> SEQ ID NO 116
<211> LENGTH: 43
<212> TYPE: DNA
<213> ORGANISM: Artificial
<220> FEATURE:
<223> OTHER INFORMATION: artificially synthesized sequence

```
<400> SEQUENCE: 116
gtgacccata tgcaaactgc ccaggacacc cggcggcggg atc                        43

<210> SEQ ID NO 117
<211> LENGTH: 98
<212> TYPE: DNA
<213> ORGANISM: Artificial
<220> FEATURE:
<223> OTHER INFORMATION: artificially synthesized sequence

<400> SEQUENCE: 117
ggcgtaatac gactcactat agcgtccgta gctcagttgg ttagagcacc accttgacat     60 ggtggggtc ggtggttcga gtccactcgg acgcacca                              98

<210> SEQ ID NO 118
<211> LENGTH: 77
<212> TYPE: RNA
<213> ORGANISM: Artificial
<220> FEATURE:
<223> OTHER INFORMATION: artificially synthesized sequence

<400> SEQUENCE: 118
gcguccguag cucaguuggu uagagcacca ccuugacaug gugggggucg gugguucgag     60
uccacucgga cgcacca                                                    77

<210> SEQ ID NO 119
<211> LENGTH: 92
<212> TYPE: DNA
<213> ORGANISM: Artificial
<220> FEATURE:
<223> OTHER INFORMATION: artificially synthesized sequence

<400> SEQUENCE: 119
ggcgtaatac gactcactat agggttaact ttaacaagga gaaaaacatg cgtgtccgtg     60
actacaagga cgacgacgac aagtaagctt cg                                   92

<210> SEQ ID NO 120
<211> LENGTH: 71
<212> TYPE: RNA
<213> ORGANISM: Artificial
<220> FEATURE:
<223> OTHER INFORMATION: artificially synthesized sequence

<400> SEQUENCE: 120
ggguuaacuu uaacaaggag aaaaacaugc guguccguga cuacaaggac gacgacgaca     60
aguaagcuuc g                                                          71

<210> SEQ ID NO 121
<211> LENGTH: 95
<212> TYPE: DNA
<213> ORGANISM: Artificial
<220> FEATURE:
<223> OTHER INFORMATION: artificially synthesized sequence

<400> SEQUENCE: 121
ggcgtaatac gactcactat agggttaact ttaacaagga gaaaaacatg cgtgtcgtcc     60
gtgactacaa ggacgacgac gacaagtaag cttcg                                95

<210> SEQ ID NO 122
<211> LENGTH: 74
<212> TYPE: RNA
```

```
<213> ORGANISM: Artificial
<220> FEATURE:
<223> OTHER INFORMATION: artificially synthesized sequence

<400> SEQUENCE: 122
ggguuaacuu uaacaaggag aaaaacaugc gugucguccg ugacuacaag gacgacgacg    60
acaaguaagc uucg                                                     74

<210> SEQ ID NO 123
<211> LENGTH: 98
<212> TYPE: DNA
<213> ORGANISM: Artificial
<220> FEATURE:
<223> OTHER INFORMATION: artificially synthesized sequence

<400> SEQUENCE: 123
ggcgtaatac gactcactat agggttaact ttaacaagga gaaaaacatg cgtgtcgtcg    60
tccgtgacta caaggacgac gacgacaagt aagcttcg                           98

<210> SEQ ID NO 124
<211> LENGTH: 77
<212> TYPE: RNA
<213> ORGANISM: Artificial
<220> FEATURE:
<223> OTHER INFORMATION: artificially synthesized sequence

<400> SEQUENCE: 124
ggguuaacuu uaacaaggag aaaaacaugc gugucgucgu ccgugacuac aaggacgacg    60
acgacaagua agcuucg                                                  77

<210> SEQ ID NO 125
<211> LENGTH: 12
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (3)..(3)
<223> OTHER INFORMATION: Xaa is valine or methyl valine

<400> SEQUENCE: 125

Met Arg Xaa Arg Asp Tyr Lys Asp Asp Asp Asp Lys
1               5                   10

<210> SEQ ID NO 126
<211> LENGTH: 13
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (3)..(4)
<223> OTHER INFORMATION: Xaa is valine or methyl valine

<400> SEQUENCE: 126

Met Arg Xaa Xaa Arg Asp Tyr Lys Asp Asp Asp Asp Lys
1               5                   10

<210> SEQ ID NO 127
<211> LENGTH: 14
<212> TYPE: PRT
<213> ORGANISM: Artificial
<220> FEATURE:
<223> OTHER INFORMATION: artificially synthesized sequence
```

```
<220> FEATURE:
<221> NAME/KEY: MISC_FEATURE
<222> LOCATION: (3)..(5)
<223> OTHER INFORMATION: Xaa is valine or methyl valine

<400> SEQUENCE: 127

Met Arg Xaa Xaa Xaa Arg Asp Tyr Lys Asp Asp Asp Lys
1               5                   10

<210> SEQ ID NO 128
<211> LENGTH: 49
<212> TYPE: DNA
<213> ORGANISM: Artificial
<220> FEATURE:
<223> OTHER INFORMATION: artificially synthesized sequence

<400> SEQUENCE: 128
gtaactatgc gctgatccca gctgcagaag ttccgctgac taacctggt         49

<210> SEQ ID NO 129
<211> LENGTH: 49
<212> TYPE: DNA
<213> ORGANISM: Artificial
<220> FEATURE:
<223> OTHER INFORMATION: artificially synthesized sequence

<400> SEQUENCE: 129
gtaactatgc gctgatccca agtgcagaag ttccgctgac taacctggt         49

<210> SEQ ID NO 130
<211> LENGTH: 49
<212> TYPE: DNA
<213> ORGANISM: Artificial
<220> FEATURE:
<223> OTHER INFORMATION: artificially synthesized sequence

<400> SEQUENCE: 130
gtaactatgc gctgatccca ggtgcagaag ttccgctgac taacctggt         49

<210> SEQ ID NO 131
<211> LENGTH: 49
<212> TYPE: DNA
<213> ORGANISM: Artificial
<220> FEATURE:
<223> OTHER INFORMATION: artificially synthesized sequence

<400> SEQUENCE: 131
gtaactatgc gctgatccca acggcagctg ttccgctgac taacctggt         49

<210> SEQ ID NO 132
<211> LENGTH: 49
<212> TYPE: DNA
<213> ORGANISM: Artificial
<220> FEATURE:
<223> OTHER INFORMATION: artificially synthesized sequence

<400> SEQUENCE: 132
gtaactatgc gctgatccca acggcagtag ttccgctgac taacctggt         49

<210> SEQ ID NO 133
<211> LENGTH: 49
<212> TYPE: DNA
<213> ORGANISM: Artificial
<220> FEATURE:
<223> OTHER INFORMATION: artificially synthesized sequence

<400> SEQUENCE: 133
```

-continued gtaactatgc gctgatccca acggcaagtg ttccgctgac taacctggt    49

<210> SEQ ID NO 134
<211> LENGTH: 33
<212> TYPE: DNA
<213> ORGANISM: Artificial
<220> FEATURE:
<223> OTHER INFORMATION: artificially synthesized sequence

<400> SEQUENCE: 134
ctggttcata ccctggctgg ttctggtctg gct    33

<210> SEQ ID NO 135
<211> LENGTH: 49
<212> TYPE: DNA
<213> ORGANISM: Artificial
<220> FEATURE:
<223> OTHER INFORMATION: artificially synthesized sequence

<400> SEQUENCE: 135
gtaactatgc gctgatccca gctgcagctg ttccgctgac taacctggt    49

<210> SEQ ID NO 136
<211> LENGTH: 49
<212> TYPE: DNA
<213> ORGANISM: Artificial
<220> FEATURE:
<223> OTHER INFORMATION: artificially synthesized sequence

<400> SEQUENCE: 136
gtaactatgc gctgatccca gctgcagtag ttccgctgac taacctggt    49

<210> SEQ ID NO 137
<211> LENGTH: 49
<212> TYPE: DNA
<213> ORGANISM: Artificial
<220> FEATURE:
<223> OTHER INFORMATION: artificially synthesized sequence

<400> SEQUENCE: 137
gtaactatgc gctgatccca gctgcaagtg ttccgctgac taacctggt    49

<210> SEQ ID NO 138
<211> LENGTH: 49
<212> TYPE: DNA
<213> ORGANISM: Artificial
<220> FEATURE:
<223> OTHER INFORMATION: artificially synthesized sequence

<400> SEQUENCE: 138
gtaactatgc gctgatccca agtgcagctg ttccgctgac taacctggt    49

<210> SEQ ID NO 139
<211> LENGTH: 49
<212> TYPE: DNA
<213> ORGANISM: Artificial
<220> FEATURE:
<223> OTHER INFORMATION: artificially synthesized sequence

<400> SEQUENCE: 139
gtaactatgc gctgatccca agtgcagtag ttccgctgac taacctggt    49

<210> SEQ ID NO 140
<211> LENGTH: 49
<212> TYPE: DNA

```
<213> ORGANISM: Artificial
<220> FEATURE:
<223> OTHER INFORMATION: artificially synthesized sequence

<400> SEQUENCE: 140
gtaactatgc gctgatccca agtgcaagtg ttccgctgac taacctggt          49

<210> SEQ ID NO 141
<211> LENGTH: 49
<212> TYPE: DNA
<213> ORGANISM: Artificial
<220> FEATURE:
<223> OTHER INFORMATION: artificially synthesized sequence

<400> SEQUENCE: 141
gtaactatgc gctgatccca ggtgcagctg ttccgctgac taacctggt          49

<210> SEQ ID NO 142
<211> LENGTH: 49
<212> TYPE: DNA
<213> ORGANISM: Artificial
<220> FEATURE:
<223> OTHER INFORMATION: artificially synthesized sequence

<400> SEQUENCE: 142
gtaactatgc gctgatccca ggtgcagtag ttccgctgac taacctggt          49

<210> SEQ ID NO 143
<211> LENGTH: 49
<212> TYPE: DNA
<213> ORGANISM: Artificial
<220> FEATURE:
<223> OTHER INFORMATION: artificially synthesized sequence

<400> SEQUENCE: 143
gtaactatgc gctgatccca ggtgcaagtg ttccgctgac taacctggt          49

<210> SEQ ID NO 144
<211> LENGTH: 33
<212> TYPE: DNA
<213> ORGANISM: Artificial
<220> FEATURE:
<223> OTHER INFORMATION: artificially synthesized sequence

<400> SEQUENCE: 144
cagttcgaca aagttgctat ggtgcagatc gtg                            33

<210> SEQ ID NO 145
<211> LENGTH: 33
<212> TYPE: DNA
<213> ORGANISM: Artificial
<220> FEATURE:
<223> OTHER INFORMATION: artificially synthesized sequence

<400> SEQUENCE: 145
atgcaccagt tcgacgctgt tgaaatggtg cag                            33

<210> SEQ ID NO 146
<211> LENGTH: 49
<212> TYPE: DNA
<213> ORGANISM: Artificial
<220> FEATURE:
<223> OTHER INFORMATION: artificially synthesized sequence

<400> SEQUENCE: 146
gtaactatgc gctgatccca acggcaggtg ttccgctgac taacctggt          49
```

<210> SEQ ID NO 147
<211> LENGTH: 49
<212> TYPE: DNA
<213> ORGANISM: Artificial
<220> FEATURE:
<223> OTHER INFORMATION: artificially synthesized sequence

<400> SEQUENCE: 147
gtaactatgc gctgatccca acggcagacg ttccgctgac taacctggt    49

<210> SEQ ID NO 148
<211> LENGTH: 49
<212> TYPE: DNA
<213> ORGANISM: Artificial
<220> FEATURE:
<223> OTHER INFORMATION: artificially synthesized sequence

<400> SEQUENCE: 148
gtaactatgc gctgatccca agtgcaggtg ttccgctgac taacctggt    49

<210> SEQ ID NO 149
<211> LENGTH: 49
<212> TYPE: DNA
<213> ORGANISM: Artificial
<220> FEATURE:
<223> OTHER INFORMATION: artificially synthesized sequence

<400> SEQUENCE: 149
gtaactatgc gctgatccca agtgcagacg ttccgctgac taacctggt    49

<210> SEQ ID NO 150
<211> LENGTH: 49
<212> TYPE: DNA
<213> ORGANISM: Artificial
<220> FEATURE:
<223> OTHER INFORMATION: artificially synthesized sequence

<400> SEQUENCE: 150
accaggttag tcagcggaac ttctgcagct gggatcagcg catagttac    49

<210> SEQ ID NO 151
<211> LENGTH: 49
<212> TYPE: DNA
<213> ORGANISM: Artificial
<220> FEATURE:
<223> OTHER INFORMATION: artificially synthesized sequence

<400> SEQUENCE: 151
accaggttag tcagcggaac ttctgcactt gggatcagcg catagttac    49

<210> SEQ ID NO 152
<211> LENGTH: 49
<212> TYPE: DNA
<213> ORGANISM: Artificial
<220> FEATURE:
<223> OTHER INFORMATION: artificially synthesized sequence

<400> SEQUENCE: 152
accaggttag tcagcggaac ttctgcacct gggatcagcg catagttac    49

<210> SEQ ID NO 153
<211> LENGTH: 49
<212> TYPE: DNA
<213> ORGANISM: Artificial
<220> FEATURE:

```
<223> OTHER INFORMATION: artificially synthesized sequence

<400> SEQUENCE: 153
accaggttag tcagcggaac agctgccgtt gggatcagcg catagttac         49

<210> SEQ ID NO 154
<211> LENGTH: 49
<212> TYPE: DNA
<213> ORGANISM: Artificial
<220> FEATURE:
<223> OTHER INFORMATION: artificially synthesized sequence

<400> SEQUENCE: 154
accaggttag tcagcggaac tactgccgtt gggatcagcg catagttac         49

<210> SEQ ID NO 155
<211> LENGTH: 49
<212> TYPE: DNA
<213> ORGANISM: Artificial
<220> FEATURE:
<223> OTHER INFORMATION: artificially synthesized sequence

<400> SEQUENCE: 155
accaggttag tcagcggaac acttgccgtt gggatcagcg catagttac         49

<210> SEQ ID NO 156
<211> LENGTH: 33
<212> TYPE: DNA
<213> ORGANISM: Artificial
<220> FEATURE:
<223> OTHER INFORMATION: artificially synthesized sequence

<400> SEQUENCE: 156
agccagacca gaaccagcca gggtatgaac cag                          33

<210> SEQ ID NO 157
<211> LENGTH: 49
<212> TYPE: DNA
<213> ORGANISM: Artificial
<220> FEATURE:
<223> OTHER INFORMATION: artificially synthesized sequence

<400> SEQUENCE: 157
accaggttag tcagcggaac agctgcagct gggatcagcg catagttac         49

<210> SEQ ID NO 158
<211> LENGTH: 49
<212> TYPE: DNA
<213> ORGANISM: Artificial
<220> FEATURE:
<223> OTHER INFORMATION: artificially synthesized sequence

<400> SEQUENCE: 158
accaggttag tcagcggaac tactgcagct gggatcagcg catagttac         49

<210> SEQ ID NO 159
<211> LENGTH: 49
<212> TYPE: DNA
<213> ORGANISM: Artificial
<220> FEATURE:
<223> OTHER INFORMATION: artificially synthesized sequence

<400> SEQUENCE: 159
accaggttag tcagcggaac acttgcagct gggatcagcg catagttac         49
```

-continued

<210> SEQ ID NO 160
<211> LENGTH: 49
<212> TYPE: DNA
<213> ORGANISM: Artificial
<220> FEATURE:
<223> OTHER INFORMATION: artificially synthesized sequence

<400> SEQUENCE: 160
accaggttag tcagcggaac agctgcactt gggatcagcg catagttac        49

<210> SEQ ID NO 161
<211> LENGTH: 49
<212> TYPE: DNA
<213> ORGANISM: Artificial
<220> FEATURE:
<223> OTHER INFORMATION: artificially synthesized sequence

<400> SEQUENCE: 161
accaggttag tcagcggaac tactgcactt gggatcagcg catagttac        49

<210> SEQ ID NO 162
<211> LENGTH: 49
<212> TYPE: DNA
<213> ORGANISM: Artificial
<220> FEATURE:
<223> OTHER INFORMATION: artificially synthesized sequence

<400> SEQUENCE: 162
accaggttag tcagcggaac acttgcactt gggatcagcg catagttac        49

<210> SEQ ID NO 163
<211> LENGTH: 49
<212> TYPE: DNA
<213> ORGANISM: Artificial
<220> FEATURE:
<223> OTHER INFORMATION: artificially synthesized sequence

<400> SEQUENCE: 163
accaggttag tcagcggaac agctgcacct gggatcagcg catagttac        49

<210> SEQ ID NO 164
<211> LENGTH: 49
<212> TYPE: DNA
<213> ORGANISM: Artificial
<220> FEATURE:
<223> OTHER INFORMATION: artificially synthesized sequence

<400> SEQUENCE: 164
accaggttag tcagcggaac tactgcacct gggatcagcg catagttac        49

<210> SEQ ID NO 165
<211> LENGTH: 49
<212> TYPE: DNA
<213> ORGANISM: Artificial
<220> FEATURE:
<223> OTHER INFORMATION: artificially synthesized sequence

<400> SEQUENCE: 165
accaggttag tcagcggaac acttgcacct gggatcagcg catagttac        49

<210> SEQ ID NO 166
<211> LENGTH: 33
<212> TYPE: DNA
<213> ORGANISM: Artificial
<220> FEATURE:
<223> OTHER INFORMATION: artificially synthesized sequence

```
<400> SEQUENCE: 166
cacgatctgc accatagcaa ctttgtcgaa ctg                                    33

<210> SEQ ID NO 167
<211> LENGTH: 33
<212> TYPE: DNA
<213> ORGANISM: Artificial
<220> FEATURE:
<223> OTHER INFORMATION: artificially synthesized sequence

<400> SEQUENCE: 167
ctgcaccatt tcaacagcgt cgaactggtg cat                                    33

<210> SEQ ID NO 168
<211> LENGTH: 49
<212> TYPE: DNA
<213> ORGANISM: Artificial
<220> FEATURE:
<223> OTHER INFORMATION: artificially synthesized sequence

<400> SEQUENCE: 168
accaggttag tcagcggaac acctgccgtt gggatcagcg catagttac                   49

<210> SEQ ID NO 169
<211> LENGTH: 49
<212> TYPE: DNA
<213> ORGANISM: Artificial
<220> FEATURE:
<223> OTHER INFORMATION: artificially synthesized sequence

<400> SEQUENCE: 169
accaggttag tcagcggaac gtctgccgtt gggatcagcg catagttac                   49

<210> SEQ ID NO 170
<211> LENGTH: 49
<212> TYPE: DNA
<213> ORGANISM: Artificial
<220> FEATURE:
<223> OTHER INFORMATION: artificially synthesized sequence

<400> SEQUENCE: 170
accaggttag tcagcggaac acctgcactt gggatcagcg catagttac                   49

<210> SEQ ID NO 171
<211> LENGTH: 49
<212> TYPE: DNA
<213> ORGANISM: Artificial
<220> FEATURE:
<223> OTHER INFORMATION: artificially synthesized sequence

<400> SEQUENCE: 171
accaggttag tcagcggaac gtctgcactt gggatcagcg catagttac                   49

<210> SEQ ID NO 172
<211> LENGTH: 114
<212> TYPE: DNA
<213> ORGANISM: Artificial
<220> FEATURE:
<223> OTHER INFORMATION: artificially synthesized sequence

<400> SEQUENCE: 172
ggcgtaatac gactcactat aggtgaggtg gccgagaggc tgaaggcgct cccctgctaa       60
gggagtatgc ggtcaaaagc tgcatccggg gttcgaatcc ccgcctcacc gcca            114
```

<210> SEQ ID NO 173
<211> LENGTH: 93
<212> TYPE: RNA
<213> ORGANISM: Artificial
<220> FEATURE:
<223> OTHER INFORMATION: artificially synthesized sequence

<400> SEQUENCE: 173
ggugaggugg ccgagaggcu gaaggcgcuc cccugcuaag ggaguaugcg gucaaaagcu    60
gcauccgggg uucgaauccc cgccucaccg cca    93

<210> SEQ ID NO 174
<211> LENGTH: 92
<212> TYPE: DNA
<213> ORGANISM: Artificial
<220> FEATURE:
<223> OTHER INFORMATION: artificially synthesized sequence

<400> SEQUENCE: 174
ggcgtaatac gactcactat agggttaact ttaacaagga gaaaacatg cgttcccgtg    60 actacaagga cgacgacgac aagtaagctt cg    92

<210> SEQ ID NO 175
<211> LENGTH: 71
<212> TYPE: RNA
<213> ORGANISM: Artificial
<220> FEATURE:
<223> OTHER INFORMATION: artificially synthesized sequence

<400> SEQUENCE: 175
ggguuaacuu uaacaaggag aaaaacaugc guucccguga cuacaaggac gacgacgaca    60
aguaagcuuc g    71

<210> SEQ ID NO 176
<211> LENGTH: 12
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (3)..(3)
<223> OTHER INFORMATION: Xaa is serine or methyl serine

<400> SEQUENCE: 176

Met Arg Xaa Arg Asp Tyr Lys Asp Asp Asp Asp Lys
1               5                   10

<210> SEQ ID NO 177
<211> LENGTH: 103
<212> TYPE: DNA
<213> ORGANISM: Artificial
<220> FEATURE:
<223> OTHER INFORMATION: artificially synthesized sequence

<400> SEQUENCE: 177
ggcgtaatac gactcactat agggttaact ttaagaagga gatatacata tgaaggctgg    60
tccgggtttt atgactaaga gtggtagtgg tagttaagct tcg    103

<210> SEQ ID NO 178
<211> LENGTH: 82
<212> TYPE: RNA
<213> ORGANISM: Artificial
<220> FEATURE:
<223> OTHER INFORMATION: artificially synthesized sequence -continued

<400> SEQUENCE: 178
ggguuaacuu uaagaaggag auauacauau gaaggcuggu ccggguuuua ugacuaagag    60
ugguaguggu aguuaagcuu cg    82

<210> SEQ ID NO 179
<211> LENGTH: 15
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (9)..(9)
<223> OTHER INFORMATION: Xaa is threonine or methyl threonine

<400> SEQUENCE: 179

Met Lys Ala Gly Pro Gly Phe Met Xaa Lys Ser Gly Ser Gly Ser
1               5                   10                  15

<210> SEQ ID NO 180
<211> LENGTH: 7
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (4)..(4)
<223> OTHER INFORMATION: Xaa is Asn (N), Tyr (Y), or Thr (T).
<220> FEATURE:
<221> NAME/KEY: MISC_FEATURE
<222> LOCATION: (5)..(5)
<223> OTHER INFORMATION: Xaa is any amino acid.
<220> FEATURE:
<221> NAME/KEY: MISC_FEATURE
<222> LOCATION: (6)..(6)
<223> OTHER INFORMATION: Xaa is Thr (T) or Ser (S).

<400> SEQUENCE: 180

Pro Pro Pro Xaa Xaa Xaa Gly
1               5

<210> SEQ ID NO 181
<211> LENGTH: 7
<212> TYPE: PRT
<213> ORGANISM: Artificial
<220> FEATURE:
<223> OTHER INFORMATION: artificially synthesized sequence
<220> FEATURE:
<221> NAME/KEY: MISC_FEATURE
<222> LOCATION: (5)..(5)
<223> OTHER INFORMATION: Xaa is any amino acid.

<400> SEQUENCE: 181

Pro Pro Pro Asn Xaa Thr Gly
1               5

<210> SEQ ID NO 182
<211> LENGTH: 951
<212> TYPE: PRT
<213> ORGANISM: Artificial
<220> FEATURE:
<223> OTHER INFORMATION: artificially synthesized sequence

<400> SEQUENCE: 182

Met Glu Lys Thr Tyr Asn Pro Gln Asp Ile Glu Gln Pro Leu Tyr Glu
1               5                   10                  15

-continued

```
His Trp Glu Lys Gln Gly Tyr Phe Lys Pro Asn Gly Asp Glu Ser Gln
             20                  25                  30

Glu Ser Phe Cys Ile Met Ile Pro Pro Gly Val Ser Gly Ser Leu
         35                  40                  45

His Met Gly His Ala Phe Gln Gln Thr Ile Met Asp Thr Met Ile Arg
 50                  55                  60

Tyr Gln Arg Met Gln Gly Lys Asn Thr Leu Trp Gln Val Gly Thr Asp
 65                  70                  75                  80

His Ala Gly Ile Ala Thr Gln Met Val Val Glu Arg Lys Ile Ala Ala
                 85                  90                  95

Glu Glu Gly Lys Thr Arg His Asp Tyr Gly Arg Glu Ala Phe Ile Asp
            100                 105                 110

Lys Ile Trp Glu Trp Lys Ala Glu Ser Gly Gly Thr Ile Thr Arg Gln
            115                 120                 125

Met Arg Arg Leu Gly Asn Ser Val Asp Trp Glu Arg Glu Arg Phe Thr
            130                 135                 140

Met Asp Glu Gly Leu Ser Asn Ala Val Lys Glu Val Phe Val Arg Leu
145                 150                 155                 160

Tyr Lys Glu Asp Leu Ile Tyr Arg Gly Lys Arg Leu Val Asn Trp Asp
                165                 170                 175

Pro Lys Leu Arg Thr Ala Ile Ser Asp Leu Glu Val Glu Asn Arg Glu
            180                 185                 190

Ser Lys Gly Ser Met Trp His Ile Arg Tyr Pro Leu Ala Asp Gly Ala
            195                 200                 205

Lys Thr Ala Asp Gly Lys Asp Tyr Leu Val Val Ala Thr Thr Arg Pro
210                 215                 220

Glu Thr Leu Leu Gly Asp Thr Gly Val Ala Val Asn Pro Glu Asp Pro
225                 230                 235                 240

Arg Tyr Lys Asp Leu Ile Gly Lys Tyr Val Ile Leu Pro Leu Val Asn
                245                 250                 255

Arg Arg Ile Pro Ile Val Gly Asp Glu His Ala Asp Met Glu Lys Gly
            260                 265                 270

Thr Gly Cys Val Lys Ile Ala Pro Ala His Asp Phe Asn Asp Tyr Glu
            275                 280                 285

Val Gly Lys Arg His Ala Leu Pro Met Ile Asn Ile Leu Thr Phe Asp
290                 295                 300

Gly Asp Ile Arg Glu Ser Ala Gln Val Phe Asp Thr Lys Gly Asn Glu
305                 310                 315                 320

Ser Asp Val Tyr Ser Ser Glu Ile Pro Ala Glu Phe Gln Lys Leu Glu
                325                 330                 335

Arg Phe Ala Ala Arg Lys Ala Val Val Ala Val Asp Ala Leu Gly
            340                 345                 350

Leu Leu Glu Glu Ile Lys Pro His Asp Leu Thr Val Pro Tyr Gly Asp
            355                 360                 365

Arg Gly Gly Val Val Ile Glu Pro Met Leu Thr Asp Gln Trp Tyr Val
            370                 375                 380

Arg Ala Asp Val Leu Ala Lys Pro Ala Val Glu Ala Val Glu Asn Gly
385                 390                 395                 400

Asp Ile Gln Phe Val Pro Lys Gln Tyr Glu Asn Met Tyr Phe Ser Trp
                405                 410                 415

Met Arg Asp Ile Gln Asp Trp Cys Ile Ser Arg Gln Leu Trp Trp Gly
            420                 425                 430

His Arg Ile Pro Ala Trp Tyr Asp Glu Ala Gly Asn Val Tyr Val Gly
```

-continued

```
            435                 440                 445
Arg Asn Glu Asp Glu Val Arg Lys Glu Asn Asn Leu Gly Ala Asp Val
450                 455                 460
Val Leu Arg Gln Asp Glu Asp Val Leu Asp Thr Trp Phe Ser Ser Ala
465                 470                 475                 480
Leu Trp Thr Phe Ser Thr Leu Gly Trp Pro Glu Asn Thr Asp Ala Leu
                    485                 490                 495
Arg Gln Phe His Pro Thr Ser Val Met Val Ser Gly Phe Asp Ile Ile
                500                 505                 510
Phe Phe Trp Ile Ala Arg Met Ile Met Thr Met His Phe Ile Lys
            515                 520                 525
Asp Glu Asn Gly Lys Pro Gln Val Pro Phe His Thr Val Tyr Met Thr
530                 535                 540
Gly Leu Ile Arg Asp Asp Glu Gly Gln Lys Met Ser Lys Ser Lys Gly
545                 550                 555                 560
Asn Val Ile Asp Pro Leu Asp Met Val Asp Gly Ile Ser Leu Pro Glu
                565                 570                 575
Leu Leu Glu Lys Arg Thr Gly Asn Met Met Gln Pro Gln Leu Ala Asp
                580                 585                 590
Lys Ile Arg Lys Arg Thr Glu Lys Gln Phe Pro Asn Gly Ile Glu Pro
            595                 600                 605
His Gly Thr Asp Ala Leu Arg Phe Thr Leu Ala Ala Leu Ala Ser Thr
            610                 615                 620
Gly Arg Asp Ile Asn Trp Asp Met Lys Arg Leu Glu Gly Tyr Arg Asn
625                 630                 635                 640
Phe Cys Asn Lys Leu Trp Asn Ala Ser Arg Phe Val Leu Met Asn Thr
                645                 650                 655
Glu Gly Gln Asp Cys Gly Phe Asn Gly Gly Glu Met Thr Leu Ser Leu
                660                 665                 670
Ala Asp Arg Trp Ile Leu Ala Glu Phe Asn Gln Thr Ile Lys Ala Tyr
            675                 680                 685
Arg Glu Ala Leu Asp Ser Phe Arg Phe Asp Ile Ala Ala Gly Ile Leu
            690                 695                 700
Tyr Glu Phe Thr Trp Asn Gln Phe Cys Asp Trp Tyr Leu Glu Leu Thr
705                 710                 715                 720
Lys Pro Val Met Asn Gly Gly Thr Glu Ala Glu Leu Arg Gly Thr Arg
                725                 730                 735
His Thr Leu Val Thr Val Leu Glu Gly Leu Leu Arg Leu Ala His Pro
                740                 745                 750
Ile Ile Pro Phe Ile Thr Glu Thr Ile Trp Gln Arg Val Lys Val Leu
            755                 760                 765
Cys Gly Ile Thr Ala Asp Thr Ile Met Leu Gln Pro Phe Pro Gln Tyr
            770                 775                 780
Asp Ala Ser Gln Val Asp Glu Ala Ala Leu Ala Asp Thr Glu Trp Leu
785                 790                 795                 800
Lys Gln Ala Ile Val Ala Val Arg Asn Ile Arg Ala Glu Met Asn Ile
                805                 810                 815
Ala Pro Gly Lys Pro Leu Glu Leu Leu Leu Arg Gly Cys Ser Ala Asp
                820                 825                 830
Ala Glu Arg Arg Val Asn Glu Asn Arg Gly Phe Leu Gln Thr Leu Ala
            835                 840                 845
Arg Leu Glu Ser Ile Thr Val Leu Pro Ala Asp Asp Lys Gly Pro Val
            850                 855                 860
```

Ser Val Thr Lys Ile Ile Asp Gly Ala Glu Leu Leu Ile Pro Met Ala
865                 870                 875                 880

Gly Leu Ile Asn Lys Glu Asp Glu Leu Ala Arg Leu Ala Lys Glu Val
            885                 890                 895

Ala Lys Ile Glu Gly Glu Ile Ser Arg Ile Glu Asn Lys Leu Ala Asn
            900                 905                 910

Glu Gly Phe Val Ala Arg Ala Pro Glu Ala Val Ile Ala Lys Glu Arg
        915                 920                 925

Glu Lys Leu Glu Gly Tyr Ala Glu Ala Lys Ala Lys Leu Ile Glu Gln
    930                 935                 940

Gln Ala Val Ile Ala Ala Leu
945                 950

<210> SEQ ID NO 183
<211> LENGTH: 951
<212> TYPE: PRT
<213> ORGANISM: Artificial
<220> FEATURE:
<223> OTHER INFORMATION: artificially synthesized sequence

<400> SEQUENCE: 183

Met Glu Lys Thr Tyr Asn Pro Gln Asp Ile Glu Gln Pro Leu Tyr Glu
1               5                   10                  15

His Trp Glu Lys Gln Gly Tyr Phe Lys Pro Asn Gly Asp Glu Ser Gln
            20                  25                  30

Glu Ser Phe Cys Ile Met Ile Pro Pro Gly Val Ser Gly Ser Leu
        35                  40                  45

His Met Gly His Ala Phe Gln Gln Thr Ile Met Asp Thr Met Ile Arg
    50                  55                  60

Tyr Gln Arg Met Gln Gly Lys Asn Thr Leu Trp Gln Val Gly Thr Asp
65                  70                  75                  80

His Ala Gly Ile Ala Thr Gln Met Val Val Glu Arg Lys Ile Ala Ala
                85                  90                  95

Glu Glu Gly Lys Thr Arg His Asp Tyr Gly Arg Glu Ala Phe Ile Asp
            100                 105                 110

Lys Ile Trp Glu Trp Lys Ala Glu Ser Gly Gly Thr Ile Thr Arg Gln
        115                 120                 125

Met Arg Arg Leu Gly Asn Ser Val Asp Trp Gln Arg Glu Arg Phe Thr
    130                 135                 140

Met Asp Glu Gly Leu Ser Asn Ala Val Lys Glu Val Phe Val Arg Leu
145                 150                 155                 160

Tyr Lys Glu Asp Leu Ile Tyr Arg Gly Lys Arg Leu Val Asn Trp Asp
                165                 170                 175

Pro Lys Leu Arg Thr Ala Ile Ser Asp Leu Glu Val Glu Asn Arg Glu
            180                 185                 190

Ser Lys Gly Ser Met Trp His Ile Arg Tyr Pro Leu Ala Asp Gly Ala
        195                 200                 205

Lys Thr Ala Asp Gly Lys Asp Tyr Leu Val Val Ala Thr Thr Arg Pro
    210                 215                 220

Glu Thr Leu Leu Gly Asp Thr Gly Val Ala Val Asn Pro Glu Asp Pro
225                 230                 235                 240

Arg Tyr Lys Asp Leu Ile Gly Lys Tyr Val Ile Leu Pro Leu Val Asn
                245                 250                 255

Arg Arg Ile Pro Ile Val Gly Asp Glu His Ala Asp Met Glu Lys Gly
            260                 265                 270

```
Thr Gly Cys Val Lys Ile Gly Pro Ala His Asp Phe Asn Asp Tyr Glu
            275                 280                 285

Val Gly Lys Arg His Ala Leu Pro Met Ile Asn Ile Leu Thr Phe Asp
        290                 295                 300

Gly Asp Ile Arg Glu Ser Ala Gln Val Phe Asp Thr Lys Gly Asn Glu
305                 310                 315                 320

Ser Asp Val Tyr Ser Ser Glu Ile Pro Ala Glu Phe Gln Lys Leu Glu
                325                 330                 335

Arg Phe Ala Ala Arg Lys Ala Val Ala Ala Val Asp Ala Leu Gly
            340                 345                 350

Leu Leu Glu Glu Ile Lys Pro His Asp Leu Thr Val Pro Tyr Gly Asp
            355                 360                 365

Arg Gly Gly Val Val Ile Glu Pro Met Leu Thr Asp Gln Trp Tyr Val
        370                 375                 380

Arg Ala Asp Val Leu Ala Lys Pro Ala Val Glu Ala Val Glu Asn Gly
385                 390                 395                 400

Asp Ile Gln Phe Val Pro Lys Gln Tyr Glu Asn Met Tyr Phe Ser Trp
                405                 410                 415

Met Arg Asp Ile Gln Asp Trp Cys Ile Ser Arg Gln Leu Trp Trp Gly
            420                 425                 430

His Arg Ile Pro Ala Trp Tyr Asp Glu Ala Gly Asn Val Tyr Val Gly
            435                 440                 445

Arg Asn Glu Asp Glu Val Arg Lys Glu Asn Asn Leu Gly Ala Asp Val
        450                 455                 460

Val Leu Arg Gln Asp Glu Asp Val Leu Asp Thr Trp Phe Ser Ser Ala
465                 470                 475                 480

Leu Trp Thr Phe Ser Thr Leu Gly Trp Pro Glu Asn Thr Asp Ala Leu
                485                 490                 495

Arg Gln Phe His Pro Thr Ser Val Met Val Ser Gly Phe Asp Ile Ile
            500                 505                 510

Phe Phe Trp Ile Ala Arg Met Ile Met Met Thr Met His Phe Ile Lys
        515                 520                 525

Asp Glu Asn Gly Lys Pro Gln Val Pro Phe His Thr Val Tyr Met Thr
530                 535                 540

Gly Leu Ile Arg Asp Asp Glu Gly Gln Lys Met Ser Lys Ser Lys Gly
545                 550                 555                 560

Asn Val Ile Asp Pro Leu Asp Met Val Asp Gly Ile Ser Leu Pro Glu
                565                 570                 575

Leu Leu Glu Lys Arg Thr Gly Asn Met Met Gln Pro Gln Leu Ala Asp
            580                 585                 590

Lys Ile Arg Lys Arg Thr Glu Lys Gln Phe Pro Asn Gly Ile Glu Pro
            595                 600                 605

His Gly Thr Asp Ala Leu Arg Phe Thr Leu Ala Ala Leu Ala Ser Thr
        610                 615                 620

Gly Arg Asp Ile Asn Trp Asp Met Lys Arg Leu Glu Gly Tyr Arg Asn
625                 630                 635                 640

Phe Cys Asn Lys Leu Trp Asn Ala Ser Arg Phe Val Leu Met Asn Thr
                645                 650                 655

Glu Gly Gln Asp Cys Gly Phe Asn Gly Gly Glu Met Thr Leu Ser Leu
            660                 665                 670

Ala Asp Arg Trp Ile Leu Ala Glu Phe Asn Gln Thr Ile Lys Ala Tyr
            675                 680                 685
```

```
Arg Glu Ala Leu Asp Ser Phe Arg Phe Asp Ile Ala Ala Gly Ile Leu
    690                 695                 700

Tyr Glu Phe Thr Trp Asn Gln Phe Cys Asp Trp Tyr Leu Glu Leu Thr
705                 710                 715                 720

Lys Pro Val Met Asn Gly Gly Thr Glu Ala Glu Leu Arg Gly Thr Arg
                725                 730                 735

His Thr Leu Val Thr Val Leu Glu Gly Leu Leu Arg Leu Ala His Pro
            740                 745                 750

Ile Ile Pro Phe Ile Thr Glu Thr Ile Trp Gln Arg Val Lys Val Leu
        755                 760                 765

Cys Gly Ile Thr Ala Asp Thr Ile Met Leu Gln Pro Phe Pro Gln Tyr
770                 775                 780

Asp Ala Ser Gln Val Asp Glu Ala Ala Leu Ala Asp Thr Glu Trp Leu
785                 790                 795                 800

Lys Gln Ala Ile Val Ala Val Arg Asn Ile Arg Ala Glu Met Asn Ile
                805                 810                 815

Ala Pro Gly Lys Pro Leu Glu Leu Leu Arg Gly Cys Ser Ala Asp
            820                 825                 830

Ala Glu Arg Arg Val Asn Glu Asn Arg Gly Phe Leu Gln Thr Leu Ala
            835                 840                 845

Arg Leu Glu Ser Ile Thr Val Leu Pro Ala Asp Asp Lys Gly Pro Val
850                 855                 860

Ser Val Thr Lys Ile Ile Asp Gly Ala Glu Leu Leu Ile Pro Met Ala
865                 870                 875                 880

Gly Leu Ile Asn Lys Glu Asp Glu Leu Ala Arg Leu Ala Lys Glu Val
                885                 890                 895

Ala Lys Ile Glu Gly Glu Ile Ser Arg Ile Glu Asn Lys Leu Ala Asn
                900                 905                 910

Glu Gly Phe Val Ala Arg Ala Pro Glu Ala Val Ile Ala Lys Glu Arg
            915                 920                 925

Glu Lys Leu Glu Gly Tyr Ala Glu Ala Lys Ala Lys Leu Ile Glu Gln
    930                 935                 940

Gln Ala Val Ile Ala Ala Leu
945                 950

<210> SEQ ID NO 184
<211> LENGTH: 334
<212> TYPE: PRT
<213> ORGANISM: Artificial
<220> FEATURE:
<223> OTHER INFORMATION: artificially synthesized sequence

<400> SEQUENCE: 184

Met Thr Lys Pro Ile Val Phe Ser Gly Ala Gln Pro Ser Gly Glu Leu
1               5                   10                  15

Thr Ile Gly Asn Tyr Met Gly Ala Leu Arg Gln Trp Val Asn Met Gln
            20                  25                  30

Asp Asp Tyr His Cys Ile Tyr Cys Ile Val Asp Gln His Ala Ile Thr
        35                  40                  45

Val Arg Gln Asp Ala Gln Lys Leu Arg Lys Ala Thr Leu Asp Thr Leu
    50                  55                  60

Ala Leu Tyr Leu Ala Cys Gly Ile Asp Pro Glu Lys Ser Thr Ile Phe
65                  70                  75                  80

Val Gln Ser His Val Pro Glu His Ala Gln Leu Gly Trp Ala Leu Asn
                85                  90                  95
```

```
Cys Tyr Thr Tyr Phe Gly Glu Leu Ser Arg Met Thr Gln Phe Lys Asp
            100                 105                 110

Lys Ser Ala Arg Tyr Ala Glu Asn Ile Asn Ala Gly Leu Phe Asp Tyr
        115                 120                 125

Pro Val Leu Met Ala Ala Asp Ile Leu Leu Tyr Gln Thr Asn Leu Val
    130                 135                 140

Pro Val Gly Glu Asp Ala Lys Gln Ala Leu Glu Leu Ser Arg Asp Ile
145                 150                 155                 160

Ala Gln Arg Phe Asn Ala Leu Tyr Gly Glu Ile Phe Lys Val Pro Glu
                165                 170                 175

Pro Phe Ile Pro Lys Ser Gly Ala Arg Val Met Ser Leu Leu Glu Pro
            180                 185                 190

Thr Lys Lys Met Ser Lys Ser Asp Asp Asn Arg Asn Asn Val Ile Gly
        195                 200                 205

Leu Leu Glu Asp Pro Lys Ser Val Val Lys Ile Lys Arg Ala Val
    210                 215                 220

Thr Asp Ser Asp Glu Pro Pro Val Val Arg Tyr Asp Val Gln Asn Lys
225                 230                 235                 240

Ala Gly Val Ser Asn Leu Leu Asp Ile Leu Ser Ala Val Thr Gly Gln
                245                 250                 255

Ser Ile Pro Glu Leu Glu Lys Gln Phe Glu Gly Lys Met Tyr Gly His
            260                 265                 270

Leu Lys Gly Glu Val Ala Asp Ala Val Ser Gly Met Leu Thr Glu Leu
        275                 280                 285

Gln Glu Arg Tyr His Arg Phe Arg Asn Asp Glu Ala Phe Leu Gln Gln
    290                 295                 300

Val Met Lys Asp Gly Ala Glu Lys Ala Ser Ala His Ala Ser Arg Thr
305                 310                 315                 320

Leu Lys Ala Val Tyr Glu Ala Ile Gly Phe Val Ala Lys Pro
                325                 330

<210> SEQ ID NO 185
<211> LENGTH: 334
<212> TYPE: PRT
<213> ORGANISM: Artificial
<220> FEATURE:
<223> OTHER INFORMATION: artificially synthesized sequence

<400> SEQUENCE: 185

Met Thr Lys Pro Ile Val Phe Ser Gly Ala Gln Pro Ser Gly Glu Leu
1               5                   10                  15

Thr Ile Gly Asn Tyr Met Gly Ala Leu Arg Gln Trp Val Asn Met Gln
            20                  25                  30

Asp Asp Tyr His Cys Ile Tyr Cys Ile Val Asp Gln His Ala Ile Thr
        35                  40                  45

Val Arg Gln Asp Ala Gln Lys Leu Arg Lys Ala Thr Leu Asp Thr Leu
    50                  55                  60

Ala Leu Tyr Leu Ala Cys Gly Ile Asp Pro Glu Lys Ser Thr Ile Phe
65                  70                  75                  80

Val Gln Ser His Val Pro Glu His Ala Gln Leu Gly Trp Ala Leu Asn
                85                  90                  95

Cys Tyr Thr Tyr Phe Gly Glu Leu Ser Arg Met Thr Gln Phe Lys Asp
            100                 105                 110

Lys Ser Ala Arg Tyr Ala Glu Asn Ile Asn Ala Gly Leu Phe Asp Tyr
        115                 120                 125
```

Pro Val Leu Ala Ala Asp Ile Leu Leu Tyr Gln Thr Asn Leu Val
    130                 135                 140

Pro Val Gly Glu Asp Gln Lys Gln His Leu Glu Leu Ser Arg Asp Ile
145                 150                 155                 160

Ala Gln Arg Phe Asn Ala Leu Tyr Gly Glu Ile Phe Lys Val Pro Glu
                165                 170                 175

Pro Phe Ile Pro Lys Ser Gly Ala Arg Val Met Ser Leu Leu Glu Pro
            180                 185                 190

Thr Lys Lys Met Ser Lys Ser Asp Asp Asn Arg Asn Asn Val Ile Gly
                195                 200                 205

Leu Leu Glu Asp Pro Lys Ser Val Val Lys Lys Ile Lys Arg Ala Val
    210                 215                 220

Thr Asp Ser Asp Glu Pro Pro Val Val Arg Tyr Asp Val Gln Asn Lys
225                 230                 235                 240

Ala Gly Val Ser Asn Leu Leu Asp Ile Leu Ser Ala Val Thr Gly Gln
                245                 250                 255

Ser Ile Pro Glu Leu Glu Lys Gln Phe Glu Gly Lys Met Tyr Gly His
            260                 265                 270

Leu Lys Gly Glu Val Ala Asp Ala Val Ser Gly Met Leu Thr Glu Leu
    275                 280                 285

Gln Glu Arg Tyr His Arg Phe Arg Asn Asp Gly Ala Phe Leu Gln Gln
    290                 295                 300

Val Met Lys Asp Gly Ala Glu Lys Ala Ser Ala His Ala Ser Arg Thr
305                 310                 315                 320

Leu Lys Ala Val Tyr Glu Ala Ile Gly Phe Val Ala Lys Pro
                325                 330

<210> SEQ ID NO 186
<211> LENGTH: 334
<212> TYPE: PRT
<213> ORGANISM: Artificial
<220> FEATURE:
<223> OTHER INFORMATION: artificially synthesized sequence

<400> SEQUENCE: 186

Met Thr Lys Pro Ile Val Phe Ser Gly Ala Gln Pro Ser Gly Glu Leu
1               5                   10                  15

Thr Ile Gly Asn Tyr Met Gly Ala Leu Arg Gln Trp Val Asn Met Gln
                20                  25                  30

Asp Asp Tyr His Cys Ile Tyr Cys Ile Val Asp Gln His Ala Ile Thr
                35                  40                  45

Val Arg Gln Asp Ala Gln Lys Leu Arg Lys Ala Thr Leu Asp Thr Leu
    50                  55                  60

Ala Leu Tyr Leu Ala Cys Gly Ile Asp Pro Glu Lys Ser Thr Ile Phe
65                  70                  75                  80

Val Gln Ser His Val Pro Glu His Ala Gln Leu Gly Trp Ala Leu Asn
                85                  90                  95

Cys Tyr Thr Tyr Phe Gly Glu Leu Ser Arg Met Thr Gln Phe Lys Asp
                100                 105                 110

Lys Ser Ala Arg Tyr Ala Glu Asn Ile Asn Ala Gly Leu Phe Asp Tyr
            115                 120                 125

Pro Val Leu Val Ala Asp Ile Leu Leu Tyr Gln Thr Asn Leu Val
    130                 135                 140

Pro Val Gly Glu Asp Ala Lys Gln Ala Leu Glu Leu Ser Arg Asp Ile
145                 150                 155                 160

```
Ala Gln Arg Phe Asn Ala Leu Tyr Gly Glu Ile Phe Lys Val Pro Glu
                165                 170                 175

Pro Phe Ile Pro Lys Ser Gly Ala Arg Val Met Ser Leu Leu Glu Pro
            180                 185                 190

Thr Lys Lys Met Ser Lys Ser Asp Asp Asn Arg Asn Asn Val Ile Gly
            195                 200                 205

Leu Leu Glu Asp Pro Lys Ser Val Val Lys Ile Lys Arg Ala Val
            210                 215                 220

Thr Asp Ser Asp Glu Pro Val Val Arg Tyr Asp Val Gln Asn Lys
225                 230                 235                 240

Ala Gly Val Ser Asn Leu Leu Asp Ile Leu Ser Ala Val Thr Gly Gln
                245                 250                 255

Ser Ile Pro Glu Leu Glu Lys Gln Phe Glu Gly Lys Met Tyr Gly His
            260                 265                 270

Leu Lys Gly Glu Val Ala Asp Ala Val Ser Gly Met Leu Thr Glu Leu
            275                 280                 285

Gln Glu Arg Tyr His Arg Phe Arg Asn Asp Glu Ala Phe Leu Gln Gln
            290                 295                 300

Val Met Lys Asp Gly Ala Glu Lys Ala Ser Ala His Ala Ser Arg Thr
305                 310                 315                 320

Leu Lys Ala Val Tyr Glu Ala Ile Gly Phe Val Ala Lys Pro
                325                 330

<210> SEQ ID NO 187
<211> LENGTH: 860
<212> TYPE: PRT
<213> ORGANISM: Artificial
<220> FEATURE:
<223> OTHER INFORMATION: artificially synthesized sequence

<400> SEQUENCE: 187

Met Gln Glu Gln Tyr Arg Pro Glu Ile Glu Ser Lys Val Gln Leu
1               5                   10                  15

His Trp Asp Glu Lys Arg Thr Phe Glu Val Thr Glu Asp Glu Ser Lys
                20                  25                  30

Glu Lys Tyr Tyr Cys Leu Ser Met Leu Pro Gly Pro Ser Gly Arg Leu
            35                  40                  45

His Met Gly His Val Arg Asn Tyr Thr Ile Gly Asp Val Ile Ala Arg
    50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175

Trp Arg Cys Asp Thr Lys Val Glu Arg Lys Glu Ile Pro Gln Trp Phe
            180                 185                 190
```

```
Ile Lys Ile Thr Ala Tyr Ala Asp Glu Leu Leu Asn Asp Leu Asp Lys
        195                 200                 205

Leu Asp His Trp Pro Asp Thr Val Lys Thr Met Gln Arg Asn Trp Ile
    210                 215                 220

Gly Arg Ser Glu Gly Val Glu Ile Thr Phe Asn Val Asn Asp Tyr Asp
225                 230                 235                 240

Asn Thr Leu Thr Val Tyr Thr Thr Arg Pro Asp Thr Phe Met Gly Cys
                245                 250                 255

Thr Tyr Leu Ala Val Ala Ala Gly His Pro Leu Ala Gln Lys Ala Ala
                260                 265                 270

Glu Asn Asn Pro Glu Leu Ala Ala Phe Ile Asp Glu Cys Arg Asn Thr
                275                 280                 285

Lys Val Ala Glu Ala Glu Met Ala Thr Met Glu Lys Lys Gly Val Asp
            290                 295                 300

Thr Gly Phe Lys Ala Val His Pro Leu Thr Gly Glu Glu Ile Pro Val
305                 310                 315                 320

Trp Ala Ala Asn Phe Val Leu Met Glu Tyr Gly Thr Gly Ala Val Met
                325                 330                 335

Ala Val Pro Gly His Asp Gln Arg Asp Tyr Glu Phe Ala Ser Lys Tyr
                340                 345                 350

Gly Leu Asn Ile Lys Pro Val Ile Leu Ala Ala Asp Gly Ser Glu Pro
                355                 360                 365

Asp Leu Ser Gln Gln Ala Leu Thr Glu Lys Gly Val Leu Phe Asn Ser
        370                 375                 380

Gly Glu Phe Asn Gly Leu Asp His Glu Ala Ala Phe Asn Ala Ile Ala
385                 390                 395                 400

Asp Lys Leu Thr Ala Met Gly Val Gly Glu Arg Lys Val Asn Tyr Arg
                405                 410                 415

Leu Arg Asp Trp Gly Val Ser Arg Gln Arg Tyr Trp Gly Ala Pro Ile
                420                 425                 430

Pro Met Val Thr Leu Glu Asp Gly Thr Val Met Pro Thr Pro Asp Asp
                435                 440                 445

Gln Leu Pro Val Ile Leu Pro Glu Asp Val Val Met Asp Gly Ile Thr
        450                 455                 460

Ser Pro Ile Lys Ala Asp Pro Glu Trp Ala Lys Thr Thr Val Asn Gly
465                 470                 475                 480

Met Pro Ala Leu Arg Glu Thr Asp Thr Phe Asp Thr Phe Met Glu Ser
                485                 490                 495

Ser Trp Tyr Tyr Ala Arg Tyr Thr Cys Pro Gln Tyr Lys Glu Gly Met
                500                 505                 510

Leu Asp Ser Glu Ala Ala Asn Tyr Trp Leu Pro Val Asp Ile Tyr Ile
        515                 520                 525

Gly Gly Ile Glu His Ala Ile Met His Leu Leu Tyr Phe Arg Phe Phe
        530                 535                 540

His Lys Leu Met Arg Asp Ala Gly Met Val Asn Ser Asp Glu Pro Ala
545                 550                 555                 560

Lys Gln Leu Leu Cys Gln Gly Met Val Leu Ala Asp Ala Phe Tyr Tyr
                565                 570                 575

Val Gly Glu Asn Gly Glu Arg Asn Trp Val Ser Pro Val Asp Ala Ile
                580                 585                 590

Val Glu Arg Asp Glu Lys Gly Arg Ile Val Lys Ala Lys Asp Ala Ala
            595                 600                 605

Gly His Glu Leu Val Tyr Thr Gly Met Ser Lys Met Ser Lys Ser Lys
```

```
                610                 615                 620
Asn Asn Gly Ile Asp Pro Gln Val Met Val Glu Arg Tyr Gly Ala Asp
625                 630                 635                 640

Thr Val Arg Leu Phe Met Met Phe Ala Ser Pro Ala Asp Met Thr Leu
                645                 650                 655

Glu Trp Gln Glu Ser Gly Val Glu Gly Ala Asn Arg Phe Leu Lys Arg
                660                 665                 670

Val Trp Lys Leu Val Tyr Glu His Thr Ala Lys Gly Asp Val Ala Ala
                675                 680                 685

Leu Asn Val Asp Ala Leu Thr Glu Asn Gln Lys Ala Leu Arg Arg Asp
690                 695                 700

Val His Lys Thr Ile Ala Lys Val Thr Asp Asp Ile Gly Arg Arg Gln
705                 710                 715                 720

Thr Phe Asn Thr Ala Ile Ala Ile Met Glu Leu Met Asn Lys Leu
                725                 730                 735

Ala Lys Ala Pro Thr Asp Gly Glu Gln Asp Arg Ala Leu Met Gln Glu
                740                 745                 750

Ala Leu Leu Ala Val Val Arg Met Leu Asn Pro Phe Thr Pro His Ile
                755                 760                 765

Cys Phe Thr Leu Trp Gln Glu Leu Lys Gly Glu Gly Asp Ile Asp Asn
770                 775                 780

Ala Pro Trp Pro Val Ala Asp Glu Lys Ala Met Val Glu Asp Ser Thr
785                 790                 795                 800

Leu Val Val Val Gln Val Asn Gly Lys Val Arg Ala Lys Ile Thr Val
                805                 810                 815

Pro Val Asp Ala Thr Glu Glu Gln Val Arg Glu Arg Ala Gly Gln Glu
                820                 825                 830

His Leu Val Ala Lys Tyr Leu Asp Gly Val Thr Val Arg Lys Val Ile
                835                 840                 845

Tyr Val Pro Gly Lys Leu Leu Asn Leu Val Val Gly
    850                 855                 860

<210> SEQ ID NO 188
<211> LENGTH: 334
<212> TYPE: PRT
<213> ORGANISM: E. coli

<400> SEQUENCE: 188

Met Thr Lys Pro Ile Val Phe Ser Gly Ala Gln Pro Ser Gly Glu Leu
1               5                   10                  15

Thr Ile Gly Asn Tyr Met Gly Ala Leu Arg Gln Trp Val Asn Met Gln
                20                  25                  30

Asp Asp Tyr His Cys Ile Tyr Cys Ile Val Asp Gln His Ala Ile Thr
            35                  40                  45

Val Arg Gln Asp Ala Gln Lys Leu Arg Lys Ala Thr Leu Asp Thr Leu
        50                  55                  60

Ala Leu Tyr Leu Ala Cys Gly Ile Asp Pro Glu Lys Ser Thr Ile Phe
65                  70                  75                  80

Val Gln Ser His Val Pro Glu His Ala Gln Leu Gly Trp Ala Leu Asn
                85                  90                  95

Cys Tyr Thr Tyr Phe Gly Glu Leu Ser Arg Met Thr Gln Phe Lys Asp
                100                 105                 110

Lys Ser Ala Arg Tyr Ala Glu Asn Ile Asn Ala Gly Leu Phe Asp Tyr
            115                 120                 125
```

```
Pro Val Leu Met Ala Ala Asp Ile Leu Leu Tyr Gln Thr Asn Leu Val
        130                 135                 140

Pro Val Gly Glu Asp Gln Lys Gln His Leu Glu Leu Ser Arg Asp Ile
145                 150                 155                 160

Ala Gln Arg Phe Asn Ala Leu Tyr Gly Glu Ile Phe Lys Val Pro Glu
                165                 170                 175

Pro Phe Ile Pro Lys Ser Gly Ala Arg Val Met Ser Leu Leu Glu Pro
            180                 185                 190

Thr Lys Lys Met Ser Lys Ser Asp Asp Asn Arg Asn Val Ile Gly
        195                 200                 205

Leu Leu Glu Asp Pro Lys Ser Val Val Lys Ile Lys Arg Ala Val
210                 215                 220

Thr Asp Ser Asp Glu Pro Val Val Arg Tyr Asp Val Gln Asn Lys
225                 230                 235                 240

Ala Gly Val Ser Asn Leu Leu Asp Ile Leu Ser Ala Val Thr Gly Gln
                245                 250                 255

Ser Ile Pro Glu Leu Glu Lys Gln Phe Glu Gly Lys Met Tyr Gly His
            260                 265                 270

Leu Lys Gly Glu Val Ala Asp Ala Val Ser Gly Met Leu Thr Glu Leu
275                 280                 285

Gln Glu Arg Tyr His Arg Phe Arg Asn Asp Glu Ala Phe Leu Gln Gln
290                 295                 300

Val Met Lys Asp Gly Ala Glu Lys Ala Ser Ala His Ala Ser Arg Thr
305                 310                 315                 320

Leu Lys Ala Val Tyr Glu Ala Ile Gly Phe Val Ala Lys Pro
                325                 330
```

<210> SEQ ID NO 189
<211> LENGTH: 860
<212> TYPE: PRT
<213> ORGANISM: E. coli

<400> SEQUENCE: 189

```
Met Gln Glu Gln Tyr Arg Pro Glu Glu Ile Glu Ser Lys Val Gln Leu
1               5                   10                  15

His Trp Asp Glu Lys Arg Thr Phe Glu Val Thr Glu Asp Glu Ser Lys
                20                  25                  30

Glu Lys Tyr Tyr Cys Leu Ser Met Leu Pro Tyr Pro Ser Gly Arg Leu
            35                  40                  45

His Met Gly His Val Arg Asn Tyr Thr Ile Gly Asp Val Ile Ala Arg
        50                  55                  60

Tyr Gln Arg Met Leu Gly Lys Asn Val Leu Gln Pro Ile Gly Trp Asp
65                  70                  75                  80

Ala Phe Gly Leu Pro Ala Glu Gly Ala Ala Val Lys Asn Asn Thr Ala
                85                  90                  95

Pro Ala Pro Trp Thr Tyr Asp Asn Ile Ala Tyr Met Lys Asn Gln Leu
            100                 105                 110

Lys Met Leu Gly Phe Gly Tyr Asp Trp Ser Arg Glu Leu Ala Thr Cys
        115                 120                 125

Thr Pro Glu Tyr Tyr Arg Trp Glu Gln Lys Phe Phe Thr Glu Leu Tyr
    130                 135                 140

Lys Lys Gly Leu Val Tyr Lys Lys Thr Ser Ala Val Asn Trp Cys Pro
145                 150                 155                 160

Asn Asp Gln Thr Val Leu Ala Asn Glu Gln Val Ile Asp Gly Cys Cys
                165                 170                 175
```

-continued

```
Trp Arg Cys Asp Thr Lys Val Glu Arg Lys Glu Ile Pro Gln Trp Phe
            180                 185                 190
Ile Lys Ile Thr Ala Tyr Ala Asp Glu Leu Leu Asn Asp Leu Asp Lys
        195                 200                 205
Leu Asp His Trp Pro Asp Thr Val Lys Thr Met Gln Arg Asn Trp Ile
210                 215                 220
Gly Arg Ser Glu Gly Val Glu Ile Thr Phe Asn Val Asn Asp Tyr Asp
225                 230                 235                 240
Asn Thr Leu Thr Val Tyr Thr Thr Arg Pro Asp Thr Phe Met Gly Cys
                245                 250                 255
Thr Tyr Leu Ala Val Ala Ala Gly His Pro Leu Ala Gln Lys Ala Ala
            260                 265                 270
Glu Asn Asn Pro Glu Leu Ala Ala Phe Ile Asp Glu Cys Arg Asn Thr
        275                 280                 285
Lys Val Ala Glu Ala Glu Met Ala Thr Met Glu Lys Lys Gly Val Asp
    290                 295                 300
Thr Gly Phe Lys Ala Val His Pro Leu Thr Gly Glu Glu Ile Pro Val
305                 310                 315                 320
Trp Ala Ala Asn Phe Val Leu Met Glu Tyr Gly Thr Gly Ala Val Met
                325                 330                 335
Ala Val Pro Gly His Asp Gln Arg Asp Tyr Glu Phe Ala Ser Lys Tyr
            340                 345                 350
Gly Leu Asn Ile Lys Pro Val Ile Leu Ala Ala Asp Gly Ser Glu Pro
        355                 360                 365
Asp Leu Ser Gln Gln Ala Leu Thr Glu Lys Gly Val Leu Phe Asn Ser
    370                 375                 380
Gly Glu Phe Asn Gly Leu Asp His Glu Ala Ala Phe Asn Ala Ile Ala
385                 390                 395                 400
Asp Lys Leu Thr Ala Met Gly Val Gly Glu Arg Lys Val Asn Tyr Arg
                405                 410                 415
Leu Arg Asp Trp Gly Val Ser Arg Gln Arg Tyr Trp Gly Ala Pro Ile
            420                 425                 430
Pro Met Val Thr Leu Glu Asp Gly Thr Val Met Pro Thr Pro Asp Asp
        435                 440                 445
Gln Leu Pro Val Ile Leu Pro Glu Asp Val Val Met Asp Gly Ile Thr
    450                 455                 460
Ser Pro Ile Lys Ala Asp Pro Glu Trp Ala Lys Thr Thr Val Asn Gly
465                 470                 475                 480
Met Pro Ala Leu Arg Glu Thr Asp Thr Phe Asp Thr Phe Met Glu Ser
                485                 490                 495
Ser Trp Tyr Tyr Ala Arg Tyr Thr Cys Pro Gln Tyr Lys Glu Gly Met
            500                 505                 510
Leu Asp Ser Glu Ala Ala Asn Tyr Trp Leu Pro Val Asp Ile Tyr Ile
        515                 520                 525
Gly Gly Ile Glu His Ala Ile Met His Leu Leu Tyr Phe Arg Phe Phe
    530                 535                 540
His Lys Leu Met Arg Asp Ala Gly Met Val Asn Ser Asp Glu Pro Ala
545                 550                 555                 560
Lys Gln Leu Leu Cys Gln Gly Met Val Leu Ala Asp Ala Phe Tyr Tyr
                565                 570                 575
Val Gly Glu Asn Gly Glu Arg Asn Trp Val Ser Pro Val Asp Ala Ile
            580                 585                 590
```

| | | | | | | | | | | | | | | |
|---|---|---|---|---|---|---|---|---|---|---|---|---|---|---|
| Val | Glu | Arg | Asp | Glu | Lys | Gly | Arg | Ile | Val | Lys | Ala | Lys | Asp | Ala | Ala |
| | | 595 | | | | 600 | | | | 605 | | | | |
| Gly | His | Glu | Leu | Val | Tyr | Thr | Gly | Met | Ser | Lys | Met | Ser | Lys | Ser | Lys |
| 610 | | | | | 615 | | | | 620 | | | | | | |
| Asn | Asn | Gly | Ile | Asp | Pro | Gln | Val | Met | Val | Glu | Arg | Tyr | Gly | Ala | Asp |
| 625 | | | | 630 | | | | 635 | | | | 640 | | | |
| Thr | Val | Arg | Leu | Phe | Met | Met | Phe | Ala | Ser | Pro | Ala | Asp | Met | Thr | Leu |
| | | | 645 | | | | 650 | | | | 655 | | | | |
| Glu | Trp | Gln | Glu | Ser | Gly | Val | Glu | Gly | Ala | Asn | Arg | Phe | Leu | Lys | Arg |
| | | 660 | | | | 665 | | | | 670 | | | | | |
| Val | Trp | Lys | Leu | Val | Tyr | Glu | His | Thr | Ala | Lys | Gly | Asp | Val | Ala | Ala |
| | 675 | | | | 680 | | | | 685 | | | | | | |
| Leu | Asn | Val | Asp | Ala | Leu | Thr | Glu | Asn | Gln | Lys | Ala | Leu | Arg | Arg | Asp |
| 690 | | | | | 695 | | | | 700 | | | | | | |
| Val | His | Lys | Thr | Ile | Ala | Lys | Val | Thr | Asp | Asp | Ile | Gly | Arg | Arg | Gln |
| 705 | | | | 710 | | | | 715 | | | | 720 | | | |
| Thr | Phe | Asn | Thr | Ala | Ile | Ala | Ile | Met | Glu | Leu | Met | Asn | Lys | Leu |
| | | | 725 | | | | 730 | | | | 735 | | | | |
| Ala | Lys | Ala | Pro | Thr | Asp | Gly | Glu | Gln | Asp | Arg | Ala | Leu | Met | Gln | Glu |
| | | 740 | | | | 745 | | | | 750 | | | | | |
| Ala | Leu | Leu | Ala | Val | Val | Arg | Met | Leu | Asn | Pro | Phe | Thr | Pro | His | Ile |
| | 755 | | | | 760 | | | | 765 | | | | | | |
| Cys | Phe | Thr | Leu | Trp | Gln | Glu | Leu | Lys | Gly | Glu | Gly | Asp | Ile | Asp | Asn |
| 770 | | | | | 775 | | | | 780 | | | | | | |
| Ala | Pro | Trp | Pro | Val | Ala | Asp | Glu | Lys | Ala | Met | Val | Glu | Asp | Ser | Thr |
| 785 | | | | 790 | | | | 795 | | | | 800 | | | |
| Leu | Val | Val | Val | Gln | Val | Asn | Gly | Lys | Val | Arg | Ala | Lys | Ile | Thr | Val |
| | | | 805 | | | | 810 | | | | 815 | | | | |
| Pro | Val | Asp | Ala | Thr | Glu | Glu | Gln | Val | Arg | Glu | Arg | Ala | Gly | Gln | Glu |
| | | 820 | | | | 825 | | | | 830 | | | | | |
| His | Leu | Val | Ala | Lys | Tyr | Leu | Asp | Gly | Val | Thr | Val | Arg | Lys | Val | Ile |
| | 835 | | | | 840 | | | | 845 | | | | | | |
| Tyr | Val | Pro | Gly | Lys | Leu | Leu | Asn | Leu | Val | Val | Gly |
| 850 | | | | | 855 | | | | 860 | | |

<210> SEQ ID NO 190
<211> LENGTH: 2853
<212> TYPE: DNA
<213> ORGANISM: Artificial
<220> FEATURE:
<223> OTHER INFORMATION: artificially synthesized sequence

<400> SEQUENCE: 190

```
atggaaaaaa cctataatcc gcaagacatt gaacaaccgc tgtatgaaca ctgggaaaaa      60
caaggctact ttaaaccgaa cggcgatgaa agtcaggaat ccttttgcat tatgattccg     120
ccgccgggcg tgtcaggttc gctgcatatg ggccacgcgt tccagcaaac gattatggat     180
accatgatcc gttatcagcg catgcaaggt aaaaacacgc tgtggcaggt tggcaccgat     240
catgcaggta tcgctacgca aatggtggtt gaacgtaaaa ttgcggccga agaaggcaaa     300
acccgtcacg actacggtcg cgaagcgttt attgataaaa tctgggaatg aaagccgaa     360 agtggcggta ccattacgcg tcagatgcgt cgcctgggta actccgtgga ctgggaacgt     420
gaacgcttta ccatggatga aggtctgagc aatgcagtta agaagttttt cgtccgtctg     480
tataaagaag atctgatcta ccgtggcaaa cgcctggtga actgggaccc gaaactgcgc     540
```

```
accgccattt ctgatctgga agttgaaaat cgtgaatcaa aaggttcgat gtggcatatc   600
cgctatccgc tggcggatgg cgccaaaacc gcagatggta aagactacct ggtcgtggca   660
accacgcgtc cggaaacgct gctgggcgat accggtgtgg ccgttaaccc ggaagacccg   720
cgctataaag atctgattgg caaatacgtg atcctgccgc tggttaatcg tcgcattccg   780
atcgtgggtg acgaacacgc ggatatggaa aaaggcaccg gttgcgttaa aattgcgccg   840
gcccatgatt ttaacgacta tgaagtcggc aaacgtcacg ccctgccgat gattaatatc   900
ctgacgtttg atggcgacat cgcgaaagt gcacaggtct tcgacaccaa gggtaatgaa   960
tccgatgtgt acagctctga atcccggcg gaatttcaaa aactggaacg tttcgcagct  1020
cgcaaagcag ttgtcgcagc agtcgatgca ctgggtctgc tggaagaaat taaaccgcat  1080
gacctgacgg ttccgtatgg tgatcgtggc ggtgtggtta tcgaaccgat gctgaccgac  1140
cagtggtatg tgcgcgccga tgtcctggct aaaccggcgg tcgaagccgt ggaaaacggt  1200
gatattcagt ttgtgccgaa acaatacgaa aacatgtact tctcatggat gcgtgatatt  1260
caggactggt gtatctcgcg tcaactgtgg tggggccatc gcattccggc atggtatgat  1320
gaagctggca acgtctacgt gggtcgtaat gaagacgaag tgcgcaaaga aaacaatctg  1380
ggtgcggatg tcgtgctgcg ccaggatgaa gacgttctgg acacctggtt tagttccgca  1440
ctgtggacct tcagtacgct gggctggccg gaaaacacgg atgcgctgcg tcagtttcac  1500
ccgaccagcg ttatggtctc tggtttcgac attatctttt tctggattgc ccgcatgatc  1560
atgatgacca tgcatttcat caaagatgaa acggcaaac cgcaggtccc gttccacacg  1620
gtgtatatga ccgcctgat ccgtgatgac gaaggtcaaa aaatgagcaa atctaaaggc  1680
aacgttatcg atccgctgga catggtcgat ggtattagcc tgccggaact gctggaaaaa  1740
cgcacgggta acatgatgca gccgcaactg gcggataaaa tccgtaaacg caccgaaaaa  1800
cagtttccga atggcattga accgcatggt acggatgcgc tgcgtttcac cctggcagct  1860
ctggcatcaa ccggtcgtga cattaattgg gatatgaaac gcctggaagg ttatcgcaac  1920
ttttgcaata aactgtggaa cgcctcacgt ttcgtgctga tgaatacgga aggccaggat  1980
tgtggtttta acgcggtga atgaccctg tcgctggcag accgctggat cctggctgaa  2040
ttcaatcaaa cgattaaagc gtaccgtgaa gccctggact cttttcgctt cgatattgcg  2100
gccggcatcc tgtatgaatt tacctggaac cagttctgcg attggtacct ggaactgacg  2160
aaaccggtga tgaatggcgg taccgaagcg gaactgcgtg gcacccgcca tacgctggtg  2220
accgttctgg aaggtctgct gcgtctgcc cacccgatta tcccgtttat taccgaaacg  2280
atctggcagc gcgtcaaagt gctgtgtggt attacggcgg ataccatcat gctgcagccg  2340
ttcccgcaat atgacgcaag tcaggttgat gaagcagctc tggctgatac cgaatggctg  2400
aaacaagcaa ttgttgctgt ccgtaacatc cgcgcggaaa tgaatattgc cccgggcaaa  2460
ccgctggaac tgctgctgcg tggttgttcc gcagatgctg aacgtcgcgt gaacgaaaat  2520
cgtggctttc tgcagacgct ggcacgcctg gaaagcatta ccgttctgcc ggctgatgac  2580
aaaggtccgg tgtctgttac caaaattatc gatggcgcag aactgctgat cccgatggct  2640
ggtctgatta caaagaaga cgaactgcg cgtctggcca agaagtggc aaaaattgaa  2700
ggcgaaatta ccgcatcga aacaaactg gctaatgaag ttttgtggc gcgtgccccg  2760
gaagcagtta tcgctaaaga acgcgaaaaa ctggaaggtt acgcagaagc aaaagccaaa  2820
ctgattgaac aacaagcggt tatcgcagca ctg                               2853
```

<210> SEQ ID NO 191
<211> LENGTH: 2853
<212> TYPE: DNA
<213> ORGANISM: Artificial
<220> FEATURE:
<223> OTHER INFORMATION: artificially synthesized sequence

<400> SEQUENCE: 191

| | |
|---|---:|
| atggaaaaaa cctataatcc gcaagacatt gaacaaccgc tgtatgaaca ctgggaaaaa | 60 |
| caaggctact ttaaaccgaa cggcgatgaa agtcaggaat cctttttgcat tatgattccg | 120 |
| ccgccgggcg tgtcaggttc gctgcatatg ggccacgcgt tccagcaaac gattatggat | 180 |
| accatgatcc gttatcagcg catgcaaggt aaaaacacgc tgtggcaggt tggcaccgat | 240 |
| catgcaggta tcgctacgca aatggtggtt gaacgtaaaa ttgcggccga agaaggcaaa | 300 |
| acccgtcacg actacggtcg cgaagcgttt attgataaaa tctgggaatg gaaagccgaa | 360 |
| agtggcggta ccattacgcg tcagatgcgt cgcctgggta actccgtgga ctgggaacgt | 420 |
| gaacgcttta ccatggatga aggtctgagc aatgcagtta agaagttttt cgtccgtctg | 480 |
| tataaagaag atctgatcta ccgtggcaaa cgcctggtga actgggaccc gaaactgcgc | 540 |
| accgccattt ctgatctgga agttgaaaat cgtgaatcaa aaggttcgat gtggcatatc | 600 |
| cgctatccgc tggcggatgg cgccaaaacc gcagatggta agactacct ggtcgtggca | 660 |
| accacgcgtc cggaaacgct gctgggcgat accggtgtgg ccgttaaccc ggaagacccg | 720 |
| cgctataaag atctgattgg caaatacgtg atcctgccgc tggttaatcg tcgcattccg | 780 |
| atcgtgggtg acgaacacgc ggatatggaa aaaggcaccg gttgcgttaa aattggtccg | 840 |
| gcccatgatt ttaacgacta tgaagtcggc aaacgtcacg ccctgccgat gattaatatc | 900 |
| ctgacgtttg atgcgacat cgcgaaagt gcacaggtct cgacaccaa gggtaatgaa | 960 |
| tccgatgtgt acagctctga atcccggcg gaatttcaaa actggaacg tttcgcagct | 1020 |
| cgcaaagcag ttgtcgcagc agtcgatgca ctgggtctgc tggaagaaat taaaccgcat | 1080 |
| gacctgacgg ttccgtatgg tgatcgtggc ggtgtggtta tcgaaccgat gctgaccgac | 1140 |
| cagtggtatg tgcgcgccga tgtcctggct aaaccggcgg tcgaagccgt ggaaaacggt | 1200 |
| gatattcagt ttgtgccgaa acaatacgaa aacatgtact tctcatggat gcgtgatatt | 1260 |
| caggactggt gtatctcgcg tcaactgtgt gggccatc gcattccggc atggtatgat | 1320 |
| gaagctggca acgtctacgt gggtcgtaat gaagacgaag tgcgcaaaga aaacaatctg | 1380 |
| ggtgcggatg tcgtgctgcg ccaggatgaa gacgttctgg acacctggtt tagttccgca | 1440 |
| ctgtggacct tcagtacgct gggctggccg gaaaacacgg atgcgctgcg tcagtttcac | 1500 |
| ccgaccagcg ttatggtctc tggtttcgac attatctttt tctggattgc ccgcatgatc | 1560 |
| atgatgacca tgcatttcat caagatgaa acggcaaac gcaggtccc gttccacacg | 1620 |
| gtgtatatga ccggcctgat ccgtgatgac gaaggtcaaa aaatgagcaa atctaaaggc | 1680 |
| aacgttatcg atccgctgga catggtcgat ggtattagcc tgccggaact gctggaaaaa | 1740 |
| cgcacgggta acatgatgca accgcaactg gcggataaaa tccgtaaacg caccgaaaaa | 1800 |
| cagtttccga atggcattga accgcatggt acggatgcgc tgcgtttcac cctggcagct | 1860 |
| ctggcatcaa ccggtcgtga cattaattgg gatatgaaac gcctggaagg ttatcgcaac | 1920 |
| ttttgcaata aactgtggaa cgcctcacgt ttcgtgctga tgaatacgga aggccaggat | 1980 |
| tgtggtttta cggcggtga atgaccctg tcgctggcag accgctggat cctggctgaa | 2040 |
| ttcaatcaaa cgattaaagc gtaccgtgaa gccctggact cttttcgctt cgatattgcg | 2100 |

| | |
|---|---|
| gccggcatcc tgtatgaatt tacctggaac cagttctgcg attggtacct ggaactgacg | 2160 |
| aaaccggtga tgaatggcgg taccgaagcg gaactgcgtg gcacccgcca tacgctggtg | 2220 |
| accgttctgg aaggtctgct gcgtctggcc cacccgatta tcccgtttat taccgaaacg | 2280 |
| atctggcagc gcgtcaaagt gctgtgtggt attacggcgg ataccatcat gctgcagccg | 2340 |
| ttcccgcaat atgacgcaag tcaggttgat gaagcagctc tggctgatac cgaatggctg | 2400 |
| aaacaagcaa ttgttgctgt ccgtaacatc cgcgcggaaa tgaatattgc cccgggcaaa | 2460 |
| ccgctggaac tgctgctgcg tggttgttcc gcagatgctg aacgtcgcgt gaacgaaaat | 2520 |
| cgtggctttc tgcagacgct ggcacgcctg gaaagcatta ccgttctgcc ggctgatgac | 2580 |
| aaaggtccgg tgtctgttac caaaattatc gatggcgcag aactgctgat cccgatggct | 2640 |
| ggtctgatta caaagaaga cgaactggcg cgtctggcca agaagtggc aaaaattgaa | 2700 |
| ggcgaaatta gccgcatcga aaacaaactg gctaatgaag ttttgtggc gcgtgccccg | 2760 |
| gaagcagtta tcgctaaaga acgcgaaaaa ctggaaggtt acgcagaagc aaaagccaaa | 2820 |
| ctgattgaac aacaagcggt tatcgcagca ctg | 2853 |

<210> SEQ ID NO 192
<211> LENGTH: 1002
<212> TYPE: DNA
<213> ORGANISM: Artificial
<220> FEATURE:
<223> OTHER INFORMATION: artificially synthesized sequence

<400> SEQUENCE: 192

| | |
|---|---|
| atgacgaaac cgattgtctt ctctggtgct caaccgtctg gtgaactgac gattggtaac | 60 |
| tacatgggtg ctctgcgcca gtgggtgaac atgcaggatg actatcattg catttactgt | 120 |
| atcgtggatc aacacgccat taccgttcgt caggacgctc aaaaactgcg caaagcgacc | 180 |
| ctggatacgc tggccctgta tctggcatgc ggtattgacc cggaaaaatc aacgatcttt | 240 |
| gtgcagtcgc atgttccgga acacgctcaa ctgggttggg cgctgaactg ttatacctac | 300 |
| tttggcgaac tgtcacgtat gacgcagttc aaagataaat cggctcgcta tgcggaaaac | 360 |
| attaatgcgg gtctgtttga ttacccggtg ctgatggcgg ccgacatcct gctgtatcag | 420 |
| accaacctgg ttccggtcgg cgaagatgca aaacaagcac tggaactgag ccgtgacatc | 480 |
| gcccagcgct tcaatgcact gtacggtgaa atttttaaag tcccggaacc gttcatcccg | 540 |
| aaaagcggcg cccgtgtgat gtctctgctg gaaccgacca agaaaatgag caaatctgat | 600 |
| gacaaccgca acaatgttat tggcctgctg gaagatccga aaagcgtggt gaagaaaatt | 660 |
| aaacgtgcgg tcaccgattc tgacgaaccg ccggtcgtgc gctatgatgt tcagaacaaa | 720 |
| gctggtgtct caaatctgct ggatattctg agtgcagtga cgggccagtc catcccggaa | 780 |
| ctggaaaaac aattcgaagg caaaatgtac ggtcatctga aggcgaagt cgcagatgct | 840 |
| gtgtccggta tgctgaccga actgcaggaa cgttatcacc gttttcgcaa tgatgaagcc | 900 |
| ttcctgcagc aagttatgaa agacggcgca gaaaaagcga gtgcccacgc atcccgcacg | 960 |
| ctgaaagcgg tctacgaagc aatcggcttt gtggcgaaac cg | 1002 |

<210> SEQ ID NO 193
<211> LENGTH: 1002
<212> TYPE: DNA
<213> ORGANISM: Artificial
<220> FEATURE:
<223> OTHER INFORMATION: artificially synthesized sequence

<400> SEQUENCE: 193

```
atgacgaaac cgattgtctt ctctggtgct caaccgtctg gtgaactgac gattggtaac    60
tacatgggtg ctctgcgcca gtgggtgaac atgcaggatg actatcattg catttactgt   120
atcgtggatc aacacgccat taccgttcgt caggacgctc aaaaactgcg caaagcgacc   180
ctggatacgt ggccctgta tctggcatgc ggtattgacc cggaaaaatc aacgatcttt    240
gtgcagtcgc atgttccgga acacgctcaa ctgggttggg cgctgaactg ttatacctac   300
tttggcgaac tgtcacgtat gacgcagttc aaagataaat cggctcgcta tgcggaaaac   360
attaatgcgg gtctgtttga ttacccggtg ctggcggcgg ccgacatcct gctgtatcag   420
accaacctgg ttccggtcgg cgaagatcag aaacaacatc tggaactgag ccgtgacatc   480
gcccagcgct tcaatgcact gtacggtgaa attttaaag tcccggaacc gttcatcccg    540
aaaagcggcg cccgtgtgat gtctctgctg gaaccgacca agaaaatgag caaatctgat   600
gacaaccgca acaatgttat tggcctgctg gaagatccga aaagcgtggt gaagaaaatt   660
aaacgtgcgg tcaccgattc tgacgaaccg ccggtcgtgc gctatgatgt tcagaacaaa   720
gctggtgtct caaatctgct ggatattctg agtgcagtga cgggccagtc catcccggaa   780
ctggaaaaac aattcgaagg caaaatgtac ggtcatctga aaggcgaagt cgcagatgct   840
gtgtccggta tgctgaccga actgcaggaa cgttatcacc gttttcgcaa tgatgaagcc   900
ttcctgcagc aagttatgaa agacggcgca gaaaaagcga gtgcccacgc atcccgcacg   960
ctgaaagcgg tctacgaagc aatcggcttt gtggcgaaac cg                     1002
```

<210> SEQ ID NO 194
<211> LENGTH: 1002
<212> TYPE: DNA
<213> ORGANISM: Artificial
<220> FEATURE:
<223> OTHER INFORMATION: artificially synthesized sequence

<400> SEQUENCE: 194

```
atgacgaaac cgattgtctt ctctggtgct caaccgtctg gtgaactgac gattggtaac    60
tacatgggtg ctctgcgcca gtgggtgaac atgcaggatg actatcattg catttactgt   120
atcgtggatc aacacgccat taccgttcgt caggacgctc aaaaactgcg caaagcgacc   180
ctggatacgc tggccctgta tctggcatgc ggtattgacc cggaaaaatc aacgatcttt   240
gtgcagtcgc atgttccgga acacgctcaa ctgggttggg cgctgaactg ttatacctac   300
tttggcgaac tgtcacgtat gacgcagttc aaagataaat cggctcgcta tgcggaaaac   360
attaatgcgg gtctgtttga ttacccggtg ctggtggcgg ccgacatcct gctgtatcag   420
accaacctgg ttccggtcgg cgaagatgca aaacaagccc tggaactgag ccgtgacatc   480
gcccagcgct tcaatgcact gtacggtgaa attttaaag tcccggaacc gttcatcccg    540
aaaagcggcg cccgtgtgat gtctctgctg gaaccgacca agaaaatgag caaatctgat   600
gacaaccgca acaatgttat tggcctgctg gaagatccga aaagcgtggt gaagaaaatt   660
aaacgtgcgg tcaccgattc tgacgaaccg ccggtcgtgc gctatgatgt tcagaacaaa   720
gctggtgtct caaatctgct ggatattctg agtgcagtga cgggccagtc catcccggaa   780
ctggaaaaac aattcgaagg caaaatgtac ggtcatctga aaggcgaagt cgcagatgct   840
gtgtccggta tgctgaccga actgcaggaa cgttatcacc gttttcgcaa tgatgaagcc   900
ttcctgcagc aagttatgaa agacggcgca gaaaaagcga gtgcccacgc atcccgcacg   960
ctgaaagcgg tctacgaagc aatcggcttt gtggcgaaac cg                     1002
```

<210> SEQ ID NO 195
<211> LENGTH: 2580
<212> TYPE: DNA
<213> ORGANISM: Artificial
<220> FEATURE:
<223> OTHER INFORMATION: artificially synthesized sequence

<400> SEQUENCE: 195

```
atgcaagaac ataccgccc ggaagaaatc gaaagtaaag tccaactgca ctgggatgaa      60
aaacgcacct ttgaagtcac ggaagacgaa tctaaagaaa atattactg cctgagcatg     120
ctgccgggtc cgtctggtcg tctgcatatg ggtcacgtgc gcaactatac cattggcgat    180
gttatcgcgc gttaccagcg catgctgggt aaaaatgttc tgcaaccgat ggctgggac    240
gcatttggtc tgccggctga aggcgcggcc gtgaaaaaca ataccgcacc ggctccgtgg    300
acgtatgata acatcgcata catgaaaaat cagctgaaaa tgctgggctt cggttatgac    360
tggtctcgtg aactggcgac ctgtacgccg aatattacc gctgggaaca aaaatttttc    420
accgaactgt acaaaaaagg tctggtctac aagaaaacca cgcgcggtga actggtgcccg   480
aatgatcaaa cggtcctggc caacgaacaa gtgattgatg ctgctgttg gcgttgtgac    540
accaaagttg aacgcaaaga aatcccgcag tggtttatta aaatcacggc gtatgccgat   600
gaactgctga cgatctgga caaactggat cattggccgg acaccgtgaa acgatgcag    660
cgtaattgga ttggccgcag cgaaggtgtt gaaatcacct taacgtcaa tgattatgac    720
aacaccctga cggtctacac cacgcgtccg gataccttca tgggttgcac gtacctggca    780
gtggcagctg tcacccgct ggctcagaaa gcagcagaaa caatccgga actggcagct    840
tttattgatg aatgtcgcaa taccaaagtg gcagaagctg aaatggcaac catggagaaa   900
aaaggcgtgg atacgggttt taagctgtc catccgctga ccggtgaaga atcccggtg    960
tgggcggcca acttcgttct gatggaatat ggtacgggtg cagtcatggc tgtgccgggt   1020
cacgatcagc gtgactatga atttgcctcc aaatacggtc tgaatattaa accgttatc    1080
ctggcagctg atggctcaga accggacctg tcgcagcaag cactgaccga aaaggtgtg    1140
ctgtttaact caggcgaatt caatggtctg atcatgaag cggccttcaa cgcgattgcc    1200
gacaaactga ccgcgatggg cgttggtgaa cgcaaagtca attatcgtct gcgcgattgg   1260
ggtgtgtcgc gtcagcgtta ctgggggtgca ccgattccga tggtgacccct ggaagatggc  1320
accgttatgc cgacgccgga tgaccaactg ccggttatcc tgccggaaga tgtggttatg   1380
gacggtatta ccagcccgat caaagctgat ccggaatggg ccaaaaccac ggtgaatggc   1440
atgccggcgc tgcgtgaaac cgatacgttt gacaccttca tggaaagctc ttggtattac   1500
gcccgctata cgtgcccgca gtacaaagaa ggcatgctgg atagcgaagc agctaactat   1560
tggctgccgg ttgacattta catcggcggt attgaacatg cgatcatgca cctgctgtat   1620
tttcgtttct tcataaaact gatgcgcgat gccggtatgg tgaattcaga cgaaccggct   1680
aaacagctgc tgtgtcaagg catggtcctg gcagatgctt tctattacgt gggcgaaaac   1740
ggtgaacgta attgggtttc gccggtcgat gcgattgttg aacgtgacga aaaaggtcgc   1800
atcgtcaaag ccaaagatgc ggccggtcac gaactggtgt ataccggcat gagcaaaatg   1860
agtaaatcca aaaacaacgg tatcgatccg caggttatgg tcgaacgtta cggcgcggac   1920
accgttcgcc tgtttatgat gttcgcgagt ccggccgata tgacgctgga atggcaagaa   1980
tccggcgtga aggtgccaa ccgttttctg aacgcgtgt ggaaactggt ttatgaacat    2040
accgcaaaag gcgatgtggc agctctgaac gttgacgcac tgacggaaaa tcagaaagct   2100
```

-continued

```
ctgcgtcgcg atgtccacaa aaccattgca aaagtgacgg atgacatcgg tcgtcgccaa    2160
acctttaaca cggcgattgc ggccatcatg gaactgatga ataaactggc gaaagcaccg    2220
accgatggtg aacaggaccg tgcactgatg caagaagcac tgctggctgt cgtgcgcatg    2280
ctgaacccgt ttaccccgca tatttgcttc acgctgtggc aggaactgaa aggcgaaggt    2340
gatatcgaca atgccccgtg gccggttgcg gatgaaaaag ccatggtcga agacagtacc    2400
ctggttgtcg tgcaggtcaa tggtaaagtg cgcgcgaaaa ttaccgtgcc ggttgatgcc    2460
acggaagaac aagtgcgtga acgcgcgggc caagaacacc tggttgccaa atatctggat    2520
ggcgtcacgg tccgcaaagt catctatgtt ccgggtaaac tgctgaatct ggtcgttggt    2580
```

<210> SEQ ID NO 196
<211> LENGTH: 92
<212> TYPE: DNA
<213> ORGANISM: Artificial
<220> FEATURE:
<223> OTHER INFORMATION: artificially synthesized sequence

<400> SEQUENCE: 196

```
ggcgtaatac gactcactat agggttaact ttaacaagga gaaaacatg cgttggcgtg     60 actacaagga cgacgacgac aagtaagctt cg                                   92
```

<210> SEQ ID NO 197
<211> LENGTH: 71
<212> TYPE: RNA
<213> ORGANISM: Artificial
<220> FEATURE:
<223> OTHER INFORMATION: artificially synthesized sequence

<400> SEQUENCE: 197

```
ggguuaacuu uaacaaggag aaaaacaugc guuggcguga cuacaaggac gacgacgaca    60
aguaagcuuc g                                                          71
```

<210> SEQ ID NO 198
<211> LENGTH: 12
<212> TYPE: PRT
<213> ORGANISM: Artificial
<220> FEATURE:
<223> OTHER INFORMATION: artificially synthesized sequence

<400> SEQUENCE: 198

```
Met Arg Trp Arg Asp Tyr Lys Asp Asp Asp Asp Lys
1               5                   10
```

<210> SEQ ID NO 199
<211> LENGTH: 12
<212> TYPE: PRT
<213> ORGANISM: Artificial
<220> FEATURE:
<223> OTHER INFORMATION: artificially synthesized sequence
<220> FEATURE:
<221> NAME/KEY: misc_feature
<222> LOCATION: (3)..(3)
<223> OTHER INFORMATION: Xaa is methyl tryptophan

<400> SEQUENCE: 199

```
Met Arg Xaa Arg Asp Tyr Lys Asp Asp Asp Asp Lys
1               5                   10
```

<210> SEQ ID NO 200
<211> LENGTH: 92
<212> TYPE: DNA

```
<213> ORGANISM: Artificial
<220> FEATURE:
<223> OTHER INFORMATION: artificially synthesized sequence

<400> SEQUENCE: 200
ggcgtaatac gactcactat agggttaact ttaacaagga gaaaaacatg cgtctccgtg      60
actacaagga cgacgacgac aagtaagctt cg                                   92

<210> SEQ ID NO 201
<211> LENGTH: 71
<212> TYPE: RNA
<213> ORGANISM: Artificial
<220> FEATURE:
<223> OTHER INFORMATION: artificially synthesized sequence

<400> SEQUENCE: 201
ggguuaacuu uaacaaggag aaaaacaugc gucuccguga cuacaaggac gacgacgaca      60
aguaagcuuc g                                                          71

<210> SEQ ID NO 202
<211> LENGTH: 12
<212> TYPE: PRT
<213> ORGANISM: Artificial
<220> FEATURE:
<223> OTHER INFORMATION: artificially synthesized sequence

<400> SEQUENCE: 202

Met Arg Leu Arg Asp Tyr Lys Asp Asp Asp Asp Lys
1               5                   10

<210> SEQ ID NO 203
<211> LENGTH: 12
<212> TYPE: PRT
<213> ORGANISM: Artificial
<220> FEATURE:
<223> OTHER INFORMATION: artificially synthesized sequence
<220> FEATURE:
<221> NAME/KEY: misc_feature
<222> LOCATION: (3)..(3)
<223> OTHER INFORMATION: Xaa is methyl leucine

<400> SEQUENCE: 203

Met Arg Xaa Arg Asp Tyr Lys Asp Asp Asp Asp Lys
1               5                   10

<210> SEQ ID NO 204
<211> LENGTH: 97
<212> TYPE: DNA
<213> ORGANISM: Artificial
<220> FEATURE:
<223> OTHER INFORMATION: artificially synthesized sequence

<400> SEQUENCE: 204
ggcgtaatac gactcactat agggtgatta gctcagctgg gagagcacct cccttacaag     60 gaggggtcg gcggttcgat cccgtcatca cccacca                               97

<210> SEQ ID NO 205
<211> LENGTH: 76
<212> TYPE: RNA
```

```
<213> ORGANISM: Artificial
<220> FEATURE:
<223> OTHER INFORMATION: artificially synthesized sequence

<400> SEQUENCE: 205
gggugauuag cucagcuggg agagcaccuc ccuuacaagg aggggucgg cgguucgauc    60 ccgucaucac ccacca                                                  76
```

MODIFIED AMINOACYL-TRNA SYNTHETASE AND USE THEREOF

CROSS-REFERENCE TO RELATED APPLICATIONS

This application is a National Stage application of PCT/JP2016/057707, filed Mar. 11, 2016, which claims priority from Japanese application JP 2015-051202, filed Mar. 13, 2015, each of which is incorporated herein by reference in its entirety.

TECHNICAL FIELD

The present invention relates to aminoacyl-tRNA synthetases (ARSs) that aminoacylate tRNA with the corresponding N-methyl amino acid more efficiently than natural aminoacyl-tRNA synthetases, and use thereof. More specifically, the present invention relates to aminoacyl-tRNA synthetases that have modified amino acid sequences, which are able to aminoacylate a tRNA with one of six N-methyl-substituted amino acids corresponding to the tRNA, namely, N-methyl-phenylalanine, N-methyl-valine, N-methyl-serine, N-methyl-threonine, N-methyl-tryptophan, and N-methyl-leucine, more efficiently than natural ARSs, and uses thereof. The aminoacyl-tRNA synthetases with modified amino acid sequences according to the present invention can be used to produce peptides that selectively and regioselectively contain N-methyl amino acids with high efficiency.

BACKGROUND ART

Generally in organisms on earth, information stored in DNA (=an information-storing substance) defines, via RNA (=an information-transmitting substance), the structures of proteins (=functional substances) and functions resulting from the structures. Polypeptides and proteins are composed of 20 types of amino acids. The information stored in DNA, which is composed of four kinds of nucleotides, is transcribed into RNA and then translated into amino acids, which make polypeptides and proteins.

During translation, tRNA plays the role of an adaptor that matches a stretch of three nucleotides to one amino acid, and aminoacyl-tRNA synthetase (aminoacyl-tRNA synthetase; ARS) is involved in the attachment of tRNA to its amino acid.

ARSs are enzymes that specifically attach an amino acid to its corresponding tRNA. There are 20 types of ARSs, each corresponding to each of the 20 types of naturally-occurring amino acids with a few exceptions, in every biological species. Of the 20 kinds of proteinaceous amino acids, ARS precisely acylates tRNA having an anticodon corresponding to an arbitrary codon, using the specific amino acid assigned to the codon. In other words, a tRNA synthetase corresponding to a certain amino acid can distinguish a tRNA corresponding to that amino acid from tRNAs corresponding to other amino acids, and does not attach other amino acids.

In translation of an mRNA into a polypeptide chain, a tRNA bound to its corresponding amino acid (aminoacyl-tRNA) pairs with the appropriate codon on the mRNA starting from the initiation codon and form hydrogen bonds with the mRNA on ribosomes. This is followed by peptidyl transfer to the amino acid on the adjacent aminoacyl-tRNA bound corresponding to the next codon. The first tRNA that released the amino acid by the transfer is liberated from the mRNA and can reattach its corresponding amino acid catalyzed by ARS. Translation is terminated upon reaching the mRNA's stop codon and upon arrival of a protein called the termination factor, which releases the polypeptide chain from the ribosome. Proteins within the living body are produced via such processes. The proteins then exert important physiological functions in the living body.

Meanwhile, in the field of pharmaceuticals of which bioactivities are exerted similarly in living bodies, the possibility of creating new pharmaceuticals using compounds having a molecular weight from 500 to 2000, called "middle molecules", is being anticipated in the field of drug discovery where it was considered difficult to create drugs with conventional low molecular weight compounds having a molecular weight less than 500. A representative example is cyclosporine A, a naturally-derived middle molecule drug, which is a peptide consisting of 11 residues that is produced by microorganisms, inhibits the intracellular target cyclophilin, and can be orally administered.

The Cyclosporine A peptide is characterized by including the non-natural amino acids "N-methyl amino acids" as components. Triggered by this, multiple studies have recently reported that the incorporation of N-methyl amino acids into peptides can increase drug-likeness of the peptides, and this is being further applied to drug discovery (Non Patent Literature 1, 2, 3). Particularly, it has come to be known that the incorporation of N-methyl amino acids leads to decrease in hydrogen bond-donating hydrogens, acquisition of protease resistance, and fixed conformation, and contributes to membrane permeability and metabolic stability (Non Patent Literature 1,4, Patent Literature 1).

This paves way to the conception of drug discovery methods that select pharmaceutical candidate substances from a library of diverse peptides containing multiple N-methyl amino acids. In terms of diversity and ease of screening, much anticipated are mRNA display libraries of N-methyl amino acid-containing peptides, and such, which use a cell-free translation system (Non Patent Literature 9, 10, Patent Literature 1). First, a display library is constructed, which is a collection of molecules forming one-for-one pairs between an enormous variety of RNA or DNA molecules (genotype) or the like and peptides encoded by these molecules (phenotype). The display library is then allowed to bind to a target protein or the like, followed by washing to remove non-bound molecules and selecting a molecule in the library, which is contained scarcely, in extremely small amounts. The selected RNA (DNA) molecule can be then sequenced to easily obtain the sequence information of the bound peptide. Particularly, an mRNA display library and a ribosome display library utilizing a cell-free translation system can be used to easily analyze $10^{12-14}$ diverse types of molecules (Non Patent Literature 11). Recently, a method that can prepare peptides containing non-proteinaceous amino acids using a reconstituted cell-free translation system has been also developed, enabling combination with display techniques to construct an N-methyl amino acid-containing peptide display library (Non Patent Literature 10).

Some methods for preparing N-methyl amino acid-containing peptides by translation of mRNAs are known so far. These methods are performed by separately preparing beforehand "N-methyl aminoacyl-tRNAs" and adding these to a translation system.

First, in the pdCpA method developed by Hecht et al. (Non Patent Literature 5), an N-methyl aminoacyl-tRNA is prepared beforehand by ligating pdCpA (5'-phospho-2'-deooxyribocytidylriboadenosine) acylated with a chemically-synthesized non-natural N-methyl amino acid to a tRNA lacking 3'-terminal CA obtained by transcription using T4 RNA ligase. This method has been used to introduce amino acids including N-methylalanine and N-methylphenylalanine (Non Patent Literature 6). However, when the present inventors attempted to introduce multiple N-methyl amino acids by preparing several complexes between non-natural N-methyl amino acids and tRNAs using the pdCpA method and adding the complexes to a cell-free translation system, translational efficiency decreased. Particularly, N-methylvaline could not be introduced (unpublished data).

As a different method, Suga et al. reported a method for aminoacylating tRNAs with N-methyl amino acids activated in advance by esterification using an artificial RNA catalyst (Flexizyme) (Patent Literature 2), and successfully introduced multiple types of N-methyl amino acids by translation. This method can be applied to various side chain structures, but aminoacylation efficiency of amino acids with nonaromatic side chains is in many cases 40 to 60% which is by no means high, and particularly, N-methylvaline introduction has not been confirmed as with the pdCpA method (Non Patent Literature 3).

Moreover, in the method of Szostak et al., aminoacyl-tRNAs are obtained by using tRNAs extracted from *Escherichia coli* and wild-type ARSs, and then preparing N-methyl aminoacyl-tRNAs via a chemical N-methylation reaction consisting of three steps. However, side chains that are efficiently translated in this method are limited to only the three side chains valine, leucine, and threonine. This method also requires cumbersome operations and further results in contamination of trace amounts of natural amino acids (the starting material) resulting from incomplete progression of the N-methylation reaction. Such difficulties in controlling the reaction directly affect the purity of products (Non Patent Literature 2).

Moreover, since these techniques add N-methyl aminoacyl-tRNAs prepared outside a translation system to a translation reaction solution, N-methyl aminoacyl-tRNAs are not re-produced in the translation system and thus are only consumed in the translation process. This requires addition of large amounts of N-methyl aminoacyl-tRNAs, but this addition itself of large amounts of tRNAs contributes to the reduction of peptide yield (Non Patent Literature 7). Further, instability of aminoacyl-tRNAs in the translation solution becomes problematic. Aminoacyl-tRNAs have been shown to be hydrolyzed under physiological conditions at pH 7.5 due to the presence of ester bonds between amino acids and tRNAs (Non Patent Literature 12). Half-life of aminoacyl-tRNAs depends on amino acid side chains, the shortest being 30 minutes. Hydrolysis of aminoacyl-tRNA is suppressed when it forms a complex with an aminoacyl-tRNA-elongation factor Tu (EF-Tu), but aminoacyl-tRNAs in excess of the concentration of EF-Tu present in the translation system are hydrolyzed. That is to say, as the translation reaction proceeds, deacylation of aminoacyl-tRNAs added at the start of translation proceeds, and at the end, aminoacyl-tRNAs having N-methyl amino acids are exhausted. In fact, Szostak et al. perceived this depletion as a problem and added N-methyl aminoacyl-tRNAs twice, at the start of translation and during the reaction, when synthesizing a polypeptide containing multiple N-methyl amino acids (Non Patent Literature 2).

The above-mentioned problems regarding introduction of N-methyl amino acids can be solved if there are ARSs for N-methyl amino acids having functions similar to natural ARSs for natural amino acids, but ARSs have an ability to precisely recognize their substrates and thus have limitations. As an exception, Murakami et al. reported that natural HisRS and PheRS could be used to introduce N-methylhistidine and N-methylphenylalanine into peptides in a cell-free translation system (Non Patent Literature 8, 13). Also, Szostak et al. confirmed that natural ARSs were used to aminoacylate tRNAs with the six N-methyl amino acids N-methylvaline, N-methylleucine, N-methyl aspartic acid, N-methylhistidine, N-methyllysine, and N-methyltryptophan (Non Patent Literature 14). However, even though a subsequent report using a cell-free translation system and natural ARSs that analyzed translational synthesis of peptides containing N-methylhistidine and N-methyl aspartic acid by mass spectrum reported a certain level of yield, in the case of peptides containing N-methylvaline, N-methylleucine, N-methyllysine, and N-methyltryptophan, it was shown that the efficiency of translational synthesis (ribosomal synthesis) is very low (Non Patent Literature 8). These reports reveal that aminoacylation with N-methyl amino acids and translational introduction of N-methyl amino acids into peptides using natural ARSs has been confirmed substantially in only the three cases of N-methylphenylalanine, N-methylhistidine, and N-methyl aspartic acid.

There are some prior art in which natural ARSs have been modified to give them the function to catalyze the attachment of non-natural amino acids to tRNAs (Patent Literature 3, 4, 5). Even though these are modified ARSs that catalyze the attachment of non-natural amino acids to tRNAs, and substrates of these modified ARSs are amino acids mainly having side chain derivatives of phenylalanine and tyrosine, modified ARSs having N-methyl amino acids as substrates, and modified ARSs that can introduce multiple N-methyl amino acid residues into peptides have not been known.

CITATION LIST

Patent Literature

Patent Literature 1: WO2013/100132
Patent Literature 2: WO2007/066627
Patent Literature 3: WO2003/014354
Patent Literature 4: WO2007/103307
Patent Literature 5: WO2002/085923

Non Patent Literature

Non Patent Literature 1: R. S. Lokey et al., Nat. Chem. Biol. 2011, 7(11), 810-817.
Non Patent Literature 2: J. W. Szostak et al., J. Am. Chem. Soc. 2008, 130, 6131-6136.
Non Patent Literature 3: T. Kawakami et al., Chemistry & Biology, 2008, Vol. 15, 32-42.
Non Patent Literature 4: H. Kessler et al., J. Am. Chem. Soc. 2012, 134, 12125-12133.
Non Patent Literature 5: S. M. Hecht et al., J. Biol. Chem. 253 (1978) 4517-4520.
Non Patent Literature 6: Z. Tan et al., J. Am. Chem. Soc. 2004, 126, 12752-12753.
Non Patent Literature 7: A. O. Subtelny et al., Angew Chem Int Ed 2011 50 3164.
Non Patent Literature 8: M. C. T. Hartman et al., PLoS one, 2007, 10, e972.
Non Patent Literature 9: S. W. Millward et al., J. Am. Chem. Soc., 2005, 127, 14142-14143.
Non Patent Literature 10: Y. Yamagishi et al., Chem. Biol., 18, 1562-1570, 2011.

Non Patent Literature 11: H. R. Hoogenboom, Nature Biotechnol. 23, 1105-1116, 2005.

Non Patent Literature 12: J. R. Peacock et al., RNA, 20, 758-64, 2014.

Non Patent Literature 13: T. Kawakami, ACS Chem Biol., 8, 1205-1214, 2013.

Non Patent Literature 14: M. C. T. Hartman et al., Proc Natl Acad Sci USA., 103, 4356-4361, 2006.

SUMMARY OF THE INVENTION

Problems to be Solved by the Invention

An objective of the present invention is to provide modified ARSs that have been modified to increase reactivity, and which use N-methyl amino acids as substrates. More specifically, an objective of the present invention is to provide a novel modified ARS that catalyzes the acylation reaction in which tRNAs attach non-natural N-methyl amino acids, particularly N-methyl-phenylalanine, N-methyl-valine, N-methyl-serine, N-methyl-threonine, N-methyltryptophan, and N-methylleucine, without using large amounts of tRNAs in order to efficiently produce peptides containing multiple N-methyl amino acids, and uses thereof.

Means for Solving the Problems

In order to obtain ARSs having increased reactivity with N-methyl amino acids, the present inventors obtained multiple ARS genes that employ different amino acids as substrates and introduced mutations into the genes to construct mutated ARS genes encoding ARSs with altered amino acid sequences. These modified ARSs were expressed and collected, and were incubated with tRNAs in the presence of unmodified amino acids or N-methyl amino acids to determine aminoacylation reaction. As a result of estimating the conformation formed in the N-methyl amino acid-ARS interaction, and after much trial and error, the present inventors successfully obtained modified ARSs, including multiple ARSs such as phenylalanyl-tRNA synthetase (PheRS), seryl-tRNA synthetase (SerRS), valyl-tRNA synthetase (ValRS), threonyl-tRNA synthetase (ThrRS), leucyl-tRNA synthetase (LeuRS), and tryptophanyl-tRNA synthetase (TrpRS), with increased activity in the aminoacylation reaction with N-methyl amino acids, compared to wild-type ARSs.

For example, 0.1 µM wild-type PheRS hardly incorporated N-methylphenylalanine into ribosomally-synthesized peptides even when 1 mM N-methylphenylalanine was added. On the other hand, 0.1 µM modified PheRS clearly incorporated N-methylphenylalanine into peptides even when 0.25 mM N-methylphenylalanine was added (Example 1). The amount of phenylalanine and N-methylphenylalanine translationally introduced (ribosomally introduced) into peptides were measured by mass spectroscopy using MALDI-TOF MS. The ratio of the peak values (the peak intensity of the peptide containing N-methylphenylalanine/the peak intensity of the peptide containing phenylalanine) at the time of 0.25 mM N-methylphenylalanine addition was 0.8 when using wild-type PheRS, whereas it dramatically increased to 12.4 when using the modified PheRS α subunit (Example 1). When sequences containing two consecutive and three consecutive phenylalanines were allowed to translate, peptides containing two consecutive and three consecutive N-methylphenylalanines were confirmed to be synthesized respectively, and the efficiency was significantly higher than that using the pdCpA method. Also, ValRS was used to perform translational synthesis in the presence of 5 mM N-methylvaline, and the peptide products were analyzed with mass spectroscopy. A peptide incorporated with unmodified valine was detected as the main product when using wild-type ValRS, whereas a peptide incorporated with N-methylvaline was observed as the main product when using modified ValRS (Example 2). Furthermore, the selectivity to N-methylvaline was successfully increased by introducing mutations into the editing domain of ValRS and decreasing aminoacylation activity with unmodified Val (Example 7). When sequences containing two consecutive and three consecutive valines were allowed to translate, peptides containing two consecutive and three consecutive N-methylvalines were confirmed to be synthesized respectively (Example 2). For SerRS, an N-methyl-serine-incorporated translation product was detected as the main product when modified SerRS was used under conditions in which an unmodified serine-incorporated translation product is detected as the main product when using wild-type SerRS (Example 3). Even for ThrRS, an N-methyl Thr-incorporated translation product was observed when modified ThrRS was used under conditions in which an unmodified Thr-incorporated translation product is detected when using wild-type ThrRS; whereas it was demonstrated that translation products incorporated with unmodified Thr were hardly observed and the peptide with N-methyl Thr introduced was synthesized with higher purity compared to that achieved with wild-type ThrRS (Example 4). For TrpRS, unmodified Trp was detected as a main product in using wild-type TrpRS, whereas the translation product with N-methyl Trp incorporated was observed as a main product using the modified TrpRS (Example 5). For LeuRS, translation products containing N-methyl Leu were not observed in using wild-type LeuRS, whereas it is revealed that translation products with N-methyl Leu incorporated were produced as much as translation products containing unmodified Leu when modified LeuRSs were used (Example 6). Thus, the modified ARSs according to the present invention can be used to introduce N-methyl amino acids into peptides more efficiently than wild-type ARS.

Accordingly, the following inventions are provided.

The present invention provides ARSs having reactivity with N-methyl amino acids. Specifically, the present invention relates to an aminoacyl-tRNA synthetase (aminoacyl-tRNA synthetase; ARS) that has an altered amino acid sequence and is able to incorporate any N-methyl amino acid, particularly the six N-methyl-substituted amino acids of N-methyl-phenylalanine, N-methyl-valine, N-methyl-serine, N-methyl-threonine, N-methyltryptophan, and N-methylleucine more efficiently than natural ARSs and use thereof. The ARS with an altered amino acid sequence according to the present invention can be used to produce peptides selectively and regioselectively containing any N-methyl amino acid from among these N-methyl amino acids with high efficiency.

The present invention further relates to a method for producing polypeptides containing non-natural amino acids using a modified ARS according to the present invention. More specifically, the present invention relates to a method for producing polypeptides containing N-methylphenylalanine, N-methylvaline, N-methylserine, N-methylthreonine, N-methyltryptophan, and N-methylleucine using ARSs for phenylalanine, valine, serine, threonine, tryptophan, and leucine, respectively, with altered amino acid sequences.

Namely, the present invention provides the following inventions:

[1] A polypeptide comprising a modified aminoacyl-tRNA synthetase (ARS), wherein the ARS is able to incorporate an N-methyl amino acid more efficiently than an original, natural ARS.

[2] A polypeptide modified to enhance an aminoacylation reaction with an N-methyl amino acid, wherein the polypeptide has aminoacyl-tRNA synthetase (ARS) activity, wherein the modification comprises at least one amino acid substitution that causes a decrease of 10 or more in molecular weight.

[3] The polypeptide according to [1] or [2], wherein the N-methyl amino acid is selected from the group consisting of valine, serine, phenylalanine, threonine, tryptophan, and leucine.

[4] The polypeptide according to any one of [1] to [3], wherein the ARS is selected from the group consisting of ValRS, SerRS, PheRS α subunit, ThrRS, TrpRS, and LeuRS.

[5] The polypeptide according to any one of [1] to [4], wherein the ValRS is modified at a position(s) corresponding to asparagine at position 43 and/or threonine at position 45 and/or threonine at position 279 of ValRS from *Escherichia coli*.

[6] The polypeptide according to any one of [1] to [4], wherein the SerRS is modified at a position(s) corresponding to glutamic acid at position 239 and/or threonine at position 237 of SerRS from *E. coli*.

[7] The polypeptide according to any one of [1] to [4], wherein the PheRS α subunit is modified at a position corresponding to glutamine at position 169 of PheRS α subunit from *E. coli*.

[8] The polypeptide according to any one of [1] to [4], wherein the ThrRS is modified at a position(s) corresponding to methionine at position 332 and/or histidine at position 511 of ThrRS from *E. coli*.

[9] The polypeptide according to any one of [1] to [4], wherein the TrpRS is modified at a position(s) corresponding to methionine at position 132 and/or glutamine at position 150 and/or histidine at position 153 of TrpRS from *E. coli*.

[10] The polypeptide according to any one of [1] to [4], wherein the LeuRS is modified at a position corresponding to tyrosine at position 43 of LeuRS from *E. coli*.

[11] The polypeptide according to any one of [1] to [4], wherein the ValRS has (a) glycine or alanine at a position corresponding to asparagine at position 43 and/or (b) serine at a position corresponding to threonine at position 45 and/or (c) glycine or alanine at a position corresponding to threonine at position 279 of ValRS from *E. coli*.

[12] The polypeptide according to any one of [1] to [4], wherein the SerRS has (a) glycine or alanine at a position corresponding to glutamic acid at position 239 and/or (b) serine at a position corresponding to threonine at position 237 of SerRS from *E. coli*.

[13] The polypeptide according to any one of [1] to [4], wherein the PheRS α subunit has glycine or alanine at a position corresponding to glutamine at position 169 of PheRS a subunit from *E. coli*.

[14] The polypeptide according to any one of [1] to [4], wherein the ThrRS has glycine at a position corresponding to methionine at position 332 and/or histidine at position 511 of ThrRS from *E. coli*.

[15] The polypeptide according to any one of [1] to [4], wherein the TrpRS has (a) alanine or valine at a position corresponding to methionine at position 132 and/or (b) alanine at a position corresponding to glutamine at position 150 and/or (c) alanine at a position corresponding to histidine at position 153 of TrpRS from *E. coli*.

[16] The polypeptide according to any one of [1] to [4], wherein the LeuRS has glycine at a position corresponding to tyrosine at position 43 of LeuRS from *E. coli*.

[17] The polypeptide according to any one of [1] to [16], wherein the ARS is derived from a bacterium.

[18] The polypeptide according to [17], wherein the bacterium is *Escherichia coli*.

[19] The polypeptide according to any one of [1] to [18], wherein the polypeptide is selected from the group consisting of the following (a) and (b):
 (a) a polypeptide comprising amino acids selected from the group consisting of SEQ ID NOs: 1 to 11 and 182 to 187, and
 (b) a polypeptide comprising an amino acid sequence having at least 90% identity to an amino acid sequence selected from the group consisting of SEQ ID NOs: 1 to 11 and 182 to 187.

[20] An isolated polypeptide comprising an amino acid sequence selected from the group consisting of SEQ ID NOs: 1 to 11 and 182 to 187.

[21] A fusion polypeptide of a polypeptide according to any one of [1] to [20] and another polypeptide.

[22] A polynucleotide encoding a polypeptide according to any one of [1] to [21].

[23] A vector comprising the polynucleotide according to [22].

[24] A host cell comprising the polynucleotide according to [22] or the vector according to [23].

[25] A method for producing a polypeptide according to any one of [1] to [21], comprising the step of culturing the host cell according to [24].

[26] A method for producing a tRNA acylated with an N-methyl amino acid, comprising the step of contacting the N-methyl amino acid with a tRNA in the presence of the polypeptide according to any one of [1] to [20].

[27] The method according to [26], wherein the step of contacting is carried out in a cell-free translation system.

[28] A method for producing a polypeptide comprising an N-methyl amino acid, comprising the step of performing translation in the presence of the polypeptide according to any one of [1] to [20] and the N-methyl amino acid.

[29] The method according to [28], wherein the step of performing translation is carried out in a cell-free translation system.

Effects of the Invention

The modified ARSs according to the present invention can be used to efficiently attach N-methylphenylalanine, N-methylvaline, N-methylthreonine, N-methylserine, N-methyltryptophan, and N-methylleucine to tRNAs corresponding to natural phenylalanine, valine, threonine, serine, tryptophan, and leucine, respectively, without complicated reactions.

Methods using modified ARSs according to the present invention require no stoichiometric amount of tRNA, can synthesize peptides into which multiple N-methyl amino acids are introduced with a high translational efficiency, and is useful for generating a highly diverse peptide library.

In order to investigate the effect on translational efficiency provided by the ARS's characteristic feature of "providing a continuous supply of aminoacyl-tRNA during the translation reaction", the present inventors compared the introduction efficiencies of N-methylphenylalanine in two methods: a method using the modified PheRS05 (SEQ ID NO: 2)

obtained by the present application invention and the pdCpA method in which aminoacyl-tRNA is not expected to be regenerated during the translation reaction. As a result, the translational efficiency of the method using the modified ARS was higher, and particularly, when two consecutive and three consecutive N-methylphenylalanines were introduced, the target peptide was synthesized approximately 4 to 8 times more (unpublished data). Thus, the present invention enables more efficient production of N-methyl amino acid-containing polypeptides, which were conventionally hard to produce.

BRIEF DESCRIPTION OF DRAWINGS

FIG. 1 shows evaluation of aminoacylation activities of modified ARSs. The bands of the synthetic peptide acylated with N-methylphenylalanine using PheRS04 and PheRS05 were detected more strongly than when using wild-type PheRS (lane 8, 9 vs. 12, 13).

FIG. 2 shows the confirmation by electrophoresis of peptides ribosomally synthesized using mutant PheRS. The bands of the N-methylphenylalanine-containing peptide synthesized using the modified PheRS were detected more strongly than that using wild-type PheRS (lanes 2, 3 vs. 5, 6).

FIG. 3-1 shows detection by mass spectroscopy of peptides ribosomally synthesized using the modified PheRS. Mass spectrum of the peptide ribosomally synthesized using (a) 0.1 μM wt PheRS and 0.25 mM Phe, (b) 0.1 μM wt PheRS and 0.25 mM MePhe, or (c) 0.1 μM wt PheRS and 1 mM MePhe.

FIG. 3-2 shows detection by mass spectroscopy of peptides ribosomally synthesized using the modified PheRS. Mass spectrum of the peptide ribosomally synthesized using (d) 0.1 μM PheRS05 and 0.25 mM Phe, (e) 0.1 μM PheRS05 and 0.25 mM MePhe, or (f) 0.1 μM PheRS05 and 1 mM MePhe.

FIG. 4 shows aminoacylation reaction performed using modified ValRSs. tRNA acylated with N-methylvaline using the mutant 13 (ValRS13) was observed more than tRNA acylated using wild-type ValRS (lane 10).

FIG. 5 shows the results of mass spectrometry analysis of peptides translated using the modified ValRSs. Mass spectrum of the peptides translated using (a) wild-type ValRS, (b) ValRS13, or (c) ValRS04. The peptide containing MeVal was observed as a main product when ValRS13 was used.

FIG. 6 shows aminoacylation reaction performed using ValRS13-11. tRNA acylated with N-methylvaline using the mutant 13-11 (ValRS13-11) was observed more than tRNA acylated using wild-type ValRS or the mutant 13 (ValRS13).

FIG. 7 shows comparison of activities between ValRS13 and ValRS13-11. Mass spectra of the N-methyl peptide-containing peptides translated using ValRS13 ((a), (c), (e)) and ValRS13-11 ((b), (d), (f)). It can be seen that the N-methylvaline-containing target peptide translated using ValRS13-11 had higher purity.

FIG. 8 shows aminoacylation reaction performed using modified SerRSs. tRNA acylated with N-methylserine was observed when mutants 03, 35, and 37 were used (lanes 3, 25, 27).

FIG. 9 shows the results of mass spectrometry analysis of peptides ribosomally synthesized using the modified SerRSs. Mass spectrum of the N-methylserine-containing peptide translated using (a) wild-type SerRS, (b) SerRS03, (c) SerRS05, (d) SerRS35, or (e) SerRS37. The MeSer-containing target peptide synthesized using each modified SerRS had higher purity compared to that synthesized using wild-type SerRS.

FIG. 10 shows the results of mass spectrometry analysis of peptides ribosomally synthesized using modified ThrRSs. Mass spectrum of the N-methylthreonine-containing peptide translated using (a) wild-type ThrRS, (b) ThrRS03, or (c) ThrRS14. The MeThr-containing target peptide synthesized using each modified ThrRS had higher purity compared to that synthesized using wild-type ThrRS.

FIG. 11 shows the results of mass spectrometry analysis of peptides ribosomally synthesized using modified TrpRSs. Mass spectrum of the peptide translated using (a) wild-type TrpRS, (b) TrpRS04, (c) TrpRS05, or (d) TrpRS18. The MeW-containing peptide was observed as a main product when TrpRS04, 05, and 18 were used.

FIG. 12 shows the results of mass spectrometry analysis of peptides ribosomally synthesized using the modified LeuRS. Mass spectrum of the peptide translated using (a) wild-type LeuRS or (b) LeuRS02. The MeL-containing peptide was observed as a main product when LeuRS02 was used.

FIG. 13 shows aminoacylation reaction with MeVal using the modified ValRSs having mutation in the editing domain. The activities of three mutants, 13-11, 66, and 67 were not much different (lanes 17, 18, 19).

FIG. 14 shows aminoacylation reaction with Val using the modified ValRSs having mutation in the editing domain. The activities of the mutants 66 and 67 were attenuated compared to the activity of the mutant 13-11 (lane 17 vs 18, 19).

MODE FOR CARRYING OUT THE INVENTION

An objective of the present invention is to provide mutant enzymes with altered enzyme-substrate specificity for aminoacyl-tRNA synthetase. More specifically, the present invention is characterized by the preparation of mutant aminoacyl-tRNA synthetases that can efficiently and selectively produce polypeptides containing N-methyl amino acids in large amounts, by altering the amino acid sequence of natural aminoacyl-tRNA synthetase.

The present invention provides polypeptides including ARSs that can react with N-methyl amino acids. More specifically, the present invention provides polypeptides comprising modified ARSs that can react with N-methyl amino acids more efficiently than the original, natural ARSs. The present invention also provides polypeptides comprising modified ARSs that can incorporate N-methyl amino acids more efficiently than the original, natural ARSs. The polypeptides according to the present invention are polypeptides that have aminoacyl-tRNA synthetase activity and are modified to enhance the aminoacylation reaction with N-methyl amino acids. As used herein, the phrase "incorporate N-methyl amino acids" refers to, for example, aminoacylation of tRNAs with N-methyl amino acids corresponding to the tRNAs and may be attachment of the N-methyl amino acids to the tRNAs or incorporation of N-methyl amino acids to proteins synthesized in a translation reaction using the aminoacyl-tRNA produced in the acylation reaction. The phrase "a polypeptide has aminoacyl-tRNA synthetase activity" includes not only the case in which the polypeptide exhibits aminoacyl-tRNA synthetase activity by itself, but also the case in which the polypeptide exhibits aminoacyl-tRNA synthetase activity together with other factors. For example, when an aminoacyl-tRNA synthetase is composed of multiple subunits, the polypeptide according to the present invention may be one subunit or may exhibit aminoacyl-tRNA synthetase activity as a complex with other subunits. In such a case, when an aminoacyl-tRNA synthetase complex is formed between a modified polypeptide according to the present invention and other wild-type subunits, the aminoacyl-tRNA synthetase complex can enhance aminoacylation reaction with N-methyl amino acids more than an aminoacyl-tRNA synthetase complex consisting of wild-type subunits. That is to say, in the present invention, polypeptides with aminoacyl-tRNA synthetase activity modified to enhance aminoacylation reaction with N-methyl amino acids include a polypeptide that is one modified subunit in an aminoacyl-tRNA synthetase complex consisting of multiple subunits and is modified to enhance aminoacylation reaction with N-methyl amino acids by the aminoacyl-tRNA synthetase complex.

A polypeptide comprising a modified ARS refers to a polypeptide comprising the polypeptide chain of the modified ARS, and specifically the polypeptide is a polypeptide comprising the amino acid sequence of the modified ARS. The original, natural ARS refers to a natural ARS from which modified ARS is derived, may be for example a wild-type ARS, and includes a naturally-occurring polymorphism. The phrase "can react with N-methyl amino acids" means that modified ARSs can perform an enzymatic reaction with N-methyl amino acids as substrates. The reaction may be, for example, an acylation reaction of tRNAs with N-methyl amino acids, and specifically a reaction that catalyzes a coupling reaction between an N-methyl amino acid and a tRNA. For example, depending on an amino acid used as a substrate by an ARS, the reaction is performed in the presence of the appropriate N-methyl amino acid and the appropriate tRNA, and the coupling between the N-methyl amino acid and the tRNA may be detected. Alternatively, a reaction with N-methyl amino acids may be incorporation of N-methyl amino acids into polypeptides in translation. Production of N-methyl amino acid-tRNA by ARSs can be detected by, for example, performing translation in the presence of the modified ARSs and N-methyl amino acids and detecting incorporation of N-methyl amino acids into the polypeptides produced by translation. The reactivity with N-methyl amino acids is considered to be higher when N-methyl amino acids are frequently incorporated into polypeptides.

The phrase "a modified ARS can react more efficiently than the original, natural ARS" may mean that the modified ARS reacts more efficiently than the original, natural ARS at least under a certain condition, or that a reaction or reaction product that cannot be observed when using the original ARS can be observed when using the modified ARS. For example, a modified ARS is considered to react with an N-methyl amino acid more efficiently than the original, natural ARS when the modified ARS produces polypeptides containing the N-methyl amino acid more than the original, natural ARS. A modified ARS is considered to react with its corresponding N-methyl amino acid more efficiently than the original, natural ARS when, for example, production of polypeptides containing the N-methyl amino acid that cannot be observed when using the original, natural ARS can be observed when using the modified ARS. For example, a modified ARS is considered to react with an N-methyl amino acid more efficiently than the original, natural ARS when, for example, production of polypeptides containing 2, 3, or more consecutive N-methyl amino acids cannot be observed when using the original, natural ARS, but can be observed when using the modified ARS.

The phrase "can react more efficiently than the original, natural ARS" may mean that a reactant of interest is purified at least under a certain condition with higher purity compared to the purity achieved with the original, natural ARS. For example, a modified ARS is considered to react with its corresponding N-methyl amino acid more efficiently than the original, natural ARS when the modified ARS produces polypeptides containing its corresponding N-methyl amino acid more than the original, natural ARS, relative to natural amino acids derived as a result of contamination, Alternatively, a modified ARS is considered to react with N-methyl amino acids more efficiently than the original ARS when it is confirmed that reaction efficiency of the modified ARS for the N-methyl amino acid remains unchanged and reaction efficiency of the modified ARS for natural amino acids decreases. For example, a modified ARS is considered to react with its corresponding N-methyl amino acid more efficiently than the original, natural ARS when reactivity of the modified ARS to the N-methyl amino acid is relatively higher than reactivity of the modified ARS to natural amino acids.

N-methyl amino acids are not particularly limited, but are appropriately selected based on ARSs. For example, when the modified ARS is valine ARS (ValRS), N-methyl amino acid is N-methylvaline; when the modified ARS is threonine ARS (Thr), N-methyl amino acid is N-methylthreonine; when the modified ARS is serine ARS (SerRS), N-methyl amino acid is N-methylserine; when the modified ARS is phenylalanine ARS α subunit (PheRS), N-methyl amino acid is N-methylphenylalanine; when the modified ARS is tryptophan ARS (TrpRS), N-methyl amino acid is N-methyltryptophan; when the modified ARS is leucine ARS (LeuRS), N-methyl amino acid is N-methylleucine.

For example in ValRS, modified sites of ARS are preferably the position(s) corresponding to asparagine at position 43 and/or threonine at position 45 and/or threonine at position 279 of ValRS from E. coli. Modified sites of ARS are preferably a combination of any two positions selected from the positions corresponding to asparagine at position 43, threonine at position 45, and threonine at position 279 (e.g., a combination of position 43 and position 45, position 43 and position 279, or position 45 and position 279), and more preferably a combination of positions corresponding to asparagine at position 43, threonine at position 45, and threonine at position 279. SerRS can be modified at the position(s) corresponding to glutamic acid at position 239 and/or threonine at position 237 of SerRS from E. coli, and more preferably, can be modified at a combination of the positions corresponding to glutamic acid at position 239 and threonine at position 237. PheRS α subunit is preferably modified at the position corresponding to glutamine at position 169 of PheRS from E. coli. ThrRS can be modified at the position(s) corresponding to methionine at position 332 and/or histidine at position 511 of ThrRS from E. coli. TrpRS can be modified at the position(s) corresponding to methionine at position 132 and/or glutamine at position 150 and/or histidine at position 153 of TrpRS from E. coli, preferably can be modified at a combination of any two positions selected from positions corresponding to methionine at position 132, glutamine at position 150, and histidine at position 153 (e.g., a combination of position 132 and position 150, position 132 and position 153, or position 150 and position 153), and more preferably can be modified at a combination of the positions corresponding to methionine at position 132, glutamine at position 150, and histidine at position 153. LeuRS can be modified at the position corresponding to tyrosine at position 43 of LeuRS from E. coli. It should be noted that these modified ARSs may be further modified at other positions. The position numbers in each ARS are indicated taking the position number of the starting methionine in each ARS from *E. coli* as 1. Specifically, the position numbers in each ARS are indicated taking the position number of the first methionine in the sequences of P07118 (SEQ ID NO: 24) for ValRS, P08312 (SEQ ID NO: 28) for PheRS α subunit, P0A8M3 (SEQ ID NO: 29) for ThrRS, P0A8L1 (SEQ ID NO: 26) for SerRS, P00954 (SEQ ID NO: 188) for TrpRS, and P07813 (SEQ ID NO: 189) for LeuRS (UniProt (http://www.uniprot.org/) as 1. In a certain ARS, a position corresponding to a certain amino acid in ARS from *E. coli* refers to the amino acid located in the site corresponding to the amino acid in ARS from *E. coli* and can be identified based on structural similarity between the certain ARS and ARS from *E. coli*. For example, the corresponding amino acid can be identified as the amino acid aligned at the position of the amino acid in ARS from *E. coli* when the amino acid sequences of an ARS of interest and ARS from *E. coli* are aligned. As used herein, a position corresponding to a certain amino acid in ARS from *E. coli* is preferably the position sterically corresponding to the certain amino acid in ARS from *E. coli*. The sterically corresponding position refers to the position of an amino acid corresponding to the position of the certain amino acid in ARS from *E. coli* in the conformation of ARS.

Those skilled in the art can easily identify the sterically corresponding position by aligning ARS from *E. coli* with all known ARSs from other biological species for example using Multiple Sequence Alignment with default parameters in ClustalW ver2.1 (http://clustalw.ddbj.nig.ac.jp). Particularly, ARSs of interest are not limited to those from prokaryotes. Generally, sequences of ARSs in eukaryotes comprise various functional domains in addition to catalytic domain, and the sequence identity between ARSs from eukaryotes and ARSs from prokaryotes is not always high. In contrast, sequences of catalytic sites, including amino acid recognition site, and editing domain are highly conserved, and the sterically corresponding position in ARSs from eukaryotes can be easily identified using publicly-available alignment techniques.

For example, the sites corresponding to positions 43 and 45 of *E. coli* ValRS may be respectively amino acid sites of "N/Y/T" and "T/S" in PPP(N/Y/T)X(T/S)G motif (SEQ ID NO: 180; "N/Y/T" is preferably N; X is any amino acid, preferably V, I, or P, and more preferably V; "T/S" is preferably T) present in ValRS from other organisms. More preferably, the sites corresponding to positions 43 and 45 of *E. coli* ValRS may be amino acids at N and T respectively in PPPNXTG motif (SEQ ID NO: 181; X is any amino acid, preferably V, I, or P, and more preferably V) present in ValRS from other organisms. For example, the position corresponding to asparagine at position 43 of *E. coli* ValRS is asparagine at position 345 in human (Uniprot P26640) and asparagine at position 191 in *Saccharomyces cerevisiae* (Uniprot P07806).

Modifications of ARSs include preferably at least one substitution with an amino acid that causes a decrease of 10 or more in molecular weight. Such modifications include, for example, a modification of an amino acid selected from the group consisting of amino acids other than Thr (T), such as Gln (Q), Asn (N), Glu (E), Met (M), Tyr (Y), and His (H), into Ala (A) or Gly (G) (preferably into Gly), for example, a modification of Thr (T) into Ser (S), and for example, a modification of Met (M) into Val (V).

Amino acids to be modified may be appropriately selected. For example in ValRS, the position corresponding to asparagine at position 43 of ValRS from *E. coli* is preferably modified into glycine or alanine, the position corresponding to threonine at position 45 of ValRS from *E. coli* is preferably modified into serine, and the position corresponding to threonine at position 279 of ValRS from *E. coli* is preferably modified into glycine or alanine. In SerRS, the position corresponding to glutamic acid at position 239 of SerRS from *E. coli* is preferably modified into glycine or alanine, and the position corresponding to threonine at position 237 of SerRS from *E. coli* is preferably modified into serine. In PheRS, the position corresponding to glutamine at position 169 of PheRS α subunit from *E. coli* is preferably modified into glycine or alanine. In ThrRS, the position corresponding to methionine at position 332 of ThrRS from *E. coli* is preferably modified into glycine, and the position corresponding to histidine at position 511 of ThrRS from *E. coli* is preferably modified into glycine. In TrpRS, the position corresponding to methionine at position 132 of TrpRS from *E. coli* is preferably modified into valine or alanine, the position corresponding to glutamine at position 150 of TrpRS from *E. coli* is preferably modified into alanine, and the position corresponding to histidine at position 153 of TrpRS from *E. coli* is preferably modified into alanine. In LeuRS, the position corresponding to tyrosine at position 43 of LeuRS from *E. coli* is preferably modified into glycine.

Specifically, the present invention includes the following polypeptides:
(a) a polypeptide comprising the amino acid sequence of any of SEQ ID NOs: 3-5, 182, and 183 (ValRS04, ValRS13, ValRS13-11, ValRS66, and ValRS67); and
(b) a polypeptide that has reactivity with N-methyl Val, has at least 90% identity to the amino acid sequence of any of SEQ ID NOs: 3-5, 182, and 183, and comprises at least one amino acid of the following (i) to (iii):
(i) Gly or Ala at the amino acid position corresponding to position 43 of SEQ ID NOs: 3-5, 182, and 183;
(ii) Ser at the amino acid position corresponding to position 45 of SEQ ID NOs: 3-5, 182, and 183; and
(iii) Gly or Ala at the amino acid position corresponding to position 279 of SEQ ID NOs: 3-5, 182, and 183.

Furthermore, the above-mentioned reactivity is preferably higher than the reactivity of a polypeptide having (i) Asn at the amino acid position corresponding to position 43 and/or (ii) Thr at the amino acid position corresponding to position 45 and/or (iii) Thr at the amino acid position corresponding to position 279. For example, the ValRS according to the present invention preferably has a reactivity with N-methyl Val higher than the reactivity of a ValRS having Asn at the amino acid position corresponding to position 43, Thr at the amino acid position corresponding to position 45, and Thr at the amino acid position corresponding to position 279 of the ValRS.

The present invention also includes the following polypeptides:
(a) a polypeptide comprising the amino acid sequence of any of SEQ ID NOs: 6-9 (SerRS03, SerRS05, SerRS35, and SerRS37) and
(b) a polypeptide that has reactivity with N-methyl Ser, has at least 90% identity to the amino acid sequence of any of SEQ ID NOs: 6-9, and comprises at least one amino acid of the following (i) and (ii);
(i) Ser at the amino acid position corresponding to position 237 of SEQ ID NOs: 6-9, and
(ii) Gly or Ala at the amino acid position corresponding to position 239 of SEQ ID NOs: 6-9.

Furthermore, the above-mentioned reactivity is preferably higher than the reactivity of a polypeptide having (i) Thr at the amino acid position corresponding to position 237 and/or (ii) Glu at the amino acid position corresponding to position 239. For example, the SerRS according to the present invention preferably has a reactivity with N-methyl Ser higher than the reactivity of a SerRS having Thr at the amino acid position corresponding to position 237 of the SerRS and Glu at the amino acid position corresponding to position 239 of the SerRS.

The present invention also includes the following polypeptides:
(a) a polypeptide comprising the amino acid sequence of any of SEQ ID NOs: 1-2 (PheRS05 and PheRS04); and
(b) a polypeptide that has reactivity with N-methyl Phe, has at least 90% identity to the amino acid sequence of any of SEQ ID NOs: 1-2, and comprises an amino acid sequence in which the amino acid at the position corresponding to position 169 of any of SEQ ID NOs: 1-2 is Gly or Ala. Furthermore, the above-mentioned reactivity is preferably higher than the reactivity of a polypeptide in which the amino acid at the above-mentioned position is Gln. The polypeptides as described above represent ARS α subunit, and therefore the polypeptides can form a complex with β subunit to result in a functional ARS. β subunit is not particularly limited, but may be, for example, a desired wild-type subunit. As an example, β subunit that can be used is one comprising the amino acid sequence of NCBI Reference Sequence WP_000672380 (e.g., WP_000672380.1) (wherein the base sequence represents 1897337-1899721 of GenBank CP009685 (e.g., CP009685.1)).

The present invention also includes the following polypeptides:
(a) a polypeptide comprising the amino acid sequence of any of SEQ ID NOs: 10-11 (ThrRS03 and ThrRS14); and
(b) a polypeptide that has reactivity with N-methyl Thr, has at least 90% identity to the amino acid sequence of any of SEQ ID NOs: 10-11, and comprises at least one amino acid of the following (i) and (ii):
(i) Gly at the amino acid position corresponding to position 332 of SEQ ID NOs: 10-11; and
(ii) Gly at the amino acid position corresponding to position 511 of SEQ ID NOs: 10-11.

Furthermore, the above-mentioned reactivity is preferably higher than the reactivity of a polypeptide having (i) Met at the amino acid position corresponding to position 332 and/or (ii) His at the amino acid position corresponding to position 511. For example, the ThrRS according to the present invention preferably has a reactivity with N-methyl Thr higher than the reactivity of a ThrRS having Met at the amino acid position corresponding to position 332 of the ThrRS and His at the amino acid position corresponding to position 511 of the ThrRS.

The present invention also includes the following polypeptides:
(a) a polypeptide comprising the amino acid sequence of any of SEQ ID NOs: 184-186 (TrpRS04, TrpRS05, and TrpRS18), and
(b) a polypeptide that has reactivity with N-methyl Trp, has at least 90% identity to the amino acid sequence of any of SEQ ID NOs: 184-186, and comprises at least one amino acid according to any of the following (i) to (iii):
(i) Val or Ala at the amino acid position corresponding to position 132 of SEQ ID NOs: 184-186;
(ii) Ala at the amino acid position corresponding to position 150 of SEQ ID NOs: 184-186; and
(iii) Ala at the amino acid position corresponding to position 153 of SEQ ID NOs: 184-186.

Furthermore, the above-mentioned reactivity is preferably higher than the reactivity of a polypeptide having (i) Met at the amino acid position corresponding to position 132 and/or (ii) Gln at the amino acid position corresponding to position 150 and/or (iii) His at the amino acid position corresponding to position 153. For example, the TrpRS according to the present invention preferably has a reactivity with N-methyl Trp higher than the reactivity of a TrpRS having Met at the amino acid position corresponding to position 132 of the TrpRS, Gln at the amino acid position corresponding to position 150 of the TrpRS, and His at the amino acid position corresponding to position 153 of the TrpRS.

The present invention also includes the following polypeptides:
(a) a polypeptide comprising the amino acid sequence of SEQ ID NO: 187 (LeuRS02); and
(b) a polypeptide that has reactivity with N-methyl Leu, has at least 90% identity to the amino acid sequence of SEQ ID NO: 187, and comprises an amino acid sequence in which the amino acid at the position corresponding to position 43 of SEQ ID NO: 187 is Gly.

Furthermore, the above-mentioned reactivity is preferably higher than the reactivity of a polypeptide having (i) Tyr at the amino acid position corresponding to position 43.

The identity of amino acid sequence is preferably 93% or more, more preferably 95% or more, more preferably 97% or more, 98% or more, or 99% or more.

The N-methyl aminoacyl-tRNA synthetases according to the present invention are characterized by the ability to efficiently acylate tRNAs with N-methyl amino acids, which are non-natural amino acids known to enhance drug-likeness of peptides. The N-methyl aminoacyl-tRNA synthetases according to the present invention may be derived from any organism including bacteria such as *E. coli*, yeast, animals, or plants, but, because of their versatility, preferable are those that have high sequence conservation with aminoacyl-tRNA synthetases exemplified in the Examples herein (SEQ ID NOs: 1-11, 182-187), and thus have mutation site(s) easily identified in other biological species. For example, polypeptides comprising the modified ARSs according to the present invention may be derived from ARSs from eukaryotes or prokaryotes. Eukaryotes include protists (including protozoan and unicellular green algae), fungi (including ascomycetes and basidiomycetes), plants (including bryophytes, pteridophytes, and seed plants (gymnosperms and angiosperms)), and animals (including invertebrates and vertebrates). Prokaryotes include archaebacteria (including thermophiles and methane bacteria) and eubacteria (including cyanobacteria and *E. coli*). Polypeptides comprising the modified ARSs according to the present invention may be derived from mammals (such as human, mouse, rat, guinea pig, rabbit, sheep, monkey, goat, donkey, cattle, horse, and pig). Polypeptides comprising the modified ARSs according to the present invention may be derived from, for example, *E. coli* or yeast, and preferably derived from prokaryotes, for example bacteria. The polypeptides according to the present invention are derived from, for example, bacteria of the family Enterobacteriaceae, for example, *E. coli*, including, but are not limited to, for example, the genera *Escherichia* (including *E. coli*, *E. albertii*, *E. fergusonii*), *Shigella* (including *S. dysenteriae*, *S. flerneri*, *S. boydii*, *S. sonnei*, *S. enterica*, *S. bongori*), *Citrobacter* (including *C. rodentium*, *C. koseri*, *C. farmeri*, *C. youngae*), *Kluyvera* (including *K. ascorbata*), *Tabulsiella* (including *T. guamensis*), *Klebsiella*, and the like.

N-methyl aminoacyl-tRNA synthetases from *E. coli* were used in the Examples herein as one example, and therefore the modified positions indicated herein are positions in *E. coli*. When N-methyl aminoacyl-tRNA synthetases from other organisms are used, positions to be modified are amino acids at positions corresponding to those in the amino acid sequence of N-methyl aminoacyl-tRNA synthetases from *E. coli* based on sequence homology. ARSs are generally very highly conserved because they are enzymes playing an essential part in the translation mechanism that exists in all organisms. Accordingly, a desired ARS can be modified based on the method according to the present invention to obtain a modified ARS with an increased ability to incorporate an N-methyl amino acid.

Amino acids to be newly introduced into N-methyl aminoacyl-tRNA synthetases are selected based on hydrophilicity, hydrogen bonds, and side chain size of amino acids in consideration of the distance to and interaction with N-methyl group. For example, when avoiding the steric repulsion between the amino acid at the position and an N-methyl group, the distance to the N-methyl amino group can be adjusted by, for example, substituting a high molecular weight amino acid with a low molecular weight amino acid. Specifically, the distance can be adjusted by reducing the molecular weight, for example, by substituting threonine (Thr) with serine (Ser).

For example, when an amino acid to be modified in an N-methyl aminoacyl-tRNA synthetase is asparagine, the low molecular weight amino acids can include, but are not limited to, for example, serine, valine, glycine, aspartic acid, and alanine. When an amino acid to be modified is glutamic acid, the low molecular weight amino acids can include, but are not limited to, for example, alanine, valine, serine, alanine, and aspartic acid. Moreover, for example, when an amino acid to be modified is Thr, the low molecular weight amino acids include preferably, for example, Ser. When an amino acid to be modified is an amino acid other than the amino acids as described above, the low molecular weight amino acids include preferably, for example, glycine (Gly) and alanine (Ala), and more preferably glycine (Gly). To give one specific example, Thr can be substituted with Ser; Gln, Glu, and Asn can be substituted with Gly or Ala: and Met, His, Gln, and the like can be substituted with Gly, but the substitutions are not limited thereto.

To give a more specific example, modification of valine aminoacyl-tRNA synthetase (ValRS) includes, for example, modification of amino acid(s) at position 43 and/or position 45 and/or position 279 of SEQ ID NO: 24 (natural ValRS), or amino acids at positions corresponding to these positions. Amino acids selected for substitution are not limited, but as mentioned above, for example, Thr can be substituted with Ser, Ala, or Gly, and amino acids (e.g., Asn) other than Thr can be substituted with Gly or Ala. For example, preferred are substitution of the amino acid at position 43 of SEQ ID NO: 24 or an amino acid at a position corresponding to position 43 of SEQ ID NO: 24 with Gly or Ala, and/or substitution of the amino acid at position 45 of SEQ ID NO: 24 or an amino acid at the position corresponding to position 45 of SEQ ID NO: 24 with Ser, and/or substitution of the amino acid at position 279 or an amino acid at a position corresponding to position 279 with Gly or Ala. These substitutions may be any one of the substitutions, a combination of any of these substitutions (e.g., substitutions at position 43 and position 45, substitutions at position 43 and position 279, or substitutions at position 45 and position 279), or all of the substitutions. Other substitutions may be further combined. As a more specific illustration, N43 and/or T45 and/or T279 of SEQ ID NO: 24, or amino acids at the positions corresponding to these, are preferably substituted, and preferably substituted to N43G and/or T45S and/or T279A.

Modification of serine aminoacyl-tRNA synthetase (SerRS) includes, for example, modification of amino acid(s) at position 237 and/or position 239 of SEQ ID NO: 26 (natural SerRS), or amino acids at the positions corresponding to these positions. Amino acids selected for substitution are not limited, but as mentioned above, for example, Thr can be substituted with Ser, and amino acids (e.g., Glu) other than Thr can be substituted with Gly or Ala. For example, preferred are substitution of the amino acid at position 237 of SEQ ID NO: 26 or an amino acid at the position corresponding to position 237 of SEQ ID NO: 26 with Ser, and/or substitution of the amino acid at position 239 of SEQ ID NO: 26 or an amino acid at the position corresponding to position 239 of SEQ ID NO: 26 with Gly or Ala. These substitutions may be any one or both of the substitutions. Other substitutions may be further combined. As a more specific illustration, T237 and/or E239 of SEQ ID NO: 26, or amino acids at positions corresponding to these, are preferably substituted, and preferably substituted to T237S and/or E239G (or E239A).

Modification of phenylalanine aminoacyl-tRNA synthetase α subunit (PheRS α) includes, for example, modification of amino acid at position 169 of SEQ ID NO: 28 (natural PheRS α subunit), or an amino acid at a position corresponding to position 169 of SEQ ID NO: 28. Amino acids selected for substitution are not limited, but as mentioned above, for example, Thr can be substituted with Ser, and amino acids other than Thr can be substituted with glycine (Gly) or alanine (Ala) (more preferably Gly). For example, preferred is substitution of the amino acid at position 169 of SEQ ID NO: 28 or an amino acid at the position corresponding to position 169 of SEQ ID NO: 28 with Gly. Other substitutions may be further combined. As a more specific illustration, Q169 of SEQ ID NO: 28, or an amino acid at the position corresponding to Q169 of SEQ ID NO: 28, is preferably substituted, and preferably substituted to Q169G (or Q169A).

Modification of threonine aminoacyl-tRNA synthetase (ThrRS) includes, for example, modification of amino acid(s) at position 332 and/or position 511 of SEQ ID NO: 29 (natural ThrRS), or amino acids at positions corresponding to these positions. Amino acids selected for substitution are not limited, but as mentioned above, for example, Thr can be substituted with Ser, and amino acids (e.g., Met and His) other than Thr can be substituted with Gly. For example, preferred is/are substitution of the amino acid at position 332 of SEQ ID NO: 29 or an amino acid at a position corresponding to position 332 of SEQ ID NO: 29 with Gly and/or substitution of the amino acid at position 511 of SEQ ID NO: 29 or an amino acid at a position corresponding to position 511 of SEQ ID NO: 29 with Gly. These substitutions may be any one or both of the substitutions. Other substitutions may be further combined. As a more specific illustration, M332 and/or H511 of SEQ ID NO: 29, or amino acids at positions corresponding to these, are preferably substituted, and preferably substituted to M332G and/or H511G.

Modification of tryptophan aminoacyl-tRNA synthetase (TrpRS) includes, for example, modification of amino acid(s) at position 132 and/or position 150 and/or position 153 of SEQ ID NO: 188 (natural TrpRS), or amino acids at a position corresponding to these positions. Amino acids selected for substitution are not limited, but as mentioned above, for example, Met can be substituted with Val or Ala, and amino acids (e.g., Gln) other than Met can be substituted with Ala. For example, preferred is/are substitution of the amino acid at position 132 of SEQ ID NO: 188 or an amino acid at a position corresponding to position 132 of SEQ ID NO: 188 with Val or Ala, and/or substitution of the amino acid at position 150 of SEQ ID NO: 188 or an amino acid at a position corresponding to position 150 of SEQ ID NO: 188 with Ala, and/or substitution of the amino acid at position 153 or an amino acid at a position corresponding to position 153 with Ala. These substitutions may be any one of the substitutions, a combination of any of these substitutions (e.g., substitutions at position 132 and position 150, substitutions at position 132 and position 153, or substitutions at position 150 and position 153), or all of the substitutions. Other substitutions may be further combined. As a more specific illustration, M132 and/or Q150 and/or H153 of SEQ ID NO: 188, or amino acids at positions corresponding to these, are preferably substituted, and preferably substituted to M132V and/or Q150A and/or H153A.

Modification of leucine aminoacyl-tRNA synthetase (LeuRS) includes, for example, modification of the amino acid at position 43 of SEQ ID NO: 189 (natural LeuRS), or an amino acid at a position corresponding to position 43 of SEQ ID NO: 189. Amino acids selected for substitution are not limited, but as mentioned above, for example, Thr can be substituted with Gly. For example, preferred is substitution of the amino acid at position 43 of SEQ ID NO: 189 or an amino acid at a position corresponding to position 43 of SEQ ID NO: 189 with Gly. Other substitutions may be further combined. As a more specific illustration, Y43 of SEQ ID NO: 189, or an amino acid at a position corresponding to Y43 of SEQ ID NO: 189, is preferably substituted, and preferably substituted to Y43G.

A method for producing a mutant N-methyl aminoacyl-tRNA synthetase, which is modified by substituting an amino acid at a specific position with another amino acid, according to the present invention, can be performed using any known genetic engineering technique. For example, DNA fragments having base sequences encoding amino acid sequences comprising amino acids at positions of interest are amplified using primers having base sequences substituted with base sequences encoding amino acid sequences comprising modified amino acids, resulting in base sequences encoding amino acid sequences comprising modified amino acids. The amplified DNA fragments are ligated together to obtain a full-length DNA encoding the mutant aminoacyl-tRNA synthetase. This full-length DNA can be expressed using a host cell such as E. coli to easily produce the mutant N-methyl aminoacyl-tRNA synthetase. Primers used in the method are 20 to 70 bases in length, and preferably about 20 to 50 bases in length. The primers have 1 to 3 base mismatches with the original unmodified base sequence, and therefore relatively long primers, for example, primers of 20 bases or more in length are preferably used.

A method for producing a mutant N-methyl aminoacyl-tRNA synthetase, which is modified by substituting an amino acid at a specific position with another amino acid, according to the present invention, is not limited to the method as described above, and various genetic engineering techniques, such as known point mutation techniques and gene synthesis techniques, and methods for introducing modified fragments using restriction enzymes, can be utilized. Expression hosts are not limited to E. coli, and animal cells and cell-free translation systems may also be used.

Modified ARSs according to the present invention include a polypeptide comprising an amino acid sequence set forth in any of SEQ ID NOs: 1-11 and 182-187 (PheRS05, PheRS04, ValRS04, ValRS13, ValRS13-11, SerRS03, SerRS05, SerRS35, SerRS37, ThrRS03, ThrRS14, ValRS66, ValRS67, TrpRS04, TrpRS05, TrpRS18, and LeuRS02) and polypeptides functionally equivalent to the polypeptide. "Functionally equivalent polypeptides" are ARSs with a high structural identity to a polypeptide comprising an amino acid sequence set forth in any of SEQ ID NOs: 1-11 and 182-187 and have reactivity with N-methyl amino acids. More specifically, "functionally equivalent polypeptides" are polypeptides that have amino acids modified according to the above description in ARSs with a high structural identity to a polypeptide comprising an amino acid sequence set forth in any of SEQ ID NOs: 1-11 and 182-187, thereby having increased reactivity with N-methyl amino acids compared to unmodified ARSs. Increased reactivity with N-methyl amino acids may be, for example, increased substrate specificity to N-methyl amino acids (e.g., increased value of reactivity with N-methyl amino acids/reactivity with unmodified amino acids).

Such polypeptides include, for example, a polypeptide in which one or more amino acids (preferably 1 to 20 amino acids, for example, 1 to 10 amino acids, 1 to 7 amino acids, 1 to 5 amino acids, 1 to 3 amino acids, 1 to 2 amino acids, or 1 amino acid) are substituted, deleted, inserted, and/or added in an amino acid sequence set forth in any of SEQ ID NOs: 1-11 and 182-187. Such polypeptides may also be, for example, a polypeptide in which one to several amino acids are substituted, deleted, inserted, and/or added in an amino acid sequence set forth in any of SEQ ID NOs: 1-11 and 182-187.

A polypeptide functionally equivalent to a modified ARS comprising an amino acid sequence set forth in any of SEQ ID NOs: 1-11 and 182-187 typically has a high identity to an amino acid sequence set forth in any of SEQ ID NOs: 1-11 and 182-187. A polynucleotide encoding a functionally equivalent polypeptide also typically has a high identity to a base sequence (e.g., SEQ ID NOs: 12-22 and 190-195) encoding an amino acid sequence set forth in any of SEQ ID NOs: 1-11 and 182-187. High identity (sequence identity) specifically refers to 70% or more, preferably 80% or more, 85% or more, 90% or more, 95% or more, 97% or more, 98% or more, or 99% or more identity.

The identity of amino acid sequences or base sequences can be determined using the BLAST algorithm by Karlin and Altschul (Proc. Natl. Acad. Sci. USA (1993) 90: 5873-7). Programs called BLASTN and BLASTX have been developed based on the algorithm (Altschul et al., J. Mol. Biol. (1990) 215: 403-10). When a base sequence is analyzed using BLAST-based BLASTN, parameters are set as, for example, score=100 and wordlength=12. When an amino acid sequence is analyzed using BLAST-based BLASTX, parameters are set as, for example, score=50 and wordlength=3. When BLAST and Gapped BLAST programs are used, default parameters of each program are used. Specific procedures of these analysis methods are known (see, information at the website of Basic Local Alignment Search Tool (BLAST) in National Center for Biotechnology Information (NCBI).

The polypeptides according to the present invention include any polypeptide of the following (a) to (d), wherein the amino acid corresponding to position 43 of SEQ ID NO: 24 (ValRS) is other than Asn, and/or the amino acid corresponding to position 45 of SEQ ID NO: 24 (ValRS) is other than Thr and/or the amino acid corresponding to position 279 of SEQ ID NO: 24 (ValRS) is other than Thr (i.e., a polypeptide in which the amino acid at at least one of these 3 positions is other than the indicated respective amino acid) and wherein the polypeptide has increased reactivity to N-methyl Val compared to a polypeptide in which the amino acids corresponding to position 43, position 45, and position 279 are Asn, Thr, and Thr, respectively:
(a) a polypeptide comprising an amino acid sequence having a high identity to an amino acid sequence set forth in any of SEQ ID NOs: 3-5, 182, and 183 (ValRS04, ValRS13, ValRS13-11, ValRS66, and ValRS67);
(b) a polypeptide comprising an amino acid sequence in which one or more amino acids are substituted, deleted, inserted, and/or added in an amino acid sequence set forth in any one of SEQ ID NOs: 3-5, 182, and 183;
(c) a polypeptide encoded by a base sequence with high identity to a base sequence set forth in any one of SEQ ID NOs: 14-16, 190, and 191 (DNA encoding ValRS04, ValRS13, ValRS13-11, ValRS66, and ValRS67); or
(d) a polypeptide encoded by a DNA fragment hybridizing with a strand complementary to a base sequence set forth in any one of SEQ ID NOs: 14-16, 190, and 191 under stringent conditions.

The above-mentioned polypeptides preferably have (i) Gly or Ala at the amino acid position corresponding to position 43 and/or (ii) Ser at the amino acid position corresponding to position 45 and/or (iii) Gly or Ala at the amino acid position corresponding to position 279. Such polypeptides include natural polypeptides and artificially-modified polypeptides, and preferably include polypeptides in which (i) the amino acid at the position corresponding to position 43 is substituted with Gly or Ala and/or (ii) the amino acid at the position corresponding to position 45 is substituted with Ser and/or (iii) the amino acid at the position corresponding to position 279 is substituted with Gly or Ala.

The polypeptides according to the present invention include any polypeptide of the following (a) to (d), wherein the amino acid corresponding to position 237 of SEQ ID NO: 26 (SerRS) is other than Thr and/or the amino acid corresponding to position 239 of SEQ ID NO: 26 (SerRS) is other than Glu (i.e., a polypeptide in which the amino acid at at least one of these 2 positions is other than the indicated respective amino acid) and wherein the polypeptide has increased reactivity with N-methyl Ser compared to a polypeptide in which the amino acids corresponding to position 237 and position 239 are Thr and Glu respectively:
(a) a polypeptide comprising an amino acid sequence having a high identity to an amino acid sequence set forth in any one of SEQ ID NOs: 6-9 (SerRS03, SerRS05, SerRS35, and SerRS37);
(b) a polypeptide comprising an amino acid sequence in which one or more amino acids are substituted, deleted, inserted, and/or added in an amino acid sequence set forth in any one of SEQ ID NOs: 6-9;
(c) a polypeptide encoded by a base sequence having a high identity to a base sequence set forth in any one of SEQ ID NOs: 17-20 (DNA encoding SerRS03, SerRS05, SerRS35, and SerRS37); or
(d) a polypeptide encoded by a DNA fragment hybridizing with a strand complementary to a base sequence set forth in any one of SEQ ID NOs: 17-20 under stringent conditions.

The above-mentioned polypeptides preferably have (i) Ser at the amino acid position corresponding to position 237 and/or (ii) Gly or Ala at the amino acid position corresponding to position 239. Such polypeptides include natural polypeptides and artificially-modified polypeptides, and preferably include polypeptides in which (i) the amino acid at the position corresponding to position 237 is substituted with Ser and/or (ii) the amino acid at the position corresponding to position 239 is substituted with Gly or Ala.

Such polypeptides according to the present invention include any polypeptide of the following (a) to (d), wherein the polypeptide has any amino acid other than Gln at the position corresponding to position 169 of SEQ ID NO: 28 (PheRS) and has increased reactivity with N-methyl Phe compared to a polypeptide in which the amino acid at position 169 of SEQ ID NO: 28 (PheRS) is Gln:
(a) a polypeptide comprising an amino acid sequence having a high identity to an amino acid sequence set forth in any one of SEQ ID NOs: 1-2 (PheRS05 and PheRS04);
(b) a polypeptide comprising an amino acid sequence in which one or more amino acids are substituted, deleted, inserted, and/or added in an amino acid sequence set forth in any one of SEQ ID NOs: 1-2;
(c) a polypeptide encoded by a base sequence having a high identity to a base sequence set forth in any one of SEQ ID NOs: 12-13 (DNA encoding PheRS05 and PheRS04); or
(d) a polypeptide encoded by a DNA fragment hybridizing with a strand complementary to a base sequence set forth in any one of SEQ ID NOs: 12-13 under stringent conditions.

The above-mentioned polypeptides preferably have Gly or Ala at the amino acid position corresponding to position 169. Such polypeptides include natural polypeptides and artificially-modified polypeptides, and preferably include polypeptides in which the amino acid at the position corresponding to position 169 is substituted with Gly or Ala.

The polypeptides according to the present invention include any polypeptide of the following (a) to (d), wherein the amino acid corresponding to position 332 of SEQ ID NO: 29 (ThrRS) is other than Met and/or the amino acid corresponding to position 511 of SEQ ID NO: 29 (ThrRS) is other than His (i.e., a polypeptide in which the amino acid at at least one of these 2 positions is other than the indicated respective amino acid) and wherein the polypeptide has increased reactivity with N-methyl Thr compared to a polypeptide in which the amino acids corresponding to position 332 and position 511 are Met and His, respectively:
(a) a polypeptide comprising an amino acid sequence having a high identity to an amino acid sequence set forth in any one of SEQ ID NOs: 10-11 (ThrRS03 and ThrRS14);
(b) a polypeptide comprising an amino acid sequence in which one or more amino acids are substituted, deleted, inserted, and/or added in an amino acid sequence set forth in any one of SEQ ID NOs: 10-11;
(c) a polypeptide encoded by a base sequence having a high identity to a base sequence set forth in any one of SEQ ID NOs: 21-22 (DNA encoding ThrRS03 and ThrRS14); or
(d) a polypeptide encoded by a DNA fragment hybridizing with a strand complementary to a nucleotide sequence set forth in any one of SEQ ID NOs: 21-22 under stringent conditions.

The above-mentioned polypeptides preferably have (i) Gly at the amino acid position corresponding to 332 and/or (ii) Gly at the amino acid position corresponding to position 511. Such polypeptides include natural polypeptides and artificially-modified polypeptides, and preferably include polypeptides in which the amino acid at the position corresponding to position 332 is substituted with Gly and/or the amino acid at the position corresponding to position 511 is substituted with Gly.

The polypeptides according to the present invention include a polypeptide that is any polypeptide of the following (a) to (d), wherein the amino acid corresponding to position 132 of SEQ ID NO: 188 (TrpRS) is other than Met and/or the amino acid corresponding to position 150 of SEQ ID NO: 188 (TrpRS) is other than Gln and/or the amino acid corresponding to position 153 of SEQ ID NO: 188 (TrpRS)

is other than His (i.e., a polypeptide in which the amino acid at at least one of these 3 positions is other than the indicated respective amino acid) and wherein the polypeptide has increased reactivity with N-methyl Trp compared to a polypeptide in which the amino acids corresponding to position 132, position 150, and position 153 are Met, Gln, and His, respectively:

(a) a polypeptide comprising an amino acid sequence having a high identity to an amino acid sequence set forth in any one of SEQ ID NOs: 184-186 (TrpRS04, TrpRS05, and TrpRS18);

(b) a polypeptide comprising an amino acid sequence in which one or more amino acids are substituted, deleted, inserted, and/or added in an amino acid sequence set forth in any one of SEQ ID NOs: 184-186;

(c) a polypeptide encoded by a base sequence having a high identity to a base sequence set forth in any one of SEQ ID NOs: 192-194 (DNA encoding TrpRS04, TrpRS05, and TrpRS18); or (d) a polypeptide encoded by a DNA fragment hybridizing with a strand complementary to a base sequence set forth in any one of SEQ ID NOs: 192-194 under stringent conditions.

The above-mentioned polypeptides preferably have (i) Val or Ala at the amino acid position corresponding to position 132 and/or (ii) Ala at the amino acid position corresponding to position 150 and/or (iii) Ala at the amino acid position corresponding to position 153. Such polypeptides include natural polypeptides and artificially-modified polypeptides, and preferably include polypeptides in which (i) the amino acid at the position corresponding to position 132 is substituted with Val or Ala and/or (ii) the amino acid at the position corresponding to position 150 is substituted with Ala and/or (iii) the amino acid at the position corresponding to position 153 is substituted with Ala.

The polypeptides according to the present invention include any polypeptide of the following (a) to (d), wherein the polypeptide has any amino acid other than Tyr at the position corresponding to position 43 of SEQ ID NO: 189 (LeuRS) and has increased reactivity with N-methyl Leu compared to a polypeptide in which the amino acid corresponding to position 43 is Tyr:

(a) a polypeptide comprising an amino acid sequence having a high identity to the amino acid sequence set forth in SEQ ID NO: 187 (LeuRS02);

(b) a polypeptide comprising an amino acid sequence in which one or more amino acids are substituted, deleted, inserted, and/or added in an amino acid sequence set forth in any one of SEQ ID NO: 187;

(c) a polypeptide encoded by a base sequence having a high identity to the base sequence set forth in SEQ ID NO: 195 (DNA encoding LeuRS02); or (d) a polypeptide encoded by a DNA fragment hybridizing with a strand complementary to the base sequence set forth in SEQ ID NO: 195 under stringent conditions.

The above-mentioned polypeptides preferably have Gly at the amino acid position corresponding to position 43. Such polypeptides include natural polypeptides and artificially-modified polypeptides, and preferably include polypeptides in which the amino acid at the position corresponding to position 43 is substituted with Gly.

In the case of polypeptides obtained by modifying natural ARSs, polypeptides according to the present invention are those with increased reactivity to N-methyl amino acids compared to unmodified ARSs. When the polypeptides are natural ARSs or artificially produced polypeptides, the polypeptides according to the present invention are those with reactivity to N-methyl amino acids, namely those having an activity to acylate tRNAs with N-methyl amino acids. When comparing the reactivities of modified ARSs and natural ARSs, and the ARSs are made up of multiple subunits, subunit(s) other than that/those compared is/are the same is/are used. These subunits may be natural (or wild-type) or a modified as long as they are the same in both ARSs.

High identity (or high sequence identity) refers to, as mentioned above, for example, 70% or more, preferably 80% or more, 85% or more, 90% or more, 95% or more, 97% or more, 98% or more, or 99% or more identity. The number of amino acids substituted, deleted, inserted, and/or added may be one or several, for example, 1 to 20, preferably 1 to 15, more preferably 1 to 10, more preferably 1 to 8, more preferably 1 to 7, more preferably 1 to 6, more preferably 1 to 5, more preferably 1 to 4, more preferably 1 to 3, more preferably 1 to 2, and more preferably 1. Stringent hybridization conditions refer to, for example, conditions of about "1×SSC, 0.1% SDS, at 37° C.", more strictly conditions of about "0.5×SSC, 0.1% SDS, at 42° C.", further more strictly conditions of about "0.2×SSC, 0.1% SDS, at 65° C.", and yet more strictly conditions of about "0.1×SSC, 0.1% SDS, at 65° C.". It is noted that the conditions of SSC, SDS, and temperature as described above are only examples of combinations. Those skilled in the art can achieve stringency similar to those described above by appropriately combining the above-mentioned or other factors that determine hybridization stringency (such as probe concentration, probe length, and duration of hybridization).

The present invention also relates to polynucleotides encoding the polypeptides according to the present invention. The polynucleotides according to the present invention comprise any polynucleotide as long as it comprises a sequence encoding a polypeptide according to the present invention as described above. The polynucleotides according to the present invention also comprise any one of genomic DNA, cDNA, and DNAs artificially produced based on the genomic DNA or cDNA. Genomic DNA comprises exons and introns. That is to say, genomic DNA may or may not comprise introns, and may or may not comprise untranslated regions (5' UTR and/or 3' UTR), transcription control elements, and the like. cDNA is a nucleic acid sequence derived from a portion of intronic sequence and may comprise a nucleic acid sequence encoding an amino acid sequence.

The polynucleotides also comprise degenerate polynucleotides comprising any codon that encodes the same amino acid. The polynucleotides according to the present invention may also be a polynucleotide derived from desired organisms.

The polynucleotides according to the present invention may be obtained using any method. For example, a complementary DNA (cDNA) prepared from mRNA, a DNA prepared from genomic DNA, a DNA obtained by chemical synthesis, a DNA obtained by amplifying RNA or DNA as a template using PCR, and a DNA constructed by appropriately combining these techniques are all included. The polynucleotides according to the present invention can be produced by cloning the genomic DNA or RNA encoding the polypeptide according to the present invention according to conventional methods and introducing mutations into the cloned genomic DNA or RNA.

For example, in a method for cloning cDNA from mRNA encoding a polypeptide according to the present invention, first, the mRNA encoding the polypeptide according to the present invention is prepared according to conventional methods from any tissue or cell where the polypeptide according to the present invention is expressed and produced. For example, total RNA prepared using a method such as the guanidine thiocyanate method, hot-phenol method, or AGPC method can be subjected to affinity chromatography on oligo (dT) cellulose, poly U-Sepharose, or the like.

The obtained mRNA is then used as a template to synthesize a cDNA strand by using a known method (Mol. Cell. Biol., Vol. 2, p. 161, 1982; Mol. Cell. Biol., Vol. 3, p. 280, 1983; Gene, Vol. 25, p. 263, 1983), for example, by using reverse transcriptase. The cDNA strand is converted into a double-stranded cDNA and incorporated into a plasmid vector, phage vector, cosmid vector, or the like. The vector is used to transform E. coli or to perform in vitro packaging followed by transfection of E. coli to generate a cDNA library.

The cDNA library can be screened using a polynucleotide according to the present invention (e.g., SEQ ID NOs: 12-22, 190-195) or a portion thereof as a probe to obtain a gene of interest. Alternatively, the cDNA library can be directly amplified by PCR using a polynucleotide according to the present invention (e.g., SEQ ID NOs: 12-22, 190-195) or a portion thereof as a primer. The sites and lengths of probes and primers may be appropriately determined.

The present invention also relates to vectors (recombinant vectors) comprising polynucleotides encoding the polypeptides according to the present invention as described above. The vectors according to the present invention are not particularly limited as long as they can replicate and can be maintained or can self-proliferate in any host prokaryotic and/or eukaryotic cell. The vectors include plasmid vectors, phage vectors, viral vectors, and the like.

Examples of vectors for cloning include, for example, pUC19, λgt10, λgt11, and the like. Furthermore, the vectors preferably have a promoter that can express the polypeptide according to the present invention when cells that can express the polynucleotide in host cells are isolated.

The recombinant vectors according to the present invention can be prepared by simply ligating a polynucleotide encoding a polypeptide according to the present invention into a vector for recombination (a plasmid DNA and bacteriophage DNA) available in the art according to conventional methods.

Examples of recombinant vectors that can be used include, for example, plasmids from E. coli (such as pBR322, pBR325, pUC12, pUC13, and pUC19), plasmids from yeast (such as pSH19 and pSH15), and plasmids from Bacillus subtilis (such as pUB110, pTP5, and pC194).

Examples of phages include bacteriophage such as λ phage, and further animal and insect viruses such as retrovirus, vaccinia virus, nucleopolyhedrovirus, and lentivirus (pVL1393, from Invitrogen).

Expression vectors are useful for expressing polynucleotides encoding the polypeptides according to the present invention and production of the polypeptides according to the present invention. The expression vectors are not particularly limited as long as they have functions to express polynucleotides encoding the polypeptides according to the present invention and produce the polypeptides in any host prokaryotic and/or eukaryotic cell.

For example, expression vectors include pMAL C2, pEF-BOS (Nucleic Acid Research, Vol. 18, 1990, p. 5322, and the like), or pME18S ("Idenshi Kougaku Handbook (Genetic Engineering Handbook)", supplementary volume of Jikken Igaku (Experimental Medicine), 1992, and the like).

The present invention also relates to fusion between polypeptides according to the present invention with another protein/other proteins. A fusion polypeptide according to the present invention is a fusion polypeptide between a polypeptide having reactivity with N-methyl amino acids according to the present invention and another polypeptide. The fusion polypeptide itself may have no reactivity with N-methyl amino acids as long as it comprises a polypeptide chain having reactivity with N-methyl amino acids according to the present invention. When prepared as a fusion protein with, for example, Glutathione S-transferase (GST), the fusion polypeptide according to the present invention can be prepared by subcloning a cDNA encoding the polypeptide according to the present invention into, for example, plasmid pGEX4T1 (from Pharmacia), transforming E. coli DH5α or the like with the plasmid, and culturing the transformant.

Alternatively, a fusion polypeptide according to the present invention can be prepared as a fusion with HA (influenza agglutinin), immunoglobulin constant region, β-galactosidase, maltose-binding protein (MBP), or the like. Moreover, a fusion polypeptide can be prepared as a fusion with, for example, any known peptide such as FLAG (Hopp, T. P. et al., BioTechnology (1988) 6, 1204-1210), a tag consisting of several (e.g., six) histidine (His) residues (such as 6×His, 10×His), influenza agglutinin (HA), a human c-myc fragment, a VSV-GP fragment, a p18HIV fragment, T7-tag, HSV-tag, E-tag, a SV40T antigen fragment, lck tag, an α-tubulin fragment, B-tag, a Protein C fragment, Stag, StrepTag, and HaloTag.

The vectors according to the present invention preferably comprise at least a promoter-operator region, the initiation codon, a polynucleotide encoding the polypeptide according to the present invention, a termination codon, a terminator region, and a replicable unit when bacteria, particularly E. coli, are used as host cells.

The expression vectors preferably comprise at least a promoter, the initiation codon, a polynucleotide encoding a polypeptide according to the present invention, and a termination codon when yeast, animal cells, or insect cells are used as hosts.

The vectors may also comprise DNA encoding a signal peptide, an enhancer sequence, 5' and 3' untranslated regions of the gene encoding a polypeptide according to the present invention, a splicing junction, a polyadenylation site, a selection marker region, a replicable unit, or the like.

The vectors may also comprise, if desired, a marker gene (such as a gene amplification gene, a drug-resistant gene) that allows selection of hosts in which gene amplification and transformation have been achieved.

Examples of marker genes include, for example, dihydrofolate reductase (DHFR) gene, thymidine kinase gene, neomycin resistant gene, glutamic acid synthetase gene, adenosine deaminase gene, ornithine decarboxylase gene, hygromycin B phosphotransferase gene, aspartate transcarbamylase gene, and the like.

The promoter-operator region for expressing a polypeptide according to the present invention in bacteria can include, a promoter, an operator, and Shine-Dalgarno (SD) sequence (such as AAGG).

An example of a promoter-operator region includes one comprising, for example, Trp promoter, lac promoter, recA promoter, λPL promoter, lpp promoter, tac promoter, or the like when the host is a bacterium of the genus Escherichia, for example.

Promoters for expressing a polypeptide according to the present invention in yeast include PH05 promoter, PGK promoter, GAP promoter, and ADH promoter.

The promoters include SL01 promoter, SP02 promoter, penP promoter, and the like when the host is a bacterium of the genus *Bacillus*.

The promoters also include promoters derived from SV40, retroviral promoters, heat shock promoters, and the like when the hosts are eukaryotic cells such as mammalian cells. The promoters are preferably those derived from SV40 and retroviral promoters. However, the promoters are not particularly limited to those described above. Also, enhancers can be effectively used for expression.

An example of a suitable initiation codon includes the methionine codon (ATG). Examples of termination codons include common termination codons (e.g., TAG, TGA, and TAA). Terminator regions that can be used include natural or synthetic terminators generally used.

The replicable unit refers to DNA having an ability to replicate the full DNA sequence of the replicable unit in host cells, and includes natural plasmids, artificially modified plasmids (DNA fragments prepared from natural plasmids), synthetic plasmids, and the like. Suitable plasmids include plasmid pBR322 or an artificially modified pBR322 (a DNA fragment obtained by digesting pBR322 with a suitable restriction enzyme) for *E. coli*; yeast 2p plasmid or yeast chromosomal DNA for yeast; and plasmid pRSVneo (ATCC 37198), plasmid pSV2dhfr (ATCC 37145), plasmid pdBPV-MMTneo (ATCC 37224), plasmid pSV2neo (ATCC 37149), and the like for mammalian cells.

Enhancer sequence, polyadenylation site, and splicing junction that can be used are those commonly used by those skilled in the art, such as for example those derived from SV40.

The expression vectors according to the present invention can be prepared by ligating at least a promoter as described above, an initiation codon, a polynucleotide encoding a polypeptide according to the present invention, a termination codon, and a terminator region to a suitable replicable unit continuously and circularly. Suitable DNA fragments (e.g., a linker, other restriction enzyme cleavage sites, and the like) can also be used in conventional techniques such as digestion with restriction enzymes and ligation with T4 DNA ligase, if desired.

The present invention also relates to recombinant cells transformed with the vectors according to the present invention as described above, and the recombinant cells according to the present invention can be prepared by introducing the expression vectors as described above into host cells.

Host cells used in the present invention are not particularly limited as long as they are compatible with the expression vectors described above and can be transformed. Examples of host cells include various cells including natural cells and artificially-established recombinant cells commonly used in the technical field of the present invention, for example, bacteria (*Escherichia* bacteria, *Bacillus* bacteria), yeast (such as *Saccharomyces*, *Pichia*), animal cells, insect cells, and the like.

The host cells are preferably *E. coli* or animal cells, and examples include, for example, *E. coli* (such as DH5α, TB1, HB101), mouse-derived cells (such as COP, L, C127, Sp2/0, NS-1, or NIH3T3), rat-derived cells (PC12, PC12h), hamster-derived cells (such as BHK and CHO), monkey-derived cells (such as COS1, COS3, COS7, CV1, and Velo), human-derived cells (such as Hela, diploid fibroblast-derived cells, myeloma cells, and HepG2), and the like.

Introduction of expression vectors into host cells (transformation (transfection)) can be performed according to conventional methods ([for *E. coli*, *Bacillus subtilis*, and the like]: Proc. Natl. Acad. Sci. USA., Vol. 69, p. 2110, 1972; Mol. Gen. Genet., Vol. 168, p. 111, 1979; J. Mol. Biol., Vol. 56, p. 209, 1971; [for *Saccharomyces cerevisiae*]: Proc. Natl. Acad. Sci. USA., Vol. 75, p. 1927, 1978; J. Bacteriol., Vol. 153, p. 163, 1983); [for animal cells]: Virology, Vol. 52, p. 456, 1973; [for insect cells]: Mol. Cell. Biol., Vol. 3, p. 2156-2165, 1983).

The polypeptides according to the present invention can be produced by culturing recombinant transformed cells including expression vectors prepared as described above (hereinafter used to mean inclusion of an inclusion body) in a nutrient medium according to any conventional method.

The polypeptides according to the present invention can be produced such as by culturing recombinant cells as described above, particularly animal cells and allowing the recombinant cells to secrete the polypeptides into culture supernatant.

The obtained culture is subjected to filtration, centrifugation, or any other similar technique to obtain a culture filtrate (supernatant). The polypeptides according to the present invention are purified and isolated from the culture filtrate according to any conventional method commonly used to purify and isolate natural or synthetic proteins.

Isolation and purification methods include, for example, methods utilizing solubility such as salt precipitation and solvent precipitation, dialysis, ultrafiltration, gel filtration, methods utilizing the difference in molecular weight such as sodium dodecyl sulphate-polyacrylamide gel electrophoresis, methods utilizing electric charge such as ion exchange chromatography and hydroxylapatite chromatography, methods utilizing specific affinity such as affinity chromatography, methods utilizing the difference in hydrophobicity such as reversed-phase high-performance liquid chromatography, methods utilizing the difference in isoelectric point such as isoelectric focusing, and the like.

Meanwhile, when a polypeptide according to the present invention is present in periplasm or cytoplasm of cultured recombinant cells (e.g., *E. coli*), the culture is subjected to any conventional method such as filtration or centrifugation to collect bacterial pellets or cells. The collected bacterial pellets or cells are suspended in a suitable buffer, and cell wall and/or cytoplasmic membrane is/are disrupted by any method such as for example sonication, lysozyme, and freeze-thawing. Any method such as centrifugation or filtration is then performed to obtain membrane fraction containing the protein according to the present invention. The membrane fraction is solubilized with any surfactant such as Triton™-X100 to give a crude solution. Then, the crude solution can be isolated and purified using any conventional method as described previously.

The present invention also relates to a polynucleotide (cDNA or genomic DNA) encoding a polypeptide according to the present invention as described above or an oligonucleotide hybridizing with a strand complementary to the polynucleotide. For example, the oligonucleotide is a base sequence at least comprising modified sites of ARSs according to the present invention or an oligonucleotide hybridizing with a strand complementary to the base sequence. An oligonucleotide according to the present invention is also a partial fragment of polynucleotides encoding a modified ARS according to the present invention, and is preferably a fragment comprising bases in modified sites of the modified ARSs or a strand complementary to the fragment.

For example, for a polynucleotide encoding a polypeptide according to the present invention having reactivity with N-methyl Val, the oligonucleotide according to the present invention may be an oligonucleotide comprising bases encoding the codon(s) for an amino acid corresponding to position 43, and/or an amino acid corresponding to position 45, and/or an amino acid corresponding to position 279 of the amino acid sequences set forth in SEQ ID NOs: 3-5, 182, and 183 (ValRS04, ValRS13, ValRS13-11, ValRS66, and ValRS67), or an oligonucleotide consisting of a sequence complementary to the oligonucleotide. In this case, an amino acid corresponding to position 43 is preferably Gly or Ala (more preferably Gly), and an amino acid corresponding to position 45 is preferably Ser, and an amino acid corresponding to position 279 is preferably Gly or Ala (more preferably Ala).

For example, for a polynucleotide encoding a polypeptide according to the present invention having reactivity with N-methyl Ser, the oligonucleotide according to the present invention may be an oligonucleotide comprising bases encoding the codon(s) for an amino acid corresponding to position 237 and/or an amino acid corresponding to position 239 of the amino acid sequences set forth in SEQ ID NOs: 6-9 (SerRS03, SerRS05, SerRS35, and SerRS37), or an oligonucleotide consisting of a sequence complementary to the oligonucleotide. In this case, an amino acid corresponding to position 237 is preferably Ser, and an amino acid corresponding to position 239 is preferably Gly or Ala (more preferably Gly).

For example, for a polynucleotide encoding a polypeptide according to the present invention having reactivity with N-methyl Phe, the oligonucleotide according to the present invention may be an oligonucleotide comprising bases encoding the codon for an amino acid corresponding to position 169 of the amino acid sequences set forth in SEQ ID NOs: 1-2 (PheRS04 and PheRS05) or an oligonucleotide consisting of a sequence complementary to the oligonucleotide. In this case, an amino acid corresponding to position 169 is preferably Gly or Ala.

For example, for a polynucleotide encoding a polypeptide according to the present invention having reactivity with N-methyl Thr, the oligonucleotide according to the present invention may be an oligonucleotide comprising bases encoding the codon(s) for an amino acid corresponding to position 332 and/or an amino acid corresponding to position 511 of the amino acid sequences set forth in SEQ ID NOs: 10-11 (ThrRS03 and ThrRS14), or an oligonucleotide consisting of a sequence complementary to the oligonucleotide. In this case, an amino acid corresponding to position 332 is preferably Gly, and an amino acid corresponding to position 511 is preferably Gly.

For example, for a polynucleotide encoding a polypeptide according to the present invention having reactivity with N-methyl Trp, the oligonucleotide according to the present invention may be an oligonucleotide comprising bases encoding the codon(s) for an amino acid corresponding to position 132, and/or an amino acid corresponding to position 150, and/or an amino acid corresponding to position 153 of the amino acid sequences set forth in SEQ ID NOs: 184-186 (TrpRS04, TrpRS05, and TrpRS18), or an oligonucleotide consisting of a sequence complementary to the oligonucleotide. In this case, an amino acid corresponding to position 132 is preferably Val or Ala (more preferably Val), an amino acid corresponding to position 150 is preferably Ala, and an amino acid corresponding to position 279 is preferably Ala.

For example, for a polynucleotide encoding a polypeptide according to the present invention having reactivity with N-methyl Leu, the oligonucleotide according to the present invention may be an oligonucleotide comprising bases encoding the codon for an amino acid corresponding to position 43 of the amino acid sequence set forth in SEQ ID NO: 187 (LeuRS02) or an oligonucleotide consisting of a sequence complementary to the oligonucleotide. In this case, an amino acid corresponding to position 43 is preferably Gly.

Length of a partial fragment of polynucleotides encoding the polypeptides according to the present invention having reactivity with N-methyl amino acids is not particularly limited, but is for example, at least 15 consecutive bases, preferably 16 or more consecutive bases, more preferably 17 or more consecutive bases, more preferably 18 or more consecutive bases, more preferably 20 or more consecutive bases, more preferably 25 or more consecutive bases, more preferably 28 or more consecutive bases, more preferably 30 or more consecutive bases, more preferably 32 or more consecutive bases, more preferably 35 or more consecutive bases, more preferably 40 or more consecutive bases, and more preferably 50 or more consecutive bases.

In addition to the partial fragment of polynucleotides encoding ARSs according to the present invention as described above, oligonucleotides according to the present invention may also further comprise (an) oligonucleotide(s) consisting of other sequences at its/their both or either end(s) (5' and/or 3' end). An oligonucleotide according to the present invention is, for example, 500 bases or less in length, more preferably 300 bases or less in length, more preferably 200 bases or less in length, more preferably 100 bases or less in length, more preferably 70 bases or less in length, more preferably 60 bases or less in length, and more preferably 50 bases or less in length.

Oligonucleotides according to the present invention are useful for producing nucleic acids encoding the polypeptides according to the present invention (e.g., useful for introducing mutations), and also useful for detecting nucleic acids encoding the polypeptides according to the present invention. For example, an oligonucleotide according to the present invention can also be used as a probe in DNA hybridization or RNA hybridization operations. An example of a DNA for the purpose of using as a probe include a partial base sequence of 20 or more consecutive bases hybridizing with a polynucleotide according to the present invention, preferably, a partial base sequence of 30 or more consecutive bases, more preferably a partial base sequence of 40 or 50 or more consecutive bases, more preferably a partial base sequence of 100 or more consecutive bases, more preferably a partial base sequence of 200 or more consecutive bases, and particularly preferably a partial base sequence of 300 or more consecutive bases.

Polypeptides, polynucleotides, and oligonucleotides according to the present invention can be included in compositions in combination with carriers or vehicles, appropriately. The compositions can be produced using any method known to those skilled in the art. The polypeptides, polynucleotides, and oligonucleotides according to the present invention can be appropriately combined with, for example, pharmacologically acceptable carriers or vehicles, specifically, sterile water, physiological saline, vegetable oil, emulsifying agents, suspending agents, surfactants, stabilizers, flavoring agents, excipients, vehicles, preservatives, bonding agents, or the like. These can be mixed together to be formulated in unit dosage form required by generally-accepted pharmaceutical practices.

The present invention also provides cells transformed with a polynucleotide (including DNA and RNA) encoding a mutant N-methyl aminoacyl-tRNA synthetase as described above. Such cells may be prokaryotic cells or eukaryotic cells.

When a mutant N-methyl aminoacyl-tRNA synthetase according to the present invention expressed in cells is directly used for protein synthesis in the cells, cells depending on the intended use can be used. Any known method can be adopted for the transformation.

The present invention also provides a method for producing polypeptide containing N-methyl amino acids using the ARS with an altered amino acid sequence according to the present invention as described above.

The ARSs with altered amino acid sequences according to the present invention are used not only in cells but also in vitro (in a cell-free system).

In either case, unlike prior art using chemical synthesis such as the pdCpA method, tRNAs can be acylated repeatedly during a translation reaction, and therefore N-methyl aminoacyl-tRNAs can be supplied continuously, and addition of a large amount of tRNAs, which may inhibit translation, can be avoided.

Accordingly, the present invention provides a method for producing non-natural amino acids efficiently, selectively, in particular regioselectively, and in large amounts.

General Method for Preparing a Modified ARS According to the Present Invention

A modified ARS according to the present invention can be produced using any known genetic recombination technique as mentioned above, and generally can be prepared as follows: first, site-directed mutation is introduced into a specific position or a specific amino acid by PCR using a plasmid comprising the natural ARS gene as a template with appropriate primers. The template plasmid is digested with a restriction enzyme, and then *E. coli* or the like is transformed with the digested plasmid. The plasmid into which the desired mutation has been introduced is cloned.

If a second amino acid mutation is introduced, subsequently the introduction of site-directed mutation using the plasmid having the mutation introduced into the specific position as a template with appropriate primers is repeated as with the description above, which results in the construction of a plasmid DNA encoding the polypeptide in which the two amino acids are substituted. A similar procedure can be followed when introducing further amino acid mutations.

*E. coli* BL21 strain or the like is co-transformed with the constructed DNA and the plasmid pREP4 encoding lac repressor (LacI) or the like, and the obtained transformed strain is isolated and cultured followed by expression induction with IPTG. The obtained strain is then disrupted, and the supernatant is passed through an affinity column for His-tag to purify the mutant ARS.

Alternatively, the following method can be used to prepare a mutant ARS. Specifically, a sequence of a certain mutant ARS is genetically synthesized and inserted into an expression vector, and proteins are allowed to be expressed. Affinity columns for different purification tags are used to purify the protein of interest.

Methods for producing a mutant N-methyl aminoacyl-tRNA synthetase according to the present invention, which is modified by substituting an amino acid at a specific position with another amino acid, are not limited to the methods as described above, and various genetic engineering techniques including known point mutation techniques and gene synthesis techniques, methods for introducing modified fragments using restriction enzymes, and the like may be used. Also, expression is not limited to expression in *E. coli*, and animal cells and cell-free translation systems may also be used. Purification methods are also not limited to methods in an affinity column for polyhistidine, and various peptide-tags and purification columns may be used.

Method for Confirming Substrate Specificity of the Obtained Modified ARS According to the Present Invention Substrate specificity of the obtained modified products can be confirmed by any of the following three assay methods, for example.

The first method can confirm by mass spectroscopy that N-methyl amino acids corresponding to codons on mRNA are introduced into a peptide by performing a translation reaction in a cell-free translation system reconstituted with the modified ARS rather than wild-type ARS and further N-methylated amino acids rather than natural amino acids, and performing aminoacylation with N-methyl amino acids in the translation system.

In the second method, peptides to be produced are labeled in a translation experiment using amino acids labeled with radioactive isotopes or fluorescent molecules, and the peptides are separated and visualized by electrophoresis or an analytical column to estimate yield of the peptides. In this method, translational introduction efficiency of corresponding N-methyl amino acids provided by using the modified ARS is increased compared to that provided by using wild-type ARS, and therefore the radioactivity or fluorescence, which is observed by electrophoresis or chromatogram, of the peptide produced using the modified ARS is observed more strongly than that of the peptide produced using wild-type ARS.

In the third method, three molecules, a modified ARS, a tRNA and an N-methyl amino acid corresponding to the modified ARS are reacted together in vitro, and the resulting N-methyl aminoacyl-tRNA is separated from unreacted tRNA by electrophoresis to quantify efficiency of the acylation reaction. The acylated tRNA produced using the modified ARS is detected more than that produced using wild-type ARS.

As mentioned above, the modified ARSs according to the present invention have increased reactivity with N-methyl amino acids compared to unmodified ARSs. The increased reactivity with N-methyl amino acids may be an increase in reaction rate, an increase in the amount of reaction products acylated with N-methyl amino acids, or an increase in substrate specificity to N-methyl amino acids. The increased reactivity with N-methyl amino acids may also be qualitative or quantitative. For example, the reactivity with N-methyl amino acids is considered to have increased in a reaction performed under the same conditions except for the use of an unmodified ARS or a modified ARS when the reactivity (such as reaction rate or the amount of reaction products) of the modified ARS to the substrate N-methyl amino acid is significantly increased compared to the reactivity of the unmodified ARS to N-methyl amino acids. Even if the reaction rate or reaction product amount in a reaction using the modified ARS and an N-methyl amino acid as substrate does not significantly increase compared to that in a reaction using the unmodified ARS, the reactivity of the modified ARS to N-methyl amino acids is considered to have increased when substrate specificity of the modified ARS to the N-methyl amino acid is increased relative to that in a reaction using unmodified amino acids. Preferably, the modified ARSs according to the present invention increase reaction rate or reaction product amount in a reaction using N-methyl amino acids as substrates compared to unmodified ARSs.

For example, the modified ARSs according to the present invention significantly increase the amount of tRNA aminoacylated with N-methyl amino acids or the amount of peptides incorporating N-methyl amino acids, as measured under the same conditions except for using either unmodified ARS or modified ARS, preferably by at least 10%, preferably by 20%, preferably by 1.3 times or more, preferably by 1.5 times or more, preferably by 2 times or more, preferably by 3 times or more, further preferably by 5 times or more, further preferably by 10 times or more, further preferably by 20 times or more, further preferably by 30 times or more, further preferably by 50 times or more, and further preferably by 100 times or more. Alternatively, the modified ARSs according to the present invention significantly increase the amount ratio of "products of the reaction with N-methyl amino acids/products of the reaction with unmodified amino acids", as measured under the same conditions except for using either unmodified ARS or modified ARS, preferably by at least 10%, preferably by 20%, preferably by 1.3 times or more, preferably by 1.5 times or more, preferably by 2 times or more, preferably by 3 times or more, further preferably by 5 times or more, further preferably by 10 times or more, further preferably by 20 times or more, further preferably by 30 times or more, further preferably by 50 times or more, further preferably by 100 times or more compared to unmodified ARSs. Alternatively, when a nucleic acid encoding a polypeptide containing consecutive N-methyl amino acids is allowed to be translated, the modified ARSs according to the present invention significantly increase the production amount of the polypeptide containing consecutive N-methyl amino acids, as measured under the same conditions except for using either unmodified ARS or modified ARS, preferably by at least 10%, preferably by 20%, preferably by 1.3 times or more, preferably by 1.5 times or more, preferably by 2 times or more, preferably by 3 times or more compared to unmodified ARSs. The consecutive N-methyl amino acids may be, for example, two and/or three consecutive N-methyl amino acids.

The reactivity with N-methyl amino acids can be determined according to a confirmation method as described above. Specifically, for example, ribosomally-produced peptides are electrophoresed, and band intensity of peptides that have incorporated N-methyl amino acids and peptides that have not incorporated N-methyl amino acids can be measured qualitatively or quantitatively to determine the reactivity. Alternatively, mass spectral peaks can be measured, and peaks of peptides that have incorporated N-methyl amino acids and peaks of peptides that have not incorporated N-methyl amino acids can be measured to determine the reactivity.

For example, substrate specificity of a modified ARSs according to the present invention is significantly increased, preferably by at least 10%, preferably by 20%, preferably by 1.3 times or more, preferably by 1.5 times or more, preferably by 2 times or more, preferably by 3 times or more, further preferably by 5 times or more, further preferably by 10 times or more, and further preferably by 20 times or more compared to unmodified ARSs when peptides are synthesized in the presence of unmodified amino acids or N-methyl amino acids and the amount ratio of "products of the reaction with N-methyl amino acids/products of the reaction with unmodified amino acids" is measured.

The reaction conditions may be appropriately determined as long as the conditions used for unmodified ARSs and for modified ARSs are the same. The substrate concentration of unmodified amino acids and N-methyl amino acids at the reaction may be appropriately adjusted, and may be any concentration condition as long as reactivity with N-methyl amino acids is increased. Preferably, unmodified amino acids may not be added (may be only endogenous amino acids originally contained in a cell-free translation system), or may be appropriately adjusted in the range from 0.1 µM to 1 mM, for example, 0.1 µM to 500 µM, 0.1 µM to 250 µM, 0.1 µM to 100 µM, or 0.1 µM to 50 µM for reactions. N-methyl amino acids may be appropriately adjusted in the range from, for example, 50 µM to 10 mM, for example, 100 µM to 5 mM, 200 µM to 2 mM, or 500 µM to 1 mM for reactions.

Modified ARSs obtained by the preparation method as described above can be used to produce peptides and peptide-mRNA fusions that have incorporated N-methyl amino acids in a site-specific manner.

Moreover, ARSs used herein are highly conserved among biological species. Therefore, it is clear that the method according to the present invention can be generally applied to modification of N-methyl amino acid-tRNA synthetases from other biological species.

The modified ARS according to the present invention can be used to produce peptides having a particular amino acid substituted with its non-natural, N-methylated amino acid, in a prokaryotic translation. Such peptides can be produced using ARSs that are derived from other organisms and modified in a similar way as the present invention.

Acylation Reaction of tRNAs Using the Modified ARSs According to the Present Invention Use of the modified ARSs according to the present invention makes it possible to employ N-methyl amino acids as substrates in acylation of tRNAs. The modified ARSs according to the present invention can acylate tRNAs with N-methyl amino acids and to ribosomally produce N-methyl amino acid-containing peptides.

In order to produce N-methyl aminoacyl-tRNAs using the modified ARSs according to the present invention, the modified ARSs, N-methyl amino acids corresponding to the modified ARSs, and tRNAs may be reacted in vitro as in chemical synthesis such as the pdCpA method. The products, N-methyl aminoacyl-tRNAs may be isolated using any known nucleic acid purification technique such as ethanol precipitation, and the isolated product may be added to a translation system. This leads to production of polypeptides or polypeptide-mRNA fusions that have introduced N-methyl amino acids at the intended positions.

Unlike chemical synthesis which requires reactions performed in a reaction solution comprising only a particular tRNA and the N-methyl amino acid corresponding to the tRNA as substrates, three molecules, a modified ARS, N-methyl amino acid, and tRNA are used to precisely and efficiently produce the intended N-methyl aminoacyl-tRNA even in a mixture of translation reaction solution comprising other tRNAs and other amino acids because the modified ARSs according to the present invention have high substrate specificity for tRNAs and amino acids. Accordingly, the isolation and purification steps as described above are not essential. A reaction solution in which tRNAs have been acylated with N-methyl amino acids can be directly used in a translation reaction, or a translation reaction can be performed at the same time as an acylation reaction of tRNAs with N-methyl amino acids. The modified ARSs according to the present invention are very convenient because the reactions using the modified ARSs require no chemical synthesis of substrates such as pdCpA amino acids and activated amino acids and can be performed using commercially available reagents.

The most important characteristics include no requirement of stoichiometric consideration for a tRNA of interest in performing peptide translation (peptide expression) using a modified ARS according to the present invention. In chemical synthesis in which aminoacyl-tRNAs are supplied, N-methyl aminoacyl-tRNAs are consumed during the reaction, decreasing the reaction efficiency. However, if ARSs are used, translational efficiency is good even in peptide synthesis in which multiple N-methyl amino acids are introduced. Aminoacyl-tRNAs are constantly deacylated in hydrolytic reactions or transpeptidation reactions in translation systems, but the modified ARSs according to the present invention recognize released tRNAs and newly acylate the tRNAs with N-α amino acids, which results in a constant supply of N-α aminoacyl-tRNAs in the translation system. Therefore, the amount of tRNA required is less than the amount of produced polypeptide. Addition of large amounts of tRNA itself contributes to reduction of peptide yield. Therefore, the modified ARSs according to the present invention are useful for producing N-α amino acid-containing peptides at a high translational efficiency and producing highly diverse peptide libraries.

Moreover, because the modified ARSs according to the present invention have increased reactivity with N-methyl amino acids compared to natural ARSs, the modified ARSs can acylate tRNAs in the presence of N-methyl amino acids at a concentration lower than a concentration of N-methyl amino acids used for natural ARSs. In other words, the absolute amount of N-methyl amino acids required for peptide expression using the modified ARSs is not as much as that of N-methyl amino acids required for peptide expression using natural ARSs.

In addition, the modified ARSs according to the present invention can be used to translate N-methyl amino acid-containing peptides at a concentration lower than a concentration of natural ARSs used for translating N-methyl amino acid-containing peptides. In other words, the absolute amount of the modified ARS according to the present invention required for peptide expression is significantly less than in translation of N-methyl amino acid-containing peptides using natural ARSs.

These characteristics are important for improving orthogonality of aminoacylation reaction. Namely, in order to translate N-methyl amino acid-containing peptides, the more the substrate N-methyl amino acid, or an ARS corresponding to the N-methyl amino acid, is needed at a concentration higher than other natural amino acids, or ARSs corresponding to the other natural amino acids, the more it makes it easier for non-specific reactions to happen, such non-specific reactions being: ARS that should be normally using an N-methyl amino acid as a substrate may use other natural amino acids for acylation reaction; or an N-methyl amino acid that is present in excess may be used in acylation reactions by ARSs corresponding to other natural amino acids. This results in the obtained translated peptides being a mixture of N-methyl amino acid-containing peptides and peptides containing corresponding natural amino acid, which may cause issues for peptide libraries. However, it is expected that this issue can be minimized by using the modified ARSs according to the present invention.

Accordingly, the characteristics of the modified ARSs according to the present invention can be described as follows:
modified ARSs that catalyze acylation of tRNAs and comprise
(a) a tRNA binding site;
(b) a binding site to an N-methyl amino acid substrate; and
(c) a catalytically active site having activity to catalyze a reaction in which an acyl group is transferred from the N-methyl amino acid substrate to 3' end of a tRNA,
wherein the modified ARSs are characterized in that they can correctly recognize tRNAs and N-methyl amino acids in a translation reaction mixture, acylates the tRNAs, and further reuse tRNAs released after the transacylation reaction to repeat acylation reactions again.

Moreover, the modified ARSs according to the present invention may comprise, in addition to (a), (b), and (c) as described above, (d) an editing site where a tRNA acylated with any undesired amino acid is hydrolyzed.

Synthesis of Acylated tRNAs Using the Modified ARSs According to the Present Invention The modified ARSs according to the present invention can be used to synthesize tRNAs acylated with desired N-methyl amino acid substrates.

A method for producing acylated tRNAs using the modified ARSs according to the present invention, comprising the following steps:
(a) providing one or more modified ARSs according to the present invention;
(b) providing tRNAs;
(c) providing N-methyl amino acids; and
(d) contacting the modified ARSs with the tRNAs and N-methyl amino acids to acylate the tRNAs.

In addition to the steps as described above, the method may further comprise the step of (e) collecting the reaction product comprising the acylated tRNAs. The acylated tRNAs require no purification in the collecting step, and the reaction mixture can be collected and used directly. By not separating or purifying the produced aminoacyl-tRNAs from the ARSs, deacylation can be prevented.

This method uses N-methyl amino acids as substrates. Particularly preferable N-methyl amino acids include N-methylphenylalanine, N-methylvaline, N-methylthreonine, N-methyltryptophan, N-methylleucine, and/or N-methylserine. A substrate of an ARS (an amino acid corresponding to the ARS) is appropriately selected as N-methyl amino acid used as a substrate.

In a method for producing an acylated tRNA using a modified ARS according to the present invention, a tRNA that can be used is a tRNA corresponding to an ARS of a corresponding natural amino acid. The term "corresponding natural amino acid" refers to an amino acid that is not N-methylated relative to an N-methyl amino acid. For example, for N-methylphenylalanine, the corresponding amino acid is phenylalanine, and the corresponding tRNA is a tRNA recognizing the codon UUU or UUC (having the anticodon corresponding to the codon). For N-methylvaline, the corresponding amino acid is valine, and the corresponding tRNA is a tRNA recognizing the codon GUU, GUC, GUA, or GUG (having the anticodon corresponding to the codon). For N-methylserine, the corresponding amino acid is serine, and the corresponding tRNA is a tRNA recognizing the codon UCU, UCC, UCA, UCG, AGU, or AGC (having the anticodon corresponding to the codon). For N-methylthreonine, the corresponding amino acid is threonine, and the corresponding tRNA is a tRNA recognizing the codon ACU, ACC, ACA, or ACG (having the anticodon corresponding to the codon). For N-methyltryptophan, the corresponding amino acid is tryptophan, and the corresponding tRNA is a tRNA recognizing the codon UGG (having the anticodon corresponding to the codon). For N-methylleucine, the corresponding amino acid is leucine, and the corresponding tRNA is a tRNA recognizing the codon UUA, UUG, CUU, CUC, CUA, or CUG (having the anticodon corresponding to the codon). Similarly, for other N-methyl amino acids, tRNAs recognizing codons corresponding to the corresponding amino acid (having the anticodons corresponding to the codons) can be used.

When a tRNA is acylated by a modified ARS in a solution, a pellet obtained by ethanol precipitation of the reaction solution may be dissolved in a suitable buffer (such as 1 mM potassium acetate, pH 5) and added to a translation system. Typical reaction conditions include, for example, a reaction performed at 37° C. for 5 minutes to 1 hour in 0.1 M reaction buffer (pH 7.5) containing a final concentration of 0.5 µM to 40 µM of a tRNA, 0.1 µM to 10 µM of a modified ARS according to the present invention, 0.1 mM to 10 mM of an N-methyl amino acid, 0.1 mM to 10 mM ATP, and 0.1 mM to 10 mM $MgCl_2$.

Furthermore, for an aminoacylation reaction, a tRNA can be refolded by, for example, heating 1 to 50 µM tRNA, 10 to 200 (e.g., 50 to 200) mM HEPES-K (pH 7.0 to 8.0 (e.g., 7.6)), 1 to 100 (e.g., 10) mM KCl solution at 95° C. for 2 minutes and then left at room temperature for 5 minutes or more. This tRNA solution can be added to an acylation buffer (a final concentration of 25 to 100 (e.g., 50) mM HEPES-K [pH 7.0 to 8.0 (e.g., 7.6)], 1 to 10 (e.g., 2) mM ATP, 10 to 100 (e.g., 100) mM potassium acetate, 1 to 20 (e.g., 10) mM magnesium acetate, 0.1 to 10 (e.g., 1) mM DTT, 0.1 mg/mL Bovine Serum Albumin) to a final concentration of 1 to 40 (e.g., 10) µM, mixed with a modified ARS (a final concentration of 0.1 to 10 (e.g., 0.5) µM) and an N-methyl amino acid (a final concentration of 0.1 to 10 (e.g., 1) mM), and incubated at 37° C. for 5 to 60 (e.g., 10) minutes.

Thus, the acylation reaction using a modified ARS according to the present invention requires no activated amino acids that need substrates and need to be synthesized. The acylation reaction can be performed with commercially available N-methyl amino acids and therefore is convenient. The modified ARSs according to the present invention can be combined with their substrates to form a kit product for obtaining acylated tRNAs. The kit may at least comprise (a) one or more modified ARSs according to the present invention, (b) N-methyl amino acid(s), and (c) tRNA(s), and may further comprise a reaction buffer, a reaction vessel, instructions for use, and the like. In the kit, each of (b) N-methyl amino acid(s) and (c) tRNA(s) acts as a substrate for (a) modified ARSs. In other words, the tRNAs recognize codons corresponding to natural amino acids equivalent to the N-methyl amino acids (the tRNAs have anticodons corresponding to the codons).

Synthesis of N-Methyl Amino Acid-Containing Polypeptides Using the Modified ARSs According to the Present Invention N-methyl amino acid-bound tRNAs can be used to produce polypeptides with N-methyl amino acids introduced into desired sites. The method comprises translating a nucleic acid encoding a polypeptide of interest in the presence of a modified ARS according to the present invention.

More specifically, for example, a method for producing an N-methyl amino acid-containing polypeptide using a modified ARS(s) according to the present invention comprises (a) providing the modified ARS(s) according to the present invention, (b) establishing a cell-free translation system reconstituted with the modified ARS(s) according to the present invention rather than wild-type ARS(s), (c) providing an mRNA having at a desired site(s) codon(s) corresponding to the anticodon(s) of a tRNA(s) that is the substrate(s) of the modified ARS(s), and (d) adding the mRNA to the cell-free translation system to produce a polypeptide with an N-methyl amino acid(s) introduced into a desired site(s). Matters particularly relevant to the production of polypeptide in (d) will be described below.

N-methyl amino acids preferably used in acylation of tRNAs with N-methyl amino acids using the modified ARSs according to the present invention include N-methylalanine, N-methylleucine, N-methyltryptophan, N-methylphenylalanine, N-methylvaline, N-methylthreonine, and/or N-methylserine, and particularly preferably N-methylphenylalanine, N-methylvaline, N-methylthreonine, N-methyltryptophan, N-methylleucine, and/or N-methylserine.

Specific methods for polypeptide synthesis may be essentially performed according to known methods, for example, performed as described in WO2013100132, and various modifications can be made. Generally, the methods can be performed according to the following description.

A suitable translation system that can be used is a cell-free translation system, typified by PURESYSTEM (Registered trademark) (BioComber, Japan), reconstituted with translation factors. In such a cell-free translation system, components of the translation system can be controlled flexibly. For example, phenylalanine and the ARS corresponding to phenylalanine are removed from the translation system and instead, N-methylphenylalanine and the modified phenylalanine-ARS according to the present invention can be added. This achieves introduction of N-methylphenylalanine into a codon, such as UUU and UUC, encoding phenylalanine in a site-specific manner.

In a cell-free translation system, ribonucleosides preferably used are ATP and GTP at 0.1 mM-10 mM. A buffer preferably used is HEPES-KOH at 5 mM-500 mM and pH 6.5-8.5. Examples of other buffers include, but are not limited to, Tris-HCl, phosphate, and the like. Salts that can be used are acetates such as potassium acetate and ammonium acetate, and glutamates such as potassium glutamate, which are preferably used at 10 mM-1000 mM. A magnesium component preferably used is magnesium acetate at 2 mM-200 mM. Examples of other magnesium components include, but are not limited to, magnesium chloride and the like. Components in an energy-regenerating system preferably used are creatine kinase at 0.4 µg/mL-40 µg/mL and creatine phosphate at 2 mM-200 mM. Other energy-regenerating systems, typified by pyruvate kinase and phosphoenol pyruvate, may also be used. A nucleoside converting enzyme preferably used is myokinase at 0.1 unit/mL-10 unit/mL or nucleoside diphosphate kinase at 0.2 µg/mL-20 µg/mL. A diphosphatase preferably used is inorganic pyrophosphatase at 0.2 unit/mL-20 unit/mL. A polyamine preferably used is spermidine at 0.2 mM-20 mM. Examples of other polyamines include, but are not limited to, spermine and the like. A reducing agent preferably used is dithiothreitol at 0.1 mM-10 mM. Examples of other reducing agents include, but are not limited to, β-mercaptoethanol and the like. A tRNA preferably used is, for example, E. coli MRE600 (RNase-negative)-derived tRNA (Roche) at 0.5 mg/mL-50 mg/mL. Other tRNAs from E. coli may also be used. A formyl donor and an enzyme preferably used to synthesize formylmethionine used in a translational initiation reaction are 10-HCO—H4 folate at 0.1 mM-10 mM and methionyl-tRNA transformylase at 0.05 µM-5 µM. A translation initiation factor preferably used is IF1 at 0.5 µM-50 µM, IF2 at 0.1 µM-50 µM, or IF3 at 0.1 µM-50 µM. A translation elongation factor preferably used is EF-G at 0.1 µM-50 µM, EF-Tu at 1 µM-200 µM, or EF-Ts at 1 µM-200 µM. A translation termination factor preferably used is RF-2, RF3, or RRF at 0.1 µM-10 µM. Ribosome is preferably used at 1 µM-100 µM. There are 20 types of aminoacyl-tRNA synthetases, but only the enzymes corresponding to amino acids included in a peptide to be synthesized may be added.

For example, ArgRS, AspRS, LysRS, MetRS, and TyrRS are all preferably used at 0.01 µM-1 µM. Amino acids used as substrates for peptide synthesis are natural 20 amino acids, which compose proteins, and derivatives thereof. Only amino acids included in a peptide to be synthesized are preferably used at 0.25 mM-10 mM. An mRNA as a template for peptide synthesis is preferably used at 0.1 µM-10 µM. When an mRNA is transcribed from a template DNA in a cell-free translation system, commercially available enzymes such as T7 RNA polymerase, T3 RNA polymerase, and SP6 RNA polymerase can be used, and the enzymes suitable for a promoter sequence in the template DNA may be appropriately selected and are preferably used at 1 µg/mL-100 µg/mL. In this case, nucleosides CTP and UTP, which are substrates, are preferably used at 0.1 mM-10 mM. A solution containing mixed these components can be left, for example, at 37° C. for 1 hour to achieve translational synthesis of peptides. Temperature and reaction time are not limited to those.

The modified ARSs according to the present invention can also be used in combination with other techniques for introducing non-natural amino acids, such as the pdCpA method or the Flexizyme method. For example, polypeptides containing both N-methylglycine and N-methylphenylalanine can be synthesized when the aminoacyl-tRNA to which N-methylglycine is attached by the pdCpA method is added to a translation system at the same time as addition of N-methylphenylalanine and the modified phenylalanine ARS.

Alternatively, polypeptides containing N-methyl amino acids can be expressed in cells by inserting the modified ARSs according to the present invention into an expression vector or genome, expressing the modified ARSs in cells, and using N-methyl amino acids added to a medium as substrates.

tRNAs that can be used include a tRNA for a natural amino acid corresponding to an N-methyl amino acid. The tRNAs may be tRNAs that contain modified bases and are purified from a living body, or tRNAs that do not contain modified bases and are produced using an in vitro transcription reaction. Mutant tRNAs, which have a mutation in a portion of tRNA other than the portion recognized by an ARS, can also be used as substrates.

EXAMPLES

The content of the present invention as mentioned above will be described in more detail in the Examples below, but the Examples are illustrative and are not intended to limit the scope of the present invention. Various variations and modifications that can be made by those skilled in the art based on the description in the specification and claims are also included in the present invention.

All prior art literatures cited here are incorporated herein by reference.

Example 1: N-Methylphenylalanine-Accepting ARS

Preparation of Plasmids for Wild-Type and Mutant PheRSs

Using a plasmid (pQE-32(2) 2_wtPheRS) comprising the ORF sequence of wild-type PheRS α subunit gene of E. coli (SEQ ID NOs: 27, 28) as starting material, mutant PheRS plasmids (having His-tag (6×His) at the N-terminus) listed in Table 1 were constructed by introducing site-directed mutations using PCR. Specifically, 2 µL of 10 ng/µL template, 10 µL of 2×KOD Fx buffer (TOYOBO, KFX-101), 0.6 µL of 10 µM forward primer, 0.6 µL of 10 µM reverse primer, 4 µL of 2 mM dNTP, 0.4 µL of KOD FX (TOYOBO, KFX-101), and 2.4 µL of $H_2O$ were mixed together. Thereafter, the resulting reaction solution was heated at 94° C. for 2 minutes and then subjected to 10 cycles, each consisting of heating at 98° C. for 10 seconds and heating at 68° C. for 7 minutes, to amplify the mutant gene. The combinations of the template plasmid, forward primer, and reverse primer used are listed in Table 2. Each sequence of primers "F.F02" through "F.F05" corresponds to SEQ ID NOs: 30-33 in ascending order, and each sequence of primers "R.F02" through "R.F05" corresponds to SEQ ID NOs: 34-37 in ascending order. 0.5 µL of 10 U/µL DpnI was then added to the PCR reaction solution and further incubated at 37° C. for 1.5 hours to digest the template DNA, and the resulting mutant DNA was purified. E. coli XL-1 Blue strain (STRATAGENE, 200236) was then co-transformed with the resulting mutant gene DNA and pREP4 (Invitrogen, V004-50) encoding the lacI gene. The transformants were seeded onto agar containing ampicillin and kanamycin. The plasmids of interest were purified from the resulting clones. The mutations were confirmed to be introduced into the plasmids.

TABLE 1

| Name | position 169 | position 171 |
|---|---|---|
| PheRS01(wt) | Q | S |
| PheRS02 | Q | A |
| PheRS03 | Q | G |
| PheRS04 | A | S |
| PheRS05 | G | S |

TABLE 2

| Name | Template | 5' primer | 3' primer |
|---|---|---|---|
| PheRS02 | PheRS01(wt) | F. F02 | R. F02 |
| PheRS03 | PheRS01(wt) | F. F03 | R. F03 |
| PheRS04 | PheRS01(wt) | F. F04 | R. F04 |
| PheRS05 | PheRS01(wt) | F. F05 | R. F05 |

Small Scale Expression of Wild-Type and Mutant PheRSs

Next, a plasmid comprising a resulting mutant gene and the gene encoding PheRS β subunit was introduced into E. coli, and a heterodimer comprising the mutant protein was expressed. First, E. coli BL21 strain transformed with the mutant plasmid and pREP4 (Invitrogen, V004-50) was cultured at 37° C. in 4 mL of LB medium containing kanamycin, ampicillin, and 0.5% glucose. Subsequently, when the OD value at 600 nm reached 0.4 to 0.8, IPTG was added to a final concentration of 0.5 mM. After further culturing at 37° C. for 4 hours, the bacterial pellets were collected using a centrifuge.

Small Scale Purification of Wild-Type and Mutant PheRSs

Next, the resulting bacterial pellets were disrupted, and the mutant protein of interest was purified from the supernatant. Specifically, the bacterial pellets as described above were suspended in 600 µL of CHAPS solution (0.5% CHAPS (DOJINDO: 349-04722), 50% TBS (TaKaRa, T903)) and mixed with 6 µL of 30 U/µl rLysozyme (Novagen, 71110-3), and 2 µL of 2.5 U/µL benzonase nuclease (Novagen, 70746-3) followed by incubation at room temperature for 30 minutes. Imidazole was then added to a final concentration of 15 mM, and an insoluble fraction was separated by centrifugation. Then, the mutant protein was purified from the resulting supernatant using QIAGEN Ni- NTA spin column kit (Qiagen, 31314) according to the product manual. Finally, excess imidazole was removed using a desalting column, PD miniTrap G-25 (GE Healthcare, 28-9180-07) according to the product manual.

Large Scale Purification of Wild-Type and Mutant PheRSs

The mutant protein confirmed to have activity was prepared in large scale. Specifically, E. coli BL21 strain transformed with a plasmid comprising the mutant α subunit gene and wild-type β subunit gene and pREP4 (Invitrogen, V004-50) was cultured at 37° C. in 3 L of LB medium containing kanamycin, ampicillin, and 0.5% glucose. Then, when the OD value at 600 nm reached 0.4, IPTG was added to a final concentration of 0.5 mM. After further culturing at 37° C. for 4 hours, the bacterial pellets were collected with a centrifuge. The bacterial pellets as described above were suspended in 1 L of CHAPS solution (0.5% CHAPS (DOJINDO: 349-04722) and 50% TBS (TaKaRa, T903)), mixed with 10 JAL of 30 KU/μl rLysozyme (Novagen, 71110-3), and stirred at room temperature for 10 minutes. Next, 2 mL of 1 M MgCl$_2$ and 320 μL of Benzonase Nuclease (Novagen, 70746-3) were added and stirred at room temperature for 20 minutes. Imidazole was then added to a final concentration of 20 mM, and an insoluble fraction was separated by centrifugation. Subsequently, the mutant protein was purified from the resulting supernatant using a column filled with 15 mL of Ni Sepharose High Performance (GE Healthcare) and AKTA10S (GE Healthcare) with an imidazole concentration gradient (initial concentration 20 mM, final concentration 500 mM). Finally, dialysis was performed three times (2 hours×2, overnight×1) using a dialysis cassette (MWCO 10,000, Slide-A-Lyzer G2 Dialysis Cassettes 70 mL, Thermo Scientific Pierce) and 3 L of stock solution (50 mM Hepes-KOH, 100 mM KCl, 10 mM MgCl$_2$, 1 mM DTT pH 7.6) to obtain the mutant protein.

Aminoacylation Reaction with N-Methylphenylalanine Using Wild-Type and Mutant PheRSs Synthesis of E. coli tRNAPhe by In Vitro Transcription Reaction E. coli tRNA (R-tRNAPhe (SEQ ID NO: 39)) was synthesized from a template DNA (D-tRNAPhe (SEQ ID NO: 38)) by in vitro transcription reaction using RiboMAX Large Scale RNA production System T7 (Promega, P1300) in the presence of 7.5 mM GMP, and purified using RNeasy Mini kit (Qiagen).

D-tRNAPhe
tRNAPhe DNA sequence:
(SEQ ID NO: 38)
GGCGTAATACGACTCACTATAGCCCGGATAGCTCAGTCGGTAGAGCAGGG

GATTGAAAATCCCCGTGTCCTTGGTTCGATTCCGAGTCCGGGCACCA

R-tRNAPhe
tRNAPhe RNA sequence:
(SEQ ID NO: 39)
GCCCGGAUAGCUCAGUCGGUAGAGCAGGGGAUUGAAAAUCCCCGUGUCCU

UGGUUCGAUUCCGAGUCCGGGCACCA

Aminoacylation Reaction

For the aminoacylation reaction, the solution containing 40 μM transcribed tRNAPhe, 10 mM HEPES-K (pH 7.6), and 10 mM KCl solution was heated at 95° C. for 2 minutes and then left at room temperature for 5 minutes or more to refold the tRNA. This tRNA solution was added to a final concentration of 10 μM to an acylation buffer (in final concentrations of 50 mM HEPES-K [pH 7.6], 2 mM ATP, 100 mM potassium acetate, 10 mM magnesium acetate, 1 mM DTI, 2 mM spermidine, 0.1 mg/mL Bovine Serum Albumin), mixed with wild-type or mutant PheRS (final concentration 0.5 μM) and phenylalanine (final concentration 0.25 mM, Watanabe Chemical Industries, Ltd., G00029) or N-methylphenylalanine (final concentration 1 mM, Watanabe Chemical Industries, Ltd., J00040), and incubated at 37° C. for 10 minutes. Four volumes of a loading buffer (90 mM sodium acetate [pH 5.2], 10 mM EDTA, 95% (w/w) formamide, 0.001% (w/v) xylene cyanol) was added to the reaction solution and analyzed with acidic PAGE (12% (w/v) polyacrylamide gel, pH 5.2) containing 6 M urea, and aminoacylation activity was detected by separating unreacted tRNA and aminoacylated tRNA. RNA was stained with SYBR Gold (Life Technologies) and detected with LAS4000 (GE Healthcare).

The activity for the aminoacylation reaction was assessed, and mutants 04 and 05 had increased activity for aminoacylation with N-methyl-phenylalanine compared to the wild-type (FIG. 1). The base sequence of mutant 04 is set forth in SEQ ID NO: 12, and the amino acid sequence of mutant 04 is set forth in SEQ ID NO: 1. The base sequence of mutant 05 is set forth in SEQ ID NO: 13, and the amino acid sequence of mutant 05 is set forth in SEQ ID NO: 2.

Translational Introduction of N-Methylphenylalanine Using Wild-Type and Mutant PheRSs Synthesis of Template DNA-F by In Vitro Transcription Reaction A template mRNA for translation (R-F (SEQ ID NO: 41)) was synthesized from a template DNA (D-F (SEQ ID NO: 40)) by in vitro transcription reaction using RiboMAX Large Scale RNA production System T7 (Promega, P1300) and purified using RNeasy Mini kit (Qiagen).

D-F
DNA sequence:
(SEQ ID NO: 40)
GGCGTAATACGACTCACTATAGGGTTAACTTTAACAAGGAGAAAAACATG

CGTTTCCGTGACTACAAGGACGACGACGACAAGTAAGCTTCG

R-F
RNA sequence:
(SEQ ID NO: 41)
GGGUUAACUUUAACAAGGAGAAAAACAUGCGUUUCCGUGACUACAAGGAC

GACGACGACAAGUAAGCUUCG

Cell-Free Translation System

In order to confirm translational introduction of N-methylphenylalanine, a desired polypeptide containing N-methylphenylalanine was ribosomally synthesized by adding an N-methyl amino acid and PheRS to a cell-free translation system. The translation system used was PURE system, a reconstituted cell-free protein synthesis system from E. coli. Specifically, wild-type or mutant PheRS and phenylalanine or N-methylphenylalanine were added to a solution containing a basic cell-free translation solution (1 mM GTP, 1 mM ATP, 20 mM creatine phosphate, 50 mM HEPES-KOH pH 7.6, 100 mM potassium acetate, 9 mM magnesium acetate, 2 mM spermidine, 1 mM dithiothreitol, 0.5 mg/ml E. coli MRE600 (RNase negative)-derived tRNA (Roche), 4 μg/ml creatine kinase, 3 μg/ml myokinase, 2 unit/ml inorganic pyrophosphatase, 1.1 μg/ml nucleoside diphosphate kinase, 0.6 μM methionyl-tRNA transformylase, 0.26 μM EF-G, 0.24 μM RF2, 0.17 μM RF3, 0.5 μM RRF, 2.7 μM IF1, 0.4 μM IF2, 1.5 μM IF3, 40 μM EF-Tu, 44 μM EF-Ts, 1.2 μM ribosome, 0.03 μM ArgRS, 0.13 μM AspRS, 0.11 μM LysRS, 0.03 μM MetRS, 0.02 μM TyrRS (wherein the proteins prepared by the inventors were essentially prepared as His-tagged proteins)), and 1 μM template mRNA, each 250 μM arginine, aspartic acid, lysine, methionine, and tyrosine, and left at 37° C. for 1 hour to ribosomally synthesize the peptide.

Detection by Electrophoresis

A peptide expression experiment was performed by using aspartic acid labeled with a radioisotope for detecting peptides into which N-methylphenylalanine is ribosomally introduced. Specifically, a solution containing 1 μM template mRNA (R-F (SEQ ID NO: 41)), arginine, lysine, methionine, and tyrosine (each final concentration 250 μM), and $^{14}$C-aspartic acid (final concentration 37 μM, Moravek Biochemicals, MC139) added to the cell-free translation system as described above was prepared. Wild-type PheRS or the mutant PheRS 05 (final concentration 0.1 μM) and phenylalanine (final concentration 250 μM) or N-methylphenylalanine (final concentration 1 mM or 250 μM) were added to the solution and incubated at 37° C. for 60 minutes. An equal volume of 2× sample buffer (TEFCO, cat No. 06-323) was added to the resulting translation reaction solution and heated at 95° C. for 3 minutes followed by electrophoresis (16% Peptide-PAGE mini, TEFCO, TB-162). After electrophoresis, the gel was dried using Clear Dry Quick Dry Starter KIT (TEFCO, 03-278), exposed to an imaging plate (GE Healthcare, 28-9564-75) for about 16 hours, detected using a Bioanalyzer System (Typhoon FLA 7000, GE Healthcare), and analyzed with ImageQuantTL (GE Healthcare).

Almost no bands of peptides that were ribosomally synthesized were observed in the presence of 0.1 μM wild-type PheRS when 0.25 mM or 1 mM N-methylphenylalanine was added (FIG. 2). Meanwhile, peptide bands were observed in the presence of 0.1 μM mutant PheRS 05 even when 0.25 mM N-methylphenylalanine was added. The results can provide confirmation that the mutant PheRS 05 had increased aminoacylation activity with N-methylphenylalanine and that peptides containing N-methylphenylalanine were ribosomally synthesized at a high yield.

Detection by Mass Spectroscopy

Mass spectroscopy was performed using MALDI-TOF MS for detecting peptides into which N-methylphenylalanine is ribosomally introduced. Specifically, a solution containing 1 μM template mRNA (R-F (SEQ ID NO: 41)) and amino acids, arginine, lysine, methionine, tyrosine, and aspartic acid (each final concentration 250 μM) added to the cell-free translation system as described above was prepared. PheRS (final concentration 0.1 μM) and phenylalanine (final concentration 250 μM) or N-methylphenylalanine (final concentration 1 mM or 250 μM) were added to the solution and incubated at 37° C. for 60 minutes. The resulting translation reaction products were purified with SPE C-TIP (Nikkyo Technos Co., Ltd) and analyzed with MALDI-TOF MS. α-Cyano-4-hydroxycinnamic acid was used as a matrix for translation products.

When a translation experiment was performed as a control experiment in the presence of 0.1 μM wild-type PheRS (SEQ ID NO: 28) or mutant PheRS 05 (SEQ ID NO: 2) with 250 μM phenylalanine added, the peak of the peptide into which phenylalanine was introduced (Calculated [M+H]+ =1631.7) was detected in both experiments using wild-type PheRS and the mutant PheRS 05 (FIG. 3(a), (d)).

Translational synthesis was then performed by using wild-type PheRS and adding 0.25 mM N-methylphenylalanine, and the peaks of the peptide containing N-methylphenylalanine (Calculated [M+H]+=1645.7) and the peptide containing phenylalanine were observed (FIG. 3 (b)). This phenomenon is thought to be due to wild-type PheRS recognizing phenylalanine contaminated in N-methylphenylalanine, the subsequent occurrence of the aminoacylation reaction, and proceeding of translational synthesis. Furthermore, the peak intensity of the peptide containing N-methylphenylalanine was increased under the condition of 1 mM N-methylphenylalanine (FIG. 3(c)). The ratio of peak intensities at each amino acid concentration was calculated (the calculating formula: the ratio of peak intensity=the peak intensity of the peptide containing N-methylphenylalanine/ the peak intensity of the peptide containing phenylalanine) to be 0.8 at 0.25 mM and 2.6 at 1 mM.

Next, a translational synthesis was performed by using the mutant PheRS 05 and adding 0.25 mM or 1 mM N-methylphenylalanine, and the peak of the peptide containing N-methylphenylalanine was strongly detected, and the ratio of peak intensity of the peptide containing N-methylphenylalanine to the peak intensity of the peptide containing phenylalanine was 12.4 at 0.25 mM and 16.0 at 1 mM (FIG. 3 (e), (f)). These results confirmed that the mutant PheRS 05 had increased aminoacylation activity with N-methylphenylalanine compared to wild-type PheRS, and consequently, translational synthesis of the peptide containing N-methylphenylalanine was promoted.

Peptide sequence P-F1
(SEQ ID NO: 42)
formylMetArgPheArgAspTyrLysAspAspAspAspLys Peptide sequence P-MeF1
(SEQ ID NO: 42)
formylMetArg[MePhe]ArgAspTyrLysAspAspAspAspLys MALDI-TOF MS:
Calc. m/z: [H+M]+=1631.7 (the peptide corresponding to the sequence P-F1)
Calc. m/z: [H+M]+=1645.7 (the peptide corresponding to the sequence P-MeF1)

Comparison with the pdCpA Method

Incorporation efficiency of N-methylphenylalanine using an ARS according to the present invention was compared with that in the pdCpA method. Translation was performed using a sequence containing one, two consecutive, or three consecutive phenylalanines in a cell-free translation system, and the synthesized peptide band was detected by electrophoresis. The amount of the peptide synthesized using a mutant PheRS according to the present invention (PhrRS05 (SEQ ID NO: 2)) was compared with the amount of the peptide synthesized using the pdCpA method. It is confirmed that the amount of the peptide synthesized using the mutant PheRS according to the present invention was detected more than the amount of the peptide synthesized using the pdCpA method in all translations and that translational efficiency obtained by using the mutant PheRS was also higher than that obtained by using the pdCpA method. Particularly, it is revealed that the amount of the peptide produced by translating sequences containing two consecutive and three consecutive N-methylphenylalanines using the mutant PheRS according to the present invention (PhrRS05) was 4 to 8 times higher than the amount of the peptide produced using the pdCpA method.

Example 2: N-Methylvaline-Accepting ARS

Preparation of Plasmids for Wild-Type and Mutant ValRSs

The mutant ValRS plasmids (having His-tag (6×His) at the N-terminus) listed in Table 3 were constructed by introducing site-directed mutations using PCR into the plasmid (PQE-32(2) 2_wtVALRS) comprising the ORF sequence of wild-type ValRS gene of *E. coli* (SEQ ID NOs: 23, 24), which was used as starting material. Specifically, 2 μL of 10 ng/μL template, 10 μL of 2×KOD Fx buffer (TOYOBO, KFX-101), 0.6 μL of 10 μM forward primer, 0.6 μL of 10 μM reverse primer, 4 μL of 2 mM dNTP, 0.4 μL of KOD FX (TOYOBO, KFX-101), and 2.4 μL of H$_2$O were mixed together. Then, the resulting reaction solution was heated at 94° C. for 2 minutes and then subjected to 10 cycles, each consisting of heating at 98° C. for 10 seconds and heating at 68° C. for 7 minutes, to amplify the mutant gene. The combinations of the template plasmid, forward primer, and reverse primer used are listed in Table 4. Each sequence of primers "F.V2" through "F.V19", "F.V46" through "F.V48", and "F.V13-01" through "F.V13-16" corresponds to SEQ ID NOs: 43-79 in ascending order. Each sequence of primers "R.V2" through "R.V19", "R.V46" through "R.V48", and "R.V13-01" through "R.V13-16" corresponds to SEQ ID NOs: 80-116 in ascending order. 0.5 μL of 10 U/μL DpnI was then added to the PCR reaction solution and further incubated at 37° C. for 1.5 hours to digest the template DNA, and the resulting mutant DNA was purified. *E. coli* XL-1 Blue strain (STRATAGENE, 200236) was then co-transformed with the resulting mutant gene DNA and pREP4 (Invitrogen, V004-50) encoding the lacI gene. The transformants were seeded onto agar containing ampicillin and kanamycin. The plasmids of interest were purified from the resulting clones. The mutations were confirmed to be introduced into the plasmids.

For plasmid construction requiring multistep mutation introduction, the procedure as described above was repeated to obtain plasmids into which mutations of interest were introduced. The combinations of the primers and template for such plasmid construction are listed in Table 4.

TABLE 3

| Name | position 80 | position 43 | position 41 | Name | position 43 | position 45 | position 85 |
|---|---|---|---|---|---|---|---|
| ValRS001 (wt) | D | N | P | ValRS13-01 | G | T | Y |
| ValRS002 | | | A | ValRS13-02 | G | T | W |
| ValRS003 | | | G | ValRS13-03 | G | T | S |
| ValRS004 | | A | P | ValRS13-04 | G | T | M |
| ValRS005 | | | A | ValRS13-05 | G | T | K |
| ValRS006 | | | G | ValRS13-06 | G | T | N |
| ValRS007 | | S | P | ValRS13-07 | G | T | V |
| ValRS008 | | | A | ValRS13-08 | G | T | L |
| ValRS009 | | | G | ValRS13-09 | G | Y | A |
| ValRS010 | | V | P | ValRS13-10 | G | W | A |
| ValRS011 | | | A | ValRS13-11 | G | S | A |
| ValRS012 | | | G | ValRS13-12 | G | M | A |
| ValRS013 | | G | P | ValRS13-13 | G | K | A |
| ValRS014 | | | A | ValRS13-14 | G | N | A |
| ValRS015 | | | G | ValRS13-15 | G | V | A |
| ValRS016 | | D | P | ValRS13-16 | G | L | A |
| ValRS017 | | | A | | | | |
| ValRS018 | | | G | | | | |
| ValRS019 | A | N | P | | | | |
| ValRS020 | | | A | | | | |
| ValRS021 | | | G | | | | |
| ValRS022 | | A | P | | | | |
| ValRS023 | | | A | | | | |
| ValRS024 | | | G | | | | |
| ValRS025 | | S | P | | | | |
| ValRS026 | | | A | | | | |
| ValRS027 | | | G | | | | |
| ValRS028 | | V | P | | | | |
| ValRS029 | | | A | | | | |
| ValRS030 | | | G | | | | |
| ValRS031 | | G | P | | | | |
| ValRS032 | | | A | | | | |
| ValRS033 | | | G | | | | |
| ValRS034 | | D | P | | | | |
| ValRS035 | | | A | | | | |
| ValRS036 | | | G | | | | |
| ValRS037 | S | D | P | | | | |
| ValRS038 | | | A | | | | |
| ValRS039 | | | G | | | | |
| ValRS040 | V | D | P | | | | |
| ValRS041 | | | A | | | | |
| ValRS042 | | | G | | | | |
| ValRS043 | G | D | P | | | | |
| ValRS044 | | | A | | | | |
| ValRS045 | | | G | | | | |
| ValRS046 | S | N | P | | | | |
| ValRS047 | V | N | P | | | | |
| ValRS048 | G | N | P | | | | |

TABLE 4

| | forward primer | reverse primer | Template | | forward primer | reverse primer | Template |
|---|---|---|---|---|---|---|---|
| ValRS001 | | | | ValRS13-01 | F. V13-01 | R. V13-01 | ValRS13 |
| ValRS002 | F. V2 | R. V2 | wild type | ValRS13-02 | F. V13-02 | R. V13-02 | ValRS13 |
| ValRS003 | F. V3 | R. V3 | wild type | ValRS13-03 | F. V13-03 | R. V13-03 | ValRS13 |
| ValRS004 | F. V4 | R. V4 | wild type | ValRS13-04 | F. V13-04 | R. V13-04 | ValRS13 |
| ValRS005 | F. V5 | R. V5 | wild type | ValRS13-05 | F. V13-05 | R. V13-05 | ValRS13 |
| ValRS006 | F. V6 | R. V6 | wild type | ValRS13-06 | F. V13-06 | R. V13-06 | ValRS13 |
| ValRS007 | F. V7 | R. V7 | wild type | ValRS13-07 | F. V13-07 | R. V13-07 | ValRS13 |
| ValRS008 | F. V8 | R. V8 | wild type | ValRS13-08 | F. V13-08 | R. V13-08 | ValRS13 |
| ValRS009 | F. V9 | R. V9 | wild type | ValRS13-09 | F. V13-09 | R. V13-09 | ValRS13 |
| ValRS010 | F. V10 | R. V10 | wild type | ValRS13-10 | F. V13-10 | R. V13-10 | ValRS13 |
| ValRS011 | F. V11 | R. V11 | wild type | ValRS13-11 | F. V13-11 | R. V13-11 | ValRS13 |
| ValRS012 | F. V12 | R. V12 | wild type | ValRS13-12 | F. V13-12 | R. V13-12 | ValRS13 |
| ValRS013 | F. V13 | R. V13 | wild type | ValRS13-13 | F. V13-13 | R. V13-13 | ValRS13 |
| ValRS014 | F. V14 | R. V14 | wild type | ValRS13-14 | F. V13-14 | R. V13-14 | ValRS13 |
| ValRS015 | F. V15 | R. V15 | wild type | ValRS13-15 | F. V13-15 | R. V13-15 | ValRS13 |
| ValRS016 | F. V16 | R. V16 | wild type | ValRS13-16 | F. V13-16 | R. V13-16 | ValRS13 |
| ValRS017 | F. V17 | R. V17 | wild type | | | | |
| ValRS018 | F. V18 | R. V18 | wild type | | | | |
| ValRS019 | F. V19 | R. V19 | wild type | | | | |
| ValRS020 | F. V2 | R. V2 | ValRS019 | | | | |
| ValRS021 | F. V3 | R. V3 | ValRS019 | | | | |
| ValRS022 | F. V4 | R. V4 | ValRS019 | | | | |
| ValRS023 | F. V5 | R. V5 | ValRS019 | | | | |
| ValRS024 | F. V6 | R. V6 | ValRS019 | | | | |
| ValRS025 | F. V7 | R. V7 | ValRS019 | | | | |
| ValRS026 | F. V8 | R. V8 | ValRS019 | | | | |
| ValRS027 | F. V9 | R. V9 | ValRS019 | | | | |
| ValRS028 | F. V10 | R. V10 | ValRS019 | | | | |
| ValRS029 | F. V11 | R. V11 | ValRS019 | | | | |
| ValRS030 | F. V12 | R. V12 | ValRS019 | | | | |
| ValRS031 | F. V13 | R. V13 | ValRS019 | | | | |
| ValRS032 | F. V14 | R. V14 | ValRS019 | | | | |
| ValRS033 | F. V15 | R. V15 | ValRS019 | | | | |
| ValRS034 | F. V16 | R. V16 | ValRS019 | | | | |
| ValRS035 | F. V17 | R. V17 | ValRS019 | | | | |
| ValRS036 | F. V18 | R. V18 | ValRS019 | | | | |
| ValRS037 | F. V16 | R. V16 | ValRS046 | | | | |
| ValRS038 | F. V17 | R. V17 | ValRS046 | | | | |
| ValRS039 | F. V18 | R. V18 | ValRS046 | | | | |
| ValRS040 | F. V16 | R. V16 | ValRS047 | | | | |
| ValRS041 | F. V17 | R. V17 | ValRS047 | | | | |
| ValRS042 | F. V18 | R. V18 | ValRS047 | | | | |
| ValRS043 | F. V16 | R. V16 | ValRS048 | | | | |
| ValRS044 | F. V17 | R. V17 | ValRS048 | | | | |
| ValRS045 | F. V18 | R. V18 | ValRS048 | | | | |
| ValRS046 | F. V46 | R. V46 | wt | | | | |
| ValRS047 | F. V47 | R. V47 | wt | | | | |
| ValRS048 | F. V48 | R. V48 | wt | | | | |

Small Scale Expression of Wild-Type and Mutant ValRSs

Next, a resulting mutant plasmid was introduced into *E. coli*, and the mutant protein was expressed. First, *E. coli* BL21 strain transformed with the mutant plasmid and pREP4 (Invitrogen, V004-50) was cultured at 37° C. in 4 mL of LB medium containing kanamycin and ampicillin. Then, when the OD value at 600 nm reached 0.4 to 0.8, IPTG was added to a final concentration of 0.5 mM. After further culturing at 37° C. for 4 hours, the bacterial pellets were collected using a centrifuge.

Small Scale Purification of Wild-Type and Mutant ValRSs

Next, the resulting bacterial pellets were disrupted, and the mutant protein of interest was purified from the supernatant. Specifically, the bacterial pellets as described above were suspended in 600 μL of CHAPS solution (0.5% CHAPS (DOJINDO: 349-04722), 50% TBS (TaKaRa, T903)) and mixed with 6 μL of 30 U/μl rLysozyme (Novagen, 71110-3) followed by incubation at room temperature for 10 minutes. The reaction was further mixed with 2 μL of 2.5 U/μL benzonase nuclease (Novagen, 70746-3) followed by incubation at room temperature for 20 minutes, and an insoluble fraction was separated by centrifugation. The mutant protein was then purified from the resulting supernatant using QIAGEN Ni-NTA spin column kit (Qiagen. 31314) according to the product manual. Finally, excess imidazole was removed using a desalting column, PD mini-Trap G-25 (GE Healthcare, 28-9180-07) according to the product manual.

Aminoacylation Reaction with N-Methylvaline Using Wild-Type and Mutant ValRSs

Synthesis of *E. coli* tRNAVal by In Vitro Transcription Reaction

*E. coli* tRNA (R-tRNAVal2A (SEQ ID NO: 118)) was synthesized from a template DNA (D-tRNAVal2A (SEQ ID NO: 117)) by in vitro transcription reaction using RiboMAX Large Scale RNA production System T7 (Promega, P1300) in the presence of 7.5 mM GMP, and purified using RNeasy Mini kit (Qiagen).

```
D-tRNAVal2A
tRNAVal2A DNA sequence:
                                        (SEQ ID NO: 117)
GGCGTAATACGACTCACTATAGCGTCCGTAGCTCAGTTGGTTAGAGCACC

ACCTTGACATGGTGGGGGTCGGTGGTTCGAGTCCACTCGGACGCACCA

R-tRNAVal2A
tRNAVal2A RNA sequence:
                                        (SEQ ID NO: 118)
GCGUCCGUAGCUCAGUUGGUUAGAGCACCACCUUGACAUGGUGGGGUCG

GUGGUUCGAGUCCACUCGGACGCACCA
```

Aminoacylation Reaction

For the aminoacylation reaction, the solution containing 40 µM transcribed tRNA, 10 mM HEPES-K (pH 7.6), and 10 mM KCl solution was heated at 95° C. for 2 minutes and then left at room temperature for 5 minutes or more to refold the tRNA. This tRNA solution was added to a final concentration of 10 µM to an acylation buffer (in final concentrations of 50 mM HEPES-K [pH 7.6], 2 mM ATP, 100 mM potassium acetate, 10 mM magnesium acetate, 1 mM DTT, 2 mM spermidine, 0.1 mg/mL Bovine Serum Albumin), mixed with wild-type or mutant ValRS (final concentration 0.2 µM-1 µM) and N-methylvaline (final concentration 5 mM), and incubated at 37° C. for 10 minutes. Four volumes of a loading buffer (90 mM sodium acetate [pH 5.2], 10 mM EDTA, 95% (w/w) formamide, 0.001% (w/v) xylene cyanol) were added to the reaction solution and analyzed with acidic PAGE containing 6 M urea, and aminoacylation activity was detected by separating unreacted tRNA and aminoacyl-tRNA. RNA was stained with SYBR Gold (Life Technologies) and detected with LAS4000 (GE Healthcare) (FIG. 4).

As a result, tRNA acylated with N-methylvaline was observed when mutant 13 was used. It was demonstrated that mutant 13 had increased activity for aminoacylation with N-methylvaline compared to wild-type ValRS (FIG. 4, lane 2 vs 10).

Translational Introduction of N-Methylvaline Using Wild-Type and Mutant ValRSs

Template mRNAs for translation (R-V, R-V2, and R-V3 (SEQ ID NOs: 120, 122, and 124, respectively)) were synthesized from template DNAs (D-V, D-V2, and D-V3 (SEQ ID NOs: 119, 121, and 123, respectively)) by in vitro transcription reaction using RiboMAX Large Scale RNA production System T7 (Promega, P1300) and purified using RNeasy Mini kit (Qiagen).

```
D-V
DNA sequence:
                                        (SEQ ID NO: 119)
GGCGTAATACGACTCACTATAGGGTTAACTTTAACAAGGAGAAAAACATG

CGTGTCCGTGACTACAAGGACGACGACGACAAGTAAGCTTCG

R-V
RNA sequence:
                                        (SEQ ID NO: 120)
GGGUUAACUUUAACAAGGAGAAAAACAUGCGUGUCCGUGACUACAAGGAC

GACGACGACAAGUAAGCUUCG

D-V2
DNA sequence:
                                        (SEQ ID NO: 121)
GGCGTAATACGACTCACTATAGGGTTAACTTTAACAAGGAGAAAAACATG

CGTGTCGTCCGTGACTACAAGGACGACGACGACAAGTAAGCTTCG

R-V2
RNA sequence:
                                        (SEQ ID NO: 122)
GGGUUAACUUUAACAAGGAGAAAAACAUGCGUGUCGUCCGUGACUACAAG

GACGACGACGACAAGUAAGCUUCG

D-V3
DNA sequence:
                                        (SEQ ID NO: 123)
GGCGTAATACGACTCACTATAGGGTTAACTTTAACAAGGAGAAAAACATG

CGTGTCGTCGTCCGTGACTACAAGGACGACGACGACAAGTAAGCTTCG

R-V3
RNA sequence:
                                        (SEQ ID NO: 124)
GGGUUAACUUUAACAAGGAGAAAAACAUGCGCGUGUCGUCGUCUGACUAC

AAGGACGACGACGACAAGUAAGCUUCG
```

Cell-Free Translation System

In order to confirm translational introduction of N-methylvaline, a desired polypeptide containing N-methylvaline was ribosomally synthesized by adding an N-methylvaline and a mutant ValRS to a cell-free translation system. The translation system used was PURE system, a reconstituted cell-free protein synthesis system from E. coli. Specifically, wild-type or mutant ValRS and N-methylvaline were added to a solution containing a basic cell-free translation solution (1 mM GTP, 1 mM ATP, 20 mM creatine phosphate, 50 mM HEPES-KOH pH 7.6, 100 mM potassium acetate, 9 mM magnesium acetate, 2 mM spermidine, 1 mM dithiothreitol, 1.5 mg/ml E. coli MRE600 (RNase negative)-derived tRNA (Roche), 0.1 mM 10-HCO—H4 folate, 4 µg/ml creatine kinase, 3 µg/ml myokinase, 2 unit/ml inorganic pyrophosphatase, 1.1 µg/ml nucleoside diphosphate kinase, 0.6 µM methionyl-tRNA transformylase, 0.26 µM EF-G, 0.24 µM RF2, 0.17 µM RF3, 0.5 µM RRF, 2.7 µM IF1, 0.4 µM IF2, 1.5 µM IF3, 40 µM EF-Tu, 84 µM EF-Ts, 1.2 µM ribosome, 0.03 µM ArgRS, 0.13 µM AspRS, 0.11 µM LysRS, 0.03 µM MetRS, 0.02 µM TyrRS (wherein the proteins prepared by the inventors were essentially prepared as His-tagged proteins)), and 1 µM template mRNA, each 250 µM arginine, aspartic acid, lysine, methionine, and tyrosine, and left at 37° C. for 1 hour to ribosomally synthesize the peptide.

Detection by Mass Spectroscopy

Mass spectroscopy was performed using MALDI-TOF MS for detecting peptides into which N-methylvaline is ribosomally introduced. Specifically, a solution containing 1 µM template mRNA (R-V (SEQ ID NO: 120)) and arginine, lysine, methionine, tyrosine, and aspartic acid (each final concentration 250 µM) added to the cell-free translation system as described above was prepared. ValRS (final concentration 0.1 µM-1 µM) and N-methylvaline (final concentration 5 mM) were added to the solution and incubated at 37° C. for 60 minutes. The resulting translation reaction products were purified with SPE C-TIP (Nikkyo Technos Co., Ltd) and analyzed with MALDI-TOF MS. Translation products were identified with MALDI-TOF MS spectrometry using α-cyano-4-hydroxycinnamic acid as a matrix.

As a result of the translation using wild-type ValRS (SEQ ID NO: 24), a peak corresponding to the peptide sequence P-V1 introduced with valine contaminated in the cell-free translation system ((FIG. 5(a), Peak V1, m/z: [H+M]+=1583.6) was observed as main product. Similar experiments were performed using different mutant ValRSs. When ValRS04 (SEQ ID NO: 3) or ValRS13 (SEQ ID NO: 4) was used, a peak corresponding to the peptide sequence P-MeV1 with N-methylvaline introduced ((FIG. 5(b), Peak MeV1, m/z: [H+M]+=1597.5, FIG. 5(c), Peak MeV2, m/z: [H+M]+=1597.5) was observed as main product. This demonstrated, also from a view point of translation reaction that ValRS04 and ValRS13 have increased activity to N-methylvaline compared to wild-type ValRS. Although peaks corresponding to the peptide P-V1 introduced with valine contaminated in the translation system (FIG. 5(b) Peak V2, (c) Peak V3) were also observed at the same time, the intensity of the peak in using ValRS13 was weaker than that in using ValRS04. Therefore, it was suggested that ValRS13 has a higher activity to N-methylvaline (FIG. 5(b), (c)).

```
Peptide sequence P-V1
                                          (SEQ ID NO: 125)
formylMetArgValArgAspTyrLysAspAspAspAspLys Peptide sequence P-MeV1
                                          (SEQ ID NO: 125)
formylMetArg[MeVal]ArgAspTyrLysAspAspAspAspLys
```

MALDI-TOF MS:
Calc. m/z: [H+M]+=1583.7 (the peptide corresponding to the sequence P-V1)
Calc. m/z: [H+M]+=1597.7 (the peptide corresponding to the sequence P-MeV1)
Production of Mutant ValRS13-11 Having Further Increased Aminoacylation Activity to N-Methylvaline Improvement in activity to N-methylvaline was aimed by further introducing mutations into ValRS13 as described above. Plasmids into which the mutations of interest are introduced were prepared as mentioned above, expressed in E. coli, and purified to prepare mutant ValRSs (Table 3). As a result of screening by performing aminoacylation reaction and translational synthesis, ValRS13-11 (SEQ ID NO: 5) exhibited higher activity to N-methylvaline compared to ValRS13.

When aminoacylation reactions with N-methylvaline using wild-type ValRS, ValRS13, and ValRS13-11 were investigated, it was observed that the amount of aminoacyl-tRNA synthesized using ValRS13-11 was more than that synthesized using ValRS13 (FIG. 6, lane 8 vs lane 9 and lane 12 vs lane 13). Particularly, the amounts of aminoacyl-tRNA synthesized using ValRS13 and ValRS13-11 with N-methylvaline at the low concentration of 1.25 mM were greatly different, demonstrating that ValRS13-11 had a high activity.

Next, mass spectroscopy was performed using MALDI-TOF MS for confirming translational synthesis of peptides having N-methylvaline using ValRS13 and ValRS13-11. Specifically, a solution containing 1 μM template mRNA (R-V (SEQ ID NO: 120)) and arginine, lysine, methionine, tyrosine, and aspartic acid (each final concentration 250 μM) added to the cell-free translation system as described above was prepared. ValRS (final concentration 4 μM) and N-methylvaline (final concentration 5 mM) were added to the solution and incubated at 37° C. for 60 minutes. Template mRNAs encoding peptide sequences containing two consecutive or three consecutive N-methylvalines (R-V2 (SEQ ID NO: 122), R-V3 (SEQ ID NO: 124)) were used to perform similar experiments. The resulting translation reaction products were purified with SPE C-TIP (Nikkyo Technos Co., Ltd) and analyzed with MALDI-TOF MS.

The intended synthesis of the peptide sequence P-MeV1 containing N-methylvaline using ValRS13 and ValRS13-11 was confirmed when the template mRNA containing one N-methylvaline (R-V (SEQ ID NO: 120)) was used (FIG. 7(a) Peak MeV1, (b) Peak MeV2). A peak corresponding to the peptide sequence P-V1 introduced with valine contaminated in the cell-free translation system was observed weakly (FIG. 7(a) Peak V1, (b) Peak V2).

Next, it was confirmed that the peptide sequence P-MeV2 containing two N-methylvaline residues was synthesized as main product by both the mutant ValRSs when a template mRNA containing two consecutive N-methylvalines (R-V2 (SEQ ID NO: 122)) was used (FIG. 7(c) Peak MeV3, (d) Peak MeV5). Meanwhile, the peptide sequence P-MeV4 containing one N-methylvaline residue and one valine residue (FIG. 7(c) Peak MeV4, (d) Peak MeV6) was observed, but the peak intensity was suppressed when using ValRS13-11 compared to ValRS13.

Finally, template mRNA containing three consecutive N-methylvalines (R-V3 (SEQ ID NO: 124)) was used to perform translation experiments. When ValRS13 was added, the synthesis of the target peptide sequence P-MeV3 containing three N-methylvaline residues was observed (FIG. 7(e), Peak MeV7), but the peptide sequence P-MeV5 comprising two N-methylvaline residues and one valine residue was produced as main product (FIG. 7(e), Peak MeV8). The peptide sequence P-MeV6 comprising one N-methylvaline residue and two valine residues was also observed (FIG. 7(e), Peak MeV9). Meanwhile, when ValRS13-11 was added, it was observed that the target peptide sequence P-MeV3 containing three N-methylvaline residues was ribosomally synthesized as main product (FIG. 7(f), Peak MeV10). The peptide sequences P-MeV5 and P-MeV6 containing valine were also observed, but the peak intensity of these peptide sequences was suppressed compared to that obtained when using ValRS13 (FIG. 7(f), Peak MeV11 and MeV12). These results indicate that ValRS13-11 has increased aminoacylation activity to N-methylvaline compared to ValRS13, leading to the increase of the ribosomally synthesized amount of the target peptide containing N-methylvaline.

```
Peptide sequence P-MeV2
                                          (SEQ ID NO: 126)
formylMetArg[MeVal][MeVal]ArgAspTyrLysAsp AspAspAspLys Peptide sequence P-MeV4
                                          (SEQ ID NO: 126)
formylMetArg[MeVal]ValArgAspTyrLysAspAspAspAsp Lys
or formylMetArgVal[MeVal]ArgAspTyrLysAspAspAspAsp Lys Peptide sequence P-MeV3
                                          (SEQ ID NO: 127)
formylMetArg[MeVal][MeVal][MeVal]ArgAspTyrLysAsp AspAspAspLys Peptide sequence P-MeV5
                                          (SEQ ID NO: 127)
formylMetArg[MeVal][MeVal]ValArgAspTyrLysAsp AspAspAspLys
or formylMetArg[MeVal]Val[MeVal]ArgAspTyrLysAsp AspAspAspLys
or
```

-continued
formylMetArgVal[MeVal][MeVal]ArgAspTyrLysAsp

AspAspAspLys

Peptide sequence P-MeV6
(SEQ ID NO: 127)
formylMetArg[MeVal]ValValArgAspTyrLysAspAspAsp AspLys
or formylMetArgVal[MeVal]ValArgAspTyrLysAspAspAsp AspLys
or formylMetArgValVal[MeVal]ArgAspTyrLysAspAspAsp AspLys MALDI-TOF MS:
Calc. m/z: [H+M]+=1710.8 (the peptide corresponding to the sequence P-MeV2)
Calc. m/z: [H+M]+=1696.8 (the peptide corresponding to the sequence P-MeV4)
Calc. m/z: [H+M]+=1823.9 (the peptide corresponding to the sequence P-MeV3)
Calc. m/z: [H+M]+=1809.9 (the peptide corresponding to the sequence P-MeV5)
Calc. m/z: [H+M]+=1795.9 (the peptide corresponding to the sequence P-MeV6)

Example 3: Development of N-Methylserine-Accenting ARS

Preparation of Plasmids for Wild-Type and Mutant SerRSs

The mutant SerRS plasmids (having His-tag (6×His) at the N-terminus) listed in Table 5 were constructed by introducing site-directed mutations using PCR into a plasmid comprising the ORF sequence (SEQ ID NOs: 25, 26) of wild-type SerRS gene of *E. coli* (PQE-32(2) 2_wtSERRS), which was used as starting material. Specifically, 2.5 µL of 10 ng/µL template, 12.5 µL of 2×KOD Fx buffer (TOYOBO, KFX-101), 0.75 µL of 10 µM forward primer, 0.75 µL of 10 µM reverse primer, 5 JAL of 2 mM dNTP, 0.5 µL of KOD FX (TOYOBO, KFX-101), and 3 µL of H$_2$O were mixed together. Next, the resulting reaction solution was heated at 94° C. for 2 minutes and then subjected to 10 cycles, each consisting of heating at 98° C. for 10 seconds and heating at 68° C. for 7 minutes, to amplify the mutant gene. The combinations of the template plasmid, forward primer, and reverse primer used are listed in Table 6. Each sequence of primers "F.S2" through "F.S8", "F.S15" through "F.S23", and "F.S33" through "F.S38" corresponds to SEQ ID NOs: 128-149 in ascending order. Each sequence of primers "R.S2" through "R.S8", "R.S15" through "R.S23", and "R.S33" through "R.S38" corresponds to SEQ ID NOs: 150-171 in ascending order. 0.5 µL of 10 U/µL DpnI was then added to the PCR reaction solution and further incubated at 37° C. for 1.5 hours to digest the template DNA, and the resulting mutant DNA was purified. *E. coli* XL-1 Blue strain (STRATAGENE, 200236) was then co-transformed with the resulting mutant gene DNA and pREP4 (Invitrogen, V004-50) encoding the lacI gene. The transformants were seeded onto agar containing ampicillin and kanamycin. The plasmids of interest were purified from the resulting clones. The mutations were confirmed to be introduced into the plasmids.

For plasmid construction requiring multistep mutation introduction, the procedure as described above was repeated to obtain plasmids into which mutations of interest were introduced. The combinations of the primers and template for such plasmid construction are listed in Table 6.

TABLE 5

| Name | position 237 | position 239 | position 389 |
| --- | --- | --- | --- |
| SerRS01(WT) | T | E | N |
| SerRS02 | A | E | N |
| SerRS03 | S | | |
| SerRS04 | G | | |
| SerRS05 | T | A | N |
| SerRS06 | | V | |
| SerRS07 | | S | |
| SerRS08 | T | E | A |
| SerRS09 | A | E | A |
| SerRS10 | S | | |
| SerRS11 | G | | |
| SerRS12 | T | A | |
| SerRS13 | | V | |
| SerRS14 | | S | |
| SerRS15 | A | A | N |
| SerRS16 | | V | |
| SerRS17 | | S | |
| SerRS18 | S | A | |
| SerRS19 | | V | |
| SerRS20 | | S | |
| SerRS21 | G | A | |
| SerRS22 | | V | |
| SerRS23 | | S | |
| SerRS24 | A | A | A |
| SerRS25 | | V | |
| SerRS26 | | S | |
| SerRS27 | S | A | |
| SerRS28 | | V | |
| SerRS29 | | S | |
| SerRS30 | G | A | |
| SerRS31 | | V | |
| SerRS32 | | S | |
| SerRS33 | E291A | | |
| SerRS34 | K289A | | |
| SerRS35 | T | G | N |
| SerRS36 | T | D | N |
| SerRS37 | S | G | N |
| SerRS38 | S | D | N |

TABLE 6

| | forward primer | revers primer | Template |
| --- | --- | --- | --- |
| SerRS001 | | | |
| SerRS002 | F. S2 | R. S2 | wt |
| SerRS003 | F. S3 | R. S3 | wt |
| SerRS004 | F. S4 | R. S4 | wt |
| SerRS005 | F. S5 | R. S5 | wt |
| SerRS006 | F. S6 | R. S6 | wt |
| SerRS007 | F. S7 | R. S7 | wt |
| SerRS008 | F. S8 | R. S8 | wt |
| SerRS009 | F. S2 | R. S2 | SerRS008 |
| SerRS010 | F. S3 | R. S3 | SerRS008 |
| SerRS011 | F. S4 | R. S4 | SerRS008 |
| SerRS012 | F. S5 | R. S5 | SerRS008 |
| SerRS013 | F. S6 | R. S6 | SerRS008 |
| SerRS014 | F. S7 | R. S7 | SerRS008 |
| SerRS015 | F. S15 | R. S15 | wt |
| SerRS016 | F. S16 | R. S16 | wt |
| SerRS017 | F. S17 | R. S17 | wt |
| SerRS018 | F. S18 | R. S18 | wt |
| SerRS019 | F. S19 | R. S19 | wt |
| SerRS020 | F. S20 | R. S20 | wt |
| SerRS021 | F. S21 | R. S21 | wt |
| SerRS022 | F. S22 | R. S22 | wt |
| SerRS023 | F. S23 | R. S23 | wt |
| SerRS024 | F. S15 | R. S15 | SerRS008 |
| SerRS025 | F. S16 | R. S16 | SerRS008 |
| SerRS026 | F. S17 | R. S17 | SerRS008 |
| SerRS027 | F. S18 | R. S18 | SerRS008 |

TABLE 6-continued

| | forward primer | revers primer | Template |
|---|---|---|---|
| SerRS028 | F. S19 | R. S19 | SerRS008 |
| SerRS029 | F. S20 | R. S20 | SerRS008 |
| SerRS030 | F. S21 | R. S21 | SerRS008 |
| SerRS031 | F. S22 | R. S22 | SerRS008 |
| SerRS032 | F. S23 | R. S23 | SerRS008 |
| SerRS033 | F. S33 | R. S33 | wt |
| SerRS034 | F. S34 | R. S34 | wt |
| SerRS035 | F. S35 | R. S35 | wt |
| SerRS036 | F. S36 | R. S36 | wt |
| SerRS037 | F. S37 | R. S37 | wt |
| SerRS038 | F. S38 | R. S38 | wt |

Small Scale Expression of Wild-Type and Mutant SerRSs

Next, the resulting mutant plasmid was introduced into E. coli to express the mutant protein. First, E. coli BL21 strain transformed with the mutant plasmid and pREP4 (Invitrogen, V004-50) was cultured at 37° C. in 4 mL of LB medium containing kanamycin and ampicillin. Then, when the OD value at 600 nm reached 0.4 to 0.8, IPTG was added to a final concentration of 0.5 mM. After further culturing at 37° C. for 4 hours, the bacterial pellets were collected with a centrifuge.

Small Scale Purification of Wild-Type and Mutant SerRSs

Next, the resulting bacterial pellets were disrupted, and the mutant protein of interest was purified from the supernatant. Specifically, the bacterial pellets as described above were suspended in 600 µL of CHAPS solution (0.5% CHAPS (DOJINDO: 349-04722), 50% TBS (TaKaRa, T903)) and mixed with 6 µL of 30 U/µl rLysozyme (Novagen, 71110-3) followed by incubation at room temperature for 10 minutes. The reaction was further mixed with 2 µL of 2.5 U/µL benzonase nuclease (Novagen, 70746-3) followed by incubation at room temperature for 20 minutes, and an insoluble fraction was separated by centrifugation. Then, the mutant protein was purified from the resulting supernatant using QIAGEN Ni-NTA spin column kit (Qiagen, 31314) according to the product manual. Finally, excess imidazole was removed using a desalting column, PD miniTrap G-25 (GE Healthcare, 28-9180-07) according to the product manual.

Aminoacylation Reaction with N-Methylserine Using Wild-Type and Mutant SerRSs

Synthesis of E. coli tRNASer by In Vitro Transcription Reaction

E. coli tRNA (R-tRNASer3 (SEQ ID NO: 173)) was synthesized from a template DNA (D-tRNASer3 (SEQ ID NO: 172)) by in vitro transcription reaction using RiboMAX Large Scale RNA production System T7 (Promega, P1300) in the presence of 7.5 mM GMP, and purified using RNeasy Mini kit (Qiagen).

D-tRNASer3
tRNASer3 DNA sequence:
(SEQ ID NO: 172)
GGCGTAATACGACTCACTATAGGTGAGGTGGCCGAGAGGCTGAAGGCGCT

CCCCTGCTAAGGGAGTATGCGGTCAAAAGCTGCATCCGGGGTTCGAATCC

CCGCCTCACCGCCA

R-tRNASer3
tRNASer3 RNA sequence:
(SEQ ID NO: 173)
GGUGAGGUGGCCGAGAGGCUGAAGGCGCUCCCCUGCUAAGGGAGUAUGCG

GUCAAAAGCUGCAUCCGGGGUUCGAAUCCCCGCCUCACCGCCA

Aminoacylation Reaction

For the aminoacylation reaction, the solution containing 40 µM transcribed tRNA, 10 mM HEPES-K (pH 7.6), and 10 mM KCl solution was heated at 95° C. for 2 minutes and then left at room temperature for 5 minutes or more to refold the tRNA. This tRNA solution was added to a final concentration of 10 µM to an acylation buffer (final concentration 50 mM HEPES-K [pH 7.6], 2 mM ATP, 100 mM potassium acetate, 10 mM magnesium acetate, 1 mM DTT, 2 mM spermidine, 0.1 mg/mL Bovine Serum Albumin), mixed with wild-type or mutant SerRS (final concentration 0.1 µM-2 µM) and N-methylserine (final concentration 1 mM), and incubated at 37° C. for 10 minutes. Four volumes of a loading buffer (90 mM sodium acetate [pH 5.2], 10 mM EDTA, 95% (w/w) formamide, 0.001% (w/v) xylene cyanol) were added to the reaction solution and analyzed with acidic PAGE containing 6 M urea, and aminoacylation activity was detected by separating unreacted tRNA and aminoacyl-tRNA. RNA was stained with SYBR Gold (Life Technologies) and detected with LAS4000 (GE Healthcare) (FIG. 8).

As a result, tRNA acylated with N-methylserine was observed when the mutants 03 (SEQ ID NO: 6), 35 (SEQ ID NO: 8), and 37 (SEQ ID NO: 9) were used. It is suggested that these mutants had increased activity for aminoacylation with N-methylserine compared to wild-type SerRS (FIG. 8, lanes 3, 25, 27).

Translational Introduction of N-Methylserine Using Wild-Type and Mutant SerRSs

Template mRNA (R-S(SEQ ID NO: 175)) was synthesized from a template DNA (D-S (SEQ ID NO: 174)) by in vitro transcription reaction using RiboMAX Large Scale RNA production System T7 (Promega, P1300) and purified using RNeasy Mini kit (Qiagen).

D-S (CT21)
DNA sequence:
(SEQ ID NO: 174)
GGCGTAATACGACTCACTATAGGGTTAACTTTAACAAGGAGAAAAACATG

CGTTCCCGTGACTACAAGGACGACGACGACAAGTAAGCTTCG

R-S
RNA sequence:
(SEQ ID NO: 175)
GGGUUAACUUUAACAAGGAGAAAAACAUGCGUUCCCGUGACUACAAGGAC

GACGACGACAAGUAAGCUUCG

Cell-Free Translation System

In order to confirm translational introduction of N-methylserine, a desired polypeptide containing N-methylserine was ribosomally synthesized by adding N-methylserine and SerRS to a cell-free translation system. The translation system used was PURE system, a reconstituted cell-free protein synthesis system from E. coli. Specifically, wild-type or mutant SerRS and N-methylserine were added to a solution containing a basic cell-free translation solution (1 mM GTP, 1 mM ATP, 20 mM creatine phosphate, 50 mM HEPES-KOH pH 7.6, 100 mM potassium acetate, 9 mM magnesium acetate, 2 mM spermidine, 1 mM dithiothreitol, 1.5 mg/ml E. coli MRE600 (RNase negative)-derived tRNA (Roche), 0.1 mM 10-HCO—H4 folate, 4 µg/ml creatine kinase, 3 µg/ml myokinase, 2 unit/ml inorganic pyrophosphatase, 1.1 µg/ml nucleoside diphosphate kinase, 0.6 µM methionyl-tRNA transformylase, 0.26 µM EF-G, 0.24 µM RF2, 0.17 µM RF3, 0.5 µM RRF, 2.7 µM IF1, 0.4 µM IF2, 1.5 µM IF3, 40 µM EF-Tu, 84 µM EF-Ts, 1.2 µM ribosome, 0.03 µM ArgRS, 0.13 µM AspRS, 0.11 µM LysRS, 0.03 µM MetRS, 0.02 µM TyrRS (wherein the proteins prepared by the inventors were essentially prepared as His-tagged proteins)), and 1 µM template mRNA, each 250 µM arginine, aspartic acid, lysine, methionine, and tyrosine, and left at 37° C. for 1 hour to ribosomally synthesize the peptide.

Detection by Mass Spectroscopy

Mass spectroscopy was performed using MALDI-TOF MS for detecting peptides into which N-methylserine is ribosomally introduced. Specifically, a solution containing 1 µM template mRNA (R-S(SEQ ID NO: 175)) and arginine, lysine, methionine, tyrosine, and aspartic acid (each final concentration 250 µM) added to the cell-free translation system as described above was prepared. SerRS (final concentration 0.1-2 µM) and N-methylserine (final concentration 5 mM) were added to the solution and incubated at 37° C. for 60 minutes. The resulting translation reaction products were purified with SPE C-TIP (Nikkyo Technos Co., Ltd) and analyzed with MALDI-TOF MS. Translation products were identified with MALDI-TOF MS spectrometry using α-cyano-4-hydroxycinnamic acid as a matrix.

As a result of the translation using wild-type SerRS (SEQ ID NO: 25)), a peak corresponding to the target peptide peak P-CT21MeSer containing N-methylserine (FIG. 9(a), Peak MeS1 m/z: [H+M]+=1585.6) was observed, but the peak corresponding to Ser-containing peptide P-CT21Ser probably derived from Ser contaminated in the translation system in trace amounts (FIG. 9(a), Peak S1 m/z: [H+M]+=1571.6) was observed as main product (FIG. 9(a)). On the other hand, when similar experiments were performed using the modified SerRS with mutations introduced (Ser03 (SEQ ID NO: 6), 05 (SEQ ID NO: 7)), the peak corresponding to P-CT21Ser (FIG. 9(b) Peak S2, (c) Peak S3) was observed similarly but as a side product, and it was revealed that the main product was P-CT21MeSer (FIG. 9(b) Peak MeS2, (c) Peak MeS3). Particularly, when SerRS35 and 37 were used, it was demonstrated that the peak corresponding to P-CT21Ser was not observed and CT21MeSer was synthesized with high purity (FIG. 9(d) Peak MeS4, (e) Peak MeS5). Consequently, these modified SerRSs were demonstrated to have increased activity to MeSer compared to wild-type SerRS.

```
Peptide sequence P-CT21Ser
                                    (SEQ ID NO: 176)
formylMetArgSerArgAspTyrLysAspAspAspAspLys Peptide sequence P-CT21MeSer
                                    (SEQ ID NO: 176)
formylMetArg[MeSer]ArgAspTyrLysAspAspAspAspLys
```

MALDI-TOF MS:

Calc. m/z: [H+M]+=1571.7 (the peptide corresponding to the sequence P-CT21Ser)

Calc. m/z: [H+M]+=1585.7 (the peptide corresponding to the sequence P-CT21MeSer)

Example 4: Development of N-Methylthreonine-Accepting ARS

Preparation of Wild-Type and Mutant ThrRS Proteins

Expression vectors having a polyhistidine sequence at the N-terminus and comprising mutations listed in Table 7 were constructed. Subsequently, an expression strain was transformed with the vectors, and the mutant proteins of interest were purified with a nickel column from supernatants obtained by disrupting cells.

TABLE 7

| Name | Position 332 | Position 334 | Position 385 | Position 462 | Position 484 | Position 511 |
|---|---|---|---|---|---|---|
| ThrRS01(wt) | M | C | H | Y | Q | H |
| ThrRS02 | A | C | H | Y | Q | H |
| ThrRS03 | G | C | H | Y | Q | H |
| ThrRS04 | M | A | H | Y | Q | H |
| ThrRS05 | M | G | H | Y | Q | H |
| ThrRS06 | M | C | A | Y | Q | H |
| ThrRS07 | M | C | H | A | Q | H |
| ThrRS08 | M | C | H | L | Q | H |
| ThrRS09 | M | C | H | V | Q | H |
| ThrRS10 | M | C | H | F | Q | H |
| ThrRS11 | M | C | H | Y | A | H |
| ThrRS12 | M | C | H | Y | N | H |
| ThrRS13 | M | C | H | Y | Q | A |
| ThrRS14 | M | C | H | Y | Q | G |

Translational Introduction of N-Methylthreonine Using Wild-Type and Mutant ThrRSs A template mRNA (R-T (SEQ ID NO: 178)) was synthesized from a template DNA (D-T (SEQ ID NO: 177)) by in vitro transcription reaction using RiboMAX Large Scale RNA production System T7 (Promega, P1300) and purified using RNeasy Mini kit (Qiagen).

```
D-T (3lib15#09)
DNA sequence:
                                    (SEQ ID NO: 177)
GGCGTAATACGACTCACTATAGGGTTAACTTTAAGAAGGAGATATACATA

TGAAGGCTGGTCCGGGTTTTATGACTAAGAGTGGTAGTGGTAGTTAAGCT

TCG

R-T
RNA sequence:
                                    (SEQ ID NO: 178)
GGGUUAACUUUAAGAAGGAGAUAUACAUAUGAAGGCUGGUCCGGGUUUUA

UGACUAAGAGUGGUAGUGGUAGUUAAGCUUCG
```

Cell-Free Translation System

In order to confirm translational introduction of N-methylthreonine, a desired polypeptide containing N-methylthreonine was ribosomally synthesized by adding N-methylthreonine and a mutant ThrRS to a cell-free translation system. The translation system used was PURE system, a reconstituted cell-free protein synthesis system from E. coli. Specifically, wild-type or mutant ThrRS and N-methylthreonine were added to a solution containing a basic cell-free translation solution (1 mM GTP, 1 mM ATP, 20 mM creatine phosphate, 50 mM HEPES-KOH pH 7.6, 100 mM potassium acetate, 9 mM magnesium acetate, 2 mM spermidine, 1 mM dithiothreitol, 1.5 mg/ml E. coli MRE600 (RNase negative)-derived tRNA (Roche), 0.1 mM 10-HCO—H4 folate, 4 µg/ml creatine kinase, 3 µg/ml myokinase, 2 unit/ml inorganic pyrophosphatase, 1.1 µg/ml nucleoside diphosphate kinase, 0.6 µM methionyl-tRNA transformylase, 0.26

μM EF-G, 0.24 μM RF2, 0.17 μM RF3, 0.5 μM RRF, 2.7 μM IF1, 0.4 μM IF2, 1.5 μM IF3, 40 μM EF-Tu, 93 μM EF-Ts, 1.2 μM ribosome, 2.73 μM AlaRS, 0.13 μM AspRS, 0.09 μM GlyRS, 0.11 M LysRS, 0.03 μM MetRS, 0.68 M PheRS, 0.16 μM ProRS, 0.25 μM SerRS (wherein the proteins prepared by the inventors were essentially prepared as His-tagged proteins)), and 1 μM template mRNA, each 250 μM glycine, proline, alanine, phenylalanine, lysine, methionine, and serine, and left at 37° C. for 1 hour to ribosomally synthesize the peptide.

Detection by Mass Spectroscopy

Mass spectroscopy was performed using MALDI-TOF MS for detecting peptides into which N-methylthreonine is ribosomally introduced. Specifically, a solution containing 1 μM template mRNA (R-T (SEQ ID NO: 178)) and glycine, proline, alanine, phenylalanine, lysine, methionine, and serine (each final concentration 250 μM) added to the cell-free translation system as described above was prepared. ThrRS (final concentration 2 μM) and N-methylthreonine (final concentration 5 mM) were added to the solution and incubated at 37° C. for 60 minutes. The resulting translation reaction products were purified with SPE C-TIP (Nikkyo Technos Co., Ltd) and analyzed with MALDI-TOF MS. Translation products were identified with MALDI-TOF MS spectrometry using α-cyano-4-hydroxycinnamic acid as a matrix.

As a result of the translation using wild-type ThrRS (SEQ ID NO: 29), a peak corresponding to the peptide peak P-3lib15MeThr of interest containing N-methylthreonine ((FIG. 10(a), Peak MeT1) and a peak corresponding to a potassium salt of the peptide (FIG. 10(a), Peak MeT2) were observed as main products, but at the same time, a peak corresponding to the peptide P-3lib15Thr derived from Thr contaminated in the translation system in trace amounts (FIG. 10(a), PeakT1) and a peak corresponding to a potassium salt of the peptide (FIG. 10(a), PeakT2) were also observed, revealing that the purity of the translation products was adversely affected (FIG. 10(a)). On the other hand, when experiments were performed using the modified ThrRS 03 (SEQ ID NO: 10) and the modified ThrRS 14 (SEQ ID NO: 11) with mutations introduced, the peaks derived from P-CT21MeThr (Peak MeT3-6, FIG. 10) were similarly observed, and the peak corresponding to the peptide sequence P-3lib15Thr was only slightly observed (FIG. 10(b), (c)). In other words, it was demonstrated that the peptide with MeThr introduced was synthesized with higher purity using the modified ThrRSs compared to using wild-type ThrRS, and it was suggested that the modified ThrRS 03 and 14 are ARSs that can introduce MeThr into peptides more efficiently compared to wild-type ThrRS.

```
Peptide sequence P-3lib15Thr
                                    (SEQ ID NO: 179)
formylMetLysAlaGlyProGlyPheMetThrLysSerGlySerGly Ser Peptide sequence P-3lib15MeThr
                                    (SEQ ID NO: 179)
formylMetLysAlaGlyProGlyPheMet[MeThr]LysSerGly SerGlySer
```

MALDI-TOF MS:
Calc. m/z: [H+M]+=1470.7, [K+M]+=1508.8 (the peptide corresponding to the sequence P-3lib15Thr)

Calc. m/z: [H+M]+=1484.7, [K+M]+=1522.8 (the peptide corresponding to the sequence P-3lib15MeThr)

Example 5: Development of N-Methyltryptophan-Accepting ARS

Preparation of Wild-Type and Mutant TrpRS Proteins

Expression vectors having a polyhistidine sequence at the N-terminus and containing mutations listed in Table 8 were constructed. Then, an expression strain was transformed with the vectors, and the mutant proteins of interest were purified with a nickel column from supernatants obtained by disrupting cells.

TABLE 8

| Name | Position 128 | Position 132 | Position 150 | Position 153 |
|---|---|---|---|---|
| ThrRS01 (wt) | Y | M | Q | H |
| ThrRS02 | Y | M | Q | A |
| ThrRS03 | Y | M | A | H |
| ThrRS04 | Y | M | A | A |
| ThrRS05 | Y | A | Q | H |
| ThrRS06 | Y | A | Q | A |
| ThrRS07 | Y | A | A | H |
| ThrRS08 | Y | A | A | A |
| ThrRS09 | A | M | Q | H |
| ThrRS10 | Y | M | S | H |
| ThrRS11 | Y | M | G | H |
| ThrRS12 | Y | M | Q | G |
| ThrRS13 | Y | M | G | A |
| ThrRS14 | Y | M | A | G |
| ThrRS15 | Y | M | G | G |
| ThrRS16 | Y | G | A | A |
| ThrRS17 | Y | I | A | A |
| ThrRS18 | Y | V | A | A |
| ThrRS19 | Y | Q | A | A |
| ThrRS20 | Y | L | A | A |

Translational Introduction of N-Methyltryptophan Using Wild-Type and Mutant TrpRSs A template mRNA(R-W (SEQ ID NO: 197)) was synthesized from a template DNA (D-W (SEQ ID NO: 196)) by in vitro transcription reaction using RiboMAX Large Scale RNA production System T7 (Promega, P1300) and purified using RNeasy Mini kit (Qiagen).

```
D-W (CT29)
DNA sequence:
                                    (SEQ ID NO: 196)
GGCGTAATACGACTCACTATAGGGTTAACTTTAACAAGGAGAAAAACATG

CGTTGGCGTGACTACAAGGACGACGACGACAAGTAAGCTTCG

R-W
RNA sequence:
                                    (SEQ ID NO: 197)
GGGUUAACUUUAACAAGGAGAAAAACAUGCGUUGGCGUGACUACAAGGAC

GACGACGACAAGUAAGCUUCG
```

Cell-Free Translation System

In order to confirm translational introduction of N-methyltryptophan, a desired polypeptide containing N-methyltryptophan was ribosomally synthesized by adding N-methyltryptophan and a mutant TrpRS to a cell-free translation system. The translation system used was PURE system, a reconstituted cell-free protein synthesis system from E. coli. Specifically, wild-type or mutant TrpRS and N-methyltryptophan were added to a solution containing a basic cell-free translation solution (1 mM GTP, 1 mM ATP, 20 mM creatine phosphate, 50 mM HEPES-KOH pH 7.6, 100 mM potassium acetate, 9 mM magnesium acetate, 2 mM spermidine, 1 mM dithiothreitol, 1.5 mg/ml E. coli MRE600 (RNase negative)-derived tRNA (Roche), 0.1 mM 10-HCO—H4 folate, 4 µg/ml creatine kinase, 3 µg/ml myokinase, 2 unit/ml inorganic pyrophosphatase, 1.1 µg/ml nucleoside diphosphate kinase, 0.6 µM methionyl-tRNA transformylase, 0.26 µM EF-G, 0.24 µM RF2, 0.17 µM RF3, 0.5 µM RRF, 2.7 µM IF1, 0.4 µM IF2, 1.5 µM IF3, 40 µM EF-Tu, 84 µM EF-Ts, 1.2 µM ribosome, 0.03 µM ArgRS, 0.13 µM AspRS, 0.11 µM LysRS, 0.03 µM MetRS, 0.02 µM TyrRS (wherein the proteins prepared by the inventors were essentially prepared as His-tagged proteins)), and 1 µM template mRNA, each 250 µM arginine, aspartic acid, lysine, methionine, and tyrosine, and left at 37° C. for 1 hour to ribosomally synthesize the peptide.

Detection by Mass Spectroscopy

Mass spectroscopy was performed using MALDI-TOF MS for detecting peptides into which N-methyltryptophan is ribosomally introduced. Specifically, a solution containing 1 µM template mRNA (R-W (SEQ ID NO: 197)) and arginine, lysine, methionine, tyrosine, and aspartic acid (each final concentration 250 µM) added to the cell-free translation system as described above was prepared. TrpRS (final concentration 5 µM) and N-methyltryptophan (final concentration 5 mM) were added to the solution and incubated at 37° C. for 60 minutes. The resulting translation reaction products were purified with SPE C-TIP (Nikkyo Technos Co., Ltd) and analyzed with MALDI-TOF MS. Translation products were identified with MALDI-TOF MS spectrometry using α-cyano-4-hydroxycinnamic acid as a matrix.

As a result of the translation using wild-type TrpRS (SEQ ID NO: 188), a peak corresponding to the target peptide peak P-CT29MeTrp containing N-methyltryptophan (FIG. 11(a), Peak MeW1) was observed, but a peak corresponding to peptide P-CT29Trp derived from Trp contaminated in the translation system in trace amounts was observed as main product (FIG. 11(a), PeakW1). On the other hand, when experiments were performed using the modified TrpRS 04 (SEQ ID NO: 184), the modified TrpRS 05 (SEQ ID NO: 185), and the modified TrpRS 18 (SEQ ID NO: 186) with mutations introduced, peaks derived from P-CT29MeTrp (Peak MeW2-4, FIG. 11(b)-(d)) were observed as main product. In other words, it is demonstrated that the peptide introduced with MeTrp was synthesized at a higher purity using modified TrpRSs compared to using wild-type TrpRS, and it was suggested that these modified TrpRSs are ARSs that can introduce MeTrp into peptides more efficiently compared to wild-type TrpRS.

```
Peptide sequence P-CT29Trp
                                        (SEQ ID NO: 198)
formylMetArgTrpArgAspTyrLysAspAspAspAspLys Peptide sequence P-CT29MeTrp
                                        (SEQ ID NO: 199)
formylMetArg[MeTrp]ArgAspTyrLysAspAspAspAspLys
```

MALDI-TOF MS:

Calc. m/z: [H+M]+=1670.7 (the peptide corresponding to the sequence P-CT29Trp)

Calc. m/z: [H+M]+=1684.7 (the peptide corresponding to the sequence P-CT29MeTrp)

Example 6: Development of N-Methylleucine-Accepting ARS

Preparation of Wild-Type and Mutant LeuRS Proteins

Expression vectors having a polyhistidine sequence at the N-terminus and containing mutations listed in Table 9 were constructed. Subsequently, an expression strain was transformed with the vectors, and the mutant proteins of interest were purified with a nickel column from supernatants obtained by disrupting cells.

TABLE 9

| Name | Position 43 | Position 80 | Position 252 |
|---|---|---|---|
| LeuRS01(wt) | Y | D | T |
| LeuRS02 | G | D | T |
| LeuRS03 | A | D | T |
| LeuRS04 | E | D | T |
| LeuRS05 | D | D | T |
| LeuRS06 | F | D | T |
| LeuRS07 | Y | G | T |
| LeuRS08 | Y | A | T |
| LeuRS09 | E | G | T |
| LeuRS10 | E | A | T |
| LeuRS11 | D | G | T |
| LeuRS12 | D | A | T |
| LeuRS13 | A | G | T |
| LeuRS14 | G | G | T |
| LeuRS15 | Y | D | A |
| LeuRS16 | A | G | A |
| LeuRS17 | G | G | A |
| LeuRS18 | G | D | A |
| LeuRS19 | Y | G | A |
| LeuRS21 | E | G | A |
| LeuRS22 | E | A | A |
| LeuRS23 | D | G | A |

Translational Introduction of N-Methylleucine Using Wild-Type and Mutant LeuRSs

A template mRNA(R-L (SEQ ID NO: 201)) was synthesized from a template DNA (D-L (SEQ ID NO: 200)) by in vitro transcription reaction using RiboMAX Large Scale RNA production System T7 (Promega, P1300) and purified using RNeasy Mini kit (Qiagen).

```
D-L (CT23)
DNA sequence:
                                        (SEQ ID NO: 200)
GGCGTAATACGACTCACTATAGGGTTAACTTTAACAAGGAGAAAAACATG

CGTCTCCGTGACTACAAGGACGACGACGACAAGTAAGCTTCG

R-L
RNA sequence:
                                        (SEQ ID NO: 201)
GGGUUAACUUUAACAAGGAGAAAAACAUGCGUCUCCGUGACUACAAGGAC

GACGACGACAAGUAAGCUUCG
```

Cell-Free Translation System

In order to confirm translational introduction of N-methylleucine, a desired polypeptide containing N-methylleucine was ribosomally synthesized by adding N-methylleucine and a mutant LeuRS to a cell-free translation system. The translation system used was PURE system, a reconstituted cell-free protein synthesis system from E. coli. Specifically, wild-type or mutant LeuRS and N-methylleucine were added to a solution containing a basic cell-free translation solution (1 mM GTP, 1 mM ATP, 20 mM creatine phosphate, 50 mM HEPES-KOH pH 7.6, 100 mM potassium acetate, 9 mM magnesium acetate, 2 mM spermidine, 1 mM dithiothreitol, 1.5 mg/ml E. coli MRE600 (RNase negative)- derived tRNA (Roche), 0.1 mM 10-HCO—H4 folate, 4 µg/ml creatine kinase, 3 µg/ml myokinase, 2 unit/ml inorganic pyrophosphatase, 1.1 µg/ml nucleoside diphosphate kinase, 0.6 µM methionyl-tRNA transformylase, 0.26 µM EF-G, 0.24 µM RF2, 0.17 µM RF3, 0.5 µM RRF, 2.7 µM IF1, 0.4 µM IF2, 1.5 µM IF3, 40 µM EF-Tu, 84 µM EF-Ts, 1.2 µM ribosome, 0.03 µM ArgRS, 0.13 µM AspRS, 0.11 µM LysRS, 0.03 µM MetRS, 0.02 µM TyrRS (wherein the proteins prepared by the inventors were essentially prepared as His-tagged proteins)), and 1 µM template mRNA, each 250 µM arginine, aspartic acid, lysine, methionine, and tyrosine, and left at 37° C. for 1 hour to ribosomally synthesize the peptide.

Detection by Mass Spectroscopy

Mass spectroscopy was performed using MALDI-TOF MS for detecting peptides into which N-methylleucine is ribosomally introduced. Specifically, a solution containing 1 µM template mRNA (R-L (SEQ ID NO: 201)) and arginine, lysine, methionine, tyrosine, and aspartic acid (each final concentration 250 µM) added to the cell-free translation system as described above was prepared. LeuRS (final concentration 0.4-2 µM) and N-methylleucine (final concentration 5 mM) were added to the solution and incubated at 37° C. for 60 minutes. The resulting translation reaction products were purified with SPE C-TIP (Nikkyo Technos Co., Ltd) and analyzed with MALDI-TOF MS. Translation products were identified with MALDI-TOF MS spectrometry using α-cyano-4-hydroxycinnamic acid as a matrix.

As a result of the translation using wild-type LeuRS (SEQ ID NO: 189), a peak corresponding to the target peptide peak P-CT23MeLeu containing N-methylleucine was not observed, but the peptide P-CT23Leu derived from Leu contaminated in the translation system in trace amounts (FIG. 12(a), PeakL1) was observed as an almost single product. On the other hand, when experiments were performed using the modified LeuRS 02 (SEQ ID NO: 187) with mutations introduced, the peak derived from P-CT29MeLeu (Peak MeL1, FIG. 12(b)) was observed, and the intensity of the peak was as strong as the intensity of the peak of the peptide P-CT23Leu containing Leu (Peak L2, FIG. 12(b)). In other words, it is demonstrated that the MeLeu-introduced peptide synthesized using the modified LeuRS 02 was more than that using wild-type LeuRS, suggesting that this modified LeuRS is an ARS that can introduce MeLeu into peptides more efficiently compared to wild-type LeuRS.

Peptide sequence P-CT23Leu (SEQ ID NO: 202)
formylMetArgLeuArgAspTyrLysAspAspAspAspLys Peptide sequence P-CT23MeLeu (SEQ ID NO: 203)
formylMetArg[MeLeu]ArgAspTyrLysAspAspAspAspLys

MALDI-TOF MS:

Calc. m/z: [H+M]+=1597.7 (the peptide corresponding to the sequence P-CT23Leu)

Calc. m/z: [H+M]+=1611.7 (the peptide corresponding to the sequence P-CT23MeLeu)

Example 7: Development of Modified ValRSs Having Increased Selectivity to N-Methylvaline Achieved by Enhancing Valine-Hydrolyzing Ability in the Editing Domain Preparation of Wild-Type and Mutant ValRS Proteins Expression vectors for modified ValRSs that have a polyhistidine sequence at the N-terminus and containing mutations (N43G, T45S) in the catalytic domain and mutation T279A(G) in the editing domain, which mutations increase activity to N-methylvaline, were constructed (Table 10). Then, an expression strain was transformed with the vectors, and the mutant proteins of interest were purified using a nickel column from supernatants obtained by disrupting cells.

TABLE 10

| | Catalytic domain | | Editing domain |
|---|---|---|---|
| Name | Position 43 | Position 45 | Position 279 |
| ValRS01(wt) | N | T | T |
| ValRS13-11 | G | S | T |
| ValRS66 | G | S | A |
| ValRS67 | G | S | G |

Aminoacylation Reaction with Valine and N-Methylvaline Using Mutant ValRSs

Synthesis of E. coli tRNAVal by In Vitro Transcription Reaction

E. coli tRNA (R-tRNAVal1 (SEQ ID NO: 205)) was synthesized from a template DNA (D-tRNAVal1 (SEQ ID NO: 204)) by in vitro transcription reaction using RiboMAX Large Scale RNA production System T7 (Promega, P1300) in the presence of 7.5 mM GMP, and purified using RNeasy Mini kit (Qiagen).

D-tRNAVal1
tRNAVal1 DNA sequence:

(SEQ ID NO: 204)
GGCGTAATACGACTCACTATAGGGTGATTAGCTCAGCTGGGAGAGCACCT

CCCTTACAAGGAGGGGGTCGGCGGTTCGATCCCGTCATCACCCACCA

R-tRNAVal1
tRNAVal1 RNA sequence:

(SEQ ID NO: 205)
GGGUGAUUAGCUCAGCUGGGAGAGCACCUCCCUUACAAGGAGGGGGUCGG

CGGUUCGAUCCCGUCAUCACCCACCA

GGGUGAUUAGCUCAGCUGGGAGAGCACCUC-
CCUUACAAGGAGGGGGUCGGCG GUUCGAUCCC-
GUCAUCACCCACCA

Aminoacylation Reaction

For the aminoacylation reaction, the solution containing 50 µM transcribed RNA, 10 mM HEPES-K (pH 7.6), and 10 mM KCl solution was heated at 95° C. for 2 minutes and then left at room temperature for 5 minutes or more to refold the tRNA. This tRNA solution was added to a final concentration of 10 µM to an acylation buffer (in final concentrations of 50 mM HEPES-K [pH 7.6], 2 mM ATP, 100 mM potassium acetate, 10 mM magnesium acetate, 1 mM DTT, 2 mM spermidine, 0.1 mg/mL Bovine Serum Albumin), mixed with a mutant ValRS (final concentration 2 µM) and N-methylvaline (final concentration 0.08 mM-5 mM) or valine (final concentration 0.031 mM-0.25 mM), and incubated at 37° C. for 10 minutes. Four volumes of a loading buffer (90 mM sodium acetate [pH 5.2], 10 mM EDTA, 95% (w/w) formamide, 0.1% (w/v) xylene cyanol) were added to the reaction solution and analyzed with acidic PAGE containing 6 M urea, and aminoacylation activity was detected by separating unreacted tRNA and aminoacyl-tRNA. RNA was stained with SYBR Gold (Life Technologies) and detected with LAS4000 (GE Healthcare).

This result proved that the acylation abilities of the mutants 13-11, 66 (SEQ ID NO: 182), and 67 (SEQ ID NO: 183) were not very different at each N-methylvaline concentration when N-methylvaline was used as substrate (FIG. 13, for example, lanes 17-19). On the other hand, it was proved that when valine was used as a substrate, the acylation abilities of mutants 66 and 67 reduced compared to mutants 13-11 (FIG. 14, for example, lanes 17-19). This demonstrated that mutants 66 and 67 having mutations newly introduced into the editing domain are modified ValRSs that have reduced aminoacylation activity to valine and therefore has increased selectivity to N-methylvaline.

INDUSTRIAL APPLICABILITY

The present invention provides modified aminoacyl-tRNA synthetases having increased reactivity with N-methyl amino acids compared to natural aminoacyl-tRNA synthetases (ARSs). The modified aminoacyl-tRNA synthetases according to the present invention can aminoacylate tRNAs with their corresponding N-methyl-substituted amino acids such as N-methyl-phenylalanine, N-methyl-valine, N-methyl-serine, N-methyl-threonine, N-methyl-tryptophan, and N-methyl-leucine more efficiently than natural aminoacyl-tRNA synthetases. The present invention can produce polypeptides containing N-methyl amino acids more efficiently.

The invention claimed is:

1. A valyl-tRNA synthetase (ValRS) polypeptide modified to enhance aminoacylation reaction with N-methyl-valine, wherein the polypeptide has aminoacyl-tRNA synthetase (ARS) activity, and wherein the modification comprises at least one amino acid substitution at a position(s) corresponding to asparagine at position 43 and/or threonine at position 45 of ValRS from *Escherichia coli*.

2. The polypeptide according to claim 1, wherein the modification further comprises a substitution at a position corresponding to threonine at position 279 of ValRS from *Escherichia coli*.

3. The polypeptide according to claim 1, wherein the polypeptide is selected from the group consisting of the following (a) and (b):
   (a) a polypeptide comprising amino acids selected from the group consisting of SEQ ID NOs: 3-5, 182, and 183, and
   (b) a polypeptide comprising an amino acid sequence having at least 90% identity to an amino acid sequence selected from the group consisting of SEQ ID NOs: 3-5, 182, and 183.

4. A polynucleotide encoding the polypeptide according to claim 1.

5. A vector comprising the polynucleotide according to claim 4.

6. A host cell comprising a polynucleotide encoding a polypeptide according to claim 1.

7. A method for producing the polypeptide according to claim 1, comprising the step of culturing a host cell comprising a polynucleotide encoding the polypeptide according to claim 1.

8. A method for producing a tRNA acylated with N-methyl-valine, comprising the step of contacting N-methyl valine with tRNA in the presence of the polypeptide according to claim 1.

9. A method for producing a polypeptide comprising N-methyl-valine, comprising the step of performing translation in the presence of the polypeptide according to claim 1 and N-methyl-valine.

10. The method according to claim 9, wherein the step of performing translation is carried out in a cell-free translation system.

11. The polypeptide according to claim 1, having (a) glycine or alanine at a position corresponding to asparagine at position 43 and/or (b) serine at a position corresponding to threonine at position 45 of ValRS from *Escherichia coli*.

12. The polypeptide according to claim 2, having (a) glycine or alanine at a position corresponding to asparagine at position 43 and/or (b) serine at a position corresponding to threonine at position 45 and/or (c) glycine or alanine at a position corresponding to threonine at position 279 of ValRS from *Escherichia coli*.

13. A host cell comprising a polynucleotide encoding a polypeptide according to claim 2.

14. A method for producing a tRNA acylated with N-methyl-valine, comprising the step of contacting N-methyl-valine with tRNA in the presence of the polypeptide according to claim 2.

15. A method for producing a polypeptide comprising N-methyl-valine, comprising the step of performing translation in the presence of the polypeptide according to claim 2 and the N-methyl-valine.

16. A host cell comprising a polynucleotide encoding a polypeptide according to claim 11.

17. A method for producing a tRNA acylated with N-methyl-valine, comprising the step of contacting N-methyl-valine with tRNA in the presence of the polypeptide according to claim 11.

18. A method for producing a polypeptide comprising N-methyl-valine, comprising the step of performing translation in the presence of the polypeptide according to claim 11 and the N-methyl-valine.

19. A host cell comprising a polynucleotide encoding a polypeptide according to claim 12.

20. A method for producing a tRNA acylated with N-methyl-valine, comprising the step of contacting N-methyl-valine with tRNA in the presence of the polypeptide according to claim 12.

21. A method for producing a polypeptide comprising N-methyl-valine, comprising the step of performing translation in the presence of the polypeptide according to claim 12 and the N-methyl-valine.

* * * * *